(12) United States Patent
Blumenfeld et al.

(10) Patent No.: US 7,427,482 B2
(45) Date of Patent: Sep. 23, 2008

(54) METHODS OF ASSESSING THE RISK FOR THE DEVELOPMENT OF SPORADIC PROSTATE CANCER

(75) Inventors: Marta Blumenfeld, Paris (FR); Ilya Chumakov, Vaux-le Penil (FR); Lydie Bougueleret, Petit-Lancy (CH); Annick Cohen-Akenine, Paris (FR)

(73) Assignee: Serono Genetics Institute S.A., Evry (FR)

( * ) Notice: Subject to any disclaimer, the term of this patent is extended or adjusted under 35 U.S.C. 154(b) by 199 days.

(21) Appl. No.: 11/285,466

(22) Filed: Nov. 22, 2005

(65) Prior Publication Data
US 2006/0073512 A1 Apr. 6, 2006

Related U.S. Application Data

(62) Division of application No. 10/376,893, filed on Feb. 27, 2003, now Pat. No. 7,041,454, which is a division of application No. 09/536,059, filed on Mar. 23, 2000, now Pat. No. 6,544,737.

(60) Provisional application No. 60/125,961, filed on Mar. 24, 1999.

(51) Int. Cl.
C07H 21/04 (2006.01)
C12Q 1/68 (2006.01)
(52) U.S. Cl. .................... 435/6; 435/91.1; 435/91.2; 536/23.1; 536/24.3
(58) Field of Classification Search ............... None
See application file for complete search history.

(56) References Cited

U.S. PATENT DOCUMENTS

| 5,719,032 A | 2/1998 | Vielkind |
| 6,544,737 B1 | 4/2003 | Blumenfeld et al. |
| 2003/0092019 A1* | 5/2003 | Meyer et al. ............ 435/6 |

FOREIGN PATENT DOCUMENTS

| EP | 0 048 970 | 4/1982 |
| WO | WO 98/20165 | 5/1998 |
| WO | WO 98/33846 | 9/1998 |
| WO | WO 99/04038 | 1/1999 |
| WO | WO 99/04265 | 1/1999 |

OTHER PUBLICATIONS

Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Beardsley, et al., "Structure and Functional Relationships in Human pur H," Purine and Pyrimidine Metabolism in Man IX, (1998):221-226.
Chee, et al., "Accessing genetic information with high-density DNA arrays", Science (1996), 274:610-614; American Association for the Advancement of Science.
Database Geneseq, Derwent Acc. No. Q77811 (Jul. 16, 1995).
Database Geneseq, Derwent Acc. No. Q93402 (Dec. 20, 1995).
Database Geneseq, Derwent Acc. No. T51562 (Nov. 6, 1997).
Database Geneseq, Derwent Acc. No. V01040 (Mar. 25, 1998).
Database Geneseq, Derwent Acc. No. T85064 (Mar. 19, 1999).
Database Geneseq, Derwent Acc. No. Z25419 (Dec. 16, 1999).
Database Empatent EMBL, Heidelberg Acc. No. A39830 (Mar. 5, 1997).
Database Empatent EMBL, Heidelberg Acc. No. I88685 (Aug. 11, 1998).
Database Empatent EMBL, Heidelberg Acc. No. I88742 (Aug. 11, 1998).
Kruglyak, L. "The use of a genetic map of biallelic markers in linkage studies", Nature Genetics (1997), 17:21-24; Nature America, New York.
Rayl, et al., "The Human purH Gene Product, 5-Aminoimidazole-4-carboxamide Ribonucleotide Formyltransferase/IMP Cyclohydrolase", J. Biol. Chem. (1996), 271(4):2225-2233.
Sapolsky, et al., "High-throughput polymorphism screening and genotyping with high-density oligonucleotide arrays", Genetic Analysis: Biomolecular Engineering (1999), 14(5-6):187-192; Elsevier Science and Publishing, U.S.
Sugita, et al., "Characterization of Molecularly Cloned Human 5-Aminoimidazole-4-carboxamide Ribonucleotide Transformylase", J. Biochem. (1997), 122(2):309-313.

* cited by examiner

Primary Examiner—Jeanine A Goldberg
(74) Attorney, Agent, or Firm—Saliwanchik, Lloyd & Saliwanchik

(57) ABSTRACT

The invention concerns the genomic sequence of the purH gene. The invention also concerns biallelic markers of a purH gene and the association established between these markers and cancer, particularly prostate cancer. The invention provides means to determine the predisposition of individuals to cancer as well as means for the diagnosis of cancer and for the prognosis/detection of an eventual treatment response to agents acting on cancer.

22 Claims, 10 Drawing Sheets

| MARKERS | 99-23437/347 | 99-23452/306 | 99-5604/376 | 99-23440/274 | 99-5582/71 | 99-5595/380 | 99-23460/199 | 99-15798/86 | 99-5596/216 | 99-5590/99 |
|---|---|---|---|---|---|---|---|---|---|---|
| haplotype 1 (3PTS) |   |   | G |   |   |   |   | C |   | T |
| haplotype 2 (4PTS) |   | G |   | A |   |   |   | T |   | T |
| haplotype 3 (2PTS) |   |   |   |   |   | A |   |   | A |   |
| haplotype 4 (2PTS) | G |   |   |   |   |   |   |   | G |   |

| SAMPLES | number cases/ controls | haplotype frequencies cases | haplotype frequencies controls | odds ratio | chi-S | P value | PERMUTATIONS TEST RESULTS Av. Chi-S | Max Chi-S | > Iter / nb of Iter. |
|---|---|---|---|---|---|---|---|---|---|

HAPLOTYPE 1 (3markers : GCT) - Familial cases

| | | | | | | | | | |
|---|---|---|---|---|---|---|---|---|---|
| cases vs controls | 420/301 | 0.130 | 0.082 | 1.68 | 8.28 | 4.0e-03 | 1.5 | 16.7 | 15/1000 |
| cases (<=65 years) vs controls | 156/301 | 0.167 | 0.082 | 2.25 | 15.02 | 1.0e-04 | 1.5 | 15.4 | 2/1000 |
| cases (>65 years) vs controls | 260/301 | 0.110 | 0.082 | 1.38 | 2.55 | 1.1e-01 | 1.4 | 16.0 | 187/1000 |
| sporadic cases vs controls | 256/301 | 0.099 | 0.082 | 1.23 | 1.00 | 2.9e-01 | 1.5 | 18.6 | 424/1000 |
| sporadic cases (<=65 years) vs controls | 81/301 | 0.110 | 0.082 | 1.39 | 1.31 | 2.4e-01 | 1.2 | 11.5 | 288/1000 |
| sporadic cases (>65 years) vs controls | 171/301 | 0.101 | 0.082 | 1.26 | 0.96 | 3.2e-01 | 1.5 | 13.8 | 414/1000 |
| sporadic informatif vs controls | 61/301 | 0.071 | 0.082 | 0.85 | 0.17 | 6.5e-01# | 1.5 | 19.1 | 727/1000 |
| familial cases vs controls | 164/301 | 0.171 | 0.082 | 2.32 | 16.96 | 3.7e-05 | 1.5 | 13.2 | 0/1000 |
| familial cases (<=65 years) vs controls | 75/301 | 0.223 | 0.082 | 3.23 | 24.60 | 7.1e-07 | 1.6 | 22.5 | 0/1000 |
| familial cases (>65 years) vs controls | 89/301 | 0.119 | 0.082 | 1.52 | 2.33 | 1.2e-01 | 1.4 | 14.1 | 196/1000 |
| familial cases (>=3caP) vs controls | 76/301 | 0.232 | 0.082 | 3.40 | 27.65 | 1.4e-07 | 1.8 | 46.3 | 1/1000 |

HAPLOTYPE 2 (4markers : GATT) - Familial cases

| | | | | | | | | | |
|---|---|---|---|---|---|---|---|---|---|
| cases vs controls | 431/288 | 0.138 | 0.077 | 1.91 | 12.63 | 3.7e-04 | 1.7 | 19.6 | 5/1000 |
| cases (<=65 years) vs controls | 162/288 | 0.181 | 0.077 | 2.63 | 21.75 | 3.0e-06 | 1.8 | 16.4 | 0/1000 |
| cases (>65 years) vs controls | 265/288 | 0.112 | 0.077 | 1.51 | 3.95 | 4.6e-02 | 1.6 | 17.1 | 120/1000 |
| sporadic cases vs controls | 268/288 | 0.118 | 0.077 | 1.59 | 5.15 | 2.3e-02 | 1.6 | 14.6 | 76/1000 |
| sporadic cases (<=65 years) vs controls | 84/288 | 0.151 | 0.077 | 2.12 | 8.32 | 3.8e-03 | 1.6 | 17.3 | 34/1000 |
| sporadic cases (>65 years) vs controls | 180/288 | 0.113 | 0.077 | 1.52 | 3.44 | 6.1e-02 | 1.6 | 20.9 | 128/1000 |
| sporadic informatif vs controls | 63/288 | 0.114 | 0.077 | 1.54 | 1.84 | 1.7e-01 | 1.6 | 24.8 | 282/1000 |
| familial cases vs controls | 163/288 | 0.186 | 0.077 | 2.73 | 23.86 | 1.0e-06 | 1.8 | 16.8 | 0/1000 |
| familial cases (<=65 years) vs controls | 78/288 | 0.246 | 0.077 | 3.90 | 34.88 | 3.5e-09 | 1.9 | 26.1 | 0/1000 |
| familial cases (>65 years) vs controls | 85/288 | 0.118 | 0.077 | 1.59 | 2.72 | 9.4e-02 | 1.5 | 21.7 | 157/1000 |
| familial cases (>=3caP) vs controls | 66/288 | 0.275 | 0.077 | 4.52 | 41.37 | 9.1e-11 | 1.9 | 23.5 | 0/1000 |

HAPLOTYPE 3 (2markers : AA) - Sporadic cases

| | | | | | | | | | |
|---|---|---|---|---|---|---|---|---|---|
| cases vs controls | 446/304 | 0.043 | 0.003 | 13.25 | 21.46 | 3.5e-06 | 1.4 | 12.5 | 0/1000 |
| cases (<=65 years) vs controls | 168/304 | 0.052 | 0.003 | 16.43 | 25.52 | 4.2e-07# | 1.3 | 16.5 | 0/1000 |
| cases (>65 years) vs controls | 274/304 | 0.037 | 0.003 | 11.49 | 17.36 | 3.0e-05 | 1.4 | 16.7 | 0/1000 |
| sporadic cases vs controls | 267/304 | 0.069 | 0.003 | 22.00 | 37.16 | 1.1e-09 | 1.3 | 14.2 | 0/1000 |
| sporadic cases (<=65 years) vs controls | 81/304 | 0.103 | 0.003 | 34.12 | 53.47 | 2.0e-13# | 1.3 | 24.7 | 0/1000 |
| sporadic cases (>65 years) vs controls | 182/304 | 0.055 | 0.003 | 17.30 | 27.37 | 1.7e-07# | 1.4 | 13.2 | 0/1000 |
| sporadic informatif vs controls | 64/304 | 0.073 | 0.003 | 23.39 | 33.64 | 6.4e-09# | 1.5 | 26.3 | 0/1000 |
| familial cases vs controls | 179/304 | 0.006 | 0.003 | 1.71 | 0.30 | 5.3e-01# | 1.0 | 7.0 | 378/1000 |
| familial cases (<=65 years) vs controls | 87/304 | 0.006 | 0.003 | 1.76 | 0.22 | 5.8e-01# | 1.0 | 10.9 | 728/1000 |
| familial cases (>65 years) vs controls | 92/304 | 0.006 | 0.003 | 1.67 | 0.18 | 6.5e-01# | 1.0 | 10.4 | 696/1000 |
| familial cases (>=3caP) vs controls | 78/304 | 0.007 | 0.003 | 1.99 | 0.34 | 5.3e-01# | 1.0 | 12.1 | 641/1000 |

HAPLOTYPE 4 (2markers : GG) - Sporadic informatifs

| | | | | | | | | | |
|---|---|---|---|---|---|---|---|---|---|
| cases vs controls | 442/297 | 0.164 | 0.118 | 1.46 | 5.92 | 1.4e-02 | 1.2 | 10.6 | 25/1000 |
| cases (<=65 years) vs controls | 166/297 | 0.154 | 0.118 | 1.36 | 2.47 | 1.1e-01 | 1.1 | 11.9 | 138/1000 |
| cases (>65 years) vs controls | 272/297 | 0.167 | 0.118 | 1.50 | 5.60 | 1.7e-02 | 1.3 | 15.7 | 36/1000 |
| sporadic cases vs controls | 265/297 | 0.175 | 0.118 | 1.59 | 7.37 | 6.5e-03 | 1.2 | 14.6 | 17/1000 |
| sporadic cases (<=65 years) vs controls | 82/297 | 0.138 | 0.118 | 1.20 | 0.50 | 4.8e-01 | 1.1 | 17.0 | 479/1000 |
| sporadic cases (>65 years) vs controls | 179/297 | 0.189 | 0.118 | 1.75 | 9.17 | 2.4e-03 | 1.3 | 19.9 | 15/1000 |
| sporadic informatif vs controls | 64/297 | 0.297 | 0.118 | 3.15 | 26.44 | 2.6e-07 | 1.7 | 13.3 | 0/1000 |
| familial cases vs controls | 177/297 | 0.146 | 0.118 | 1.28 | 1.53 | 2.1e-01 | 1.2 | 13.7 | 256/1000 |
| familial cases (<=65 years) vs controls | 84/297 | 0.174 | 0.118 | 1.57 | 3.57 | 5.8e-02 | 1.1 | 13.4 | 73/1000 |
| familial cases (>65 years) vs controls | 93/297 | 0.118 | 0.118 | 1.00 | 0.00 | 7.5e-01 | 1.2 | 15.5 | 993/1000 |
| familial cases (>=3caP) vs controls | 77/297 | 0.164 | 0.118 | 1.46 | 2.30 | 1.2e-01 | 1.2 | 13.4 | 164/1000 | theoritical size cell is under the limit of 5

| MARKERS | 5-297/209 ox14 | 99-15798/86 In13 | 99-15528/333 In12 | 5-294/285 In11 | 99-5596/216 In8 | 99-22573/321 In6 | 99-5602/372 ex5 |
|---|---|---|---|---|---|---|---|
| cases / controls | 288 vs 300 | 286 vs 301 | 291 vs 304 | 270 vs 292 | 274 vs 308 | 283 vs 296 | 278 vs 308 |
| (frequency % (case/controls)) | 97/97 (A) | 66/66 (T) | 46/45 (G) | 51/51 (G) | 69/68 (G) | 47/47 (A) | 67/65 (C) |
| diff freq. all. (cases - controls) | 0.2 | 0.5 | 1.7 | 0.5 | 1.3 | 0.1 | 1.5 |
| pvalue | 7.5e-01 | 7.5e-01 | 5.3e-01 | 7.5e-01 | 5.8e-01 | 7.5e-01 | 5.3e-01 |
| Odds ratio | 1.1 | 1.0 | 1.1 | 1.0 | 1.1 | 1.0 | 1.1 |
| Test Hardy Weinberg cases vs controls | -0.00 HW / -0.00 HW | -0.01 HW / 0.02 HW | -0.01 HW / 0.02 HW | -0.00 HW / -0.02 HW | 0.01 HW / -0.00 HW | 0.01 HW / -0.01 HW | -0.02 HW / 0.01 HW |

| | 5-297/209 ox14 | 99-15798/86 In13 | 99-15528/333 In12 | 5-294/285 In11 | 99-5596/216 In8 | 99-22573/321 In6 | 99-5602/372 ex5 | Estimation frequency of haplotype | | | Statistical test | | | | Likelihood Ratio Test | Pvalue (3df) | omnibus test Pvalue (100 permutations) |
|---|---|---|---|---|---|---|---|---|---|---|---|---|---|---|---|---|---|
| | | | | | | | | freq. cases (%) | freq. controls (%) | frequency difference | p-excess | Odds ratio | CHI²S | pvalue (1df) | Pvalue (100 permutations) | Nb of permutations | | | |
| haplotype 1 | | | | | G | A | | 4.50 | 0.00 | 4.5 | 4.47 | 100.00 | 26.38 | 2.80E-07 | <1.0e-07 | 0/100 | 32.94 | 3.20E-07 | 1.00E-02 |
| haplotype 2 | | | G | | A | | | 3.90 | 0.00 | 3.9 | 3.89 | 100.00 | 23.84 | 1.00E-06 | <1.0e-02 | 0/100 | 25.70 | 1.10E-05 | 1.00E-02 |
| haplotype 3 | | | | | G | | | 21.30 | 16.20 | 5.1 | 6.12 | 1.40 | 4.83 | 2.70E-02 | 1.00E-02 | 1/100 | 29.49 | 1.80E-06 | 1.00E-02 |
| haplotype 4 | | T | | | G | | C | 39.0 | 34.40 | 4.6 | 6.96 | 1.22 | 2.54 | 1.10E-01 | 8.00E-02 | 8/100 | 16.88 | 7.40E-04 | 1.00E-02 |
| haplotype 5 | | | | | G | | C | 38.8 | 34.40 | 4.4 | 6.69 | 1.21 | 2.33 | 1.20E-01 | 6.00E-02 | 6/100 | 12.43 | 5.90E-03 | 2.00E-02 |
| haplotype 6 | | T | G | | | | | 13.5 | 11.10 | 2.4 | 2.66 | 1.24 | 1.50 | 2.20E-01 | 1.70E-01 | 17/100 | 1.51 | 6.60E-01 | 4.50E-01 |
| haplotype 7 | | | G | | | | | 14.1 | 11.70 | 2.4 | 2.73 | 1.24 | 1.50 | 2.10E-01 | 1.90E-01 | 19/100 | 4.04 | 2.50E-01 | 2.90E-01 |
| haplotype 8 | | | | | | G | | 20.3 | 17.70 | 2.6 | 3.05 | 1.18 | 1.15 | 2.70E-01 | 1.40E-01 | 14/100 | 1.53 | 6.60E-01 | 4.70E-01 |
| haplotype 9 | A | | | | | | C | 65.5 | 63.10 | 2.4 | 6.45 | 1.11 | 0.70 | 3.70E-01 | 1.60E-01 | 16/100 | 0.82 | 8.30E-01 | 6.70E-01 |
| haplotype 10 | | T | | | | | C | 19.8 | 17.90 | 1.9 | 2.25 | 1.13 | 0.63 | 4.00E-01 | 2.90E-01 | 29/100 | 1.20 | 7.30E-01 | 7.30E-01 |
| haplotype 11 | A | | | | | | C | 46.5 | 44.60 | 1.9 | 3.53 | 1.08 | 0.45 | 4.80E-01 | 2.90E-01 | 29/100 | 0.48 | 9.20E-01 | 8.10E-01 |
| haplotype 12 | | | | G | | | | 19.2 | 17.90 | 1.3 | 1.53 | 1.09 | 0.29 | 5.80E-01 | 5.30E-01 | 53/100 | 2.88 | 4.10E-01 | 6.00E-01 |
| haplotype 13 | | T | | | | | C | 67.1 | 65.80 | 1.3 | 3.87 | 1.06 | 0.22 | 5.80E-01 | 3.50E-01 | 35/100 | 5.32 | 1.40E-01 | 3.10E-01 |
| haplotype 14 | | | G | G | | | | 45.7 | 44.30 | 1.4 | 2.39 | 1.06 | 0.20 | 6.50E-01 | 5.10E-01 | 51/100 | 0.83 | 8.30E-01 | 8.50E-01 |
| haplotype 15 | | T | | | | | | 18.90 | 18.00 | 0.9 | 1.16 | 1.07 | 0.16 | 6.50E-01 | 5.70E-01 | 57/100 | 0.45 | 9.20E-01 | 9.30E-01 |
| haplotype 16 | A | | | | | | | 64.70 | 63.60 | 1.1 | 3.14 | 1.05 | 0.16 | 6.50E-01 | 3.70E-01 | 37/100 | 0.20 | 9.80E-01 | 9.20E-01 |
| haplotype 17 | A | | | G | | | | 51.50 | 50.50 | 1.0 | 1.96 | 1.04 | 0.10 | 6.50E-01 | 4.90E-01 | 49/100 | 0.42 | 9.20E-01 | 7.70E-01 |

| MARKERS | 5-287/209 ex14 | 99-15798/86 In13 | 99-15528/333 In12 | 5-294/285 In11 | 99-5598/216 In8 | 99-22573/321 In6 | 99-5602/372 ex5 | \multicolumn HAPLOTYPE FREQUENCY TEST | | | | | | | | OMNIBUS LR TEST | |
|---|---|---|---|---|---|---|---|---|---|---|---|---|---|---|---|---|---|
| cases / controls | 288 vs 300 | 286 vs 301 | 291 vs 304 | 270 vs 292 | 274 vs 308 | 283 vs 296 | 278 vs 308 | Estimation frequency of haplotype | | frequency difference | p-excess | Odds ratio | Statistical test | | | | Likelihood Ratio Test | omnibus test |
| frequency % (case/controls) | 97/97 (A) | 66/66 (T) | 46/45 (G) | 51/51 (G) | 69/68 (G) | 47/47 (A) | 67/65 (C) | frequency cases (%) | frequency controls (%) | | | | CHI-S | Pvalue (1df) | Pvalue (100 permutations) | Nb of permutations | Pvalue (7df) | Pvalue (100 permutations) |
| diff freq. all. (cases - controls) pvalue | 0.2 / 7.5e-01 | 0.5 / 7.5e-01 | 1.7 / 5.3e-01 | 0.5 / 7.5e-01 | 1.3 / 5.8e-01 | 0.1 / 7.5e-01 | 1.5 / 5.3e-01 | | | | | | | | | | | |
| Odds ratio cases vs controls | 1.1 | 1.0 | 1.1 | 1.0 | 1.1 | 1.0 | 1.1 | | | | | | | | | | | |
| Test Hardy Weinberg cases | -0.00 HW | -0.01 HW | -0.01 HW | -0.00 HW | -0.01 HW | 0.01 HW | -0.02 HW | | | | | | | | | | | |
| Test Hardy Weinberg controls | -0.00 HW | 0.02 HW | 0.02 HW | -0.02 HW | -0.00 HW | 0.01 HW | 0.01 HW | | | | | | | | | | | |
| haplotype 18 (249 vs 280) | A | | | | | | | 4.50 | 0.00 | 4.5 | 4.50 | 100.00 | 25.75 | 3.80E-07 | <1.0e-02 | 0/100 | 37.62 | 3.50E-06 | 1.00E-02 |
| haplotype 19 (269 vs 291) | A | | G | | A | | | 4.00 | 0.00 | 4.0 | 3.95 | 100.00 | 23.45 | 1.20E-06 | <1.0e-02 | 0/100 | 29.53 | 1.10E-04 | 1.00E-02 |
| haplotype 20 (244 vs 275) | | | | C | G | A | | 22.40 | 15.50 | 6.9 | 8.19 | 1.58 | 8.15 | 4.20E-03 | <1.0e-02 | 0/100 | 38.70 | 2.10E-06 | 1.00E-02 |
| haplotype 21 (251 vs 282) | | | A | C | G | | | 21.70 | 15.70 | 6.0 | 7.10 | 1.48 | 6.28 | 1.20E-02 | <1.0e-02 | 0/100 | 37.39 | 3.90E-06 | 1.00E-02 |
| haplotype 22 (243 vs 286) | | | | C | G | | C | 22.20 | 16.40 | 5.8 | 7.04 | 1.46 | 5.91 | 1.40E-02 | 1.00E-02 | 1/100 | 33.94 | 1.70E-05 | 1.00E-02 |
| haplotype 23 (250 vs 279) | | T | | C | G | | | 22.30 | 16.40 | 5.9 | 6.99 | 1.46 | 5.81 | 1.50E-02 | 2.00E-02 | 2/100 | 35.88 | 7.60E-06 | 1.00E-02 |
| haplotype 24 (265 vs 287) | | | A | | G | A | | 21.10 | 15.70 | 5.4 | 6.41 | 1.44 | 5.40 | 1.90E-02 | 1.00E-02 | 1/100 | 33.35 | 2.20E-05 | 1.00E-02 |
| haplotype 25 (262 vs 285) | | T | | | G | A | | 21.70 | 16.30 | 5.4 | 6.44 | 1.42 | 5.18 | 2.30E-02 | 1.00E-02 | 1/100 | 34.64 | 1.30E-05 | 1.00E-02 |
| haplotype 26 (252 vs 290) | | | | | G | A | | 21.30 | 16.40 | 4.9 | 5.90 | 1.38 | 4.32 | 3.60E-02 | 6.00E-02 | 6/100 | 29.23 | 1.30E-04 | 1.00E-02 |
| haplotype 27 (262 vs 283) | A | | | | | A | | 20.40 | 16.10 | 4.3 | 5.11 | 1.34 | 3.37 | 6.50E-02 | 3.00E-02 | 3/100 | 33.57 | 2.00E-05 | 2.00E-02 |
| haplotype 28 (256 vs 295) | | T | G | | | | | 38.80 | 34.20 | 4.6 | 6.95 | 1.22 | 2.47 | 1.10E-01 | 8.00E-02 | 8/100 | 18.08 | 1.20E-02 | 2.00E-02 |
| haplotype 29 (281 vs 266) | A | | G | | | | | 13.70 | 10.70 | 3.0 | 3.40 | 1.33 | 2.45 | 1.10E-01 | 9.00E-02 | 9/100 | 2.49 | 9.30E-01 | 5.10E-01 |
| haplotype 30 (273 vs 291) | A | T | | C | | | | 14.30 | 11.20 | 3.1 | 3.47 | 1.32 | 2.41 | 1.20E-01 | 9.00E-02 | 9/100 | 5.24 | 6.20E-01 | 2.20E-01 |
| haplotype 31 (266 vs 288) | A | | | | G | | C | 38.20 | 33.90 | 4.3 | 6.62 | 1.21 | 2.30 | 1.20E-01 | 5.00E-02 | 5/100 | 22.59 | 2.00E-03 | 1.00E-02 |
| haplotype 32 (259 vs 298) | | | A | | G | | C | 26.70 | 22.80 | 3.9 | 5.03 | 1.23 | 2.26 | 1.30E-01 | 8.00E-02 | 8/100 | 26.75 | 3.60E-04 | 1.00E-02 |
| haplotype 33 (256 vs 294) | A | | | | G | | C | 38.00 | 33.80 | 4.2 | 6.32 | 1.20 | 2.08 | 1.50E-01 | 1.10E-01 | 11/100 | 18.68 | 9.20E-03 | 1.00E-02 |
| haplotype 34 (265 vs 283) | | | | | | G | C | 20.60 | 17.30 | 3.3 | 3.93 | 1.24 | 1.89 | 1.70E-01 | 1.80E-01 | 18/100 | 2.92 | 8.90E-01 | 3.80E-01 |
| haplotype 35 (269 vs 293) | | | A | | | G | C | 26.60 | 23.20 | 3.4 | 4.41 | 1.20 | 1.72 | 1.80E-01 | 1.40E-01 | 14/100 | 26.52 | 3.90E-04 | 1.00E-02 |
| haplotype 36 (263 vs 285) | | T | | | | | C | 20.20 | 17.40 | 2.8 | 3.37 | 1.20 | 1.39 | 2.40E-01 | 1.90E-01 | 19/100 | 6.75 | 4.50E-01 | 2.50E-01 |
| haplotype 37 (271 vs 293) | | T | G | | | | C | 13.50 | 11.20 | 2.3 | 2.58 | 1.24 | 1.37 | 2.40E-01 | 1.70E-01 | 17/100 | 6.51 | 4.70E-01 | 2.20E-01 |

FIG. 5

| MARKERS | 5-294/285 | 99-5596/216 |
|---|---|---|
| HAPLOTYPE | in11 | in8 |
| | G | A |
| pvalue (1df) Sporadic cases vs controls | 7.50E-01 | 5.80E-01 |
| % frequency difference (sample sizes) | 0,5 (270 vs 292) | 1,3 (274 vs 308) |

| HAPLOTYPE FREQUENCY TEST | | | | | | | | | | OMNIBUS LR TEST | | |
|---|---|---|---|---|---|---|---|---|---|---|---|---|
| HAPLOTYPE (GA) | Estimation frequency of haplotype | | | | | Statistical test | | | | Likelihood Ratio Test | | omnibus test |
| | sample sizes cases vs controls | frequency cases (%) | frequency controls (%) | frequency difference (%) | Odds ratio | p-excess | Chi-S | Pvalue (1df) | Nb of permutations | Likelihood Ratio Test | Pvalue (3 df) | Pvalue (1000 permutations) |
| cases vs controls | 405 vs 289 | 2.7 | 0.0 | 2.7 | 100.0 | 2.7 | 15.7 | 7.4e-05 # | 0/1000 | 21.8 | 6.80E-05 | 1.00E-03 |
| cases (<=65 years) vs controls | 153 vs 289 | 1.6 | 0.0 | 1.6 | 100.0 | 1.6 | 9.4 | 2.2e-03 # | 5/1000 | 9.3 | 2.60E-02 | 2.60E-02 |
| cases (>65 years) vs controls | 249 vs 289 | 3.4 | 0.0 | 3.4 | 100.0 | 3.4 | 20.1 | 7.3e-06 # | 1/1000 | 24.9 | 1.60E-05 | 1.00E-03 |
| sporadic cases vs controls | 252 vs 289 | 4.5 | 0.0 | 4.5 | 100.0 | 4.5 | 26.4 | 2.80E-07 | 0/1000 | 32.9 | 3.20E-07 | 1.00E-03 |
| sporadic cases (<=65 years) vs controls | 76 vs 289 | 3.2 | 0.0 | 3.2 | 100.0 | 3.2 | 18.8 | 1.5e-05 # | 0/1000 | 14.9 | 1.80E-03 | 2.00E-03 |
| sporadic cases (>65 years) vs controls | 173 vs 289 | 5.3 | 0.0 | 5.3 | 100.0 | 5.4 | 31.6 | 1.9e-08 # | 0/1000 | 37.5 | 3.60E-08 | 1.00E-03 |
| sporadic informatif vs controls | 62 vs 289 | 7.8 | 0.0 | 7.8 | 100.0 | 7.8 | 45.5 | 1.2e-11 # | 0/1000 | 29.7 | 1.50E-06 | 1.00E-03 |
| familial cases vs controls | 153 vs 289 | 0.0 | 0.0 | 0.0 | | | | | | | | |
| familial cases (<=65 years) vs controls | 77 vs 289 | 0.0 | 0.0 | 0.0 | | | | | | | | |
| familial cases (>65 years) vs controls | 76 vs 289 | 0.0 | 0.0 | 0.0 | | | | | | | | |
| familial cases (>=3caP) vs controls | 60 vs 289 | 0.0 | 0.0 | 0.0 | | | | | | | | |

Theoritical size cell is under the limit of 5

SEQUENCE LISTING

<160> NUMBER OF SEQ ID NOS: 24

<210> SEQ ID NO 1
<211> LENGTH: 41684
<212> TYPE: DNA
<213> ORGANISM: Homo sapiens
<220> FEATURE:
<221> NAME/KEY: misc_feature
<222> LOCATION: 1..2000
<223> OTHER INFORMATION: 5'regulatory region
<220> FEATURE:
<221> NAME/KEY: exon
<222> LOCATION: 2001..2096
<223> OTHER INFORMATION: exon 1
<220> FEATURE:
<221> NAME/KEY: exon
<222> LOCATION: 2433..2559
<223> OTHER INFORMATION: exon 2
<220> FEATURE:
<221> NAME/KEY: exon
<222> LOCATION: 8092..8168
<223> OTHER INFORMATION: exon 3
<220> FEATURE:
<221> NAME/KEY: exon
<222> LOCATION: 9600..9666
<223> OTHER INFORMATION: exon 4
<220> FEATURE:
<221> NAME/KEY: exon
<222> LOCATION: 15178..15266
<223> OTHER INFORMATION: exon 5
<220> FEATURE:
<221> NAME/KEY: exon
<222> LOCATION: 15924..16075
<223> OTHER INFORMATION: exon 6
<220> FEATURE:
<221> NAME/KEY: exon
<222> LOCATION: 16759..16915
<223> OTHER INFORMATION: exon 7
<220> FEATURE:
<221> NAME/KEY: exon
<222> LOCATION: 22309..22434
<223> OTHER INFORMATION: exon 8
<220> FEATURE:
<221> NAME/KEY: exon
<222> LOCATION: 23277..23384
<223> OTHER INFORMATION: exon 9
<220> FEATURE:
<221> NAME/KEY: exon
<222> LOCATION: 24841..24926
<223> OTHER INFORMATION: exon 10
<220> FEATURE:
<221> NAME/KEY: exon
<222> LOCATION: 25957..26046
<223> OTHER INFORMATION: exon 11
<220> FEATURE:
<221> NAME/KEY: exon
<222> LOCATION: 28700..28828
<223> OTHER INFORMATION: exon 12
<220> FEATURE:
<221> NAME/KEY: exon
<222> LOCATION: 34699..34791
<223> OTHER INFORMATION: exon 13
<220> FEATURE:
<221> NAME/KEY: exon
<222> LOCATION: 36679..36861
<223> OTHER INFORMATION: exon 14
<220> FEATURE:
<221> NAME/KEY: exon
<222> LOCATION: 39014..39169
<223> OTHER INFORMATION: exon 15
<220> FEATURE:
<221> NAME/KEY: exon
<222> LOCATION: 39456..39684
<223> OTHER INFORMATION: exon 16

```
<220> FEATURE:
<221> NAME/KEY: misc_feature
<222> LOCATION: 39685..41684
<223> OTHER INFORMATION: 3'regulatory region
<220> FEATURE:
<221> NAME/KEY: allele
<222> LOCATION: 6491
<223> OTHER INFORMATION: 99-32284-107   : polymorphic base C or T
<220> FEATURE:
<221> NAME/KEY: allele
<222> LOCATION: 15234
<223> OTHER INFORMATION: 99-5602-372   : polymorphic base G or C
<220> FEATURE:
<221> NAME/KEY: allele
<222> LOCATION: 15868
<223> OTHER INFORMATION: 5-290-32   : polymorphic base C or T
<220> FEATURE:
<221> NAME/KEY: allele
<222> LOCATION: 16729
<223> OTHER INFORMATION: 99-22573-321   : polymorphic base C or T
<220> FEATURE:
<221> NAME/KEY: allele
<222> LOCATION: 18311
<223> OTHER INFORMATION: 99-22586-300   : polymorphic base G or C
<220> FEATURE:
<221> NAME/KEY: allele
<222> LOCATION: 18572
<223> OTHER INFORMATION: 99-22586-39   : polymorphic base C or T
<220> FEATURE:
<221> NAME/KEY: allele
<222> LOCATION: 22906
<223> OTHER INFORMATION: 99-5596-197   : polymorphic base A or G
<220> FEATURE:
<221> NAME/KEY: allele
<222> LOCATION: 23175
<223> OTHER INFORMATION: 5-293-76   : polymorphic base C or T
<220> FEATURE:
<221> NAME/KEY: allele
<222> LOCATION: 23253
<223> OTHER INFORMATION: 5-293-155   : polymorphic base A or G
<220> FEATURE:
<221> NAME/KEY: allele
<222> LOCATION: 26106
<223> OTHER INFORMATION: 5-294-285   : polymorphic base G or C
<220> FEATURE:
<221> NAME/KEY: allele
<222> LOCATION: 30464
<223> OTHER INFORMATION: 99-23454-317   : polymorphic base A or G
<220> FEATURE:
<221> NAME/KEY: allele
<222> LOCATION: 30669
<223> OTHER INFORMATION: 99-23454-105   : polymorphic base G or C
<220> FEATURE:
<221> NAME/KEY: allele
<222> LOCATION: 31250
<223> OTHER INFORMATION: 99-15528-333   : polymorphic base A or G
<220> FEATURE:
<221> NAME/KEY: allele
<222> LOCATION: 35148
<223> OTHER INFORMATION: 99-15798-86   : polymorphic base A or G
<220> FEATURE:
<221> NAME/KEY: allele
<222> LOCATION: 36801
<223> OTHER INFORMATION: 5-297-209   : polymorphic base A or G
<220> FEATURE:
<221> NAME/KEY: allele
<222> LOCATION: 37286
<223> OTHER INFORMATION: 99-32281-276   : polymorphic base C or T
<220> FEATURE:
<221> NAME/KEY: allele
<222> LOCATION: 37536
<223> OTHER INFORMATION: 99-32281-26   : polymorphic base C or T
<220> FEATURE:
<221> NAME/KEY: allele
<222> LOCATION: 39321
<223> OTHER INFORMATION: 5-298-376   : polymorphic base A or G
```

-continued

```
<220> FEATURE:
<221> NAME/KEY: allele
<222> LOCATION: 39689
<223> OTHER INFORMATION: 99-23460-199  : polymorphic base G or T
<220> FEATURE:
<221> NAME/KEY: primer_bind
<222> LOCATION: 6137..6157
<223> OTHER INFORMATION: 99-32284.rp
<220> FEATURE:
<221> NAME/KEY: primer_bind
<222> LOCATION: 6577..6597
<223> OTHER INFORMATION: 99-32284.pu complement
<220> FEATURE:
<221> NAME/KEY: primer_bind
<222> LOCATION: 14864..14882
<223> OTHER INFORMATION: 99-5602.pu
<220> FEATURE:
<221> NAME/KEY: primer_bind
<222> LOCATION: 15292..15312
<223> OTHER INFORMATION: 99-5602.rp   complement
<220> FEATURE:
<221> NAME/KEY: primer_bind
<222> LOCATION: 15837..15855
<223> OTHER INFORMATION: 5-290.pu
<220> FEATURE:
<221> NAME/KEY: primer_bind
<222> LOCATION: 16249..16266
<223> OTHER INFORMATION: 5-290.rp   complement
<220> FEATURE:
<221> NAME/KEY: primer_bind
<222> LOCATION: 16599..16617
<223> OTHER INFORMATION: 99-22573.rp
<220> FEATURE:
<221> NAME/KEY: primer_bind
<222> LOCATION: 17030..17049
<223> OTHER INFORMATION: 99-22573.pu complement
<220> FEATURE:
<221> NAME/KEY: primer_bind
<222> LOCATION: 18131..18150
<223> OTHER INFORMATION: 99-22586.rp
<220> FEATURE:
<221> NAME/KEY: primer_bind
<222> LOCATION: 18592..18610
<223> OTHER INFORMATION: 99-22586.pu complement
<220> FEATURE:
<221> NAME/KEY: primer_bind
<222> LOCATION: 22710..22727
<223> OTHER INFORMATION: 99-5596.pu
<220> FEATURE:
<221> NAME/KEY: primer_bind
<222> LOCATION: 23100..23118
<223> OTHER INFORMATION: 5-293.pu
<220> FEATURE:
<221> NAME/KEY: primer_bind
<222> LOCATION: 23130..23149
<223> OTHER INFORMATION: 99-5596.rp   complement
<220> FEATURE:
<221> NAME/KEY: primer_bind
<222> LOCATION: 23512..23530
<223> OTHER INFORMATION: 5-293.rp   complement
<220> FEATURE:
<221> NAME/KEY: primer_bind
<222> LOCATION: 25822..25840
<223> OTHER INFORMATION: 5-294.pu
<220> FEATURE:
<221> NAME/KEY: primer_bind
<222> LOCATION: 26222..26241
<223> OTHER INFORMATION: 5-294.rp   complement
<220> FEATURE:
<221> NAME/KEY: primer_bind
<222> LOCATION: 30332..30352
<223> OTHER INFORMATION: 99-23454.rp
<220> FEATURE:
<221> NAME/KEY: primer_bind
<222> LOCATION: 30754..30773
<223> OTHER INFORMATION: 99-23454.pu complement
```

```
<220> FEATURE:
<221> NAME/KEY: primer_bind
<222> LOCATION: 30918..30935
<223> OTHER INFORMATION: 99-15528.pu
<220> FEATURE:
<221> NAME/KEY: primer_bind
<222> LOCATION: 31390..31408
<223> OTHER INFORMATION: 99-15528.rp   complement
<220> FEATURE:
<221> NAME/KEY: primer_bind
<222> LOCATION: 34780..34799
<223> OTHER INFORMATION: 99-15798.rp
<220> FEATURE:
<221> NAME/KEY: primer_bind
<222> LOCATION: 35215..35233
<223> OTHER INFORMATION: 99-15798.pu complement
<220> FEATURE:
<221> NAME/KEY: primer_bind
<222> LOCATION: 36593..36610
<223> OTHER INFORMATION: 5-297.pu
<220> FEATURE:
<221> NAME/KEY: primer_bind
<222> LOCATION: 37017..37036
<223> OTHER INFORMATION: 5-297.rp   complement
<220> FEATURE:
<221> NAME/KEY: primer_bind
<222> LOCATION: 37060..37080
<223> OTHER INFORMATION: 99-32281.rp
<220> FEATURE:
<221> NAME/KEY: primer_bind
<222> LOCATION: 37541..37561
<223> OTHER INFORMATION: 99-32281.pu complement
<220> FEATURE:
<221> NAME/KEY: primer_bind
<222> LOCATION: 38946..38965
<223> OTHER INFORMATION: 5-298.pu
<220> FEATURE:
<221> NAME/KEY: primer_bind
<222> LOCATION: 39346..39365
<223> OTHER INFORMATION: 5-298.rp   complement
<220> FEATURE:
<221> NAME/KEY: primer_bind
<222> LOCATION: 39439..39459
<223> OTHER INFORMATION: 99-23460.rp
<220> FEATURE:
<221> NAME/KEY: primer_bind
<222> LOCATION: 39868..39886
<223> OTHER INFORMATION: 99-23460.pu complement
<220> FEATURE:
<221> NAME/KEY: primer_bind
<222> LOCATION: 6472..6490
<223> OTHER INFORMATION: 99-32284-107.mis
<220> FEATURE:
<221> NAME/KEY: primer_bind
<222> LOCATION: 6492..6510
<223> OTHER INFORMATION: 99-32284-107.mis complement
<220> FEATURE:
<221> NAME/KEY: primer_bind
<222> LOCATION: 15215..15233
<223> OTHER INFORMATION: 99-5602-372.mis
<220> FEATURE:
<221> NAME/KEY: primer_bind
<222> LOCATION: 15235..15253
<223> OTHER INFORMATION: 99-5602-372.mis complement
<220> FEATURE:
<221> NAME/KEY: primer_bind
<222> LOCATION: 15849..15867
<223> OTHER INFORMATION: 5-290-32.mis
<220> FEATURE:
<221> NAME/KEY: primer_bind
<222> LOCATION: 15869..15887
<223> OTHER INFORMATION: 5-290-32.mis complement
<220> FEATURE:
<221> NAME/KEY: primer_bind
<222> LOCATION: 16710..16728
<223> OTHER INFORMATION: 99-22573-321.mis
```

```
<220> FEATURE:
<221> NAME/KEY: primer_bind
<222> LOCATION: 16730..16748
<223> OTHER INFORMATION: 99-22573-321.mis complement
<220> FEATURE:
<221> NAME/KEY: primer_bind
<222> LOCATION: 18292..18310
<223> OTHER INFORMATION: 99-22586-300.mis
<220> FEATURE:
<221> NAME/KEY: primer_bind
<222> LOCATION: 18312..18330
<223> OTHER INFORMATION: 99-22586-300.mis complement
<220> FEATURE:
<221> NAME/KEY: primer_bind
<222> LOCATION: 18553..18571
<223> OTHER INFORMATION: 99-22586-39.mis
<220> FEATURE:
<221> NAME/KEY: primer_bind
<222> LOCATION: 18573..18591
<223> OTHER INFORMATION: 99-22586-39.mis complement
<220> FEATURE:
<221> NAME/KEY: primer_bind
<222> LOCATION: 22887..22905
<223> OTHER INFORMATION: 99-5596-197.mis
<220> FEATURE:
<221> NAME/KEY: primer_bind
<222> LOCATION: 22907..22925
<223> OTHER INFORMATION: 99-5596-197.mis complement
<220> FEATURE:
<221> NAME/KEY: primer_bind
<222> LOCATION: 23156..23174
<223> OTHER INFORMATION: 5-293-76.mis
<220> FEATURE:
<221> NAME/KEY: primer_bind
<222> LOCATION: 23176..23194
<223> OTHER INFORMATION: 5-293-76.mis complement
<220> FEATURE:
<221> NAME/KEY: primer_bind
<222> LOCATION: 23234..23252
<223> OTHER INFORMATION: 5-293-155.mis
<220> FEATURE:
<221> NAME/KEY: primer_bind
<222> LOCATION: 23254..23272
<223> OTHER INFORMATION: 5-293-155.mis complement
<220> FEATURE:
<221> NAME/KEY: primer_bind
<222> LOCATION: 26087..26105
<223> OTHER INFORMATION: 5-294-285.mis
<220> FEATURE:
<221> NAME/KEY: primer_bind
<222> LOCATION: 26107..26125
<223> OTHER INFORMATION: 5-294-285.mis complement
<220> FEATURE:
<221> NAME/KEY: primer_bind
<222> LOCATION: 30445..30463
<223> OTHER INFORMATION: 99-23454-317.mis
<220> FEATURE:
<221> NAME/KEY: primer_bind
<222> LOCATION: 30465..30483
<223> OTHER INFORMATION: 99-23454-317.mis complement
<220> FEATURE:
<221> NAME/KEY: primer_bind
<222> LOCATION: 30650..30668
<223> OTHER INFORMATION: 99-23454-105.mis
<220> FEATURE:
<221> NAME/KEY: primer_bind
<222> LOCATION: 30670..30688
<223> OTHER INFORMATION: 99-23454-105.mis complement
<220> FEATURE:
<221> NAME/KEY: primer_bind
<222> LOCATION: 31231..31249
<223> OTHER INFORMATION: 99-15528-333.mis
<220> FEATURE:
<221> NAME/KEY: primer_bind
<222> LOCATION: 31251..31269
<223> OTHER INFORMATION: 99-15528-333.mis complement
```

```
<220> FEATURE:
<221> NAME/KEY: primer_bind
<222> LOCATION: 35129..35147
<223> OTHER INFORMATION: 99-15798-86.mis
<220> FEATURE:
<221> NAME/KEY: primer_bind
<222> LOCATION: 35149..35167
<223> OTHER INFORMATION: 99-15798-86.mis complement
<220> FEATURE:
<221> NAME/KEY: primer_bind
<222> LOCATION: 36782..36800
<223> OTHER INFORMATION: 5-297-209.mis
<220> FEATURE:
<221> NAME/KEY: primer_bind
<222> LOCATION: 36802..36820
<223> OTHER INFORMATION: 5-297-209.mis complement
<220> FEATURE:
<221> NAME/KEY: primer_bind
<222> LOCATION: 37267..37285
<223> OTHER INFORMATION: 99-32281-276.mis
<220> FEATURE:
<221> NAME/KEY: primer_bind
<222> LOCATION: 37287..37305
<223> OTHER INFORMATION: 99-32281-276.mis complement
<220> FEATURE:
<221> NAME/KEY: primer_bind
<222> LOCATION: 37517..37535
<223> OTHER INFORMATION: 99-32281-26.mis
<220> FEATURE:
<221> NAME/KEY: primer_bind
<222> LOCATION: 37537..37555
<223> OTHER INFORMATION: 99-32281-26.mis complement
<220> FEATURE:
<221> NAME/KEY: primer_bind
<222> LOCATION: 39302..39320
<223> OTHER INFORMATION: 5-298-376.mis
<220> FEATURE:
<221> NAME/KEY: primer_bind
<222> LOCATION: 39322..39340
<223> OTHER INFORMATION: 5-298-376.mis complement
<220> FEATURE:
<221> NAME/KEY: primer_bind
<222> LOCATION: 39670..39688
<223> OTHER INFORMATION: 99-23460-199.mis
<220> FEATURE:
<221> NAME/KEY: primer_bind
<222> LOCATION: 39690..39708
<223> OTHER INFORMATION: 99-23460-199.mis complement
<220> FEATURE:
<221> NAME/KEY: misc_binding
<222> LOCATION: 6479..6503
<223> OTHER INFORMATION: 99-32284-107.probe
<220> FEATURE:
<221> NAME/KEY: misc_binding
<222> LOCATION: 15222..15246
<223> OTHER INFORMATION: 99-5602-372.probe
<220> FEATURE:
<221> NAME/KEY: misc_binding
<222> LOCATION: 15856..15880
<223> OTHER INFORMATION: 5-290-32.probe
<220> FEATURE:
<221> NAME/KEY: misc_binding
<222> LOCATION: 16717..16741
<223> OTHER INFORMATION: 99-22573-321.probe
<220> FEATURE:
<221> NAME/KEY: misc_binding
<222> LOCATION: 18299..18323
<223> OTHER INFORMATION: 99-22586-300.probe
<220> FEATURE:
<221> NAME/KEY: misc_binding
<222> LOCATION: 18560..18584
<223> OTHER INFORMATION: 99-22586-39.probe
<220> FEATURE:
<221> NAME/KEY: misc_binding
<222> LOCATION: 22894..22918
<223> OTHER INFORMATION: 99-5596-197.probe
```

```
<220> FEATURE:
<221> NAME/KEY: misc_binding
<222> LOCATION: 23163..23187
<223> OTHER INFORMATION: 5-293-76.probe
<220> FEATURE:
<221> NAME/KEY: misc_binding
<222> LOCATION: 23241..23265
<223> OTHER INFORMATION: 5-293-155.probe
<220> FEATURE:
<221> NAME/KEY: misc_binding
<222> LOCATION: 26094..26118
<223> OTHER INFORMATION: 5-294-285.probe
<220> FEATURE:
<221> NAME/KEY: misc_binding
<222> LOCATION: 30452..30476
<223> OTHER INFORMATION: 99-23454-317.probe
<220> FEATURE:
<221> NAME/KEY: misc_binding
<222> LOCATION: 30657..30681
<223> OTHER INFORMATION: 99-23454-105.probe
<220> FEATURE:
<221> NAME/KEY: misc_binding
<222> LOCATION: 31238..31262
<223> OTHER INFORMATION: 99-15528-333.probe
<220> FEATURE:
<221> NAME/KEY: misc_binding
<222> LOCATION: 35136..35160
<223> OTHER INFORMATION: 99-15798-86.probe
<220> FEATURE:
<221> NAME/KEY: misc_binding
<222> LOCATION: 36789..36813
<223> OTHER INFORMATION: 5-297-209.probe
<220> FEATURE:
<221> NAME/KEY: misc_binding
<222> LOCATION: 37274..37298
<223> OTHER INFORMATION: 99-32281-276.probe
<220> FEATURE:
<221> NAME/KEY: misc_binding
<222> LOCATION: 37524..37548
<223> OTHER INFORMATION: 99-32281-26.probe
<220> FEATURE:
<221> NAME/KEY: misc_binding
<222> LOCATION: 39309..39333
<223> OTHER INFORMATION: 5-298-376.probe
<220> FEATURE:
<221> NAME/KEY: misc_binding
<222> LOCATION: 39677..39701
<223> OTHER INFORMATION: 99-23460-199.probe
<220> FEATURE:
<221> NAME/KEY: misc_feature
<222> LOCATION: 17427
<223> OTHER INFORMATION: n=a, g, c or t

<400> SEQUENCE: 1
aaattgattc caggctggac gcggtggctc acgcctgcaa tcccagccct ttgggaggcc      60
aaggcaggtg gatcacctga ggtcaggagt tcgagaccag cgtggccaac atggcgaaac     120
cccatctcta ctaaaaatac aaaaattagc caggcatggt ggcacgcgcc tgtagtgcca     180
gatactcggg aggctgaggc aggagaatcg cttgaacctg ggaggcagag gttgcagtga     240
gccgagatcg cgctactgca ctccagtgtg ggtgacagag cgagactctg tctcaaaaaa     300
aaaaaaaaaa aattgattct agtcaatagg tatttatttt ggggagtaaa gagatgggaa     360
gaattagaga aggaagagg aaaaacaaaa ataaatagca tgcagataat gagaaaatag      420
actcattttt acagctgtga gctcagacta aaagataaac aatgctatta ctttggaata     480
taattctaat aacacaaaaa agactcacag accacaatat gtatttattt tgtggcaaag     540
gtgtcatttt tagaaagaaa caatgtgtt caattttgct ttccctgttt ttaatgaatt      600
aagaaaggtc ttctcttacc ttcttttgac tgtcatcatt cctctcatcc aggaatattt     660
acaggtttgc aagaagacac catctttaag tagttttttag gcactttta aatactgact     720
```

-continued

```
aaattgtata aaatagtatt ataaattaat atttaaatta taattttatg acgtgaaaat      780
caacaacgaa tgtcaatttc acttcgtttt gactgtcatc tgtggcctct ggagtccctc      840
acttaaatca ttggtccttg gttttatttt ttaagcctat taaaaaggag gatggggccg      900
ggcactgtgg ctcacacctg taatcccagc actttgggag gctgaggtgg acagatcatt      960
tgaggtcagg agttgaagac cggcctggcc aacaccgtga aaccccatct ctactaaata     1020
tacaaaaaaa aaaaaataca acaacaacaa aaaattagac gggtgtggag gcagaggcag     1080
gagaatttct tgaacctggg aggcagaggt tgcagtgagc tgagatggtg ccactgctct     1140
ccagtctggg agacagagcg agaccctgtc tcaaaacaaa caagcaaaca agcaagcaag     1200
caaacaaaca aaaaacaagt tgggcatggt ggctcacccc tgtaatccca gcactttggg     1260
aagccgaggc aggcggatca cctgaggtca ggagtttgag accagcttgg ccaacatggc     1320
gaaaccccat gtctactaaa aatacaaaaa ttagccgggc atcgtggcgc ctgcctataa     1380
ttccagctac tcgggaggct gaggcaggat aaactcttga acccgggatg tggaggttgc     1440
aggttgcacg tgacatagcc gagatcgcgc cattgcactc cagcctgggc aacaaaagcg     1500
aaactccatc tcaaaaaaaa aaaaaaacca aaaaaaaaaa caaaaaaacc agaaaaacaa     1560
aaaaacaaca aacaaaaagg gaggatggta gataactgtc cagatacttt ccagctttgc     1620
cgctatatga actattcctt ttgtttagtt ttcagcatgg gagcttctgg cacttttacg     1680
tactttccag cttctgggga ccggctgcct agaataacag gcatttgccc cagaggccgt     1740
ggagtggcct cactttgggg tcgtgggcag atcgctggct cccacgcctg gacttcggga     1800
tcgcaggcag gatcccttcc agcccaagca ctccgcccag gcgcgccagg cagagccccg     1860
ccccatcccg ccgttccctt cagccccggg gcgcggatct tgcatctgaa actgagcaga     1920
gcagggcgcc gggcagggcc ggcgggccac gtgataagcc cggaaacagc tccgcccccct    1980
cgcttcctga gccgccacat cccggcagcc ctcctacctg cgcacgtggt gccgccgctg     2040
ctgcctcccg ctcgccctga acccagtgcc tgcagccatg gctcccggcc agctcggtga     2100
ggccctagcg gagcggcgcg gtctgcgtcc tcgcctgcgg ccccccacgc tcccgccttg     2160
gcggcggccg gcgggacccg gcactgcagg ggcggcgctg cgggattgaa agccagcgtc     2220
cccgctcccc ggccgggccg cagcctgcgt ggggcccgcc ttagagcagc tcgcgggtgt     2280
aagacctggg gaggcccgga ccaggcctgc gaacgcaggg tccaggtgct ggccttgcga     2340
ttcgagaatc tcctcccccca gaccctccca aggccttgca gaacacagtg caatgtgctg    2400
cgaatcatga gaaaaaatgt cttctctttc agccttattt agtgtctctg acaaaaccgg     2460
ccttgtggaa tttgcaagaa acctgaccgc tcttggtttg aatctggtcg cttccggagg     2520
gactgcaaaa gctctcaggg atgctggtct ggcagtcagg taaggcatag ctagttccat     2580
cagaaaggag tgtgatcaca ttaaccagga agtattgtat tccaggcacc agcagcaaaa     2640
cgccttattt actcctccca gtagcgctgt gaggttggtg taatacttcc ccactttatg     2700
gggaaaaaaa gtgaggctca gagagattta gcaacttta agaccctgga cggctgggct     2760
aggtggctca cgcatgtaat cccagcactt tgggaggccg aggtgggctg atcacttacg     2820
gtcaagagtt cgagaccagc ctggccaaca tggtgaaacc cgtctctact aaaaatacaa     2880
aaattagccg gtatggtggc acgcctgt aatcccagct actgggaagg ctgaggcagg      2940
agaatcgctt gaacctagga ggcggaggtt gtggtgagcc gagatggcac tactgcactc     3000
catcctgggt gacagagaaa gaccctggac aacacactgg acagatttag catcttctgc     3060
acaagtttaa acagttgagt aagggaaaag taggattgga acccgtgctg ttcctgattt     3120
```

```
taggacacta gtcttagccc cttccttaaa cagattaact taggtgggcc acttgttatg    3180
caaggaaaac ttcagttact ttgactggtg atttaataaa actcgacatc atgaagattc    3240
caatttacct gccttccctt agaatctctg gtaaccatat gaaggtgcaa atcattcatt    3300
cccacgttca caagcccttc attagctgac taggccatgg aaagaaggga cttagaaatg    3360
attaaccagg atgccattgc tgatgtcaag gagtggcatt ctgggaggag agggaggaag    3420
tctactgaaa ggtagaaaaa tgaaaaaaac tataggatag ctatttaata aacggcagtg    3480
agagttggga ggaacgagat gaccacccct gaaacatatt ttagaatgaa agagatgaag    3540
gatatctgtc tgcttttttgt tgccatgtgg aaaatttgct tcttggtttc tagatccatg    3600
tagaggtagg ttattacctt ttctttgtgc agttcccagc tatgtgagca gtacacagct    3660
tccctaagtt taacaagttc agatggtaag aatgccttac tttattaaca aatacataac    3720
tgtatatttt cggatgtctt tttgcgtctt gtctctgtgg ttttcatggg aaacctgtga    3780
gaatcgtggc aggcaagttg gctctttgct catcagcaac cgaatgagaa ttcaaagtcc    3840
agacctgcgt gctttccatt gggccaagtt gggtcctcct atggtaatgg aaccttcgta    3900
aagcaaaatc ctcatctgta gtctcttttt tttccccacc aaactttgta ttatggaaac    3960
atttcagaca caatcaaaag tagaaaagta taatgatccc ttgggtccta tatctgtcac    4020
ccactttagg tacttatcaa ctgattagtc ttgtttctgt acctataccc actcctcact    4080
tatcttcatt atggtcatat cttctttaaa aactggaaat gtaaatgtgt ttctcttcta    4140
tgaaaggata agaagttcac catgagtgat ttatttagac cccagcacag taaagttcac    4200
tgaatgaaat gtaaacaact tggagcaatt gttttttctt caacaaaggc cacattcagt    4260
tgcagtggta ttttattcag ttgcagtggt attttacata tataaactct tatagtcctt    4320
ataacaactt tttagtttag gtagtgttat cctcatttta taggtgagga aactaagcac    4380
aacgtagtta agtaactcgc tcgagattac acagctagtt aagaggccaa gattttttt    4440
ttttttctct gagacagagt ttcactcttg ttgctcaggc tggagtgcaa tggcactgtc    4500
tcagctcact gcaacctctg cctcccaggt tcaaacgatt ctcctgcctc agcctcccaa    4560
gtagctagga ttacaggcgc ccgccaccac gcctggctaa tttttttgta tttttggtag    4620
agacagagtt tcaccatgtt ggccaggctg atctcgaact cctgacctca agtgatcgcc    4680
cgccttggcc tgctgggatt acaggtgtga gccaccgcac ccgaggccaa gattttgtag    4740
gggtggaaag gtgtgatcct ttgctctcca tcgtaaacgt cacggccaat attttttataa    4800
gagaagacag gttataataa gagaaaagca taacaaattt atttaacaaa gttttacatg    4860
acatgagagc cttcagaatg aagacccaaa gacagaggaa aaaccatcca tttttatgtt    4920
taggttcaac aaagaatgga cagaaaggtg gaagtatgat tggacagcaa ggatatggtg    4980
tatgctagta gactgaggtg gagaaagcca ggaaagcctg tctgtccaga ttcttcttgg    5040
cttctctaaa attctttctc caccccctaa ggatctcctg acctactaat gggcaaggag    5100
atgagaggat ttctttacgt ccagctccta gacagaaagc cagtggaaag ttagaatcat    5160
aagtttaaat cttatgactg gctttgggga aaaagagttt tagtttctgt aaactgccct    5220
ggggaagaga aattctcatt tctgtgactt cagggaagaa tgaagggtga gaggcaagag    5280
ggcaggagaa agctatatat atatttttttt tgagagggt ttactctgtc acccaggctg    5340
gagtgcagtg gcacaatcat ggctaattgc agcctcgatc tcccaggctg aggcaatcct    5400
tccacctcag cctcctgagt atctgggact acaggtgcac accagcatgc ccaactaatt    5460
tttgtatttt tcatagagat ggtttcacca tgttgtctgt ctggtcttga actctagggc    5520
```

```
ttaagcaatt ttgcctgcct tggcctccca aagtgctggg attacaagtg tgatccacca   5580
tgcctggaca aggtcttggt tctggctggg cgcagtggct cacccctgta atcccagcac   5640
tttgggaggc tgaggctgct ggatcatctg aggtcaggag tttgagccca gcctggccaa   5700
catggtgcaa ctccatctct gctaaaaata caaaaaagaa tcagccgggt gtggtggcgt   5760
gcacctgtaa tcccagctac tcaggaggct gaggcaggag aattgcttga acccaggagg   5820
tggaggttgc agtgagccga gattccacca ctacactcca gcctgatgac agagagaaa    5880
cactgtctca aaaaaaaaa aaaagatctt ggttctgagg ctgcttctga gcatatttt    5940
gggtgttgtt atctgcaata attttatccc aggaagttaa ccattacctt gtcatgaggt   6000
aaactgatgg atttttaatta gtgagtatac agcagtgagc atacatagaa ttatttcccg   6060
agactacagc cattatgtat aaattcttca gttcaaagga gtagcaagct ttttaattac   6120
cccaaatgtt taattctaga aataaatccg ccttctctaa gttttaagtg actgtcttca   6180
tttgaggaa atggatttta tttcctgaac cccaggaaaa gaattttga atttgaaaac    6240
acttatgtca ccagtttgtg gatgttggaa ctgtgtgtgt cattggtcaa acaccagtca   6300
tttgcaaatg ctcccctta acaggagaat ctacccagga aattccgtat cttactggca   6360
gaacttgctg ctttaaagtg tttattatag tctcagctac ttggaggatt acttaataag   6420
cccaggagtt ctaggctgcc atggactgta atcttgcctg tgaataatca ctgtactcca   6480
ggctgggcaa yatagtgaga tcccatctca aaaactatat atgttgattg tagaaaattc   6540
gaaaatatgg acaactataa agaaggtagt aaaaatggat tgtaattctt aacatgctag   6600
tatattttc ttcaagcatt tttataagca tgtactttat ttcatagctt acacagaaga   6660
tagatgcagt tttgcttcct gctttattta ttttatgta tttatttatt ttttgagacg    6720
gagttttgct gttgttgccc aggttgaaat gcagtggcac aatcttggct cactgcaacc   6780
tccgcctccc gggttcaagc gattctcctg cctcagcctc ccaagtagct gggattatag   6840
gcatgcccca ccatgcctgg ctaatttgt attttagta gaggcggggt ttcaccatgt    6900
tggtcaggct ggtctggaac tcccttacct caggtgatcc attcgccttg gcctcccaaa   6960
gtgctgggat tacaggtgtg agccacccca cctggcccct gctttatttt tcttatata    7020
ttgtgggcat ttttacacac cattacaact tataaagtct gccagagtgt tcgtggttat   7080
gactttctag gggtctgctt tgtgatatgg attaatattt actgtccttc acttgaccct   7140
ttgtcacatt gtgtgattat ttttctagt ttactttttt ttcccatgta aaactttta    7200
tttaacattt ctgtaatcag aactctcaat cttttgttta aaacttggaa agcattcctc   7260
acatatttaa ttttgctaca tgcatgattt tttaaatgct aaacctttga ttcataagga   7320
atatattttt gtttgggttt aacccgttat tccaatagca acaccacttt attaaacagt   7380
cttttatgtc ttcactcact tgatatgcca tcttcatgtg ttgttgttgt tgttttttga   7440
gatggagtct tgctctgtcg cccaggctgg agtgcagtgg catgatctcg gctcactgcg   7500
acctccaact cttgggttca agtgattctc ctgcctcagc ctcccagta gctgggatta    7560
caggtgcccg ccatcacgct cggctaattt tttgtatttt tttagtagag ctggggtttc   7620
atcatgttgg ccaggctggt ctcaaactcc cctcctcagg tgatccacct gcctcagcct   7680
tccaaagtgc tgggtttaca gccatgagcc accgtgcccg gccaaggata ttttaatgc    7740
tttttgttac atactgccaa attctcagtt gtatgtctta gtaatatta atgagtatgg    7800
cttatgattc agtttctaaa tgctctgaaa attataaaac cagtgctgta gtagttacca   7860
attatccctg aacatacaca acagttagga aataaattaa ataaactttt tttcggaagt   7920
```

```
aaatagaatt ttacttaaga aataaaatat agtgaaatac tttaaaaaat cagaattttc      7980
ttgttgaatt caggctcaaa atctcttgaa atgaaaacag tagatgcttt gaatagtgaa      8040
aattacaatt cagccacacc agtagtacca ttctgtttat ctgttttta gagatgtctc       8100 tgagttgacg ggatttcctg aaatgttggg gggacgtgtg aaaactttgc atcctgcagt     8160
ccatgctggt aagtggttgg tatctttaat gtaaaaacag tcagtggttt ccaggaatat     8220
tttagttgat agcgtcctaa aataaaggaa gaaaaaggct caagagaaat ttacatataa     8280
agttaatgtt atgaagttgc tgccagattt cataatacgt tagaactggt ttaaaatcca     8340
gcttgtctta ctacttgatg aattcagatt gttttcctct gcttgctatt agtcctgacc     8400
tgatacctaa tttagagtct ggtgtttcct gctcaagttg ctgaagatat ttagatttca     8460
tcgtatgaaa atacttttaa aatagttcaa acttagaaga aagcatcaca gcgtaactga     8520
cttgcaaagg aattttttt tcaaagtgc tttacatttg ttcgttcacc taagaatgaa       8580
ttgtatataa accgaaacgg caagaaactg gtatcctcct agtttgtcag ttgtggtaca     8640
atttggtgaa taaagctgaa tggctacaga tcatcagaca agccattgac ttacagaaac     8700
gcatagactt ttctggaact agcaacagtt ttgtaaaatt cctttacct ttttacatt       8760 ttattgctca agaaactggg atcaagaact gaagaaaaag atttttaaat atatctctct    8820 ttttttttt tgagacagga ttatactctt gcccaggctg gagtgcagtg gtgcgatcat     8880
ggctcgctgc agcctctgtc tgcttcccag gctcaagcag ttctcccacc tcagcctccc    8940
aagtagctgg gactataggc atgtgccacc acacccagct aattttttgta ttttttatag   9000 agacggggtc tcaccttgtt gcccaggctg gtctcgaaca cctgggctca gcgatcccc     9060 cacctagcc tcccaaagtg ctggtattac agacatgagc cactgtggcc agccagatat    9120
atctgttaat cctaattttt ttgtttgata actccccaac tacatgtttg atattcttta   9180
attaagaata ttatgctggg catggtggct cttgcctgta gtcccagcac ttggagagct   9240
gagacaggag aaccgcttga gcccaggagt ttaagatcac cctgggcaag atggcaacac    9300
cccccttctc tttaaaaaat tgaaaagacc agctgggtgt ggtgatgcat tcctgtagtc   9360
ccagctactt gggaggctga ggtaggagga tcacttgagc cctggaggtc agggctatag   9420
tgagttgtga ttacgccact acaatccagc ctgggcgata gagtgagacc atctcaaaaa   9480
aataaatttt ttttttaatc aatgggattt aatttgattg aagacactat gttgaaagac   9540
attccttaat ctgacttgtt ttttgaagct aatgactttg tttaacttttt ttaaattagg   9600 aatcctagct cgtaatattc cagaagataa tgctgacatg ccagacttg atttcaatct    9660 tataaggtaa aaacctgaaa ttaaactttt aacgcattac gaaccaacga caaagactat   9720
gccaaacctg gtgtccctgt gttttcttac tcactataaa cctttactgc gtaccttctg   9780
tgtgactttg tatgtgtgta agcattttgg tttggccaga tttatatacc aaaatacata   9840
ctgaagtttt ttaggaagtt acaatctaaa tcttagtatg tataggttga gtatcccta   9900 tctgaaatgc ttgggaccca gaagtgtctt ggatttcaga tttcttcaga ttttggaata   9960
tttgcaggta acatgccagt tgagcgtccc tcagaaatcc gaaatgcttc agtgagcatt   10020
tcctccaagt gtcatgttga cgctcaaaaa gtttcagatt ttggagcatt tcagatttca   10080
ggttttcata ttaggaatta tcaacttgca caactaactg agttatttgc ataaagtac    10140 tggctgtttc tcttaaatat acgtaacagc tttattgaga tctaatccac ataccataca   10200
actcaccaat ttaaaatgta caaatcagtg gttcacagaa gttgtgcaac cattactgtg   10260
ttagtctgtt ctgcattgct ataaaggaat actagaagct gggtaattta tgaaaatagg   10320
```

```
tttattttgg ctcgtgattc tatagacagt acaagaagtg tggtgccagc atcaacttct   10380
ggtgagggcc tcaggaagtt tataatcaca gtggaaagca gaggggagc tggcatatcc    10440 catgagagaa gaagcaagag agagggagag gaggagttgc ccagctcttt tacttttaa    10500 cttttattct taatttaatt taattttatt ttgagacagg gtctcgctct gttgctcagg   10560
ttggagttca gtggcatgac cttggctcac tgcaacctct gcctcctgtg ttcaagtgat   10620
tctcctgcct cagcctcctg agtagctgag attacaggcg tttgtcacca cgcccaactc   10680
atttttacta tttttagtag agatgggggtt tcaccatgtt ggtcaggctg ctcttggaac  10740
tcctgacctc aaatgatgca cccaccccgg cctcccaaag tgctgggatt aggtgtgagc   10800
caccacgccc ggcctgcccg gctctgttaa acaaccagct ctacatgaac tcagagtgag   10860
gactcattat ggggagggca ccaagccatt cataagggat ctcccccgtg acccaatcat   10920
ctcccaccag gccccacctc aacattggg gatcacattg caaaatgaga tttggagagg    10980
acacacatcc aaaccatatt aattgccaca tccaatatta aaacatattc atcacccccca  11040 ccctaaaccc tatcccata cgcatttatt ctccatttcc ccaacgtcct ccagcctcgg    11100
caaccaccaa ttgttacgtg tctgatttgc ctgtagtgga cattttcata taaatagaat   11160
ctaacaatat atggttttt tgttcctggc ttctttcact tagcatgttt tcaaggttta    11220
tccatgttat agcatagtat caatagttca tttcgtttt agtgctgaaa aataatccat    11280
tgtgtggtca taccctgttt tgtttatcag ttcatttgtt gatggacatt tgggttgttt   11340
ctactttttg aatattatga ataatgcagc tataaatatt tgtgtataag ttttttgtgtg  11400 gacatacaca ttcgtttcat tggggtatat acctaggagt ggaattcctt ggtcatatgg   11460
taactatgtt tagcttttga ggaactgcga ccctgtattt cagagtgctg caccatttta   11520
catttccagc agcagtgtgc tggatggggc tccagtttct ccacatcctc atcaacgtta   11580
ctatctgtct ttttgattct agtcattcta ggggttctga agtggcatct cattgtggtt   11640
ataatttgct ttccaaataa tgtggaacac cgttggatgt gcttcctagc cagttgttta   11700
cctcctttgg agaaatgtct gttgagacct cttgtccatt tttagttgag gtatttatct   11760
gtttattatt gagttgtaag tttatttcct ctcattctat ggattgtgtt agcctttctt   11820
gatggtttcc tttgatcatc acaagttttt tctttttttt gagacggagt cttactctcg   11880
cccaggctgg agcacagtgg cgtcatcttg gctcactgca acctccacct cccggattca   11940
agcgattctg cctcagtctc atgagtagct ggggttacag gtgcccgcca ccacacttgg   12000
ctaatttttt tggattttta atagagatag ggtttcacta tgttggccag gttggtcttg   12060
aattcctgac ctcgggttat ctgcccgcct tggcctccca aagtgctggg attacaggct   12120
tgagccacca tgcccggccc acaaaagttt ttaattttga tgatgttgaa tttatttttt   12180
cttttgttgc ttgtgttaat ggtgtcatgt ctaagaaacc attgcctaat cctcagtgat   12240 gaagatttt gtgtatattt tctttctttt ttttttttt tttgagatgg agtttcgctc     12300
ttgttgccca ggctggagtg cagtggcgtg atctcggctc actgcaactt tcgcctcctg   12360
ggttcaagcg attctcatgc ctcagcctcg caagtagctg tgattacagg tgcccgccac   12420
cacgcccagc taattttttt gtgtttttag tagagacggg gtttctccat gttggccagg   12480
ctggtcttga actcctgacc tcaggtgatc cacctgcctc ggtctcccaa agtgctggga   12540
ttacaagtgt gagccaccgc acccggcgtg tgtacatttc ttttaagagt tattttagtg   12600
ttagctctta tacttaagtc tttggttcat tttaagttaa ttttcatata cagacatgaa   12660
atagaagtct tattttattt tgtatgtggc tgtctagttg tctcagcatc atttgttgaa   12720
```

```
aagactgttc tttgcccaat cgaatggtct tggcaccctt ggtccatgtg cctgctgtta   12780
tgccagtact acactattac tataggctgg taacaaattt tgaaatcagc aagcgtgagt   12840
cctccaactt catttttctg ttttttgttt gtttgtttgt tttgttttgt tttgtttttg   12900
agacggagtc tggctctgtt gcccaggctg gagtgcagtg gcgcgatctt ggctcactgc   12960
aagctctgcc tcccgggttc acgccttct  cctgcctcag cctcccgagt agctgggacc   13020
ataggcgccc gctaccatgc gcagctaatt ttttgtatt  tttagtagag acagggtttc   13080
accgtgttcg ccaggatggt ctcgatctcc tgacctcgtg atccgcccgc ctcggcctcc   13140
caaagtgcta ggattacagg cgtgagccac tgcgcccggc cccaacttcg ttttttttat   13200
tcaagatgac tttgactctt cagagtccct tgcatttcca catgattttt agaatcagct   13260
tgtccatttc tgcaaaacaa cgcagttgga attttcatag gtattgtgtt gaatctgtag   13320
atcaatttgg gaaatgttac catcctaaga atattaaatc ttccagtctg tgaacatggg   13380
gtgtctttaa tttctttaac attgtcttgt gaagtagaat tgtttttctta atttttttct   13440 cattcactgc taatgtatat tttaatacaa ttgattttta tatattgatc atatatcctg   13500
cggctttgct gaactcattt attagtgcta aaaggttatt tttgtgaatt tgggattttc   13560
tgtatactag gtggtatcat ctgcaaatag atataacttc actgctttct ttccagtcct   13620
gatgcctttt attttcttttt ctttgctaat tgctctggct agaacttcta gtacagtgtt   13680
cagtagaagt ggtaagaatg gacattattg ttttgtttct tttttttaag atggcgtttt   13740
gctcttgttg cccaaggcgg agtgcagttg cgtgatcttg gctcactgtg acctccgcct   13800
cccgggttta agtgattatc ctgcttcagc ctggggttac aggcatgtgc caccttgcct   13860 ggctaattt  gtattttag tagagatggg gtttctccat gttggtcagg ctggtcttga   13920
acttccaacc tcagttgatc catcctcctg agcctcccaa agtgctggga ttgcaggcgt   13980
gcgccacctt gcccggctaa ttttttgtatt tttagtagag atggggtttt accatattgg   14040
ccacgctggt ctcgaacttc tgacctcagg tgatctgcct ggctcagcct cccaaagtgc   14100
tgggattata ggcatgagcc actgcgcctg gcctcttgtc ttgtttctga gttgagtaga   14160
caagtatttt agtctttcac catcaagtat gatgttagct gtgggttttt cttacacttt   14220
gtcatgttca gtaagttccc ttctatttt  aatttgctga gtgtttctat atgaatacct   14280
gttgaattgt gtcagatcct ttttgtacat ctattgagat gatcaggtgg ttttgcatt    14340 tttctggatt cagtttgtta gtgttttgtt gagagttttt gtgtgaagat acctaagaga   14400
tactggtctc tagttttctt gtgacatttg tctggttta  gtaggagggc agtagactta   14460
ataaagatga gctgcaaaat gtttccctc  caattctgtt cttctgtttt tgttttttgtt   14520 ttttttaatt agttttcagc agttaggctt gtttggagcc tgcccgtaga gctcctcgca   14580
ctacaggcct aggagtggaa ctgtacttca ctgattgtta atttagatt  acttctgtat   14640 tttaaattat tcttttggca ttcctgttac catcattttt atgacctctc tgaaggcaaa   14700
acaaatgttt caccttaga  atgctctgat atttttcatc attgtgccaa tccactggaa   14760
aaagaatcta aattctaatg ttctggataa tagtgatcac attccaaaat gagaatgtta   14820
tctgtaatct tgtactttat acttctatta aaatgttcta taaattttc  atggcttggt   14880 ggttctgggt agctaaggtt atgcaagcag cagcgttgca gtgtgacgtg gagggagtac   14940
tgtgtattca gatccgggga gcacctgctg actaaattac ctctgctcga ccccagcagg   15000
acaccctgac tttttaacac actcgttaga attctaaagt gtcaggctca cagtttatgt   15060
attagttctc tatggctttt gtttacgtta atagtactga cttgtttttt tcctagatag   15120
```

```
ctgtaaacca catgagtgga cttttaatg acagccagat tcgtctttgt tttatagagt   15180
tgttgcctgc aatctctatc cctttgtaaa gacagtggct tctccaggtg taastgttga   15240
ggaggctgtg gagcaaattg acattggtaa gtcagaaaaa ccatttaga agactgagag    15300
gagaggatta tttaaatttt agtgagattt cattttgaat tttattactg aggaaataga   15360
aagaaaatag ctacttctgg attgtgtttt gggattacta taattcattt atattttctt   15420
tttttcattt atattttcta agctttttt gtatgcagag atgcatctgg gttattttcc    15480
tgatttattt atttatttat tttatttta ttttttgag atgaagtctt gctgtgtcac     15540
ccaggctgga gtacagtggc acagttttgg ctgactgcaa cctctgcctc ctgggctcaa   15600
gtgattctct tgcctcagcc tcctgagtag ctgggattac aggtgcacac caccacgcct   15660
ggctaattt ttttgtattt tttatagaga tggaatttcg ccatgttggc cagagtggtc    15720
tcgaactcct gacctcaggt gatccacctg cctcagcctc ccaaagtgct gggattccag   15780
gcatgagcca ctgcgcccag cttatttcc tgatttttaa gtcaggaatt aaaatggaag    15840
tacatgcaca atgactttat ttaaaagygg ttcataagct gatagggaca tacaaaaatc   15900
aatacgtctt tgttcttca aggtggagt aaccttactg agagctgcag ccaaaaacca     15960
cgctcgagtg acagtggtgt gtgaaccaga ggactatgtg gtggtgtcca cggagatgca   16020
gagctccgag agtaaggaca cctccttgga gactagacgc cagttagcct tgaaggtggg   16080
atgcactttc atgatattgt aagttacatc catggagtgc agtgtttgcc agaccaagca   16140
gtattcagtt cttggtagat tgcattacct accaaagctt tgcttggagc tgctatcctt   16200
ttgttaaaaa tggagaaacc agctattaca gaggtgttct gtcaaaaaga ttgaaagaga   16260
gctgggcgcg gtggctcacg cctgtaatcc tagcactttg ggaggccgag gcgggcggat   16320
cacctgaggt caggagtttg agaccagcct ggccaatgtg gtgaaaccct gtctctactg   16380
aaaatacaaa aattagccga gtgtggtgtg gtgtggtacg cctgtaatcc cagctactcg   16440
ggagactgag gcaggagaat cgcttgaacc caggaggtgg aagttgcagt aagctgacat   16500
cacaccactg cactctagcc tgggcagcag agtgagactt tgtctcaaaa aaaaaaaaa    16560
agattgaaaa agaattggaa aggggtaatt tgttgggcca ttcagtgctt tgctgtcatt   16620
catggtgtca tcgtgttgtg cagccaccac atagcactga atagtgagga gatgttgttt   16680
gctgtggacg tagaaaacca tcttgtcccc acttggaaa gtgctgctyg tgtctcacaa    16740
aacttatgct ttttgtaggc attcactcat acggcacaat atgatgaagc aatttcagat   16800
tatttcagga aacagtacag caaaggcgta tctcagatgc ccttgagata tggaatgaac   16860
ccacatcaga cccctgccca gctgtacaca ctgcagccca agcttcccat cacaggtaaa   16920
gcccgagcgt tctgtggcat ggtttgctgt gcctggagag tgtgtgtttc tctgtattgc   16980
atctgatgtg gttcacattc agaagatgat acattccgta atgcctcctg tagccatctg   17040
ataaccatct ggtttgagac gccatttgga ctgaagagca cagaagttga gtagtctgga   17100
gttctgaaaa gatgtcatgg gggagatgga gattggaatg tctctgccac gtagatcttt   17160
ttgaagacat gagacaggat gggatggcct ggattttata gagaagaggg tcaagaaagc   17220
cttggggtaa aggcttggta ggtgtactgt ggaggaacca gcagaagaaa agttgtgaaa   17280
ttccaacctt ttagaatgca tttgagaaca gaaaaggaac tgtttgtttt gcacatattg   17340
taagaagccg ttgccttgga atattggatc tagaagccca attgaagtag gccaaagcag   17400
aaatgtgatg ttaagaacta acaacgnata agaggtttct tggaacaaga aagtaggact   17460
ttctctgggt ttgtagagtt tagagagggt ttttaaatgt gtgtcctgtt ctgttccaaa   17520
```

```
ggtaggctgt gagagcctgt cctgctctgg tacaagggag agtaggggca gggacagagg   17580
tgagagtccc aggcatggag gccttggaat cccaagcact accggtgcag ctggccttgg   17640
ctgagagcaa gggcagcctc cttcctgcct ggggcggtca gcatttggtg aggggtgca    17700
gcctgggctt cctttccctg tcatcagctg agagagcgat gggggagggg agcagcgtgc   17760
caggtgggag gagaatctga aagtttcttc acgtttgccg cgttctattg ttctgcctca   17820
gatagatttt tttttttttt ttaaattaag acaacggagt ctcgctctgt cacccaggct   17880
ggagtgcagt ggcgcaatct ctggttcaag cgattctcct gcctcagcct cctgagtagc   17940
tgggattaca ggtgcgcacc acaatgcctg gctagttttt ctgttttag tagagatggg    18000
gtttcaccat gttggccagg ctggtctcaa actcctgacc tcaagttatc tgcctatctc   18060
agcctcccag agtgctggga ttacaggcgt gagccaccac acctggcctc agatctcaga   18120
tacactttga cactaacact tcccaaatcc ccacagacac cctgtgaagt cctgtaggct   18180
gaagtaatct aagtaatttg ttttctctct cctttctggg cttcacagca cagtaatctt   18240
ttaaaaatgg aaatcggatg atgtcagacc ctacttaaag ccattccttg gcttttctta   18300
agcactttgc sctgccccac aaaccctgtg ctgcctgcct gcctcctatc tgcccctca    18360
gcagctctcc ctgcgcctgc tgctagcccc tccgccctgt gcctccaagt gggcccagct   18420
cttccactc cagcgcctct ggctccttgt cccttcacc cagaattctt ccctctgccc     18480
ttcaccgtcc tggtttcttg ttattcaggc ctcacctcct cagagaagcc ttccttgacc   18540
gcttagacca aagtagcagc ccatcatgct tycatcccat caccctgttt tgctgcatgt   18600
gtttctattc aatctgttca aattgtcttc ccccattagg atggcagctt cctttttttt   18660
tttttttttg agatagagtt tcactctttt cgcccaggct ggagtgcagt ggtgcgatct   18720
tggctcgctg caaactccac ctcccgggtt gaagtgattc tcctgcctcg gcctctcaag   18780
tagctgggac tacaggcgcc tgccaccaca cctggctaat tttgtatttt tagtagagat   18840
agggtttcac cacgttggcc aggctggttt tgaactcctg acctcaggtg atctgcctgc   18900
ctcggcctcc cagagtgctg ggattacagg catgagccac agcgcccagc caggatgtca   18960
gcttttgaga gcagaagctg catctgtttt tgtttgtcgc tgaatcccca gggcttagaa   19020
gactgcttgg cacattccct aaatgtttac tgaatgaata attagcaacc tgacattttg   19080
cacaaatttt tccttgtagg acttcttgaa actgatttgt ctgctgttat atctgaccta   19140
tttcctgctt atagtttata ttctccatta agattctgag acaaaaaaat ccccatgtac   19200
tgtcagttct tatacttttc attttccaaa gcattttcat tggactatat aaaagccttc   19260
attgttcctt agactgtgtg tgcgtttctt ttgaagttta agtattatt tgtggtaaac    19320
atggcagagg cggccctgga cacgtaaata agcgtttctt gtgcgagatt cccaggattt   19380
ctccccaaca tgggcttatt tccacaatag aaaaggcact ttgcctttc atgtggtttg    19440
agtatttggc agtgatgtta ttacagagtg tatggttgcg attgtatcta aaacaaaatt   19500
gaagcaagaa caaagatggg gttgtgtgag tgtgtgtatg tgtctgagat tttaatgact   19560
ggtttgctta tgattggaaa gaagaaaatt cctatttatt tcagctattt actagattaa   19620
gcaactttca gcatttctct ggcactttct atttcagtta ttaatgtctt tgaaaatttg   19680
atatttgaag gggaaccgga tactcttttt ttttgagtc agagtcttgc tctgtcgtcc    19740
aggctggagt gcagtggcat gatctcggct caccacaacc tccgcctccc aggttcaagt   19800
gatctcctgc ctcagcctcc tgagtagttg ggattacagg catgtaccac caggcccagc   19860
taattttgt attttagta aagacagagt ttcaccatat tggccagacc agtctgaaac    19920
```

```
tcccaacctc aggtgatcca cccaccttgg cctcccaaag tgttggggat tacaggcatg   19980
agccaccgca cccatccaga tacgcttaac tatgagatgt ttcagaaacc aaaagttttc   20040
tcccacttat caaccttagc ctaaaccatc tatgaggagt gggagggaga tgggggagtt   20100
gtacatatgg tgttttgttt tattatgcct gttgtatgcc ttaggggata ttttacttct   20160
attgtttact atttattgcc tagtttgttt tcttctgtgc ctctcgcata aatttcatga   20220
ggacagtgat tttatttgac ttgatttttg gttgggggaa ttattttttc aagttctttt   20280
taaaacgggc tttatttttt tagagtagtt acaggtttac agaaaaaata cacggtgatt   20340
atagggaatt tccatatacc ccgcttcccc gcagtttctc ctattaacat catgcattag   20400
tgtggtgtat ttgttacaac tgatgaaccg attttgattc attattaacc aaggttcata   20460
gtttaacatt cattctttgt gttgtacatt ctgtgtattt ggaaaaatgc acagtggcat   20520
gtctccccca ttacagtatc atgcagaata gtttcaatgc cctaaaactc ccttgtgctc   20580
ctccgcctca tccctccttt ccttctccc caacccttg caaccactgt tatctttttc   20640
tcttttcttt tttttttttt tggaatggag tcttgctatg ttgtctgagc tggttttgat   20700
atcctgggac tcaagcagtc cttccgcctt ggcctctcaa gtagctggga ttacaggcat   20760
gcaccaccat gcccagctgt ttttactgac tctgtaccca tttccagaat gtcagatagt   20820
tgggatcata cagtatggag cacttttagg cactttcagt taacaacatg cattaagttt   20880
cttccacatc tttttgtggg ttggtagctt atttcttaat gctgaataat atttcactgt   20940
gtatgaatgt accacagttt atccatggac atattgaagg gcatcaaaac ttcaaggaca   21000 gttttggta gtttatgaac aaaattgcta taatcatttg tgtgcaagtt ttcaactcat   21060
tttgataaat acctaatatt ttcttttatt gtatactatt tattgcctat tttttatttg   21120
cctccccagt aagctccata aggacagtga cttttttta agagggttcc agggccggtt   21180 ttttcactg atgtatcctg aatacctaga acagtgctta acatcgtagt aggcaactca   21240
gtaaatattt ggcaagttct ttaaaaacta tcttaaccca tgaaggacat gaaattacac   21300 attttgttt tttgggttgt tttttttttt tttttgaga cggagtctcg ctcttgttgg   21360
ccaggctgga gtgcagtggc gcggtttcgg ctcactgcaa cctccacctt ccaggttcaa   21420
gcgattctcc tgcctcagcc tcctagtag ctgggattac atgcgcctgc caccacaccc   21480
agctaatttt tgtgttttta gtagagacgg gggtttcacc atgttgacca ggctgatctc   21540
gaactcctga ccttgtgatc cacccacctc ggcctcccaa agtgctgggg tcatgggggt   21600
gagccattgt acccggctca tttttgtttt taattagtgc tggcccacca tttctttctg   21660
tgtgctgaac ttcttatgtt tattcacaag agatactagc tcctaaaaaa atctgccagt   21720
gttgagaaac taggtaatgg aaaactctga agttgcagtc tccttttaac tacagttctg   21780
ctttaggcag agtctgttga gtttgccatc aaagaagaaa gaaaaaacac attatttctt   21840
ctcttcttcc acccacagct gttgctttag cttgtaatat aatttcttac atcgataggg   21900
tttataactt taattttgta ctgtctctgt gattacctca attgtttaat cttagttctg   21960
tatttacatg aattcctgac tgatcactag tcttgtcata gtttctccca tccctaaatc   22020
tcttattgtg gatttatttc tagactggct ggttctggtc ctccagtcgt gtgtgtgtgt   22080
gtgtgtgtgt gtgtgtgtgt gttcatgtac atgtgcattt ttttaaaga tgggctcagg   22140 ctcagttgct ttgttctttta tcatcaagat tttatgtttg tgtgtatctg tttggctctt   22200
aattatactt aaaacatttg tttagtcatg ttattttttt gagaagtgtg catacatctg   22260
accttactga tcctgcttag taatgtgcat gtatattttt acatttagtt ctaaatggag   22320
```

```
ccctggatt tataaacttg tgcgatgctt tgaacgcctg gcagctggtg aaggaactca    22380
aggaggcttt aggtattcca gccgctgcct ctttcaaaca tgtcagccca gcaggtaaag    22440
ctctgtgctc tggaaagctc cagaattgtt cgaaaggcat ttcttcttaa attttttga    22500 atattaacaa gttctaatgt gaatatagac atgctatgaa atctgaaagt catctgttga    22560
taacagtatc aatgtaataa tataaaatct gatacacaca cacacacaga attgtgtaat    22620
attgtcagga aaatgaggca ggaatttgtt tgtggggtgg aaccataaaa gtttagaaaa    22680
taaaagtgaa atgtcctaat gcaatagact aagtcttgtg ccacatcttt gaaaatgtaa    22740
tggagtaaac ataagaagt tcttctttgg actctttatc tgaaacttct tatagtcgtt    22800
gtatgagata ctttgcttct gtgtttaaat catgaactcc gcaattgagt tgtctgtaca    22860
ccacatcttg ctgacagtcc tccagcacat gatttgttct caggtrttta ttgggtgtta    22920
aagtgatgtg agtggggaag aaataaatga tgtgtgatat caaagtgata tcaagcagaa    22980
catagagaaa gagtgagtca gtaatgaagt aaacgagctt cacctacacg ctgggtactg    23040
tcaggcttca gtggctctgt ggttttggag ggcagagagg agatttccct cacactgctc    23100
ccacaaccat atttttagtg tataattatc tggctaaata gatttctgtt taatttagca    23160
caggcactag aaaaygtgct gcgtagactg ggtgttaaga aaactgtctt gatttaggag    23220
ttgacaggta gtaactttag ctttctttgt ttrtgatttt actattttct aaccaggtgc    23280
tgctgttgga attccactca gtgaagatga ggccaaagtc tgcatggttt atgatctcta    23340
taaaaccctc acacccatct cagcggcata tgcaagagca agaggtcaga ctcatagggc    23400
tttttgattt ggggagaaa gaaaaagcaa tattttatcc taaatagaat aaagaggata    23460
gaataaagaa aaatatata gatattctgt ataatatata gatgaaatta aggacttcta    23520
tctctatgta aatatacagt tattctatat aatatagttt gattaaagta aaatacccatt    23580 tgtttcatta taggatttcc tatttaattt gttttattaa tatttgagat tgattctgtg    23640
agtacctcaa aatacatttc tttataaaag tgtatgttag tattttaggc cgggcgcagt    23700
gtctcacgcc tgtagtacca ggactttggg aggctgaggc aggcagatca cgaggtcagg    23760
agatcgagac catcctggct aacacggtga acccccgtct ctactaaaaa tacaaaaaat    23820
tagctgggcg tgatgggggg tccctgtagt cccaggtact caggaggctg aggcaggaga    23880
atggtgtgaa cccggcaggc ggaacttgca gtgagccaag atagcgccag tgcactccag    23940
cctgggtgac agagcgatac tccgtctcaa aaaaaaaaaa aagtatttgt tagtattta    24000 gtgtaataaa tggaaacaat tggaatttgg tcaatgtaat tttgctaatt tagcctattg    24060
aatgcatttg ttattgtta atatgtgacc aaaattgaaa ttacaaaaag ctattctttt    24120
tttttttttt tttgagacag cttcttgctc tgttgtccag gctggagtgc agtggcgcca    24180
tctcagctca ctgcaacctc cacctcctgg gttcaagcga ttctcctgcc tcagcgtcct    24240
gagtagctgg gattacaggt gcgtgccacc acacctggct aatttttttg tattttagt    24300 agagacatgg tttcaccatg ttggccaggc tggtcttgag ctcctgacct caagtgattc    24360
acctgcctca gcctcccaga gggctgggat tacaggcgtg atttatggct cttctaactt    24420 tactacatt ggttagagtc atgttttatc agagacattt acttgttgaa tttaataacc    24480
catgaatatt cctttaatat ttctgaaagt tcttgagaaa ctgttaccat agtttatcat    24540
ctacagcagt ggtcagcaac ttcagctgaa tccagcctgc caccctgttt ttgtgaatat    24600
agtatatata aattggtcct tcacagaaaa agttttctga gtgtcactct agagggtaaa    24660
attaaagaat actttcttac tggttacttc agttaaatga cttattgatc tgttaaaatc    24720
```

```
ttacgtaaac agtaagatta gctttagaga aatgaatttt atatgacagt ggagaatttt   24780
attacttttt ctgtatcagg atactttgtg ataaatacct cattttaatt ttatttacag   24840
gggctgatag gatgtcttca tttggtgatt ttgttgcatt gtccgatgtt tgtgatgtac   24900
caactgcaaa aattatttcc agagaagtta gtggacattc atgtatctta atctgtgtgt   24960
tgaataaagc tttatttgtt cataatgtta attgaaacca taacctataa tatttatatt   25020
tataatatct tttaattagc taagtttatc atttaatgtt catattttaa atagaacatg   25080
aatcttaaat tgttaatttt gaaatgtagt gaattattgt ttcagatgga tatttggctg   25140
ttatgatgtt ttttacttat atatttattt taaattcttt gttgtcttca tgccaaagtt   25200
attgtttctg aagagcagaa gttgtaattt taggtggtga tgcgatataa tccatcttac   25260
tgcatagtgg gtaaaaaaca gaaactacat taataaactt accccatcag ttgaatacca   25320
aacaggtatt ccagacaggt gggggtactg ttggtagtag gaagacagga agaaaagaga   25380
aaaagattaa atagctcaga aaggggaaaa aaataagcag aggtgaaggc tgaaggagca   25440
tgtggcttgg cactatttttg ttgctttagg attcttttcca tggccactgc catccctggg   25500
ttacaggtta caggagggct gtgacatttg tatctttcgt catgtcaaat ctctgattta   25560
atctggtctt gctgttaagg aaaacgcctt gccggaagag gtcatttaac catgtactag   25620
gagagtcagg actagaatgt gctcttgctc attcaaaaca ctccctgaag aaatatttcc   25680
tcctgaggta catgtgttaa gagcaaatca gtcatatttt cttagtttaa actgaaacga   25740
acaaaaactt ggagaggaca gaaagttagg atctgctata cagaaagctg tattctaata   25800
gatttctctt ttcaagtata gcgttagcat tgtttgttgg aggcagaaac cagaatatgc   25860
tgccacatta tttaagactg ataattgctg ctagattttt ttaagaggtg ttctctgatt   25920
tttaaaaata gaaattaaaa tttaatattt ttgcaggtat ctgatggtat aattgcccca   25980
ggatatgaag aagaagcctt gacaatactt tccaaaaaga aaatggaaa ctattgtgtc   26040 cttcaggtga gtgcaattca tgtttgaagc ggtaatttgc tcttttattc tgtgtctctt   26100
tctccsttgt ttactctttc ctttatactc atacccttct agtttatcct tattatagtt   26160
tattttcccc aatcctgcat ttaaaaaaat actattaact tggggttttg agatgagagt   26220
agctttctta ccctcaattt taacttttg ctggttgtga tggcttatgc ctataatttc   26280
agccacttga gaggctgatg tgggaggatg gcttgaggcc aagaattgga ggctgtattg   26340
tggtactatg atgcctgtga ataacgactg cactccagcc ttggcagtgt agtaagacca   26400
tgtctctaaa atactaataa tagtaacaat atttaatgga aagtctctcc atccttctgt   26460
taccttttga aaagataact attttaaatt tcttgcttat ctttcctgaa atagtctata   26520
tattcagcaa atatttgcat gtgcatttct ttttctattt tcctattgac acaagtgcac   26580
cctgcttcac cttcttggaa gtttgtcctg tatctgtgta ttttaactta cctagacagt   26640
caccaatctt tagctactac aaataccct gcagtgaata acctagaaaa gtcctgagag   26700
tgaaattaag gcttaataac aagctctatg tatattggta atcttaattg atactgcccc   26760
ttttagatgt tgtaggcaaa ttcattgtcc taactgaaat atataaggat gcctgtttcc   26820
caacactttt gtcagcattg tggttttata cttttaaaaa gtctctgcag ttagaaaatg   26880
gcatctcaat gtagttttaa cattgtgtgt ggtatgagca tcttttcatg tttgaatgtt   26940
tttattcctt tctatgaact gtcttttccat attctttgat gattttttcta ctaagttgtt   27000 gttgctttt tttttttttt aactgatttt tatgagctct tctgtattgg gaaaagtagc   27060
tcatggtcta agattatgca ttgataaagc aaagagttat ttcaatttaa agtaaaaatt   27120
```

```
cctaatgcta cttttcatag tattgatatc agaactctgt ggaatcctaa ttccttacaa    27180
ggaaacttat taagtatatt cttttgattg taagatacca ataattttat agttcaccat    27240
agattccatg tcagctattt aaggaaagaa gagaatacca cattaaagtt aatacttatt    27300
ttttttagc cacttgacag tctgttgccc aggctagagt gcagtggtgt gatcttggct    27360
cactgcaacc tctgcctcct gagttcaagc gattttcctg cctcaccctc ccaagtacct    27420
gggactacag gcatgtacta ccaggcctgg ctgagttttg tattttagt agagacaggg    27480
tttcaccatg ttggccaggc tggtctcaaa ctcctgacct caagggatct gcccgcctcg    27540
gcctcccaaa gtgttgggat tacaggcgtg agccaccgcg cctggccccc agtttcttaa    27600
tcaagttttt ttgttgttgt tgttgttaag agtgttatgt acttaacaac cattagcatt    27660
ttcttgtagc atcatggaaa atattttcca aaacctgagt catttccttg atctctttaa    27720
cacctgatag ttggagagtg tcaaaggaat atcaggactt cattggtatt ttacttattt    27780
gagaatttgg cttagtttgc acattggacg catgattata agcatgagac aacttatccc    27840
tctacctgac taatgataag tttctcctag catcagttaa taggagagca tatcaattt    27900
agaaattta tagtgcataa tacaaaggaa catttagaa ttcaagaaaa tgtagattaa    27960
acagaactaa tatttacggg gtcttgctta taaattatat gtcagggctt tctaaatcaa    28020
agatcatcca aagcataaag aagaaatagt gtcaagttta aaaaaatatc agggagaga    28080
gtagtgttac acgtattgtt ccacacacct taatgttctt tcggctcaaa atttgggaga    28140
ggaagatggc agtaaatgat acaaattcct tccaaatagc aaagacacag attacaaatc    28200
ctgttttctc acttttagct ttcagttcct gggttagctg gtattttgt aacagatttt    28260
tagaaaggaa aattagaatt taatttttgt gccattgctt atttaattag cacatctgtt    28320
ttatctgctg accttccaaa agaaccatat aggtagtaac ttaaccaaaa atacactcac    28380
tggaatcatt gttttttaac atgttgtata taggttgtaa aatctataaa atactattgg    28440
gtagtaaaat ctataaaaga ctttggagaa aaatattagc gcctggctgt tgtgtcatac    28500
cagaatgttg aattgtatca taccagaatg atttaacaca tcatttgttg tgtgagaaaa    28560
attagaaaat tagaaaactg taaaaaatta gaaacatgca tataacttta cttacaatga    28620
aatcttttgt atataaatta aatgaaaaat ttgagggaag tggagagatt aactttaact    28680
tttaaaattt gtattttaga tggaccaatc ttacaaacca gatgaaaatg aagttcgaac    28740
tctctttggt cttcatttaa gccagaagag aaataatggt gtcgtcgaca agtcattatt    28800
tagcaatgtt gttaccaaaa ataaagatgt aagttgggaa gtatctgaac tgactgctag    28860
taacttccat tggtctgttt tcaatactta atgagcttta catttattaa ggtctggatt    28920
tggaactggt ctgtatgcac acggctagct agcttatctt tgagttgtca cataagcttt    28980
ggagtttaag aaatgaatca aaggccatgt tagaagcttc tgtgcatatg tacacactag    29040
agataagtag ctttaattgt gtataaatgg gatctgtctt ccataatctg gctcctgtaa    29100
cttggctttt ttccatgtgc taggctacaa atgtgttttt atatcaatac atatagatgc    29160
tgggtgcagt agctgacatt tgtaatccca acactttggt aggccaaggg gcagctctct    29220
tgaggtcagg agtttaagac cagcctgacc atgtagtgaa accttgtctt tagaaaaagt    29280
acaaaaatta gccggcgtg gtagctgcgc ctgtaggtcc agctactcga gaggctgagg    29340
tgagaggatt gcatgagtct gggagatcaa ggctgcagtg agccgtgttt gtgccactgc    29400
actcctatct gggtgacaga acaagatcct atctcgaaaa taaatgcata ttcatatctt    29460
tatctgaaag tccatgtggc agtcagtcca tgtgtagatg tactacgatg gatatttatt    29520
```

```
gttcttatttt taccctgat tgattgattt attttttat tttatttttt ctgagacaga    29580
gtctcgctct gtcacccagg ctggagtgca gtggtgcgat ctcgggtcac tgcaagctcc    29640
gcctcccggg ttcacgccat tctcctgctt cagcctccca agtagctggg actacaggcg    29700
cccgccacaa cgcctggcta attttttttg tattttagt agagacggtg tttcactgtg     29760
ttagccagga tggtctcgat ctcctaacct cgtgatctgc ccacctcagc ctcccaaagt    29820
gctggggtta caggcgtgag ccaccatgcc cagcctttat tatttttttt aagagacttt    29880
tgaatgtttt tatccctttg aagctcgctc tgtttgaatg ttttattcc tttgaagctt    29940 gctctgttgc ccaggctgga gtgcagtggt gcgatcatag ctcactgcaa cgtggatctt    30000
ctgatggata tttagattgc ttacattttc agtgctatga tcaatgtttt tatatagaca    30060
agtttttggg cttgtgctct tgttaccttt gtagtaagga cacgttccta ggataataat    30120
ggtgattttt gtgttttgga tatattatct catttaacac ttaggtcact ctatgggggt    30180
gactaccatc gtgtcaattg tgaagatcac aaaattgtac cataaaggac aattaagaaa    30240
tttgaccgga gttacacaat aaagaatgga caagctgaca tttattttt ggagtatctt     30300 aattgggcct tcagtttgaa ggatgtttgt cctaggtcta aagtaggctg tgcttgttgt    30360
tcaatacttt gcaggaatca ttccattgct ttctggtctg tctggctgat agcctggaat    30420
tttttattga gtgctaggca ttgggtatga aaaactgta gcgrtatttt gagggctgga    30480
tggtgttatt tttctctcca gagttgactt gtccttcttt tgggcagata aggtgtagga    30540
ggtatcttca ttctgtcagg aattgttgag cttcctaaag gctaaatagg aatttagcct    30600
tcagtctttg tgaggactgg tctgttcatg gttcattcct gctcctgaat ccctaggtat    30660
ctactgctst acgctgaact cggcttttgt cccttagtcc tctaagactg ccaaaagttg    30720
tgctcagcca atttaccttt agtttattgc atgcaacttg gaaaatgcct tgaggagaaa    30780
agcatagact gtcaggccca tttcttactg cttccatttt ctctgggatc tttgtctgtt    30840
agcacttgct gtctgtccgc tctgcccagc atttctgttt gttactaaaa gaggattggt    30900
ctcttaagct atttgctgta acagaaggag atgaggggct gcagcttgct cccaggtctg    30960
aatcctgagg cctttttcagt agaattgctg gaaataagcc ttaaaatctt tatccagaga    31020
gttctgtctg ttgataagca tacgacgatt aacatatctt ttttgtttga tttaatggat    31080 attcttttcat ttctatcttt gacaattaat ggtgtcctga agtaaagaaa catgtaggca    31140
ttatacatag aaatatcttt cagccctttg gaatccactc tggttggttc atgtactttg    31200
aaaaatactg aatggatatt gacctagatt ccatggtacc atgttgagar ttgtgcctag    31260
ctactgagag tcttttttct aaggtttgta gatattggat tcattaataa tttagtgatc    31320
ttgataggtt ttgtgcctct ggatattttt tataagagtg gtaggtatga tcttaatcgt    31380
ttatctaaac tcttccttg cttcatatga attcttagta gaaatttgga aacttaagga     31440
tgagagaatg atagctttgt tctcctttct gttttacccg tctttttaag tggatttttg    31500
ttaacattcc agcctcagaa ttattaggtc tggaaccatt tcagtcctga gagagccaga    31560
caggtggatg gaatgtttat taatactgaa catgtttgaa ttatttcctc ttctcccatt    31620
tttcttgaat agtgctttaa ttgtgttaac tatttgtagc atgtttctaa gactggattc    31680
ccttactccc agtccactgg catttctcgt atgccttgat cccaacccag gatgccaagt    31740
gtattagttt ttatcacgct gctatgaaga aattcctgag actgggcaat ttataaagaa    31800
aagaggttta attgactcac agttccacac ggttggggag gcctcaggaa tcttataatc    31860
atggcagaag gcacctcttc agagggcggc aggagaggga atgagtgcaa gcgagagaaa    31920
```

```
tgccagacgc ttactgtcag atctcatgag actcattcat tgtcatgaga actacatggg    31980
ggaaactgcc cccatgatcc agttacctcc acctagtccc gcctgttgac acatggggat    32040
tattataatt cagggtgaga tttaggtggg gacacagcca aaccgtatca ccaagattat    32100
ctttgaaggt ctagacatct atgaagctgg cttttgctac taagttttct gggaaccaga    32160
ggaatcagat ttatagttga tgactcaaat agcagataaa gataaaagat atataacatt    32220
aataatacct tagagtaata aattcttaag aaatcctaat agctttttt aaattaaact     32280 tttttaatttt gagataaaag ttgtagattc atatacagtt gtaagagttc ccatgtaacc   32340
gttaccctat ttctcctaat gctagctttt gtcacactac agtacagttc cacaaccatg    32400
ccattgacat tgataacagt taaagacaca gggcatttcc aacactgcag tgatccctca    32460
tgttcttttg tatccgggct cacttgatat ggcttccacc ctctccttac ccttgggcaa    32520
ccacaaatct gttttccctt tctataattt tcattcatcg tgcattcatg tacagttttt    32580
gtgtgtgtgt gtgagcataa ggttttttgtc ttttggggaa acagggtcca actctgttgt   32640
ccaggctgga gtgcaatggc tcggtcttgg ctcactgcaa tctccgcctc ccgggttcaa    32700
gcgattctcc tgcctcagcc tcccaaggag ctgggattac aggcatgcgg caccacacct    32760
ggctaatctt tgtattttca gtagagacgg ggtttcacca tgttggtcag gctggtcttg    32820
aactcctgac tcaggtgatc tacccgcctg ggattacagg catgagccac tgtgcccagc    32880
ctaaacgtaa gttttttattt ctctttgata aatgcccagg gttgttaact gctttgtggt   32940
atggtagttg catgtttagt ttactaagaa actgctgaat tgttttccag agtggcttgt    33000 accatttgt attcccacca gcaatggatg agtgatccaa tgtctctgca tccttactag     33060
cttttggtat tactactttt ttttttttttt taaagacatg ggatagttgt gtagcaatct   33120
ctcactgatt ttaatttgca taatagctca tgatgttgaa cattttttttg tgtacttatt   33180 tgctacatgt gtatccttttt tggtgaaaat gtctgtctttt tgcccattttt ctaattaaat 33240 ttttgattgt tactgagtttt ttttgttttg tttttgagatg aagtctcgct ctgtcaccta  33300
gactggagtg cagtggcatg atcttgtctc actgcagcct ccaccacccg ggttcaagtg    33360
gttctcctgt ctcagcttcc caagtagctg ggattacagg aatgcgccac cacacctggc    33420
aaatttttat attttttagta gagatggggt tcaccatgtt ggtcaggctg gcctggaact   33480
tctgacctca ggtggtccac cgccttggc ctcccaaagt gctaggatta caggcatgtg     33540
ccactgcgcc tgtcctgtta cagagttttt aaagtttttt tatgttttag gtgctagttt    33600
gttgttggat atgaggtttg ttaataattt tctcctagtt cgtagcttgt cttttcatcc    33660
tctttaatga ggaatctttt acagaggaaa agttcttaat tttactgaag tcaaatttat    33720
caacttatct gttggctgta gcaaatatcc tctgtccatt tagcatacag acgtggacta    33780
tcatccttct tttccatttg tattcatgcc tgatactaaa gatagtgata ttttttgggcg  33840 ttattcttgt tgttctatttt ggactggtaa ttcctaatgg tttttgaaca gtttcaactt   33900
aagttattct aaacaaaaga gaaaatgatc gtaatttgat ttttccaaag tcttggctgt    33960
ctgtgtgcat cataacgatt tgtgatgtct atgaaacaat tctccgcatt ggttctgaac    34020 gtaaattta ccatgtctcc agatatttaa aagtactctg gtcaagaaaa tattgtttgt     34080
cagttttgga atggatatgg tagttcttac ctcatgtgat ataaaaaggc ttaatccaca    34140
attgctacaa aataacatga gtttgtgtct atggatgcat tgtgctaagt tccacccccaa   34200 atgtgttaaa tatttaagta aatcatggta gtgtgtagga gaacagttaa tttccctctg    34260
tcatttgagt ggtataacta tgttgtaggt cttttacatt aaatagaact aagaaactta    34320
```

```
aagttggcca ggtgtggtgg ctcacacctg ttgtaatcct ggcactctgg gaggctgagg   34380
cacgtagatg acttgagctc aggagttcga gaccagcctg gccaacatgg tgaaacccca   34440
tctctactaa aaatacaaaa attagccagg catggtggtg catgcgcctg taattgaagc   34500
gtgagaatct cttgcacccg ggaggtggag gttacagtga gccgagattg tgccgttgga   34560
gattgtccca ttgtgcctgg gagacagagt gagactctga ctcaaaaaaa ccacaaaaaa   34620
taatatttaa aaaagaagc ttaaagttaa atgagtttaa aaggccccat gcaatttacc    34680
attgtgtatg tgtttcagtt gccagagtct gccctccgag acctcatcgt agccaccatt   34740
gctgtcaagt acactcagtc taactctgtg tgctacgcca agaacgggca ggtaagtggg   34800
ctgttggact cgccttcggg ggactgttgt tttacgaaat gatatttaaa catccgtctg   34860
ccttagatat tggacagctt gaaagggaat atttgccaaa tgtttgtctt ttgtgtttgt   34920
cagtgtttcc tcagtaccct ggtgggctgt taaaactaat gatgatcaga aaatatcttt   34980
ggaaccaggt actcaaagta gttgtgctgc ttcttgcctt gaataggttg gcacattttg   35040
gattagtgag actctaatag ctgttacaaa actggattat ttcctttcct tttccccat    35100 tggtattatt tccagggaag aggaggtaag ttacggtact gccacccrcc agcctatatt   35160
tttgcagcct gcagggtatt ttcacattat ttcttatgtt gtcttatcaa gaatctgctg   35220
agtagaaaga ctgctagact aggagttaac ttcatcttta aaaagttagg ttcattgagg   35280
cataatttgt atacagtaga attcacccttt ttaaagtaca gtttgaccag ttttcacaaa   35340
tttcacagta tgtgaccgct gccacaatta aataccaaac atttctcact gtgtgacgtt   35400
aagcaagata ttacacttct ttcctagtgt cccgagcctc agaatacaag atggagctgg   35460
ttcatctctg aggtctctgc tagccttttc ttcacatggt gtcctgagct tatctcttgg   35520
catttgttaa attatttggc ccacaagtga cagggaggtg ggtggatatg aattagccta   35580
tggcctggaa gacccagat tgccagtctc tgtagtaaca aactcctggg agattgtgtc    35640
tactggtgtc aggttctaag aagttctgta agtccatgta gaatgagtgc ttcattcctg   35700
atgttgagga ggaggcggct gcccaggtat tgtggtctc tttattctc ttgtagctgt     35760 gggcagggtt gccagcagct gtgctcagaa agagatggac tgttgggcag acagcttagg   35820
ggctgttcat tataggaact aaaaccagaa aacacacctg tgcatttaag tccttgttgc   35880
ttagaattca acccatagaa atagaggaaa gaaggaagaa catttgtacc tggcggaatt   35940
gtttctactt ttagctaccc atgtcagatc cttatctcaa tttctgagag ttgatatttt   36000
aactgtaatt tatacactgg ggcaaacaaa agactttcaa gtaaccatag ttatttttgt   36060
ggtcattagt tttattat tatttattta tttttatag agacagggtc ttgctctgtt      36120
gcccaggcca gagtacagtg acatgatcat agctcattgt agccttcgac tcctggcctc   36180
aagcggtcct accacttcag cctcctgagt agctgggact gcaggtgtgc gccactaccc   36240
ctagctattt tttaattctt attttttgta gagatgagat gttgccatct gcccaggct    36300 ggtctcctga gctcaagcaa tccttctgtc ctaacctcac aaagtgctgg gattacaggc   36360
atgagccagt gcacccagca ttggtcattt atttaactt ttttttttt ttgacctcaa     36420 accatcaatt ttattgaatt gtagattatt aatagtcata tgtcacatat cactgaagag   36480
gtataaatag tagtttataa caaacctctt actccacccc ttttaatgac ttaaaaatta   36540
tttatatttc tcttattttg gcctgatatg ttcttccaca aaactaataa ataggttttg   36600
gagaatgtgc acaaaagatc cttttgagaa gaaagtgtct ttggaagagg tgttcacttt   36660
aatgtctgtg ttcctcaggt tatcggcatt ggagcaggac agcagtctcg tatacactgc   36720
```

```
actcgccttg caggagataa ggcaaactat tggtggctta gacaccatcc acaagtgctt    36780
tcgatgaagt ttaaaacagg rgtgaagaga gcagaaatct ccaatgccat cgatcaatat    36840
gtgactggaa ccattggcga ggtgaaagac ttggcattgg ttctcggct gtgttaatat    36900 tcagttcatc cctttatgtg taacagattt taacttcatc accacacaga gaaaagata     36960 ctttcattga aattctatgt tgtctaaaat tgatcattga aacttcttac acatttctca    37020
tgttcttctg tctcatgtaa ctttcttcat tgttttttgac cccttctga aaccacagtc    37080 ctctgtcttt ttaaattgca gccttggtgt aggtttgtat atttgtactt cccctgttga    37140
ttataagctt ttgatgacaa ggactgcttt tcacctacgt cgaggtgcct gccaccacgt    37200
catgcatggt gcttgctgtc cgatgggtct gtattcaaca ttaaatacaa attgcctgac    37260
ggcaggtaac cctggggtct tctccyacca cattttctac atgtgccatt aataacttga    37320
tacattttgt tacatttcat gttcttctgt ttgaagaagg tatgtgggaa cattacaatc    37380
gcaaacgtta ggtaggtagc ccgccagaag aaaagatcta gcccagtttc tggacatatt    37440
gcgtgcctaa caaaatgctg gatggaaaac agaagcctgc taatcaaata ctagatggtc    37500
ttctgaagag ccaattgact accctcagtt ttttaytcag gagcaggaat caacataagt    37560
gtcattgaag agtgaggctg cagaatgtaa ctgaagtcct taagatatct ttttttttttc   37620 aactttgata cttggatttt tctgtttgat attaccagtc aacccctgct actagtcctg    37680
aaagagtcct ggaagtgaac aagaataaaa gtatgtcaaa gctaaaacat gacccaagat    37740
agaagcacct tgtaaaatat gattaactgt ctgtgccact atgacacaat actgcaggct    37800
gggtaactta taaaccatag acatttattt ttcatagttc tggaggctgt gaagtcccag    37860
atcaaggtac tggtgggctg agagtctggg gaggcctacc ctctgcttcc cagatggcac    37920
agccctctct ggaaaggaca aacactgtgt ccttacttca cagaaggggc atacttcccc    37980
tgaagccctt ttataagtct gtaatccatt catgagggcc ccaccctcat tgcccaataa    38040
ctttctaaag gccttatact tcttaatact gttgcattgg ggattaagtt tcaacatgaa    38100
ttttggagtg gatacacaca ctcaaaccat agcaaatatt atgaattgtg ttttgtctac    38160
aactgccttt acatttagaa taattttgt ataaatgtag ttaaagaact actcatctct     38220
ttcctagatt ggatatagag ggttttttg aaaaccttg gaacacaatt tttatttgct      38280
ttctttgcta cagtagtacc aaagcagtag atttaaatta gacggtagtc taatagacat    38340
aaagtagtag atacgaagta gatttaaatt agagatttta aaacagtgta tttttatgta    38400
agtagcttag ccaaaaataa aaaaaattac atatgtactt ggaataaact gatttggaaa    38460
gtaaaatggt attatcttta tttggtaaac ttagaatcac tttttttcct taatgaaaat    38520
atttctaaaa gcatcaaaga gattctagat atgtgaactt ccatgtaaat aatggtcatt    38580
atttacaatt aagaaatcct ggccgggcgc ggtggctcat gcctataatc ccagcacttt    38640
gggaggccga ggtgagtgga tcatgaggtc aagagattga gacctcctg gccaacatgg      38700 tgaaactctg tctccaaaaa tacaaaaatt agctgggtgt ggtggtgtgc acttgtggtc    38760
ccaggtactt gggaggctga ggcaggagaa ttgcttgaac ctgggaggtg gaggttgcgg    38820
tgagccgaga tcgcaccact gcactccagc ctggtgatag tgcaaaactc cgtctaaaaa    38880
aaaaataata ataataataa taaaaacaag tcctaagaaa aatgcccagg tgctttctgg    38940
catggtgatt tgcaccacat agaactaaag acgatgtcag accaagcttc ttcctttctc    39000
tctccccgca taggatgaag atttgataaa gtggaaggca ctgtttgagg aagtccctga    39060
gttactcact gaggcagaga agaaggaatg ggttgagaaa ctgactgaag tttctatcag    39120
```

```
ctctgatgcc ttcttcccct tccgagataa cgtagacaga gctaaaaggg taagtatgga   39180
attgggtgca tttgcttaga gttgagcatt atgtagaaac tgtttcagaa atcctgcttt   39240
tgatttttaa aaggtgtggc aaagtgatac agatcagtaa tattcagaga accatttgac   39300
ttctccattg ggtggatgga raacccaaat cctgttgtta ttttgccttt ttgactgagt   39360
gtatctttgt tagcatatgc tttttagagg gggattttga gttttgcagg ttttttacata   39420 aaatcgcgtt ttgaaaatca atatacttcc cccagagtgg tgtggcgtac attgcggctc   39480
cctccggttc tgctgctgac aaagttgtga ttgaggcctg cgacgaactg ggaatcatcc   39540
tcgctcatac gaaccttcgg ctcttccacc actgattta ccacacactg ttttttggct    39600
tgcttatgtg taggtgaaca gtcacgcctg aaactttgag gataactttt taaaaaaata   39660
aaacagtatc tcttaatcac tggatccaka gtttttggta gttgtgtttt atgttaaaga   39720
tgcaggctct ttgaactgac acatgacaca taacacataa atgaggaatt ccagagcacc   39780
cctgcctacc ggagctcagc ccatcccaca gcactgcccg tgtgaaacat aaacattagc   39840
aggaaccaaa cgagctgagc agccagagga catggcacaa gtcactgtgt acaggccaca   39900
cttaaggact gggagttata cccatcttaa aggtggagta ttgatgtaaa ttacctagaa   39960
ttcttctgca tgggagttgt atattaaggg tccatgttgc ctcctagggg agtcttctca   40020
tgccgttttt gtttgtttgt ttttcatttt tttgatttgt tattttgaga gggagtctca   40080
aaaaaatagc tctgtcactc aggctagagt cagtggcacc gtcttggctc actgcaacct   40140
ccgcctcccg ggttcaagcg attctcctgc ctcagtctcc tgagtagctg ggactacagg   40200
catgtgccac catgcctggc taattttgt atttagtaga gacagggttt caccatgttg    40260
gtcaggctgg tctcgaactc ttgacctcat gatccacctg ccctggcctc ccaaagtgct   40320
gggattacgg gcgtgagcca ccgtgcccgg ccctcatgcc atttattttt aatcacactt   40380
ctgagaagct tggttgtcta cttttccaaac aaacagcaga ttggcacctg tgaactggaa   40440
ccttagaggg gattggttta agtcttgttg acccccctcta tggataatct gatgtatatt   40500
tttctcagtg ctaagtgaaa tgtttcccag aatttcagca gcccgagatt caccctctgg   40560
agctgcataa aaatgtagtc aatatttggt gctcagaaat tgtacccaat attccaatta   40620
caggcttaat cactacagtg ggcacagtgg gagggcagtg ccttccttca tcaggacaga   40680
cctgtgcatc tgtgtgtcct gcctgtgtgc tcctgaccat tcccgtgcat tgcacctgtg   40740
ttcaactaaa accctttgcc attgttcacc tttaccaatg agtcctaccc tcttcccaag   40800 tcttaactt atcccttgc taaataaaaa tttctgaagt tttttcttaa tggtcatctt     40860
tctaagttat ttctggttca gctaatcttc cagccctggc ctaggacctg cccacattga   40920
aacaaggctg acttgtgtga tcagtaaaat actgcagaaa aaataagact tttgaggcta   40980
ggtcctaata cattgcaact tcagccttag tttcttggat tacttcctct gggataagcc    41040
aagaccacgt tgtaagagtt aagcagccct ccacaaggag agacgccatc ttgcttacac   41100
tagttgccag ccacatgagt gagccacctc agaggtggat cctccagctt cagtcccagg   41160
caacatctgg cttcaacctc ttcagagacc tgagccagaa ctgcccaaaa gagctcttga   41220
attcctgacc cacagataca gagagatgca tactgttgtt aagccacaaa gttctggggt   41280
aattatgtag cagtaaatag ctaatacaga ttttggcttg taaattaagt gtgtgttgtc   41340
tttttcatgg ttctttggct tgaccaaagg ttaacattaa gggtatgata atgggaacag   41400
gctgagcact gtgtctcctg tctataatcc cagcactttg ggaggattgc ttgaggccag   41460
gagttcaaga ccagcctggg caacatagcg acatcctcat ctctaaaaaa agagaaaatt   41520
```

-continued

```
ttaattagct gggcgtggtg gctcctgttt gtagtgttct tcacatagat gaagaataaa    41580
taagtggaga atatgcaact cccatgcaga agaattctag gtaatttaca tcaatactct    41640 actgagggt ataactccca gtccttaagt gtggcctgta caca                     41684
```

<210> SEQ ID NO 2
<211> LENGTH: 1965
<212> TYPE: DNA
<213> ORGANISM: Homo sapiens
<220> FEATURE:
<221> NAME/KEY: 5'UTR
<222> LOCATION: 1..77
<220> FEATURE:
<221> NAME/KEY: CDS
<222> LOCATION: 78..1856
<220> FEATURE:
<221> NAME/KEY: 3'UTR
<222> LOCATION: 1857..1965
<220> FEATURE:
<221> NAME/KEY: polyA_signal
<222> LOCATION: 1938..1943
<220> FEATURE:
<221> NAME/KEY: allele
<222> LOCATION: 424
<223> OTHER INFORMATION: 99-5602-372  : polymorphic base G or C
<220> FEATURE:
<221> NAME/KEY: allele
<222> LOCATION: 1520
<223> OTHER INFORMATION: 5-297-209  : polymorphic base A or G

<400> SEQUENCE: 2

```
cccggcagcc ctcctacctg cgcacgtggt gccgccgctg ctgcctcccg ctcgccctga    60
acccagtgcc tgcagcc atg gct ccc ggc cag ctc gcc tta ttt agt gtc     110
                   Met Ala Pro Gly Gln Leu Ala Leu Phe Ser Val
                    1               5                  10 tct gac aaa acc ggc ctt gtg gaa ttt gca aga aac ctg acc gct ctt    158
Ser Asp Lys Thr Gly Leu Val Glu Phe Ala Arg Asn Leu Thr Ala Leu
            15                  20                  25 ggt ttg aat ctg gtc gct tcc gga ggg act gca aaa gct ctc agg gat    206
Gly Leu Asn Leu Val Ala Ser Gly Gly Thr Ala Lys Ala Leu Arg Asp
        30                  35                  40 gct ggt ctg gca gtc aga gat gtc tct gag ttg acg gga ttt cct gaa    254
Ala Gly Leu Ala Val Arg Asp Val Ser Glu Leu Thr Gly Phe Pro Glu
    45                  50                  55 atg ttg ggg gga cgt gtg aaa act ttg cat cct gca gtc cat gct gga    302
Met Leu Gly Gly Arg Val Lys Thr Leu His Pro Ala Val His Ala Gly
60                  65                  70                  75 atc cta gct cgt aat att cca gaa gat aat gct gac atg gcc aga ctt    350
Ile Leu Ala Arg Asn Ile Pro Glu Asp Asn Ala Asp Met Ala Arg Leu
                80                  85                  90 gat ttc aat ctt ata aga gtt gtt gcc tgc aat ctc tat ccc ttt gta    398
Asp Phe Asn Leu Ile Arg Val Val Ala Cys Asn Leu Tyr Pro Phe Val
            95                 100                 105 aag aca gtg gct tct cca ggt gta ast gtt gag gag gct gtg gag caa    446
Lys Thr Val Ala Ser Pro Gly Val Xaa Val Glu Glu Ala Val Glu Gln
        110                 115                 120 att gac att ggt gga gta acc tta ctg aga gct gca gcc aaa aac cac    494
Ile Asp Ile Gly Gly Val Thr Leu Leu Arg Ala Ala Ala Lys Asn His
    125                 130                 135 gct cga gtg aca gtg gtg tgt gaa cca gag gac tat gtg gtg gtg tcc    542
Ala Arg Val Thr Val Val Cys Glu Pro Glu Asp Tyr Val Val Val Ser
140                 145                 150                 155 acg gag atg cag agc tcc gag agt aag gac acc tcc ttg gag act aga    590
Thr Glu Met Gln Ser Ser Glu Ser Lys Asp Thr Ser Leu Glu Thr Arg
                160                 165                 170
```

```
cgc cag tta gcc ttg aag gca ttc act cat acg gca caa tat gat gaa      638
Arg Gln Leu Ala Leu Lys Ala Phe Thr His Thr Ala Gln Tyr Asp Glu
            175                 180                 185 gca att tca gat tat ttc agg aaa cag tac agc aaa ggc gta tct cag      686
Ala Ile Ser Asp Tyr Phe Arg Lys Gln Tyr Ser Lys Gly Val Ser Gln
        190                 195                 200 atg ccc ttg aga tat gga atg aac cca cat cag acc cct gcc cag ctg     734
Met Pro Leu Arg Tyr Gly Met Asn Pro His Gln Thr Pro Ala Gln Leu
    205                 210                 215 tac aca ctg cag ccc aag ctt ccc atc aca gtt cta aat gga gcc cct      782
Tyr Thr Leu Gln Pro Lys Leu Pro Ile Thr Val Leu Asn Gly Ala Pro
220                 225                 230                 235 gga ttt ata aac ttg tgc gat gct ttg aac gcc tgg cag ctg gtg aag      830
Gly Phe Ile Asn Leu Cys Asp Ala Leu Asn Ala Trp Gln Leu Val Lys
                240                 245                 250 gaa ctc aag gag gct tta ggt att cca gcc gct gcc tct ttc aaa cat      878
Glu Leu Lys Glu Ala Leu Gly Ile Pro Ala Ala Ala Ser Phe Lys His
            255                 260                 265 gtc agc cca gca ggt gct gct gtt gga att cca ctc agt gaa gat gag      926
Val Ser Pro Ala Gly Ala Ala Val Gly Ile Pro Leu Ser Glu Asp Glu
        270                 275                 280 gcc aaa gtc tgc atg gtt tat gat ctc tat aaa acc ctc aca ccc atc      974
Ala Lys Val Cys Met Val Tyr Asp Leu Tyr Lys Thr Leu Thr Pro Ile
    285                 290                 295 tca gcg gca tat gca aga gca aga ggg gct gat agg atg tct tca ttt     1022
Ser Ala Ala Tyr Ala Arg Ala Arg Gly Ala Asp Arg Met Ser Ser Phe
300                 305                 310                 315 ggt gat ttt gtt gca ttg tcc gat gtt tgt gat gta cca act gca aaa     1070
Gly Asp Phe Val Ala Leu Ser Asp Val Cys Asp Val Pro Thr Ala Lys
                320                 325                 330 att att tcc aga gaa gta tct gat ggt ata att gcc cca gga tat gaa     1118
Ile Ile Ser Arg Glu Val Ser Asp Gly Ile Ile Ala Pro Gly Tyr Glu
            335                 340                 345 gaa gaa gcc ttg aca ata ctt tcc aaa aag aaa aat gga aac tat tgt     1166
Glu Glu Ala Leu Thr Ile Leu Ser Lys Lys Lys Asn Gly Asn Tyr Cys
        350                 355                 360 gtc ctt cag atg gac caa tct tac aaa cca gat gaa aat gaa gtt cga     1214
Val Leu Gln Met Asp Gln Ser Tyr Lys Pro Asp Glu Asn Glu Val Arg
    365                 370                 375 act ctc ttt ggt ctt cat tta agc cag aag aga aat aat ggt gtc gtc     1262
Thr Leu Phe Gly Leu His Leu Ser Gln Lys Arg Asn Asn Gly Val Val
380                 385                 390                 395 gac aag tca tta ttt agc aat gtt gtt acc aaa aat aaa gat ttg cca     1310
Asp Lys Ser Leu Phe Ser Asn Val Val Thr Lys Asn Lys Asp Leu Pro
                400                 405                 410 gag tct gcc ctc cga gac ctc atc gta gcc acc att gct gtc aag tac     1358
Glu Ser Ala Leu Arg Asp Leu Ile Val Ala Thr Ile Ala Val Lys Tyr
            415                 420                 425 act cag tct aac tct gtg tgc tac gcc aag aac ggg cag gtt atc ggc     1406
Thr Gln Ser Asn Ser Val Cys Tyr Ala Lys Asn Gly Gln Val Ile Gly
        430                 435                 440 att gga gca gga cag cag tct cgt ata cac tgc act cgc ctt gca gga     1454
Ile Gly Ala Gly Gln Gln Ser Arg Ile His Cys Thr Arg Leu Ala Gly
    445                 450                 455 gat aag gca aac tat tgg tgg ctt aga cac cat cca caa gtg ctt tcg     1502
Asp Lys Ala Asn Tyr Trp Trp Leu Arg His His Pro Gln Val Leu Ser
460                 465                 470                 475 atg aag ttt aaa aca ggr gtg aag aga gca gaa atc tcc aat gcc atc     1550
Met Lys Phe Lys Thr Gly Val Lys Arg Ala Glu Ile Ser Asn Ala Ile
                480                 485                 490
```

```
gat caa tat gtg act gga acc att ggc gag gat gaa gat ttg ata aag    1598
Asp Gln Tyr Val Thr Gly Thr Ile Gly Glu Asp Glu Asp Leu Ile Lys
            495                 500                 505 tgg aag gca ctg ttt gag gaa gtc cct gag tta ctc act gag gca gag    1646
Trp Lys Ala Leu Phe Glu Glu Val Pro Glu Leu Leu Thr Glu Ala Glu
        510                 515                 520 aag aag gaa tgg gtt gag aaa ctg act gaa gtt tct atc agc tct gat    1694
Lys Lys Glu Trp Val Glu Lys Leu Thr Glu Val Ser Ile Ser Ser Asp
    525                 530                 535 gcc ttc ttc cct ttc cga gat aac gta gac aga gct aaa agg agt ggt    1742
Ala Phe Phe Pro Phe Arg Asp Asn Val Asp Arg Ala Lys Arg Ser Gly
540                 545                 550                 555 gtg gcg tac att gcg gct ccc tcc ggt tct gct gct gac aaa gtt gtg    1790
Val Ala Tyr Ile Ala Ala Pro Ser Gly Ser Ala Ala Asp Lys Val Val
                560                 565                 570 att gag gcc tgc gac gaa ctg gga atc atc ctc gct cat acg aac ctt    1838
Ile Glu Ala Cys Asp Glu Leu Gly Ile Ile Leu Ala His Thr Asn Leu
            575                 580                 585 cgg ctc ttc cac cac tga ttttaccaca cactgttttt tggcttgctt           1886
Arg Leu Phe His His *
        590 atgtgtaggt gaacagtcac gcctgaaact ttgaggataa cttttaaaa aaataaaaca   1946 gtatctctta atcactgga                                                1965

<210> SEQ ID NO 3
<211> LENGTH: 592
<212> TYPE: PRT
<213> ORGANISM: Homo sapiens
<220> FEATURE:
<221> NAME/KEY: VARIANT
<222> LOCATION: 116
<223> OTHER INFORMATION: Xaa=Thr or Ser

<400> SEQUENCE: 3

Met Ala Pro Gly Gln Leu Ala Leu Phe Ser Val Ser Asp Lys Thr Gly
1               5                   10                  15

Leu Val Glu Phe Ala Arg Asn Leu Thr Ala Leu Gly Leu Asn Leu Val
            20                  25                  30

Ala Ser Gly Gly Thr Ala Lys Ala Leu Arg Asp Ala Gly Leu Ala Val
        35                  40                  45

Arg Asp Val Ser Glu Leu Thr Gly Phe Pro Glu Met Leu Gly Gly Arg
    50                  55                  60

Val Lys Thr Leu His Pro Ala Val His Ala Gly Ile Leu Ala Arg Asn
65                  70                  75                  80

Ile Pro Glu Asp Asn Ala Asp Met Ala Arg Leu Asp Phe Asn Leu Ile
                85                  90                  95

Arg Val Val Ala Cys Asn Leu Tyr Pro Phe Val Lys Thr Val Ala Ser
            100                 105                 110

Pro Gly Val Xaa Val Glu Glu Ala Val Glu Gln Ile Asp Ile Gly Gly
        115                 120                 125

Val Thr Leu Leu Arg Ala Ala Lys Asn His Ala Arg Val Thr Val
    130                 135                 140

Val Cys Glu Pro Glu Asp Tyr Val Val Ser Thr Glu Met Gln Ser
145                 150                 155                 160

Ser Glu Ser Lys Asp Thr Ser Leu Glu Thr Arg Arg Gln Leu Ala Leu
                165                 170                 175

Lys Ala Phe Thr His Thr Ala Gln Tyr Asp Glu Ala Ile Ser Asp Tyr
            180                 185                 190
```

```
Phe Arg Lys Gln Tyr Ser Lys Gly Val Ser Gln Met Pro Leu Arg Tyr
            195                 200                 205

Gly Met Asn Pro His Gln Thr Pro Ala Gln Leu Tyr Thr Leu Gln Pro
    210                 215                 220

Lys Leu Pro Ile Thr Val Leu Asn Gly Ala Pro Gly Phe Ile Asn Leu
225                 230                 235                 240

Cys Asp Ala Leu Asn Ala Trp Gln Leu Val Lys Glu Leu Lys Glu Ala
                245                 250                 255

Leu Gly Ile Pro Ala Ala Ser Phe Lys His Val Ser Pro Ala Gly
            260                 265                 270

Ala Ala Val Gly Ile Pro Leu Ser Glu Asp Glu Ala Lys Val Cys Met
    275                 280                 285

Val Tyr Asp Leu Tyr Lys Thr Leu Thr Pro Ile Ser Ala Ala Tyr Ala
290                 295                 300

Arg Ala Arg Gly Ala Asp Arg Met Ser Ser Phe Gly Asp Phe Val Ala
305                 310                 315                 320

Leu Ser Asp Val Cys Asp Val Pro Thr Ala Lys Ile Ile Ser Arg Glu
                325                 330                 335

Val Ser Asp Gly Ile Ile Ala Pro Gly Tyr Glu Glu Ala Leu Thr
            340                 345                 350

Ile Leu Ser Lys Lys Asn Gly Asn Tyr Cys Val Leu Gln Met Asp
            355                 360                 365

Gln Ser Tyr Lys Pro Asp Glu Asn Glu Val Arg Thr Leu Phe Gly Leu
    370                 375                 380

His Leu Ser Gln Lys Arg Asn Asn Gly Val Val Asp Lys Ser Leu Phe
385                 390                 395                 400

Ser Asn Val Val Thr Lys Asn Lys Asp Leu Pro Glu Ser Ala Leu Arg
                405                 410                 415

Asp Leu Ile Val Ala Thr Ile Ala Val Lys Tyr Thr Gln Ser Asn Ser
            420                 425                 430

Val Cys Tyr Ala Lys Asn Gly Gln Val Ile Gly Ile Gly Ala Gly Gln
    435                 440                 445

Gln Ser Arg Ile His Cys Thr Arg Leu Ala Gly Asp Lys Ala Asn Tyr
    450                 455                 460

Trp Trp Leu Arg His His Pro Gln Val Leu Ser Met Lys Phe Lys Thr
465                 470                 475                 480

Gly Val Lys Arg Ala Glu Ile Ser Asn Ala Ile Asp Gln Tyr Val Thr
                485                 490                 495

Gly Thr Ile Gly Glu Asp Glu Asp Leu Ile Lys Trp Lys Ala Leu Phe
            500                 505                 510

Glu Glu Val Pro Glu Leu Leu Thr Glu Ala Glu Lys Lys Glu Trp Val
    515                 520                 525

Glu Lys Leu Thr Glu Val Ser Ile Ser Ser Asp Ala Phe Phe Pro Phe
530                 535                 540

Arg Asp Asn Val Asp Arg Ala Lys Arg Ser Gly Val Ala Tyr Ile Ala
545                 550                 555                 560

Ala Pro Ser Gly Ser Ala Ala Asp Lys Val Val Ile Glu Ala Cys Asp
                565                 570                 575

Glu Leu Gly Ile Ile Leu Ala His Thr Asn Leu Arg Leu Phe His His
            580                 585                 590
```

```
<210> SEQ ID NO 4
<211> LENGTH: 450
<212> TYPE: DNA
<213> ORGANISM: Homo sapiens
<220> FEATURE:
<221> NAME/KEY: allele
<222> LOCATION: 78
<223> OTHER INFORMATION: 99-22578-78 : polymorphic base C or T
<220> FEATURE:
<221> NAME/KEY: misc_binding
<222> LOCATION: 66..90
<223> OTHER INFORMATION: 99-22578-78.probe
<220> FEATURE:
<221> NAME/KEY: primer_bind
<222> LOCATION: 59..77
<223> OTHER INFORMATION: 99-22578-78.mis
<220> FEATURE:
<221> NAME/KEY: primer_bind
<222> LOCATION: 79..97
<223> OTHER INFORMATION: 99-22578-78.mis complement
<220> FEATURE:
<221> NAME/KEY: primer_bind
<222> LOCATION: 1..18
<223> OTHER INFORMATION: 99-22578.pu
<220> FEATURE:
<221> NAME/KEY: primer_bind
<222> LOCATION: 430..450
<223> OTHER INFORMATION: 99-22578.rp complement

<400> SEQUENCE: 4
tgccccttga aaatctacac tccaaatgag tacattacaa ctatggtgca atgagtgatt      60
ttccccaagg taccatgytc attggttttcc acaggacagg caacctagca gggcattccc    120
tccatgaggt tatgaaaaca cgctgtgctc ctgtagaccc acacacagca ccctccccat    180
tgtacttatt gccaaacact gggcttccta atcactttgt gttcagtcag agatccagga    240
aatccaaacc cagccagaaa aatgcacaac agctcagcat aagcagcttt aataggagct    300
taaggaagct tccattgctc ccatcctgga aaagcatgtg ttgtagcaga aagagcacaa    360
gctctagcaa tggacaggcc tcaggtcata tcctggatct ggctgggttg ctgggttacg    420
tgctgggttg tctcagataa ggtcaagtct                                      450

<210> SEQ ID NO 5
<211> LENGTH: 506
<212> TYPE: DNA
<213> ORGANISM: Homo sapiens
<220> FEATURE:
<221> NAME/KEY: allele
<222> LOCATION: 72
<223> OTHER INFORMATION: 99-22580-72 : polymorphic base A or T
<220> FEATURE:
<221> NAME/KEY: misc_binding
<222> LOCATION: 60..84
<223> OTHER INFORMATION: 99-22580-72.probe
<220> FEATURE:
<221> NAME/KEY: primer_bind
<222> LOCATION: 53..71
<223> OTHER INFORMATION: 99-22580-72.mis
<220> FEATURE:
<221> NAME/KEY: primer_bind
<222> LOCATION: 73..91
<223> OTHER INFORMATION: 99-22580-72.mis complement
<220> FEATURE:
<221> NAME/KEY: primer_bind
<222> LOCATION: 1..18
<223> OTHER INFORMATION: 99-22580.pu
<220> FEATURE:
<221> NAME/KEY: primer_bind
<222> LOCATION: 488..506
<223> OTHER INFORMATION: 99-22580.rp complement
```

-continued

```
<400> SEQUENCE: 5
tctcaggaaa tggacaacat attgtcaagt ttgaaagcat atggagctaa acgggattct      60
agtaaaggct cwtggtctta taatccaata tttataagca attaaagttc accaaagtct     120
ataaaaacat actgcagctg tgaatcaaat tagtgccttg acctacccaa ttagacaaag     180
aaaacatcaa tataataatt aggcagacaa tttccatctt agaattaatg taaatagtga     240
ttatgcctta aaaacaaatg ccgtatttt caaactagga gaaaattcat gtgctaaaag      300
atacaacatc ccaggttaga gagagtacct ccatgtttga ttagtgaatt gacaaggaga     360
attgtttttt ggtcactcag caaaatttc cttttgattt caattagtct ctctctcctt      420
ttacaaggat tgactgtcca tagattgaaa gtcattgctt tgtcagttca ggtttaaaga     480
gcaaagagtt tcaagccttc taatag                                           506

<210> SEQ ID NO 6
<211> LENGTH: 514
<212> TYPE: DNA
<213> ORGANISM: Homo sapiens
<220> FEATURE:
<221> NAME/KEY: allele
<222> LOCATION: 462
<223> OTHER INFORMATION: 99-22585-462 : polymorphic base G or C
<220> FEATURE:
<221> NAME/KEY: misc_binding
<222> LOCATION: 450..474
<223> OTHER INFORMATION: 99-22585-462.probe
<220> FEATURE:
<221> NAME/KEY: primer_bind
<222> LOCATION: 443..461
<223> OTHER INFORMATION: 99-22585-462.mis
<220> FEATURE:
<221> NAME/KEY: primer_bind
<222> LOCATION: 463..481
<223> OTHER INFORMATION: 99-22585-462.mis complement
<220> FEATURE:
<221> NAME/KEY: primer_bind
<222> LOCATION: 1..21
<223> OTHER INFORMATION: 99-22585.pu
<220> FEATURE:
<221> NAME/KEY: primer_bind
<222> LOCATION: 494..514
<223> OTHER INFORMATION: 99-22585.rp complement

<400> SEQUENCE: 6
gtagttactt ccattatctt cataatgaga atattgaggg gtgtacacaa cttgtctaaa      60
tgcacataac tattaagtga ataagtcagg gaacaaactc aggaagtctg acactataac     120
tcttaatgat caaggtacat tttcgtccat gtaatgatga taatactcat ctacctcaag     180
ccttgtggca aaatatagca aaagtagctt ggaaaatgta aagagctata gtaaaatgtc     240
ttatcaattt aactgcaaaa gaattttgaa agacacgtg gtttgaataa tttacctctg      300
gattatcttt ggtttatgat ccaaggaaaa gaggacctca tggaaaaatc tttcagggtg     360
cttagctact ctttccagaa actgcttctg tccatctggg cacatgcacg gccagttctt     420
caagagtaga tgttgcctgg gacttgccac tggaattttt csttaaaatg ttaaaacagt     480
atttaattca catggtttgg tggaaaaatg aagt                                  514

<210> SEQ ID NO 7
<211> LENGTH: 497
<212> TYPE: DNA
<213> ORGANISM: Homo sapiens
<220> FEATURE:
<221> NAME/KEY: allele
<222> LOCATION: 347
<223> OTHER INFORMATION: 99-23437-347 : polymorphic base A or G
```

```
<220> FEATURE:
<221> NAME/KEY: misc_binding
<222> LOCATION: 335..359
<223> OTHER INFORMATION: 99-23437-347.probe
<220> FEATURE:
<221> NAME/KEY: primer_bind
<222> LOCATION: 328..346
<223> OTHER INFORMATION: 99-23437-347.mis
<220> FEATURE:
<221> NAME/KEY: primer_bind
<222> LOCATION: 348..366
<223> OTHER INFORMATION: 99-23437-347.mis complement
<220> FEATURE:
<221> NAME/KEY: primer_bind
<222> LOCATION: 1..20
<223> OTHER INFORMATION: 99-23437.pu
<220> FEATURE:
<221> NAME/KEY: primer_bind
<222> LOCATION: 478..497
<223> OTHER INFORMATION: 99-23437.rp complement

<400> SEQUENCE: 7
cccatttcaa tcttagatag ctcttaccgt taggaagttc atctttatag tgaaataaaa      60
tcctacctcc ctgtaatttt tatctttagt catgaaagtc aaactgtact taagatgtgg    120
ttattttgtt cttaccttgc tagttatagt ttaattacca gtctttaagc actgtgaaaa    180
ttctaacatt ctcattctat caaactacat tctacattgt acagcaattt gtatctccat    240
agaaacaatt ccaacacata gaattgtaat tcccaaatgg cataattgta aacattttct    300
cagataactt caaagccatt tctgaaattt cttctaaaac attcacrtga actcagattg    360
tgaaaatgag ttatacctcc tttgaaatca agtcgttttt taattcctcc aaatataaat    420
gttaaaaact aaaatgtcaa aataagcaat ggtagtatta acacagttaa tactgaaggt    480
aaatgttaaa cacatgc                                                    497

<210> SEQ ID NO 8
<211> LENGTH: 448
<212> TYPE: DNA
<213> ORGANISM: Homo sapiens
<220> FEATURE:
<221> NAME/KEY: allele
<222> LOCATION: 273
<223> OTHER INFORMATION: 99-23440-274 : polymorphic base A or G
<220> FEATURE:
<221> NAME/KEY: misc_binding
<222> LOCATION: 261..285
<223> OTHER INFORMATION: 99-23440-274.probe
<220> FEATURE:
<221> NAME/KEY: primer_bind
<222> LOCATION: 254..272
<223> OTHER INFORMATION: 99-23440-274.mis
<220> FEATURE:
<221> NAME/KEY: primer_bind
<222> LOCATION: 274..292
<223> OTHER INFORMATION: 99-23440-274.mis complement
<220> FEATURE:
<221> NAME/KEY: primer_bind
<222> LOCATION: 1..21
<223> OTHER INFORMATION: 99-23440.pu
<220> FEATURE:
<221> NAME/KEY: primer_bind
<222> LOCATION: 428..448
<223> OTHER INFORMATION: 99-23440.rp complement

<400> SEQUENCE: 8
gtggcttttt tccagtaaag gttaattatt aagaccacta gtcctggcct gggtcaatcc      60
cagtatgatc ctgggcaagt aaattaaaga agataacttc tctgtgcctc agttttttt     120 tgttttgttt tttgtttttt catttacaaa atggagataa ttgtagtaaa tcaaattttt    180
```

```
agaggtgata ggtttgttca tttcttgaat gcggtgatgg tctcccaagt cacacatatg    240
taaaaaccca tcactttaaa gatatgcagt acrttgtatg acaagaaatt gcttttaaaa    300
ggagcaaact accttccagg gttgttgtga ggcataaatg gcaatccaca gcaccacagc    360
aaggattatc atgtgccctc cagagacata ctctcaggtg gatgcgagaa atatccagct    420
gttgcagcaa cttcatccca ctcgaaat                                       448
```

```
<210> SEQ ID NO 9
<211> LENGTH: 457
<212> TYPE: DNA
<213> ORGANISM: Homo sapiens
<220> FEATURE:
<221> NAME/KEY: allele
<222> LOCATION: 190
<223> OTHER INFORMATION: 99-23442-190 : polymorphic base C or T
<220> FEATURE:
<221> NAME/KEY: misc_binding
<222> LOCATION: 178..202
<223> OTHER INFORMATION: 99-23442-190.probe
<220> FEATURE:
<221> NAME/KEY: primer_bind
<222> LOCATION: 171..189
<223> OTHER INFORMATION: 99-23442-190.mis
<220> FEATURE:
<221> NAME/KEY: primer_bind
<222> LOCATION: 191..209
<223> OTHER INFORMATION: 99-23442-190.mis complement
<220> FEATURE:
<221> NAME/KEY: primer_bind
<222> LOCATION: 1..20
<223> OTHER INFORMATION: 99-23442.pu
<220> FEATURE:
<221> NAME/KEY: primer_bind
<222> LOCATION: 437..457
<223> OTHER INFORMATION: 99-23442.rp complement
<220> FEATURE:
<221> NAME/KEY: allele
<222> LOCATION: 396
<223> OTHER INFORMATION: 99-23442-396 : polymorphic base A or C
<220> FEATURE:
<221> NAME/KEY: misc_binding
<222> LOCATION: 384..408
<223> OTHER INFORMATION: 99-23442-396.probe
<220> FEATURE:
<221> NAME/KEY: primer_bind
<222> LOCATION: 377..395
<223> OTHER INFORMATION: 99-23442-396.mis
<220> FEATURE:
<221> NAME/KEY: primer_bind
<222> LOCATION: 397..415
<223> OTHER INFORMATION: 99-23442-396.mis complement

<400> SEQUENCE: 9
```

```
cttttgagta tagaaacccc tagtaacaat ttaagttcct tccattttc ttttaaactc      60 cttattccca gcagcagtat tctacattct aaccaggttc tcccagcttt gagacgtctc    120
agacttacca gttctccaaa acgctatttt ctttaagggt gacaccttt aaaaattagg    180 cacctcaaay atctactgct tttgagcttt tgagttttgc actgtaaaaa gaaaaataca    240
cagtgggatt ttaagtcaaa ttagtttatc taatttttag ggataatttt gaagcatgct    300
ttgtttgcat agattttttt aaaataagct tttccaaatc ataaagagat aagatcttag    360
gtaacatgaa gagactccct tacttattcc taaatmatct atattccaag ggcatttct    420 tatttggaac agttgacctc actgataaag ctgtctc                             457
```

```
<210> SEQ ID NO 10
<211> LENGTH: 399
<212> TYPE: DNA
<213> ORGANISM: Homo sapiens
```

```
<220> FEATURE:
<221> NAME/KEY: allele
<222> LOCATION: 203
<223> OTHER INFORMATION: 99-23444-203 : polymorphic base A or G
<220> FEATURE:
<221> NAME/KEY: misc_binding
<222> LOCATION: 191..215
<223> OTHER INFORMATION: 99-23444-203.probe
<220> FEATURE:
<221> NAME/KEY: primer_bind
<222> LOCATION: 184..202
<223> OTHER INFORMATION: 99-23444-203.mis
<220> FEATURE:
<221> NAME/KEY: primer_bind
<222> LOCATION: 204..222
<223> OTHER INFORMATION: 99-23444-203.mis complement
<220> FEATURE:
<221> NAME/KEY: primer_bind
<222> LOCATION: 1..19
<223> OTHER INFORMATION: 99-23444.pu
<220> FEATURE:
<221> NAME/KEY: primer_bind
<222> LOCATION: 379..399
<223> OTHER INFORMATION: 99-23444.rp complement

<400> SEQUENCE: 10
cttcatagtc aacgaaggct tgaaccaacc tacggatgac tcgtgctttg acccctacac      60
agtttcccat tatgccgttg gagatgagtg ggaacgaatg tctgaatcag gctttaaact     120
gttgtgccag tgcttaggct ttggaagtgg tcatttcaga tgtgattcat ctagtgagta     180
gttgctttgt ccatccactt ccrtgtttgt ctcctcaagt tccatgcatg cactcatgtg     240
ccaaggaagc atgtttggrr aagacacagg ttcttccaaa catgaagcma aacaagagaa     300
tactgtttga ctcgaagtaa twatttttgca tcatagaaaa atgatgggaa attttacttg     360
ttggacattg cttcatttca agggttgtat gccaataca                            399

<210> SEQ ID NO 11
<211> LENGTH: 547
<212> TYPE: DNA
<213> ORGANISM: Homo sapiens
<220> FEATURE:
<221> NAME/KEY: allele
<222> LOCATION: 77
<223> OTHER INFORMATION: 99-23451-78 : polymorphic base A or G
<220> FEATURE:
<221> NAME/KEY: misc_binding
<222> LOCATION: 65..89
<223> OTHER INFORMATION: 99-23451-78.probe
<220> FEATURE:
<221> NAME/KEY: primer_bind
<222> LOCATION: 58..76
<223> OTHER INFORMATION: 99-23451-78.mis
<220> FEATURE:
<221> NAME/KEY: primer_bind
<222> LOCATION: 78..96
<223> OTHER INFORMATION: 99-23451-78.mis complement
<220> FEATURE:
<221> NAME/KEY: primer_bind
<222> LOCATION: 1..20
<223> OTHER INFORMATION: 99-23451.pu
<220> FEATURE:
<221> NAME/KEY: primer_bind
<222> LOCATION: 529..547
<223> OTHER INFORMATION: 99-23451.rp complement

<400> SEQUENCE: 11
ggatatgtaa attgcccccc acaaccttt aaaataagca caatacatct aaaagagctg       60
cacaaaatcc aaagctrttt ataaaattct gtcccaatag tcatctggaa aacttaggtc    120
aacataaagg aattccgttg atataaaatt acaataagat tatttgatgc agaggaaaag    180
```

```
aacagttaga tttattatga tattatattt tcaccacctt agaaactgtg ttagagatga    240
tctccatctt tattccaacg aacaacggtc atgtcttacc ataagtcctg atacaaccac    300
ggatgagctg tcaggagcaa ggttgatttc tttcattggt ccggtcttct ccttgggggt    360
cacccgcact cgatatccag tgagctgaac attgggtggt gtccactggg cgctcaggct    420
tgtgggtgtg acctgagtga acttcaggtc agttggtgca ggaatagctg tcgagattgt    480
cattggttag aggttatctt ataggaaatg ggggaaaagg aaaataaagt gagtycmaag    540
aagtaga                                                              547
```

```
<210> SEQ ID NO 12
<211> LENGTH: 400
<212> TYPE: DNA
<213> ORGANISM: Homo sapiens
<220> FEATURE:
<221> NAME/KEY: allele
<222> LOCATION: 306
<223> OTHER INFORMATION: 99-23452-306 : polymorphic base G or T
<220> FEATURE:
<221> NAME/KEY: misc_binding
<222> LOCATION: 294..318
<223> OTHER INFORMATION: 99-23452-306.probe
<220> FEATURE:
<221> NAME/KEY: primer_bind
<222> LOCATION: 287..305
<223> OTHER INFORMATION: 99-23452-306.mis
<220> FEATURE:
<221> NAME/KEY: primer_bind
<222> LOCATION: 307..325
<223> OTHER INFORMATION: 99-23452-306.mis complement
<220> FEATURE:
<221> NAME/KEY: primer_bind
<222> LOCATION: 1..20
<223> OTHER INFORMATION: 99-23452.pu
<220> FEATURE:
<221> NAME/KEY: primer_bind
<222> LOCATION: 380..400
<223> OTHER INFORMATION: 99-23452.rp complement

<400> SEQUENCE: 12
tcctctccca attctcaccc aatgaaaaaa tatgttacat cctctatcca ctgcttggtt     60
aaactgaggt tctccataaa aatacttgtt atctatatgc tatgcaatca tctgtgagtt    120
tgagttttga atatgtgcat tgattctctc tcacagtgca gcctgggagc tctattccac    180
cttacaacac cgaggtgact gagaccacca ttgtgatcac atggacgcct gctccaagaa    240
ttggttttaa ggtaaactgc agatgttcct aatctctgtg atacagccct gaagctgtcc    300
ttgtgkttcc catgtagtgg aaacagggtg ctcaggagtc aggagacctg ggttttgtca    360
cctgcttctg tccatacatc tttgactaca ttgtcagggc                         400
```

```
<210> SEQ ID NO 13
<211> LENGTH: 450
<212> TYPE: DNA
<213> ORGANISM: Homo sapiens
<220> FEATURE:
<221> NAME/KEY: allele
<222> LOCATION: 417
<223> OTHER INFORMATION: 99-28437-417 : polymorphic base C or T
<220> FEATURE:
<221> NAME/KEY: misc_binding
<222> LOCATION: 405..429
<223> OTHER INFORMATION: 99-28437-417.probe
<220> FEATURE:
<221> NAME/KEY: primer_bind
<222> LOCATION: 398..416
<223> OTHER INFORMATION: 99-28437-417.mis
```

```
<220> FEATURE:
<221> NAME/KEY: primer_bind
<222> LOCATION: 418..436
<223> OTHER INFORMATION: 99-28437-417.mis complement
<220> FEATURE:
<221> NAME/KEY: primer_bind
<222> LOCATION: 1..20
<223> OTHER INFORMATION: 99-28437.pu
<220> FEATURE:
<221> NAME/KEY: primer_bind
<222> LOCATION: 431..450
<223> OTHER INFORMATION: 99-28437.rp complement

<400> SEQUENCE: 13
gtgaatatta aacatcgacc atctttattt tccaagtaat gtgttatggt tttaagaaaa     60
agtaggaaca cttttgggat agttgcattt ttctggagga aatcttagag gaaaataaat    120
gtcagcctaa tataaaaaac taagtagttt gggcactgtt gtggagaaaa acaccaacac    180
ctattacttt tattaccaat aaaatgaaac ttcatgttca gcattagaat ttttctccct    240
cttttcatca gagtaagcac cactgttttc cttgctgtgc gctctgtgtt tgtacaaagc    300
catttgtaat ggcagaagga gtcttctcca tctgtcccaa cagttccaag cacaagcata    360
acaggatata tttaagaaaa gaactcctcc ctgtattcca gagttttctc tcattcygtg    420
aaatgattaa gatttggata tgatgaaggt                                      450

<210> SEQ ID NO 14
<211> LENGTH: 494
<212> TYPE: DNA
<213> ORGANISM: Homo sapiens
<220> FEATURE:
<221> NAME/KEY: allele
<222> LOCATION: 218
<223> OTHER INFORMATION: 99-32278-218 : polymorphic base A or G
<220> FEATURE:
<221> NAME/KEY: misc_binding
<222> LOCATION: 206..230
<223> OTHER INFORMATION: 99-32278-218.probe
<220> FEATURE:
<221> NAME/KEY: primer_bind
<222> LOCATION: 199..217
<223> OTHER INFORMATION: 99-32278-218.mis
<220> FEATURE:
<221> NAME/KEY: primer_bind
<222> LOCATION: 219..237
<223> OTHER INFORMATION: 99-32278-218.mis complement
<220> FEATURE:
<221> NAME/KEY: primer_bind
<222> LOCATION: 1..20
<223> OTHER INFORMATION: 99-32278.pu
<220> FEATURE:
<221> NAME/KEY: primer_bind
<222> LOCATION: 474..494
<223> OTHER INFORMATION: 99-32278.rp complement
<220> FEATURE:
<221> NAME/KEY: allele
<222> LOCATION: 414
<223> OTHER INFORMATION: 99-32278-414 : polymorphic base C or T
<220> FEATURE:
<221> NAME/KEY: misc_binding
<222> LOCATION: 402..426
<223> OTHER INFORMATION: 99-32278-414.probe
<220> FEATURE:
<221> NAME/KEY: primer_bind
<222> LOCATION: 395..413
<223> OTHER INFORMATION: 99-32278-414.mis
<220> FEATURE:
<221> NAME/KEY: primer_bind
<222> LOCATION: 415..433
<223> OTHER INFORMATION: 99-32278-414.mis complement
```

<400> SEQUENCE: 14

```
gcactttttct atatgcctac ttcattacaa tttcttttaa agataaattt gtgcctggca      60
cagtgtttgg caaaaataag gtataaaaat gtccatgaat ggaaagcact gcgagcttaa     120
agacctgcag ggttctgtgc tctgaggaag ggacataggc tgggctttag aaaggtggcc     180
tggagagaag caggtgtcaa agggcaaggc aacgggarga agaatggagg atcccttttca    240 tggactgttt tctccctgtg cccaggggat cccccaatag aaatacactc agtattggtc     300
aggacgttgt tacattatgg atcttctgtc cttctgctgg aaacaacaga cataagatca     360
ttatgcattt cacttaaaca ccagtgaaac tccactcttg acgtttcgaa tgaytgaatt     420
atactagaca tatatatgtt aatggggttc cagtgccaga ccctcccaaa gtgctcaact     480
tccttggtta ctgg                                                       494
```

<210> SEQ ID NO 15
<211> LENGTH: 533
<212> TYPE: DNA
<213> ORGANISM: Homo sapiens
<220> FEATURE:
<221> NAME/KEY: allele
<222> LOCATION: 382
<223> OTHER INFORMATION: 99-5574-388 : deletion AA
<220> FEATURE:
<221> NAME/KEY: primer_bind
<222> LOCATION: 1..20
<223> OTHER INFORMATION: 99-5574.pu
<220> FEATURE:
<221> NAME/KEY: primer_bind
<222> LOCATION: 513..533
<223> OTHER INFORMATION: 99-5574.rp complement

<400> SEQUENCE: 15

```
ttgacatttg cccagcggag tcatcacctg gaaaccacgg gcagctgaac cctgggaact      60
tgcctcggtg tttataaata cctcagttgc atcaggaccc tacaggtgaa agatcttgat     120
accacacagg tataattaca atctgcaaac ctactcaagg ggagttgcag gtgaagataa     180
ggaagtcagc ctcattccat tacctaatca gattctcagc caaagacaaa cagcaacata     240
tgggacttta aggtgagcag ggagccgaca gcagcgctac tcaaaatgtg gtccgtgatc     300
tgcatggctc tcagaattgt ttgttattgg ttcatggcaa gtaaagcaca gaaaatgaga     360
gtaaggattt aaaacatttg gaaaagtttg acaatagttg tgtatctgtt gaaactaatc     420
atttataaat gtgtttctat tttkscatga cttttcatt ttccattgtt ttgcttcttc      480
agttttatca aagtattggt ctgtaacaaa ttgtgtgtgt tttgttgggg act             533
```

<210> SEQ ID NO 16
<211> LENGTH: 472
<212> TYPE: DNA
<213> ORGANISM: Homo sapiens
<220> FEATURE:
<221> NAME/KEY: allele
<222> LOCATION: 327
<223> OTHER INFORMATION: 99-5575-330 : polymorphic base C or T
<220> FEATURE:
<221> NAME/KEY: misc_binding
<222> LOCATION: 315..339
<223> OTHER INFORMATION: 99-5575-330.probe
<220> FEATURE:
<221> NAME/KEY: primer_bind
<222> LOCATION: 308..326
<223> OTHER INFORMATION: 99-5575-330.mis
<220> FEATURE:
<221> NAME/KEY: primer_bind
<222> LOCATION: 328..346
<223> OTHER INFORMATION: 99-5575-330.mis complement -continued

```
<220> FEATURE:
<221> NAME/KEY: primer_bind
<222> LOCATION: 1..20
<223> OTHER INFORMATION: 99-5575.pu
<220> FEATURE:
<221> NAME/KEY: primer_bind
<222> LOCATION: 452..472
<223> OTHER INFORMATION: 99-5575.rp complement

<400> SEQUENCE: 16
gaaaaattgt ttgtgctctg tcacttgtta taagttgtag ctttatctga cacttaccta      60
ccctcaggct tctttttaac tcactctgac ttatttgtct tatccagaga ttgtggattc     120
cctgtcatca aagcagtcta aagggtgtta aaacacctgc ggcccttatt tctttgccat     180
aggctttagg tgacttaaaa aaaaatagta ctgtcctctc actgtctaag gactaccttc     240
cttagtatct ttacataagg aagaaattgg tttttctgtt ttatctgaca aaagagagag     300
atatgaggga gagactgaat tctttcytga aacagaaata ttcctatctc ttatcaagta     360
ttttgattgt ttaatttcct acactaagtc caacaggatt ttataccaaa agcagtagct     420
tccctaaagt ctacttggta gttgttcgtt gccaaagtct attctctctt aa             472

<210> SEQ ID NO 17
<211> LENGTH: 516
<212> TYPE: DNA
<213> ORGANISM: Homo sapiens
<220> FEATURE:
<221> NAME/KEY: allele
<222> LOCATION: 354
<223> OTHER INFORMATION: 99-5582-354 : polymorphic base A or G
<220> FEATURE:
<221> NAME/KEY: misc_binding
<222> LOCATION: 342..366
<223> OTHER INFORMATION: 99-5582-354.probe
<220> FEATURE:
<221> NAME/KEY: primer_bind
<222> LOCATION: 335..353
<223> OTHER INFORMATION: 99-5582-354.mis
<220> FEATURE:
<221> NAME/KEY: primer_bind
<222> LOCATION: 355..373
<223> OTHER INFORMATION: 99-5582-354.mis complement
<220> FEATURE:
<221> NAME/KEY: primer_bind
<222> LOCATION: 1..19
<223> OTHER INFORMATION: 99-5582.pu
<220> FEATURE:
<221> NAME/KEY: primer_bind
<222> LOCATION: 497..516
<223> OTHER INFORMATION: 99-5582.rp complement
<220> FEATURE:
<221> NAME/KEY: allele
<222> LOCATION: 71
<223> OTHER INFORMATION: 99-5582-71 : polymorphic base G or C
<220> FEATURE:
<221> NAME/KEY: misc_binding
<222> LOCATION: 59..83
<223> OTHER INFORMATION: 99-5582-71.probe
<220> FEATURE:
<221> NAME/KEY: primer_bind
<222> LOCATION: 52..70
<223> OTHER INFORMATION: 99-5582-71.mis
<220> FEATURE:
<221> NAME/KEY: primer_bind
<222> LOCATION: 72..90
<223> OTHER INFORMATION: 99-5582-71.mis complement

<400> SEQUENCE: 17
tcatcagttc aaatagtcct gggcgtgctt tagtttctca tgcttttgag cagagtttta      60
aaataagccc satttgcccc tacagatctc ctgcctggta cagaatatgt agtgagtgtc    120
```

-continued

| | |
|---|---|
| tccagtgtct acgaacaaca tgagagcaca cctcttagag gaagacagaa aacaggtgag | 180 |
| tggtgttggc agtatgacta tccagtagct tttgcctatc aattctgtat aacaaatgaa | 240 |
| atgctacttc taaaaataca tctccatttt ttgttgtcat ggtgtgtgta cctttgtcat | 300 |
| cacagtatga ttttatcgct ggtctcaaaa actaaaagat accttactca acartcacct | 360 |
| agactttcag tcactaacaa attaagaaat ttgttgtctg tccttttaaa aaacattttc | 420 |
| taagaagatc tttgttattt agatttagca gacattcctt ttcattaggc agctctgtct | 480 |
| aatggctgac ccaacactca ttgtcatcta tttgtc | 516 |

```
<210> SEQ ID NO 18
<211> LENGTH: 461
<212> TYPE: DNA
<213> ORGANISM: Homo sapiens
<220> FEATURE:
<221> NAME/KEY: allele
<222> LOCATION: 424
<223> OTHER INFORMATION: 99-5590-425 : polymorphic base G or C
<220> FEATURE:
<221> NAME/KEY: misc_binding
<222> LOCATION: 412..436
<223> OTHER INFORMATION: 99-5590-425.probe
<220> FEATURE:
<221> NAME/KEY: primer_bind
<222> LOCATION: 405..423
<223> OTHER INFORMATION: 99-5590-425.mis
<220> FEATURE:
<221> NAME/KEY: primer_bind
<222> LOCATION: 425..443
<223> OTHER INFORMATION: 99-5590-425.mis complement
<220> FEATURE:
<221> NAME/KEY: primer_bind
<222> LOCATION: 1..19
<223> OTHER INFORMATION: 99-5590.pu
<220> FEATURE:
<221> NAME/KEY: primer_bind
<222> LOCATION: 441..461
<223> OTHER INFORMATION: 99-5590.rp complement
<220> FEATURE:
<221> NAME/KEY: allele
<222> LOCATION: 99
<223> OTHER INFORMATION: 99-5590-99 : polymorphic base C or T
<220> FEATURE:
<221> NAME/KEY: misc_binding
<222> LOCATION: 87..111
<223> OTHER INFORMATION: 99-5590-99.probe
<220> FEATURE:
<221> NAME/KEY: primer_bind
<222> LOCATION: 80..98
<223> OTHER INFORMATION: 99-5590-99.mis
<220> FEATURE:
<221> NAME/KEY: primer_bind
<222> LOCATION: 100..118
<223> OTHER INFORMATION: 99-5590-99.mis complement

<400> SEQUENCE: 18
```

| | |
|---|---|
| atgcccattg ratttctacg aattttactt aaactgaaaa tataaataaa gcataatgtt | 60 |
| gaccaacaat aactagcata tgatattgaa taaatatayt gttattcaac gttcatttaa | 120 |
| caaccagaaa aaaagaaaa aaattgttat tgttttattg ttctgtttca aacagaaact | 180 |
| tcaaactcct agaaaatata atttacgaaa attcaatggt ttaaagctaa tgacagaatg | 240 |
| ggtggtttac cctctctgtc aatataagac atatatattt ttattcaata tatgaattga | 300 |
| cctgtaatca aaaactataa acaagctgta gctaataatc tcagtgatct tttgatgaat | 360 |
| gagggatata aagagatgcc ttcagtacaa aaaattcaag ttacaaaagt gtaatactca | 420 |
| agastgactt cctgaaacaa gtaagttctc tatgaaaagg a | 461 |

```
<210> SEQ ID NO 19
<211> LENGTH: 453
<212> TYPE: DNA
<213> ORGANISM: Homo sapiens
<220> FEATURE:
<221> NAME/KEY: allele
<222> LOCATION: 379
<223> OTHER INFORMATION: 99-5595-380 : polymorphic base A or G
<220> FEATURE:
<221> NAME/KEY: misc_binding
<222> LOCATION: 367..391
<223> OTHER INFORMATION: 99-5595-380.probe
<220> FEATURE:
<221> NAME/KEY: primer_bind
<222> LOCATION: 360..378
<223> OTHER INFORMATION: 99-5595-380.mis
<220> FEATURE:
<221> NAME/KEY: primer_bind
<222> LOCATION: 380..398
<223> OTHER INFORMATION: 99-5595-380.mis complement
<220> FEATURE:
<221> NAME/KEY: primer_bind
<222> LOCATION: 1..18
<223> OTHER INFORMATION: 99-5595.pu
<220> FEATURE:
<221> NAME/KEY: primer_bind
<222> LOCATION: 436..453
<223> OTHER INFORMATION: 99-5595.rp complement

<400> SEQUENCE: 19
cagatcatgg ttctgaagac cctgtgacac gtcccagttc acctactgtc ttgtgagtca      60
gaatatacaa ataacttttt ggtcctgact ttccccaccc ctacaggatg gtgccatgac     120
aatggtgtga actacaagat tggagagaag tgggaccgtc agggagaaaa tggccagatg     180
atgagctgca catgtcttgg gaacggaaaa ggagaattca agtgtgaccc tcgtatgtca     240
tcacagatca tttttagtgc cttattaagc attctcactt tcattatcag gctgtaactc     300
tcattcacag aaatgattgg agactttagg tctccttgag gagtgaacag tgggtttctt     360
aatcttttga tttgggaarg tggagacaag cttcaaaaat gagtcatgat ttaatgttat     420
tacaggacac tttagcactt gtccaacctg agt                                  453

<210> SEQ ID NO 20
<211> LENGTH: 467
<212> TYPE: DNA
<213> ORGANISM: Homo sapiens
<220> FEATURE:
<221> NAME/KEY: allele
<222> LOCATION: 374
<223> OTHER INFORMATION: 99-5604-376 : polymorphic base A or G
<220> FEATURE:
<221> NAME/KEY: misc_binding
<222> LOCATION: 362..386
<223> OTHER INFORMATION: 99-5604-376.probe
<220> FEATURE:
<221> NAME/KEY: primer_bind
<222> LOCATION: 355..373
<223> OTHER INFORMATION: 99-5604-376.mis
<220> FEATURE:
<221> NAME/KEY: primer_bind
<222> LOCATION: 375..393
<223> OTHER INFORMATION: 99-5604-376.mis complement
<220> FEATURE:
<221> NAME/KEY: primer_bind
<222> LOCATION: 1..20
<223> OTHER INFORMATION: 99-5604.pu
<220> FEATURE:
<221> NAME/KEY: primer_bind
<222> LOCATION: 447..467
<223> OTHER INFORMATION: 99-5604.rp complement
```

-continued

```
<400> SEQUENCE: 20
ctttaccaaa atcactctac ttcagaggga gattaaaaga gatattctga gctagtttca      60
ttctgtgtgt ttgcatacat taatcagatt tagagatgat agccttagct ctgtgccccg     120
gcaaagataa gaactatata atacttttt ttaaacaaaa atttcacaag aattttacag     180
taaaattaga aatagctaaa taataaccta aacatatccc ttaaattaac aagtatatga     240
ggtaagaatg caatcaacat taattggaac tttatttttt gtttaagatt tttctccata     300
ggtttgttga gacttccatg tggttttggc aaaagtaatg ggtatctaaa atttcctgtt     360
attgctatag tacrtcatgc tgtttgaata ttgttaacaa ctatctttat acattttagc     420
attttataaa taatttcaa atatatgtga acaagraatt tagacaa                  467

<210> SEQ ID NO 21
<211> LENGTH: 399
<212> TYPE: DNA
<213> ORGANISM: Homo sapiens
<220> FEATURE:
<221> NAME/KEY: allele
<222> LOCATION: 135
<223> OTHER INFORMATION: 99-5605-135 : polymorphic base G or T
<220> FEATURE:
<221> NAME/KEY: misc_binding
<222> LOCATION: 123..147
<223> OTHER INFORMATION: 99-5605-135.probe
<220> FEATURE:
<221> NAME/KEY: primer_bind
<222> LOCATION: 116..134
<223> OTHER INFORMATION: 99-5605-135.mis
<220> FEATURE:
<221> NAME/KEY: primer_bind
<222> LOCATION: 136..154
<223> OTHER INFORMATION: 99-5605-135.mis complement
<220> FEATURE:
<221> NAME/KEY: primer_bind
<222> LOCATION: 1..18
<223> OTHER INFORMATION: 99-5605.pu
<220> FEATURE:
<221> NAME/KEY: primer_bind
<222> LOCATION: 380..399
<223> OTHER INFORMATION: 99-5605.rp complement
<220> FEATURE:
<221> NAME/KEY: allele
<222> LOCATION: 90
<223> OTHER INFORMATION: 99-5605-90 : polymorphic base G or T
<220> FEATURE:
<221> NAME/KEY: misc_binding
<222> LOCATION: 78..102
<223> OTHER INFORMATION: 99-5605-90.probe
<220> FEATURE:
<221> NAME/KEY: primer_bind
<222> LOCATION: 71..89
<223> OTHER INFORMATION: 99-5605-90.mis
<220> FEATURE:
<221> NAME/KEY: primer_bind
<222> LOCATION: 91..109
<223> OTHER INFORMATION: 99-5605-90.mis complement

<400> SEQUENCE: 21
aagactccag tggctttggg gctctcttgg ttgcccttta tggccacgag ggatacggtg      60
tactcagatg caggctgcag attcctcagk gggtacttgg agacagaggg acccacattg     120
tactgcctgg gctgkcctct tcgggtaagg cccacggtca gtcggtatcc tgttatctgg     180
gcccgaggtg gagtccatct caccaggaca gtagaatcag tttcattgac aaactggagg     240
ttagtgggag catccagttc taggaaaaaa gatgaaacat gccaagaaat atttagatca     300
gtaatgatca taactcaagt cctgaaactt gattgaatgt ctaagttttc tctcctcaag     360
gttgtaacta tgtgaaagtc aaaccctgr aaaaactga                            399
```

<210> SEQ ID NO 22
<211> LENGTH: 529
<212> TYPE: DNA
<213> ORGANISM: Homo sapiens
<220> FEATURE:
<221> NAME/KEY: allele
<222> LOCATION: 323
<223> OTHER INFORMATION: 99-5608-324 : polymorphic base A or G
<220> FEATURE:
<221> NAME/KEY: misc_binding
<222> LOCATION: 311..335
<223> OTHER INFORMATION: 99-5608-324.probe
<220> FEATURE:
<221> NAME/KEY: primer_bind
<222> LOCATION: 304..322
<223> OTHER INFORMATION: 99-5608-324.mis
<220> FEATURE:
<221> NAME/KEY: primer_bind
<222> LOCATION: 324..342
<223> OTHER INFORMATION: 99-5608-324.mis complement
<220> FEATURE:
<221> NAME/KEY: primer_bind
<222> LOCATION: 1..19
<223> OTHER INFORMATION: 99-5608.pu
<220> FEATURE:
<221> NAME/KEY: primer_bind
<222> LOCATION: 509..529
<223> OTHER INFORMATION: 99-5608.rp complement

<400> SEQUENCE: 22

```
caaatcaagt gtagcaaggc aatgtaaaac tttaaaacga tgatatttct ttttaaagtc    60
tgattaacat ttactagttt tacctaattt ttcttgcatt gttgatttct tgcctaaata   120
tagatttttc ttttagtaat gccttttcaa tcttgcccgc ttaaaacaat tctcggggga   180
agcaataacc tgaatcaata aaaacggcaa aagatctttg gaaatagttg gttctcctgt   240
ttgagatcag gagtaaacaa actgtttagc tgggagctta tcaagccatg ctaaaagtgt   300
cagctgacac aaagtaagac gcrttagatt ggggttatca tacaatgggg tttccccaag   360
acaaaactct atactatgct atttgctgag aaatgatcag tacaaaagaa agtttcatca   420
ttcttgcatt gtgatgctaa aagaaaaggc cttgtaaatg tgtttaattt gctattcgtt   480
hacttcataa atttaatgta tcactttgga gaatccaaca gacattttg             529
```

<210> SEQ ID NO 23
<211> LENGTH: 18
<212> TYPE: DNA
<213> ORGANISM: Artificial Sequence
<220> FEATURE:
<223> OTHER INFORMATION: sequencing oligonucleotide PrimerPU

<400> SEQUENCE: 23

```
tgtaaaacga cggccagt                                                  18
```

<210> SEQ ID NO 24
<211> LENGTH: 18
<212> TYPE: DNA
<213> ORGANISM: Artificial Sequence
<220> FEATURE:
<223> OTHER INFORMATION: sequencing oligonucleotide PrimerRP

<400> SEQUENCE: 24

```
caggaaacag ctatgacc                                                  18
```

METHODS OF ASSESSING THE RISK FOR THE DEVELOPMENT OF SPORADIC PROSTATE CANCER

RELATED APPLICATIONS

This application is a divisional of U.S. application Ser. No. 10/376,893, filed Feb. 27, 2003, which is a divisional of U.S. application Ser. No. 09/536,059, filed Mar. 23, 2000, now U.S. Pat. No. 6,544,737, which claims priority to U.S. Provisional Patent Application Ser. No. 60/125,961, filed Mar. 24, 1999; all of which are hereby incorporated by reference herein in their entireties, including any figures, tables, nucleic acid sequences, amino acid sequences, or drawings.

FIELD OF THE INVENTION

The invention concerns the genomic and cDNA sequences of the purH gene, biallelic markers of the purH gene and the association established between these markers and prostate cancer. The invention provides means to determine the predisposition of individuals to prostate cancer as well as means for the diagnosis of this cancer and for the prognosis/detection of an eventual treatment response to therapeutic agents acting against prostate cancer.

BACKGROUND OF THE INVENTION

Prostate Cancer

The incidence of prostate cancer has dramatically increased over the last decades. It averages 30-50/100,000 males in Western European countries as well as within the US White male population. In these countries, it has recently become the most commonly diagnosed malignancy, being one of every four cancers diagnosed in American males. Prostate cancer's incidence is very much population specific, since it varies from 2/100,000 in China, to over 80/100,000 among African-American males.

In France, the incidence of prostate cancer is 35/100,000 males and it is increasing by 10/100,000 per decade. Mortality due to prostate cancer is also growing accordingly. It is the second cause of cancer death among French males, and the first one among French males aged over 70. This makes prostate cancer a serious burden in terms of public health.

Prostate cancer is a latent disease. Many men carry prostate cancer cells without overt signs of disease. Autopsies of individuals dying of other causes show prostate cancer cells in 30% of men at age 50 and in 60% of men at age 80. Furthermore, prostate cancer can take up to 10 years to kill a patient after the initial diagnosis.

The progression of the disease usually goes from a well-defined mass within the prostate to a breakdown and invasion of the lateral margins of the prostate, followed by metastasis to regional lymph nodes, and metastasis to the bone marrow. Cancer metastasis to bone is common and often associated with uncontrollable pain.

Unfortunately, in 80% of cases, diagnosis of prostate cancer is established when the disease has already metastasized to the bones. Of special interest is the observation that prostate cancers frequently grow more rapidly in sites of metastasis than within the prostate itself.

Early-stage diagnosis of prostate cancer mainly relies today on Prostate Specific Antigen (PSA) dosage, and allows the detection of prostate cancer seven years before clinical symptoms become apparent. The effectiveness of PSA dosage diagnosis is, however, limited due to its inability to discriminate between malignant and non-malignant affections of the organ and because not all prostate cancers give rise to an elevated serum PSA concentration. Furthermore, PSA dosage and other currently available approaches such as physical examination, tissue biopsy and bone scans are of limited value in predicting disease progression. Therefore, there is a strong need for a reliable diagnostic procedure which would enable a more systematic early-stage prostate cancer prognosis.

Although an early-stage prostate cancer prognosis is important, the possibility of measuring the period of time during which treatment can be deferred is also interesting as currently available medicaments are expensive and generate important adverse effects. However, the aggressiveness of prostate tumors varies widely. Some tumors are relatively aggressive, doubling every six months whereas others are slow-growing, doubling once every five years. In fact, the majority of prostate cancers grows relatively slowly and are never clinically manifested. Very often, affected patients are among the elderly and die from another disease before prostate cancer actually develops. Thus, a significant question in treating prostate carcinoma is how to discriminate between tumors that will progress and those that will not progress during the expected lifetime of the patient.

Hence, there is also a strong need for detection means which may be used to evaluate the aggressiveness or the development potential of prostate cancer tumors once diagnosed.

Furthermore, at the present time, there is no means to predict prostate cancer susceptibility. It would also be very beneficial to detect individual susceptibility to prostate cancer. This could allow preventive treatment and a careful follow up of the development of the tumor.

A further consequence of the slow growth rate of prostate cancer is that few cancer cells are actively dividing at any one time, rendering prostate cancer generally resistant to radiation and chemotherapy. Surgery is the mainstay of treatment but it is largely ineffective and removes the ejaculatory ducts, resulting in impotence. Oral oestrogens and luteinizing releasing hormone analogs are also used for treatment of prostate cancer. These hormonal treatments provide marked improvement for many patients, but they only provide temporary relief. Indeed, most of these cancers soon relapse with the development of hormone-resistant tumor cells and the oestrogen treatment can lead to serious cardiovascular complications. Consequently, there is a strong need for preventive and curative treatment of prostate cancer.

Developing reliable means of accessing efficacy and tolerance prognoses could be of extreme value in prostate cancer therapy. Indeed, hormonal therapy, the main treatment currently available, presents important side effects. The use of chemotherapy is limited because of the small number of patients with chemosensitive tumors. Furthermore the age profile of the prostate cancer patient and intolerance to chemotherapy make the systematic use of this treatment very difficult.

Therefore, a valuable assessment of the eventual efficacy of a medicament to be administered to a prostate cancer patient as well as the patient's eventual tolerance to it may permit one to enhance the benefit/risk ratio of prostate cancer treatment.

SUMMARY OF THE INVENTION purH Gene

The purH gene encodes a bifunctional protein which exhibits the final two activities of the purine nucleotide bio-synthetic pathway, AICARFT and IMPCH (Rayl et al., 1996; Sugita et al, 1997), the disclosures of which are incorporated herein by reference. The human gene is located on the long arm of chromosome 2, between bands q34 and q35. The human purH cDNA previously described is 1776 base pairs in length encoding for a 591-amino acid polypeptide. IMPCHase and AICARFT activities are located within the N-terminal and C-terminal regions, respectively.

The present invention stems from the isolation and characterization of the whole genomic sequence of the purH gene including its regulatory regions. Oligonucleotide probes and primers hybridizing specifically with a genomic sequence of purH are also part of the invention. A further object of the invention consists of recombinant vectors comprising any of the nucleic acid sequences described in the present invention, and in particular of recombinant vectors comprising the regulatory region of purH or a sequence encoding the purH enzyme, as well as cell hosts comprising said nucleic acid sequences or recombinant vectors. The invention also encompasses methods of screening of molecules which modulate or inhibit the expression of the purH gene. The invention also comprises a new allelic variant of the purH protein.

The invention is also directed to biallelic markers that are located within the purH genomic sequence or that are in linkage disequilibrium with the purH gene, these biallelic markers representing useful tools in order to identify a statistically significant association between specific alleles of purH gene and diseases such as cancer, more particularly prostate cancer. These association methods are within the scope of the invention.

More particularly, the present invention stems from the identification of genetic associations between alleles of biallelic markers of the purH gene and cancer, more particularly prostate cancer, as confirmed and characterized in a panel of human subjects.

Methods and products are provided for the molecular detection of a genetic susceptibility to cancer, more particularly prostate cancer, the level of aggressiveness of cancer, or prostate cancer tumors, an early onset of cancer, or prostate cancer, a beneficial response to or side effects related to treatment against cancer, or prostate cancer. They can be used for diagnosis, staging, prognosis, and monitoring of such a disease, which processes can be further included within treatment approaches. The invention also provides for the efficient design and evaluation of suitable therapeutic solutions including individualized strategies for optimizing drug usage, and screening of potential new medicament candidates.

BRIEF DESCRIPTION OF THE FIGURES

FIG. 1 is a table demonstrating the results of a haplotype association analysis between sporadic prostate cancer and haplotypes which consist of biallelic markers of the invention. In this haplotype analysis, 294 sporadic cases and 313 controls were considered.

FIG. 2 is a table demonstrating the results of a haplotype association analysis between familial prostate cancer and haplotypes which consist of biallelic markers of the invention. In this haplotype analysis, 197 familial cases and 313 controls were considered.

FIG. 3 is a table demonstrating the results of a haplotype frequency analysis including permutation testing.

FIG. 4 is a table demonstrating the results of a haplotype association analysis between sporadic prostate cancer and haplotypes which consist of biallelic markers of the purH gene. In this haplotype analysis, 294 sporadic cases and 313 controls were considered. FIG. 4A presents the results with the 2-biallelic marker haplotypes and FIG. 4B presents the results with the 3-biallelic marker haplotypes.

FIG. 5 is a table demonstrating the haplotype frequency analysis for the preferred 2-biallelic marker haplotype comprising biallelic markers of the purH gene.

BRIEF DESCRIPTION OF THE SEQUENCES PROVIDED IN THE SEQUENCE LISTING

Figure 6:
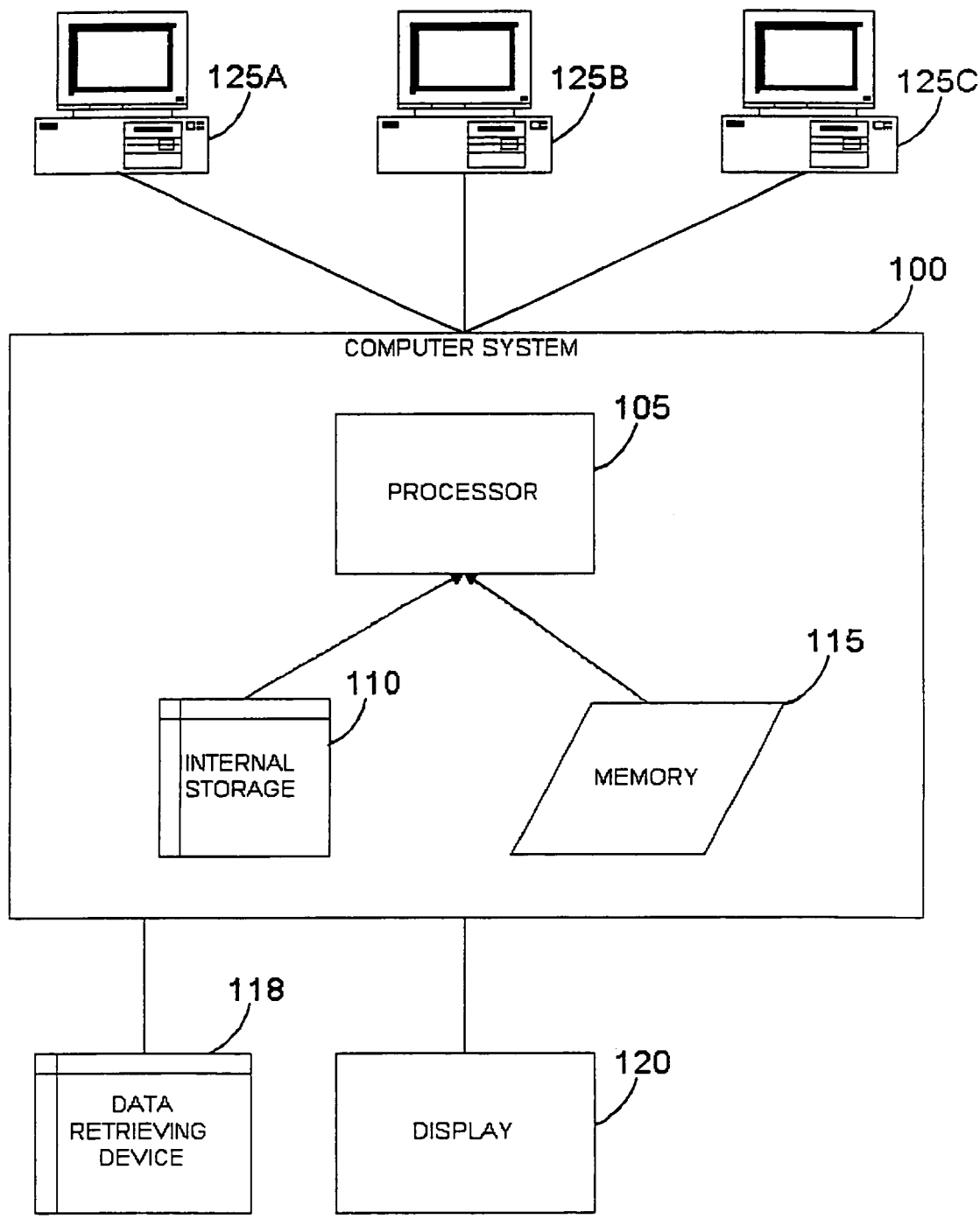
FIG. 6 is a block diagram of an exemplary computer system.
Figure 7:
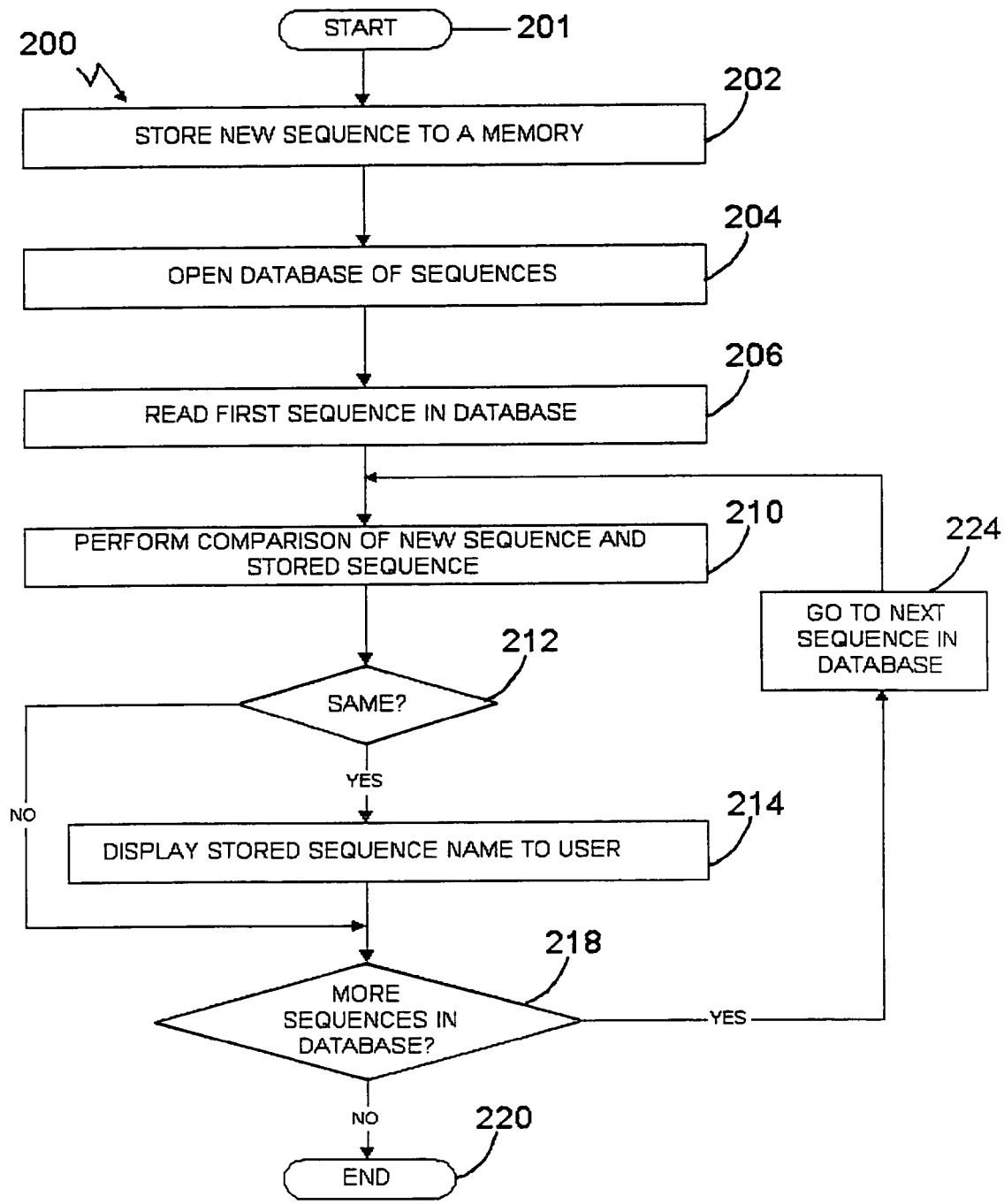
FIG. 7 is a flow diagram illustrating one embodiment of a process 200 for comparing a new nucleotide or protein sequence with a database of sequences in order to determine the homology levels between the new sequence and the sequences in the database.
Figure 8:
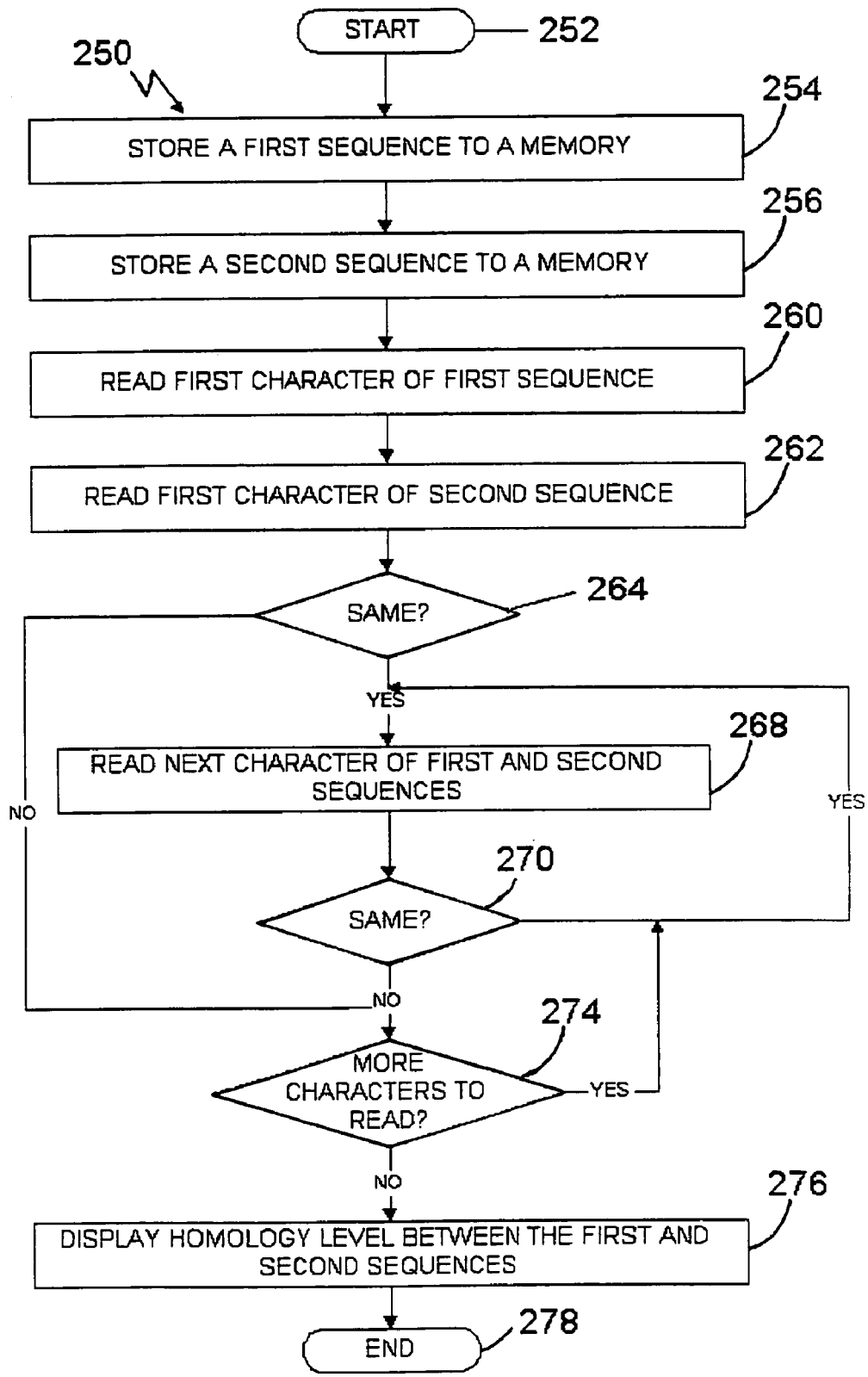
FIG. 8 is a flow diagram illustrating one embodiment of a process 250 in a computer for determining whether two sequences are homologous.
Figure 9:
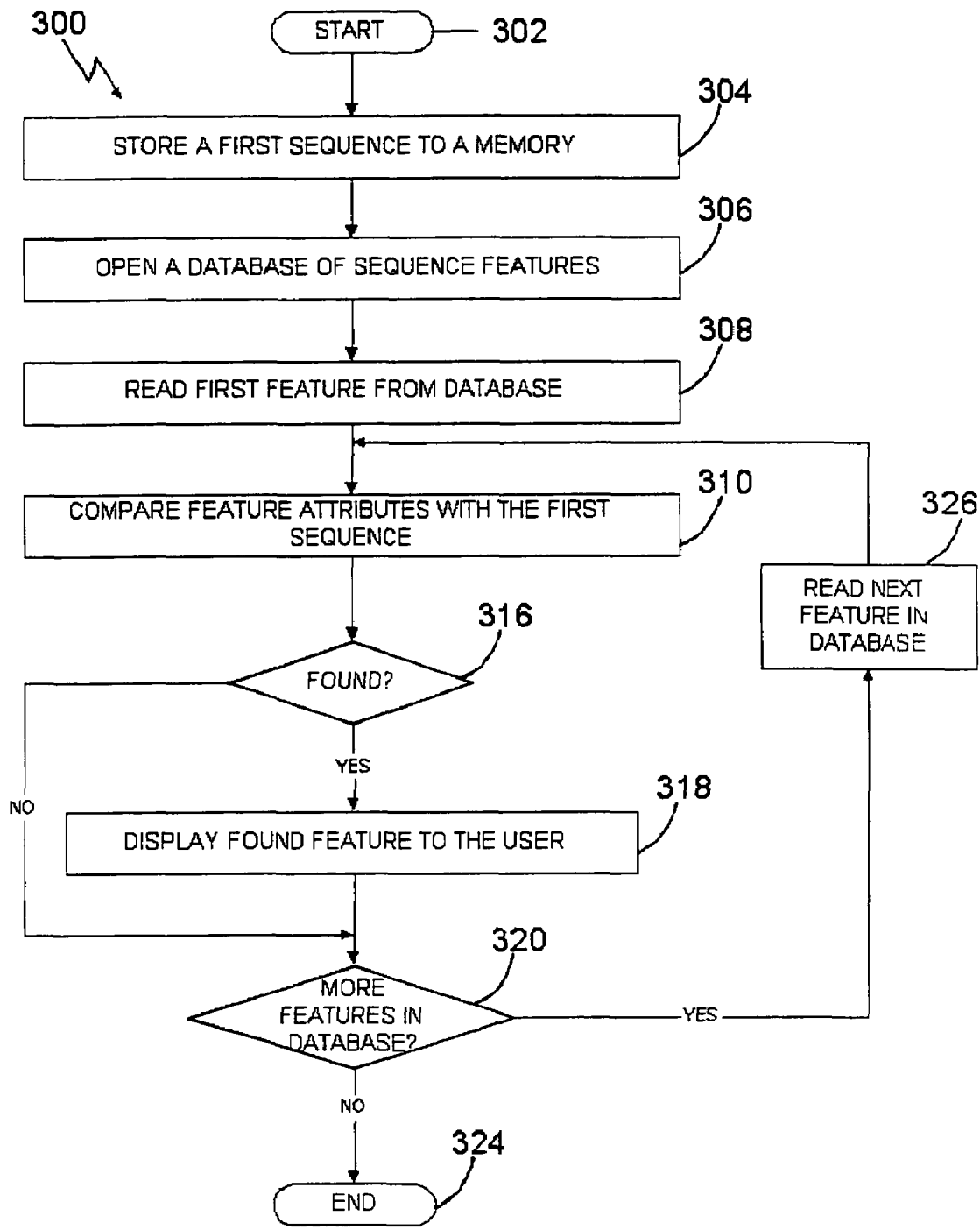
FIG. 9 is a flow diagram illustrating one embodiment of an identifier process 300 for detecting the presence of a feature in a sequence.

SEQ ID NO: 1 contains a genomic sequence of purH comprising the 5' regulatory region (upstream untranscribed region), the exons and introns, and the 3' regulatory region (downstream untranscribed region).

SEQ ID NO: 2 contains a cDNA sequence of purH.

SEQ ID NO: 3 contains the amino acid sequence encoded by the cDNA of SEQ ID NO: 2.

SEQ ID NOs: 4, 5, 6, 7, 8, 9, 10, 11, 12, 13, 14, 15, 16, 17, 18, 19, 20, 21, and 22, respectively contain the nucleotide sequence of the amplicons 99-22578, 99-22580, 99-22585, 99-23437, 99-23440, 99-23442, 99-23444, 99-23451, 99-23452, 99-28437, 99-32278, 99-5574, 99-5575, 99-5582, 99-5590, 99-5595, 99-5604, 99-5605, and 99-5608, said amplicons comprising the non-genic purH-related biallelic markers.

SEQ ID NO: 23 contains a primer containing the additional PU 5' sequence described further in Example 2

SEQ ID NO: 24 contains a primer containing the additional RP 5' sequence described further in Example 2.

In accordance with the regulations relating to Sequence Listings, the following codes have been used in the Sequence Listing to indicate the locations of biallelic markers within the sequences and to identify each of the alleles present at the polymorphic base. The code "r" in the sequences indicates that one allele of the polymorphic base is a guanine, while the other allele is an adenine. The code "y" in the sequences indicates that one allele of the polymorphic base is a thymine, while the other allele is a cytosine. The code "m" in the sequences indicates that one allele of the polymorphic base is an adenine, while the other allele is an cytosine. The code "k" in the sequences indicates that one allele of the polymorphic base is a guanine, while the other allele is a thymine. The code "s" in the sequences indicates that one allele of the polymorphic base is a guanine, while the other allele is a cytosine. The code "w" in the sequences indicates that one allele of the polymorphic base is an adenine, while the other allele is an thymine. The nucleotide code of the original allele for each biallelic marker is the following:

| Biallelic marker | Original allele |
|---|---|
| 99-32284-107 | C |
| 99-5602-372 | C |

-continued

| Biallelic marker | Original allele |
|---|---|
| 5-290-32 | C |
| 99-22573-321 | C |
| 99-22586-300 | G |
| 99-22586-39 | C |
| 99-5596-197 | G |
| 5-293-76 | C |
| 5-293-155 | A |
| 5-294-285 | G |
| 99-23454-317 | A |
| 99-23454-105 | G |
| 99-15528-333 | G |
| 99-15798-86 | A |
| 5-297-209 | A |
| 99-32281-276 | C |
| 99-32281-26 | T |
| 5-298-376 | G |
| 99-23460-199 | G |

In some instances, the polymorphic bases of the biallelic markers alter the identity of an amino acids in the encoded polypeptide. This is indicated in the accompanying Sequence Listing by use of the feature VARIANT, placement of an Xaa at the position of the polymorphic amino acid, and definition of Xaa as the two alternative amino acids. For example if one allele of a biallelic marker is the codon CAC, which encodes histidine, while the other allele of the biallelic marker is CAA, which encodes glutamine, the Sequence Listing for the encoded polypeptide will contain an Xaa at the location of the polymorphic amino acid. In this instance, Xaa would be defined as being histidine or glutamine.

In other instances, Xaa may indicate an amino acid whose identity is unknown because of nucleotide sequence ambiguity. In this instance, the feature UNSURE is used, placement of an Xaa at the position of the unknown amino acid and definition of Xaa as being any of the 20 amino acids or a limited number of amino acids suggested by the genetic code.

DETAILED DESCRIPTION

The present invention provides the genomic sequence of the purH gene and further provides biallelic markers derived from the purH locus. The purH-related biallelic markers of the present invention offer the possibility of rapid, high throughput genotyping of a large number of individuals. The biallelic markers of the present invention can be used in any method of genetic analysis including linkage studies in families, linkage disequilibrium studies in populations and association studies of case-control populations. An important aspect of the present invention is that biallelic markers allow association studies to be performed to identify genes involved in complex traits. As part of the present invention an association between alleles of purH-related biallelic markers and prostate cancer was established.

DEFINITIONS

Before describing the invention in greater detail, the following definitions are set forth to illustrate and define the meaning and scope of the terms used to describe the invention herein.

The term "purH gene", when used herein, encompasses genomic, mRNA and cDNA sequences encoding the purH protein, including the untranslated regulatory regions of the genomic DNA.

The term "heterologous protein", when used herein, is intended to designate any protein or polypeptide other than the purH protein. More particularly, the heterologous protein is a compound which can be used as a marker in further experiments with a purH regulatory region.

The term "isolated" requires that the material be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

The term "purified" does not require absolute purity; rather, it is intended as a relative definition. Purification of starting material or natural material to at least one order of magnitude, preferably two or three orders, and more preferably four or five orders of magnitude is expressly contemplated. As an example, purification from 0.1% concentration to 10% concentration is two orders of magnitude. The term "purified" is used herein to describe a polynucleotide or polynucleotide vector of the invention which has been separated from other compounds including, but not limited to other nucleic acids, carbohydrates, lipids and proteins (such as the enzymes used in the synthesis of the polynucleotide), or the separation of covalently closed polynucleotides from linear polynucleotides. A polynucleotide is substantially pure when at least about 50%, preferably 60 to 75% of a sample exhibits a single polynucleotide sequence and conformation (linear versus covalently close). A substantially pure polynucleotide typically comprises about 50%, preferably 60 to 90% weight/weight of a nucleic acid sample, more usually about 95%, and preferably is over about 99% pure. Polynucleotide purity or homogeneity is indicated by a number of means well known in the art, such as agarose or polyacrylamide gel electrophoresis of a sample, followed by visualizing a single polynucleotide band upon staining the gel. For certain purposes higher resolution can be provided by using HPLC or other means well known in the art.

The term "polypeptide" refers to a polymer of amino acids without regard to the length of the polymer; thus, peptides, oligopeptides, and proteins are included within the definition of polypeptide. This term also does not specify or exclude post-expression modifications of polypeptides, for example, polypeptides which include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

The term "recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide.

The term "purified" is used herein to describe a polypeptide of the invention which has been separated from other compounds including, but not limited to nucleic acids, lipids, carbohydrates and other proteins. A polypeptide is substantially pure when at least about 50%, preferably 60 to 75% of a sample exhibits a single polypeptide sequence. A substantially pure polypeptide typically comprises about 50%, preferably 60 to 90% weight/weight of a protein sample, more usually about 95%, and preferably is over about 99% pure. Polypeptide purity or homogeneity is indicated by a number of means well known in the art, such as agarose or polyacrylamide gel electrophoresis of a sample, followed by visualizing a single polypeptide band upon staining the gel. For certain purposes higher resolution can be provided by using HPLC or other means well known in the art.

As used herein, the term "non-human animal" refers to any non-human vertebrate, birds and more usually mammals, preferably primates, farm animals such as swine, goats, sheep, donkeys, and horses, rabbits or rodents, more preferably rats or mice. As used herein, the term "animal" is used to refer to any vertebrate, preferable a mammal. Both the terms "animal" and "mammal" expressly embrace human subjects unless preceded with the term "non-human".

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', F(ab)$_2$, and F(ab')$_2$ fragments.

As used herein, an "antigenic determinant" is the portion of an antigen molecule, in this case a purH polypeptide, that determines the specificity of the antigen-antibody reaction. An "epitope" refers to an antigenic determinant of a polypeptide. An epitope can comprise as few as 3 amino acids in a spatial conformation which is unique to the epitope. Generally an epitope consists of at least 6 such amino acids, and more usually at least 8-10 such amino acids. Methods for determining the amino acids which make up an epitope include x-ray crystallography, 2-dimensional nuclear magnetic resonance, and epitope mapping e.g. the Pepscan method described by Geysen et al. 1984; PCT Publication No. WO 84/03564; and PCT Publication No. WO 84/03506, the disclosures of which are incorporated herein by reference.

Throughout the present specification, the expression "nucleotide sequence" may be employed to designate either a polynucleotide or a nucleic acid. More precisely, the expression "nucleotide sequence" encompasses the nucleic material itself and is thus not restricted to the sequence information (i.e. the succession of letters chosen among the four base letters) that biochemically characterizes a specific DNA or RNA molecule.

As used interchangeably herein, the terms "nucleic acids", "oligonucleotides", and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No. WO 95/04064. The polynucleotide sequences of the invention may be prepared by any known method, including synthetic, recombinant, ex vivo generation, or a combination thereof, as well as utilizing any purification methods known in the art.

A sequence which is "operably linked" to a regulatory sequence such as a promoter means that said regulatory element is in the correct location and orientation in relation to the nucleic acid to control RNA polymerase initiation and expression of the nucleic acid of interest. As used herein, the term "operably linked" refers to a linkage of polynucleotide elements in a functional relationship. For instance, a promoter or enhancer is operably linked to a coding sequence if it affects the transcription of the coding sequence.

The terms "trait" and "phenotype" are used interchangeably herein and refer to any visible, detectable or otherwise measurable property of an organism such as symptoms of, or susceptibility to a disease for example. Typically the terms "trait" or "phenotype" are used herein to refer to symptoms of, or susceptibility to cancer or prostate cancer, the level of aggressiveness of cancer or prostate cancer tumors, an early onset of cancer or prostate cancer, a beneficial response to or side effects related to treatment against cancer or prostate cancer.

The term "allele" is used herein to refer to variants of a nucleotide sequence. A biallelic polymorphism has two forms. Typically the first identified allele is designated as the original allele whereas other alleles are designated as alternative alleles. Diploid organisms may be homozygous or heterozygous for an allelic form.

The term "heterozygosity rate" is used herein to refer to the incidence of individuals in a population which are heterozygous at a particular allele. In a biallelic system, the heterozygosity rate is on average equal to $2P_a(1-P_a)$, where $P_a$ is the frequency of the least common allele. In order to be useful in genetic studies, a genetic marker should have an adequate level of heterozygosity to allow a reasonable probability that a randomly selected person will be heterozygous.

The term "genotype" as used herein refers to the identity of the alleles present in an individual or a sample. In the context of the present invention, a genotype preferably refers to the description of the biallelic marker alleles present in an individual or a sample. The term "genotyping" a sample or an individual for a biallelic marker consists of determining the specific allele or the specific nucleotide carried by an individual at a biallelic marker.

The term "mutation" as used herein refers to a difference in DNA sequence between or among different genomes or individuals which has a frequency below 1%.

The term "haplotype" refers to a combination of alleles present in an individual or a sample. In the context of the present invention, a haplotype preferably refers to a combination of biallelic marker alleles found in a given individual and which may be associated with a phenotype.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism is the replacement of one nucleotide by another nucleotide at the polymorphic site. Deletion of a single nucleotide or insertion of a single nucleotide also gives rise to single nucleotide polymorphisms. In the context of the present invention, "single nucleotide polymorphism" preferably refers to a single nucleotide substitution. Typically, between different individuals, the polymorphic site may be occupied by two different nucleotides.

The term "biallelic polymorphism" and "biallelic marker" are used interchangeably herein to refer to a polymorphism, usually a single nucleotide, having two alleles at a fairly high frequency in the population. A "biallelic marker allele" refers to the nucleotide variants present at a biallelic marker site. Typically, the frequency of the less common allele of the biallelic markers of the present invention has been validated to be greater than 1%, preferably the frequency is greater than 10%, more preferably the frequency is at least 20% (i.e. heterozygosity rate of at least 0.32), even more preferably the frequency is at least 30% (i.e. heterozygosity rate of at least 0.42). A biallelic marker wherein the frequency of the less common allele is 30% or more is termed a "high quality biallelic marker".

As used herein the term "purH-related biallelic marker" relates to a set of biallelic markers in linkage disequilibrium with the purH gene. The term purH-related biallelic marker encompasses all of the biallelic markers A1 to A43 disclosed in Table 2.

The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center", and so on. For polymorphisms which involve the substitution, insertion or deletion of 1 or more nucleotides, the polymorphism, allele or biallelic marker is "at the center" of a polynucleotide if the difference between the distance from the substituted, inserted, or deleted polynucleotides of the polymorphism and the 3' end of the polynucleotide, and the distance from the substituted, inserted, or deleted polynucleotides of the polymorphism and the 5' end of the polynucleotide is zero or one nucleotide. If this difference is 0 to 3, then the polymorphism is considered to be "within 1 nucleotide of the center." If the difference is 0 to 5, the polymorphism is considered to be "within 2 nucleotides of the center." If the difference is 0 to 7, the polymorphism is considered to be "within 3 nucleotides of the center," and so on.

The terms "complementary" or "complement thereof" are used herein to refer to the sequences of polynucleotides which are capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym for "complementary polynucleotide", "complementary nucleic acid" and "complementary nucleotide sequence". These terms are applied to pairs of polynucleotides based solely upon their sequences and not any particular set of conditions under which the two polynucleotides would actually bind.

The term "non-genic" is used herein to describe purH-related biallelic markers, as well as polynucleotides and primers which occur outside the nucleotide positions shown in the human purH genomic sequence of SEQ ID NO: 1. The non-genic biallelic marker of the purH gene could either be located in an intergenic region or in an other gene. The term "genic" is used herein to describe purH-related biallelic markers as well as polynucleotides and primers which do occur in the nucleotide positions shown in the human purH genomic sequence of SEQ ID NO: 1.

Variants and Fragments

1—Polynucleotides

The invention also relates to variants and fragments of the polynucleotides described herein, particularly of a purH gene containing one or more biallelic markers according to the invention.

Variants of polynucleotides, as the term is used herein, are polynucleotides that differ from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Variants of polynucleotides according to the invention include, without being limited to, nucleotide sequences which are at least 95% identical to a polynucleotide selected from the group consisting of the nucleotide sequences of SEQ ID NO: 1 or to any polynucleotide fragment of at least 12, 15, 18, 20, 25, 30, 50, 80, 100, 150, 200, 250, 300, 350, 400, 450, 500, 600 or 1000 consecutive nucleotides of a polynucleotide selected from the group consisting of the nucleotide sequences of SEQ ID NO: 1, and preferably at least 99% identical, more particularly at least 99.5% identical, and most preferably at least 99.8% identical to a polynucleotide selected from the group consisting of the nucleotide sequences of SEQ ID NO: 1 or to any polynucleotide fragment of at least 12, 15, 18, 20, 25, 30, 50, 80, 100, 150, 200, 250, 300, 350, 400, 450, 500, 600 or 1000 consecutive nucleotides of a polynucleotide selected from the group consisting of the nucleotide sequences of SEQ ID NO: 1.

Nucleotide changes present in a variant polynucleotide may be silent, which means that they do not alter the amino acids encoded by the polynucleotide. However, nucleotide changes may also result in amino acid substitutions, additions, deletions, fusions and truncations in the polypeptide encoded by the reference sequence. The substitutions, deletions or additions may involve one or more nucleotides. The variants may be altered in coding or non-coding regions or both. Alterations in the coding regions may produce conservative or non-conservative amino acid substitutions, deletions or additions.

In the context of the present invention, particularly preferred embodiments are those in which the polynucleotides encode polypeptides which retain substantially the same biological function or activity as the mature purH protein, or those in which the polynucleotides encode polypeptides which maintain or increase a particular biological activity, while reducing a second biological activity.

A polynucleotide fragment is a polynucleotide having a sequence that is entirely the same as part but not all of a given nucleotide sequence, preferably the nucleotide sequence of a purH gene, and variants thereof. The fragment can be a portion of an intron of a purH gene. It can also be a portion of the regulatory regions of purH, preferably of the promoter sequence of the purH gene. Preferably, such fragments comprise at least one of the biallelic markers A1 to A43 or the complements thereto.

Such fragments may be "free-standing", i.e. not part of or fused to other polynucleotides, or they may be comprised within a single larger polynucleotide of which they form a part or region. Indeed, several of these fragments may be present within a single larger polynucleotide.

Optionally, such fragments may consist of, or consist essentially of a contiguous span of at least 8, 10, 12, 15, 18, 20, 25, 35, 40, 50, 70, 80, 100, 250, 500 or 1000 nucleotides in length.

2—Polypeptides

The invention also relates to variants, fragments, analogs and derivatives of the polypeptides described herein, including mutated purH proteins.

The variant may be 1) one in which one or more of the amino acid residues are substituted with a conserved or non-conserved amino acid residue and such substituted amino acid residue may or may not be one encoded by the genetic code, or 2) one in which one or more of the amino acid residues includes a substituent group, or 3) one in which the mutated purH is fused with another compound, such as a compound to increase the half-life of the polypeptide (for example, polyethylene glycol), or 4) one in which the additional amino acids are fused to the mutated purH, such as a leader or secretory sequence or a sequence which is employed for purification of the mutated purH or a preprotein sequence. Such variants are deemed to be within the scope of those skilled in the art.

A polypeptide fragment is a polypeptide having a sequence that entirely is the same as part but not all of a given polypeptide sequence, preferably a polypeptide encoded by a purH gene and variants thereof.

A specific embodiment of a modified purH peptide molecule of interest according to the present invention, includes, but is not limited to, a peptide molecule which is resistant to proteolysis, is a peptide in which the —CONH— peptide bond is modified and replaced by a (CH2NH) reduced bond, a (NHCO) retro inverso bond, a (CH2-O) methylene-oxy bond, a (CH2-S) thiomethylene bond, a (CH2CH2) carba bond, a (CO—CH2) cetomethylene bond, a (CHOH—CH2) hydroxyethylene bond, a (N—N) bond, a E-alcene bond or also a —CH=CH— bond. The invention also encompasses a human purH polypeptide or a fragment or a variant thereof in which at least one peptide bond has been modified as described above.

Such fragments may be "free-standing", i.e. not part of or fused to other polypeptides, or they may be comprised within a single larger polypeptide of which they form a part or region. However, several fragments may be comprised within a single larger polypeptide.

As representative examples of polypeptide fragments of the invention, there may be mentioned those which have at least 6 amino acids, preferably at least 8 to 10 amino acids, more preferably at least 12, 15, 20, 25, 30, 40, 50, or 100 amino acids long. A specific embodiment of a purH fragment is a fragment containing at least one amino acid mutation in the purH protein.

Identity Between Nucleic Acids or Polypeptides

The terms "percentage of sequence identity" and "percentage homology" are used interchangeably herein to refer to comparisons among polynucleotides and among polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988; Altschul et al., 1990; Thompson et al., 1994; Higgins et al., 1996; Altschul et al., 1993), the disclosures of which are incorporated herein by reference. In a particularly preferred embodiment, protein and nucleic acid sequence homologies are evaluated using the Basic Local Alignment Search Tool ("BLAST") which is well known in the art (see, e.g., Karlin and Altschul, 1990; Altschul et al., 1990, 1993, 1997), the disclosures of which are incorporated herein by reference. In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992; Henikoff and Henikoff, 1993), the disclosures of which are incorporated herein by reference. Less preferably, the PAM or PAM250 matrices may also be used (see, e.g., Schwartz and Dayhoff, eds., 1978), the disclosure of which is incorporated herein by reference. The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990), the disclosure of which is incorporated herein by reference.

Stringent Hybridization Conditions

For the purpose of defining such a hybridizing nucleic acid according to the invention, the stringent hybridization conditions are the following:

the hybridization step is realized at 65° C. in the presence of 6×SSC buffer, 5× Denhardt's solution, 0.5% SDS and 100 μg/ml of salmon sperm DNA.

The hybridization step is followed by four washing steps:
two washings during 5 min, preferably at 65° C. in a 2×SSC and 0.1% SDS buffer;
one washing during 30 min, preferably at 65° C. in a 2×SSC and 0.1% SDS buffer,
one washing during 10 min, preferably at 65° C. in a 0.1×SSC and 0.1% SDS buffer,
these hybridization conditions being suitable for a nucleic acid molecule of about 20 nucleotides in length. There is no need to say that the hybridization conditions described above are to be adapted according to the length of the desired nucleic acid, following techniques well known to the one skilled in the art. The suitable hybridization conditions may for example be adapted according to the teachings disclosed in the book of Hames and Higgins (1985), the disclosure of which is incorporated herein by reference.

Genomic Sequences of the purH Gene

The present invention concerns the genomic sequence of purH. The present invention encompasses the purH gene, or purH genomic sequences consisting of, consisting essentially of, or comprising the sequence of SEQ ID NO: 1, a sequence complementary thereto, as well as fragments and variants thereof. These polynucleotides may be purified, isolated, or recombinant.

The invention also encompasses a purified, isolated, or recombinant polynucleotide comprising a nucleotide sequence having at least 70, 75, 80, 85, 90, or 95% nucleotide identity with a nucleotide sequence of SEQ ID NO: 1 or a complementary sequence thereto or a fragment thereof. The nucleotide differences as regards to the nucleotide sequence of SEQ ID NO: 1 may be generally randomly distributed throughout the entire nucleic acid. Nevertheless, preferred nucleic acids are those wherein the nucleotide differences as regards to the nucleotide sequence of SEQ ID NO: 1 are predominantly located outside the coding sequences contained in the exons. These nucleic acids, as well as their fragments and variants, may be used as oligonucleotide primers or probes in order to detect the presence of a copy of the purH gene in a test sample, or alternatively in order to amplify a target nucleotide sequence within the purH sequences.

Another object of the invention consists of a purified, isolated, or recombinant nucleic acid that hybridizes with the nucleotide sequence of SEQ ID NO: 1 or a complementary sequence thereto or a variant thereof, under the stringent hybridization conditions as defined above.

Preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 400, 500, or 1000 nucleotides of SEQ ID NO: 1 or the complements thereof. Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 400, 500, or 1000 nucleotides of SEQ ID NO: 1 or the complements thereof, wherein said contiguous span comprises at least 1, 2, 3, 5, or 10 of the following nucleotide positions of SEQ ID NO: 1: 1-1587, 1729-2000, 2095-2414, 2558-3235, 3848-3991, 4156-7043, 7396-7958, 8237-9596, 9666-9874, 9921-10039, 10083-11742, 11825-15173, 15267-15916, 16075-16750, 16916-22304, 22443-23269, 23384-24834, 24927-25952, 26048-28683, 28829-34694, 37282-37458, 37765-37894, 38563-38932, 39178-39451, 39692-39821, 40038-40445, and 40846-41587. Additional preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 400, 500, or 1000 nucleotides of SEQ ID NO: 1 or the complements thereof, wherein said contiguous span comprises either a G at position 15234, or a G at position 36801 of SEQ ID NO: 1. Further preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 400, 500, or 1000 nucleotides of SEQ ID NO: 1 or the complements thereof, wherein said contiguous span comprises at least 1, 2, 3, 5, or 10 of the following nucleotide positions of SEQ ID NO: 1: 1-1587, 1729-2000, 2095-2414, 2558-3235, 3848-3991, 4156-5000, 5001-6000, 6001-7043, 7396-7958, 8237-9596, 9666-9874, 9921-10039, 10083-11742, 11825-13000, 13001-14000, 14001-15173, 15267-15916, 16075-16750, 16916-18000, 18001-19000, 19001-20000, 20001-21000, 21001-22304, 22443-23269, 23384-24834, 24927-25952, 26048-27000, 27001-28000, 28001-28683, 28829-30000, 30001-31000, 31001-32000, 32001-33000, 33001-34694, 37282-37458, 37765-37894, 38563-38932, 39178-39451, 39692-39821, 40038-40445, and 40846-41587. It should be noted that nucleic acid fragments of any size and sequence may also be comprised by the polynucleotides described in this section.

The purH genomic nucleic acid comprises 16 exons. The exon positions in SEQ ID NO: 1 are detailed below in Table A.

Thus, the invention embodies purified, isolated, or recombinant polynucleotides comprising a nucleotide sequence selected from the group consisting of the 16 exons of the purH gene, or a sequence complementary thereto. The invention also deals with purified, isolated, or recombinant nucleic acids comprising a combination of at least two exons of the purH gene, wherein the polynucleotides are arranged within the nucleic acid, from the 5'-end to the 3'-end of said nucleic acid, in the same order as in SEQ ID NO: 1.

Intron 1 refers to the nucleotide sequence located between Exon 1 and Exon 2, and so on. The position of the introns is detailed in Table A. Thus, the invention embodies purified, isolated, or recombinant polynucleotides comprising a nucleotide sequence selected from the group consisting of the 15 introns of the purH gene, or a sequence complementary thereto.

TABLE A

| Exon | Position in SEQ ID NO: 1 Beginning | End | Intron | Position in SEQ ID NO: 1 Beginning | End |
|---|---|---|---|---|---|
| 1 | 2001 | 2096 | 1 | 2097 | 2432 |
| 2 | 2433 | 2559 | 2 | 2560 | 8091 |
| 3 | 8092 | 8168 | 3 | 8169 | 9599 |
| 4 | 9600 | 9666 | 4 | 9667 | 15177 |
| 5 | 15178 | 15266 | 5 | 15267 | 15923 |
| 6 | 15924 | 16075 | 6 | 16076 | 16758 |
| 7 | 16759 | 16915 | 7 | 16916 | 22308 |
| 8 | 22309 | 22434 | 8 | 22435 | 23276 |
| 9 | 23277 | 23384 | 9 | 23385 | 24840 |
| 10 | 24841 | 24926 | 10 | 24927 | 25956 |
| 11 | 25957 | 26046 | 11 | 26047 | 28699 |
| 12 | 28700 | 28828 | 12 | 28829 | 34698 |
| 13 | 34699 | 34791 | 13 | 34792 | 36678 |
| 14 | 36679 | 36861 | 14 | 36862 | 39013 |
| 15 | 39014 | 39169 | 15 | 39170 | 39455 |
| 16 | 39456 | 39684 | | | |

The invention also concerns the polypeptide encoded by the nucleotide sequence of SEQ ID NO: 1, or a fragment thereof or a complementary sequence thereto.

While this section is entitled "Genomic Sequences of purH," it should be noted that nucleic acid fragments of any size and sequence may also be comprised by the polynucleotides described in this section, flanking the genomic sequences of purH on either side or between two or more such genomic purH cDNA Sequences

The expression of the purH gene has been shown to lead to the production of at least one mRNA species, the nucleic acid sequence of which is set forth in SEQ ID NO: 2.

Another object of the invention is a purified, isolated, or recombinant nucleic acid comprising the nucleotide sequence of SEQ ID NO: 2, complementary sequences thereto, as well as allelic variants, and fragments thereof. Moreover, preferred polynucleotides of the invention include purified, isolated, or recombinant purH cDNAs consisting of, consisting essentially of, or comprising the sequence of SEQ ID NO: 2. Particularly preferred embodiments of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID NO: 2 or the complements thereof, wherein said contiguous span comprises a nucleotide selected in the group consisting of a G at position 424, and a G at position 1520 of SEQ ID NO: 2.

The cDNA of SEQ ID NO: 2 includes a 5'-UTR region starting from the nucleotide at position 1 and ending at the nucleotide in position 77 of SEQ ID NO: 2. The cDNA of SEQ ID NO: 2 includes a 3'-UTR region starting from the nucleotide at position 1857 and ending at the nucleotide at position 1965 of SEQ ID NO: 2. The polyadenylation site starts from the nucleotide at position 1938 and ends at the nucleotide in position 1943 of SEQ ID NO: 2.

Consequently, the invention concerns a purified, isolated, and recombinant nucleic acid comprising a nucleotide sequence of the 5'UTR of the purH cDNA, a sequence complementary thereto, or an allelic variant thereof.

The invention also concerns the polypeptide encoded by the nucleotide sequence of SEQ ID NO: 2, or a fragment thereof or a complementary sequence thereto.

While this section is entitled "purH cDNA Sequences," it should be noted that nucleic acid fragments of any size and sequence may also be comprised by the polynucleotides described in this section, flanking the genomic sequences of purH on either side or between two or more such genomic sequences.

Regulatory Sequences of purH

As mentioned, the genomic sequence of the purH gene contains regulatory sequences both in the non-coding 5'-flanking region and in the non-coding 3'-flanking region that border the purH coding region containing the three exons of this gene.

The 5'-regulatory sequence of the purH gene is localized between the nucleotide in position 1 and the nucleotide in position 2000 of the nucleotide sequence of SEQ ID NO: 1. This polynucleotide contains the promoter site. Three potential GC boxes are found in the 5' regulatory sequence. They are located at 1833-1838, 1858-1863, and 1872-1877 of the sequence of SEQ ID NO: 1. There is also a TATA box which is located at 1710-1717 of the sequence of SEQ ID NO: 1. The GC boxes and TATA box are known to be related to a gene promoter. Moreover, two others TATA box have been found in positions 727-734 (TATAAAAT) and 740-746 (TATAAAAT).

The 3'-regulatory sequence of the purH gene is localized between nucleotide position 39685 and nucleotide position 41684 of SEQ ID NO: 1.

Polynucleotides derived from the 5' and 3' regulatory regions are useful in order to detect the presence of at least a copy of a nucleotide sequence of SEQ ID NO: 1 or a fragment thereof in a test sample.

The promoter activity of the 5' regulatory regions contained in purH can be assessed as described below.

In order to identify the relevant biologically active polynucleotide fragments or variants of SEQ ID NO: 1, one of skill in the art will refer to the book of Sambrook et al. (Sambrook, 1989), the disclosure of which is incorporated herein by reference, which describes the use of a recombinant vector carrying a marker gene (i.e. beta galactosidase, chloramphenicol acetyl transferase, etc.) the expression of which will be detected when placed under the control of a biologically active polynucleotide fragments or variants of SEQ ID NO: 1. Genomic sequences located upstream of the first exon of the purH gene are cloned into a suitable promoter reporter vector, such as the pSEAP-Basic, pSEAP-Enhancer, pβgal-Basic, pβgal-Enhancer, or pEGFP-1 Promoter Reporter vectors available from Clontech, or pGL2-basic or pGL3-basic promoterless luciferase reporter gene vector from Promega. Briefly, each of these promoter reporter vectors include multiple cloning sites positioned upstream of a reporter gene encoding a readily assayable protein such as secreted alkaline phosphatase, luciferase, β galactosidase, or green fluorescent protein. The sequences upstream of the purH coding region are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for increasing transcription levels from weak promoter sequences. A significant level of expression above that observed with the vector lacking an insert indicates that a promoter sequence is present in the inserted upstream sequence.

Promoter sequence within the upstream genomic DNA may be further defined by constructing nested 5' and/or 3' deletions in the upstream DNA using conventional techniques such as Exonuclease III or appropriate restriction endonuclease digestion. The resulting deletion fragments can be inserted into the promoter reporter vector to determine whether the deletion has reduced or obliterated promoter activity, such as described, for example, by Coles et al. (1998), the disclosure of which is incorporated herein by reference in its entirety. In this way, the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into cloning sites in promoter reporter vectors. This type of assay is well-known to those skilled in the art and is described in WO 97/17359; U.S. Pat. No. 5,374,544; EP 582 796; U.S. Pat. No. 5,698,389; U.S. Pat. No.

5,643,746; U.S. Pat. No. 5,502,176; and U.S. Pat. No. 5,266,488; the disclosures of which are incorporated by reference herein in their entirety.

The strength and the specificity of the promoter of the purH gene can be assessed through the expression levels of a detectable polynucleotide operably linked to the purH promoter in different types of cells and tissues. The detectable polynucleotide may be either a polynucleotide that specifically hybridizes with a predefined oligonucleotide probe, or a polynucleotide encoding a detectable protein, including a purH polypeptide or a fragment or a variant thereof. This type of assay is well-known to those skilled in the art and is described in U.S. Pat. No. 5,502,176; and U.S. Pat. No. 5,266,488; the disclosures of which are incorporated by reference herein in their entirety. Some of the methods are discussed in more detail below.

Polynucleotides carrying the regulatory elements located at the 5' end and at the 3' end of the purH coding region may be advantageously used to control the transcriptional and translational activity of an heterologous polynucleotide of interest.

Thus, the present invention also concerns a purified or isolated nucleic acid comprising a polynucleotide which is selected from the group consisting of the 5' and 3' regulatory regions, or a sequence complementary thereto or a biologically active fragment or variant thereof.

The invention also pertains to a purified or isolated nucleic acid comprising a polynucleotide having at least 95% nucleotide identity with a polynucleotide selected from the group consisting of the 5' and 3' regulatory regions, advantageously 99% nucleotide identity, preferably 99.5% nucleotide identity and most preferably 99.8% nucleotide identity with a polynucleotide selected from the group consisting of the 5' and 3' regulatory regions, or a sequence complementary thereto or a variant thereof or a biologically active fragment thereof.

Another object of the invention consists of purified, isolated or recombinant nucleic acids comprising a polynucleotide that hybridizes, under the stringent hybridization conditions defined herein, with a polynucleotide selected from the group consisting of the nucleotide sequences of the 5'- and 3' regulatory regions, or a sequence complementary thereto or a variant thereof or a biologically active fragment thereof.

Preferred fragments of the 5' regulatory region have a length of about 1500 or 1000 nucleotides, preferably of about 500 nucleotides, more preferably about 400 nucleotides, even more preferably 300 nucleotides and most preferably about 200 nucleotides.

Preferred fragments of the 3' regulatory region are at least 50, 100, 150, 200, 300 or 400 bases in length.

"Biologically active" polynucleotide derivatives of SEQ ID NO: 1 are polynucleotides comprising or alternatively consisting in a fragment of said polynucleotide which is functional as a regulatory region for expressing a recombinant polypeptide or a recombinant polynucleotide in a recombinant cell host. It could act either as an enhancer or as a repressor.

For the purpose of the invention, a nucleic acid or polynucleotide is "functional" as a regulatory region for expressing a recombinant polypeptide or a recombinant polynucleotide if said regulatory polynucleotide contains nucleotide sequences which contain transcriptional and translational regulatory information, and such sequences are "operably linked" to nucleotide sequences which encode the desired polypeptide or the desired polynucleotide.

The regulatory polynucleotides of the invention may be prepared from the nucleotide sequence of SEQ ID NO: 1 by cleavage using suitable restriction enzymes, as described for example in the book of Sambrook et al. (1989). The regulatory polynucleotides may also be prepared by digestion of SEQ ID NO: 1 by an exonuclease enzyme, such as Bal31 (Wabiko et al., 1986), the disclosure of which is incorporated herein by reference. These regulatory polynucleotides can also be prepared by nucleic acid chemical synthesis, as described elsewhere in the specification.

The regulatory polynucleotides according to the invention may be part of a recombinant expression vector that may be used to express a coding sequence in a desired host cell or host organism. The recombinant expression vectors according to the invention are described elsewhere in the specification.

A preferred 5'-regulatory polynucleotide of the invention includes the 5'-UTR of the purH cDNA, or a biologically active fragment or variant thereof.

A preferred 3'-regulatory polynucleotide of the invention includes the 3'-UTR of the purH cDNA, or a biologically active fragment or variant thereof.

A further object of the invention consists of a purified or isolated nucleic acid comprising:

a) a nucleic acid comprising a regulatory nucleotide sequence selected from the group consisting of:

(i) a nucleotide sequence comprising a polynucleotide of the 5' regulatory region or a complementary sequence thereto;

(ii) a nucleotide sequence comprising a polynucleotide having at least 95% of nucleotide identity with the nucleotide sequence of the 5' regulatory region or a complementary sequence thereto;

(iii) a nucleotide sequence comprising a polynucleotide that hybridizes under stringent hybridization conditions with the nucleotide sequence of the 5' regulatory region or a complementary sequence thereto; and (iv) a biologically active fragment or variant of the polynucleotides in (i), (ii) and (iii);

b) a polynucleotide encoding a desired polypeptide or a nucleic acid of interest, operably linked to the nucleic acid defined in (a) above;

c) Optionally, a nucleic acid comprising a 3'-regulatory polynucleotide, preferably a 3'-regulatory polynucleotide of the purH gene.

The regulatory polynucleotide of the 5' regulatory region, or its biologically active fragments or variants, is operably linked at the 5'-end of the polynucleotide encoding the desired polypeptide or polynucleotide.

The regulatory polynucleotide of the 3' regulatory region, or its biologically active fragments or variants, is advantageously operably linked at the 3'-end of the polynucleotide encoding the desired polypeptide or polynucleotide.

The desired polypeptide encoded by the above-described nucleic acid may be of various nature or origin, encompassing proteins of prokaryotic or eukaryotic origin. Among the polypeptides expressed under the control of a purH regulatory region are bacterial, fungal or viral antigens. Also encompassed are eukaryotic proteins such as intracellular proteins, like "house keeping" proteins, membrane-bound proteins, like receptors, and secreted proteins like endogenous mediators such as cytokines. The desired polypeptide may be the purH protein, especially the protein of the amino acid sequence of SEQ ID NO: 3, or a fragment or a variant thereof.

The desired nucleic acids encoded by the above-described polynucleotide, usually an RNA molecule, may be complementary to a desired coding polynucleotide, for example to the purH coding sequence, and thus useful as an antisense polynucleotide.

Such a polynucleotide may be included in a recombinant expression vector in order to express the desired polypeptide or the desired nucleic acid in a host cell or in a host organism. Suitable recombinant vectors that contain a polynucleotide such as described herein are disclosed elsewhere in the specification.

Coding Regions

The purH open reading frame is contained in the corresponding mRNA of SEQ ID NO: 2. More precisely, the effective purH coding sequence (CDS) includes the region between nucleotide position 78 (first nucleotide of the ATG codon) and nucleotide position 1856 (end nucleotide of the TGA codon) of SEQ ID NO: 2. The present invention also embodies isolated, purified, and recombinant polynucleotides which encode a polypeptides comprising a contiguous span of at least 6 amino acids, preferably at least 8 or 10 amino acids, more preferably at least 12, 15, 20, 25, 30, 40, 50, or 100 amino acids of SEQ ID NO: 3, wherein said contiguous span includes a serine residue at amino acid position 116 in SEQ ID NO: 3.

The above disclosed polynucleotide that contains the coding sequence of the purH gene may be expressed in a desired host cell or a desired host organism, when this polynucleotide is placed under the control of suitable expression signals. The expression signals may be either the expression signals contained in the regulatory regions in the purH gene of the invention or in contrast the signals may be exogenous regulatory nucleic sequences. Such a polynucleotide, when placed under the suitable expression signals, may also be inserted in a vector for its expression and/or amplification.

Polynucleotide Constructs

The terms "polynucleotide construct" and "recombinant polynucleotide" are used interchangeably herein to refer to linear or circular, purified or isolated polynucleotides that have been artificially designed and which comprise at least two nucleotide sequences that are not found as contiguous nucleotide sequences in their initial natural environment.

DNA Construct that Enables Directing Temporal and Spatial purH Gene Expression in Recombinant Cell Hosts and in Transgenic Animals.

In order to study the physiological and phenotypic consequences of a lack of synthesis of the purH protein, both at the cell level and at the multi cellular organism level, the invention also encompasses DNA constructs and recombinant vectors enabling a conditional expression of a specific allele of the purH genomic sequence or cDNA and also of a copy of this genomic sequence or cDNA harboring substitutions, deletions, or additions of one or more bases as regards to the purH nucleotide sequence of SEQ ID NOs: 1 and 2, or a fragment thereof, these base substitutions, deletions or additions being located either in an exon, an intron or a regulatory sequence, but preferably in the 5'-regulatory sequence or in an exon of the purH genomic sequence or within the purH cDNA of SEQ ID NO: 2. In a preferred embodiment, the purH sequence comprises a biallelic marker of the present invention. In a preferred embodiment, the purH sequence comprises a biallelic marker of the present invention, preferably one of the biallelic markers A1 to A17, A34 and A35.

The present invention embodies recombinant vectors comprising any one of the polynucleotides described in the present invention. More particularly, the polynucleotide constructs according to the present invention can comprise any of the polynucleotides described in the "Genomic Sequences Of The Human purH Gene" section, the "purH cDNA Sequences" section, the "Coding Regions" section, and the "Oligonucleotide Probes And Primers" section.

A first preferred DNA construct is based on the tetracycline resistance operon tet from *E. coli* transposon Tn10 for controlling the purH gene expression, such as described by Gossen et al. (1992, 1995) and Furth et al. (1994), the disclosures of which are incorporated herein by reference. Such a DNA construct contains seven tet operator sequences from Tn10 (tetop) that are fused to either a minimal promoter or a 5'-regulatory sequence of the purH gene, said minimal promoter or said purH regulatory sequence being operably linked to a polynucleotide of interest that codes either for a sense or an antisense oligonucleotide or for a polypeptide, including a purH polypeptide or a peptide fragment thereof. This DNA construct is functional as a conditional expression system for the nucleotide sequence of interest when the same cell also comprises a nucleotide sequence coding for either the wild type (tTA) or the mutant (rTA) repressor fused to the activating domain of viral protein VP16 of herpes simplex virus, placed under the control of a promoter, such as the HCMVIE1 enhancer/promoter or the MMTV-LTR. Indeed, a preferred DNA construct of the invention comprises both the polynucleotide containing the tet operator sequences and the polynucleotide containing a sequence coding for the tTA or the rTA repressor.

In a specific embodiment, the conditional expression DNA construct contains the sequence encoding the mutant tetracycline repressor rTA, the expression of the polynucleotide of interest is silent in the absence of tetracycline and induced in its presence.

DNA Constructs Allowing Homologous Recombination: Replacement Vectors

A second preferred DNA construct will comprise, from 5'-end to 3'-end: (a) a first nucleotide sequence that is comprised in the purH genomic sequence; (b) a nucleotide sequence comprising a positive selection marker, such as the marker for neomycine resistance (neo); and (c) a second nucleotide sequence that is comprised in the purH genomic sequence, and is located on the genome downstream from the first purH nucleotide sequence (a).

In a preferred embodiment, this DNA construct also comprises a negative selection marker located upstream from the nucleotide sequence (a) or downstream from the nucleotide sequence (c). Preferably, the negative selection marker consists of the thymidine kinase (tk) gene (Thomas et al., 1986), the hygromycine beta gene (Te Riele et al., 1990), the hprt gene (Van der Lugt et al., 1991; Reid et al., 1990) or the Diphteria toxin A fragment (Dt-A) gene (Nada et al., 1993; Yagi et al., 1990), the disclosures of which are incorporated herein by reference. Preferably, the positive selection marker is located within a purH exon sequence so as to interrupt the sequence encoding a purH protein. These replacement vectors are described, for example, by Thomas et al. (1986; 1987), Mansour et al. (1988) and Koller et al. (1992), the disclosures of which are incorporated herein by reference.

The first and second nucleotide sequences (a) and (c) may be indifferently located within a purH regulatory sequence, an intronic sequence, an exon sequence or a sequence containing both regulatory and/or intronic and/or exon sequences. The size of the nucleotide sequences (a) and (c) ranges from 1 to 50 kb, preferably from 1 to 10 kb, more preferably from 2 to 6 kb and most preferably from 2 to 4 kb.

DNA Constructs Allowing Homologous Recombination: Cre-LoxP System.

These new DNA constructs make use of the site specific recombination system of the P1 phage. The P1 phage possesses a recombinase called Cre which interacts specifically with a 34 base pairs loxP site. The loxP site is composed of two palindromic sequences of 13 bp separated by a 8 bp conserved sequence (Hoess et al., 1986), the disclosure of which is incorporated herein by reference. The recombination by the Cre enzyme between two loxP sites having an identical orientation leads to the deletion of the DNA fragment.

The Cre-loxP system used in combination with a homologous recombination technique has been first described by Gu et al. (1993, 1994), the disclosures of which are incorporated herein by reference. Briefly, a nucleotide sequence of interest to be inserted in a targeted location of the genome harbors at least two loxP sites in the same orientation and located at the respective ends of a nucleotide sequence to be excised from the recombinant genome. The excision event requires the presence of the recombinase (Cre) enzyme within the nucleus of the recombinant cell host. The recombinase enzyme may be brought at the desired time either by (a) incubating the recombinant cell hosts in a culture medium containing this enzyme, by injecting the Cre enzyme directly into the desired cell, such as described by Araki et al. (1995), the disclosure of which is incorporated herein by reference, or by lipofection of the enzyme into the cells, such as described by Baubonis et al. (1993), the disclosure of which is incorporated herein by reference; (b) transfecting the cell host with a vector comprising the Cre coding sequence operably linked to a promoter functional in the recombinant cell host, which promoter being optionally inducible, said vector being introduced in the recombinant cell host, such as described by Gu et al. (1993) and Sauer et al. (1988), the disclosures of which are incorporated herein by reference; (c) introducing in the genome of the cell host a polynucleotide comprising the Cre coding sequence operably linked to a promoter functional in the recombinant cell host, which promoter is optionally inducible, and said polynucleotide being inserted in the genome of the cell host either by a random insertion event or an homologous recombination event, such as described by Gu et al. (1994), the disclosure of which is incorporated herein by reference.

In a specific embodiment, the vector containing the sequence to be inserted in the purH gene by homologous recombination is constructed in such a way that selectable markers are flanked by loxP sites of the same orientation, it is possible, by treatment by the Cre enzyme, to eliminate the selectable markers while leaving the purH sequences of interest that have been inserted by an homologous recombination event. Again, two selectable markers are needed: a positive selection marker to select for the recombination event and a negative selection marker to select for the homologous recombination event. Vectors and methods using the Cre-loxP system are described by Zou et al. (1994), the disclosure of which is incorporated herein by reference.

Thus, a third preferred DNA construct of the invention comprises, from 5'-end to 3'-end: (a) a first nucleotide sequence that is comprised in the purH genomic sequence; (b) a nucleotide sequence comprising a polynucleotide encoding a positive selection marker, said nucleotide sequence comprising additionally two sequences defining a site recognized by a recombinase, such as a loxP site, the two sites being placed in the same orientation; and (c) a second nucleotide sequence that is comprised in the purH genomic sequence, and is located on the genome downstream of the first purH nucleotide sequence (a).

The sequences defining a site recognized by a recombinase, such as a loxP site, are preferably located within the nucleotide sequence (b) at suitable locations bordering the nucleotide sequence for which the conditional excision is sought. In one specific embodiment, two loxP sites are located at each side of the positive selection marker sequence, in order to allow its excision at a desired time after the occurrence of the homologous recombination event.

In a preferred embodiment of a method using the third DNA construct described above, the excision of the polynucleotide fragment bordered by the two sites recognized by a recombinase, preferably two loxP sites, is performed at a desired time, due to the presence within the genome of the recombinant host cell of a sequence encoding the Cre enzyme operably linked to a promoter sequence, preferably an inducible promoter, more preferably a tissue-specific promoter sequence and most preferably a promoter sequence which is both inducible and tissue-specific, such as described by Gu et al. (1994).

The presence of the Cre enzyme within the genome of the recombinant cell host may result from the breeding of two transgenic animals, the first transgenic animal bearing the purH-derived sequence of interest containing the loxP sites as described above and the second transgenic animal bearing the Cre coding sequence operably linked to a suitable promoter sequence, such as described by Gu et al. (1994).

Spatio-temporal control of the Cre enzyme expression may also be achieved with an adenovirus based vector that contains the Cre gene thus allowing infection of cells, or in vivo infection of organs, for delivery of the Cre enzyme, such as described by Anton and Graham (1995) and Kanegae et al. (1995), the disclosures of which are incorporated herein by reference.

The DNA constructs described above may be used to introduce a desired nucleotide sequence of the invention, preferably a purH genomic sequence or a purH cDNA sequence, and most preferably an altered copy of a purH genomic or cDNA sequence, within a predetermined location of the targeted genome, leading either to the generation of an altered copy of a targeted gene (knock-out homologous recombination) or to the replacement of a copy of the targeted gene by another copy sufficiently homologous to allow an homologous recombination event to occur (knock-in homologous recombination). In a specific embodiment, the DNA constructs described above may be used to introduce a purH genomic sequence or a purH cDNA sequence comprising at least one biallelic marker of the present invention, preferably at least one biallelic marker selected from the group consisting of A1 to A17, A34 and A35.

Nuclear Antisense DNA Constructs

Other compositions containing a vector of the invention comprising an oligonucleotide fragment of the nucleic sequence SEQ ID NO: 2, preferably a fragment including the start codon of the purH gene, can be used as an antisense tool that inhibits the expression of the corresponding purH gene. Preferred methods using antisense polynucleotide according to the present invention are the procedures described by Sczakiel et al. (1995) or those described in PCT Application No WO 95/24223, the disclosures of which are incorporated by reference herein in their entirety.

Preferably, the antisense tools are chosen among the polynucleotides (15-200 bp long) that are complementary to the 5' end of the purH mRNA. In one embodiment, a combination of different antisense polynucleotides complementary to different parts of the desired targeted gene are used.

Preferred antisense polynucleotides according to the present invention are complementary to a sequence of the mRNAs of purH that contains either the translation initiation codon ATG or a splicing site. Further preferred antisense polynucleotides according to the invention are complementary of the splicing site of the purH mRNA.

Preferably, the antisense polynucleotides of the invention have a 3' polyadenylation signal that has been replaced with a self-cleaving ribozyme sequence, such that RNA polymerase II transcripts are produced without poly(A) at their 3' ends, these antisense polynucleotides being incapable of export from the nucleus, such as described by Liu et al. (1994), the disclosure of which is incorporated herein by reference. In a preferred embodiment, these purH antisense polynucleotides also comprise, within the ribozyme cassette, a histone stem-loop structure to stabilize cleaved transcripts against 3'-5' exonucleolytic degradation, such as the structure described by Eckner et al. (1991), the disclosure of which is incorporated herein by reference.

Oligonucleotide Probes and Primers

Polynucleotides derived from the purH gene are useful in order to detect the presence of at least a copy of a nucleotide sequence of SEQ ID NO: 1, or a fragment, complement, or variant thereof in a test sample.

Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID NO: 1 or the complements thereof, wherein said contiguous span comprises at least 1, 2, 3, 5, or 10 of the following nucleotide positions of SEQ ID NO: 1: 1-1587, 1729-2000, 2095-2414, 2558-3235, 3848-3991, 4156-7043, 7396-7958, 8237-9596, 9666-9874, 9921-10039, 10083-11742, 11825-15173, 15267-15916, 16075-16750, 16916-22304, 22443-23269, 23384-24834, 24927-25952, 26048-28683, 28829-34694, 37282-37458, 37765-37894, 38563-38932, 39178-39451, 39692-39821, 40038-40445, and 40846-41587. Additional preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID NO: 1 or the complements thereof, wherein said contiguous span comprises either a G at position 15234, or a G at position 36801 of SEQ ID NO: 1. Further preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID NO: 1 or the complements thereof, wherein said contiguous span comprises at least 1, 2, 3, 5, or 10 of the following nucleotide positions of SEQ ID NO: 1: 1-1587, 1729-2000, 2095-2414, 2558-3235, 3848-3991, 4156-5000, 5001-6000, 6001-7043, 7396-7958, 8237-9596, 9666-9874, 9921-10039, 10083-11742, 11825-13000, 13001-14000, 14001-15173, 15267-15916, 16075-16750, 16916-18000, 18001-19000, 19001-20000, 20001-21000, 21001-22304, 22443-23269, 23384-24834, 24927-25952, 26048-27000, 27001-28000, 28001-28683, 28829-30000, 30001-31000, 31001-32000, 32001-33000, 33001-34694, 37282-37458, 37765-37894, 38563-38932, 39178-39451, 39692-39821, 40038-40445, and 40846-41587.

Another object of the invention is a purified, isolated, or recombinant polynucleotide comprising the nucleotide sequence of SEQ ID NO: 2, complementary sequences thereto, as well as allelic variants, and fragments thereof. Moreover, preferred primers and probes of the invention include purified, isolated, or recombinant purH cDNAs consisting of, consisting essentially of, or comprising the sequence of SEQ ID NO: 2. Particularly preferred probes and primers of the invention comprise a contiguous span of at least 12, 15, 18, 20, 25, 30, 35, 40, 50, 60, 70, 80, 90, 100, 150, 200, 500, or 1000 nucleotides of SEQ ID NO: 2 or the complements thereof, wherein said contiguous span comprises a nucleotide selected in the group consisting of a G at position 424, and a G at position 1520 of SEQ ID NO: 2.

A further embodiment of the invention includes isolated, purified, or recombinant polynucleotides comprising a contiguous span of at least 12, 15, 18, 20, 25, 30, 35, 40, 50, 60, 70, 80, 90, 100, 150, 200, or 500 nucleotides, to the extent that such lengths are consistent with the specific sequence, of a sequence selected from the group consisting of SEQ ID NOs: 4 to 22, and the complements thereof, optionally wherein said contiguous span comprises either allele 1 or allele 2 of a purH-related biallelic marker selected from the group consisting of A18 to A33 and A36 to A43.

Thus, the invention also relates to nucleic acid probes characterized in that they hybridize specifically, under the stringent hybridization conditions defined above, with a nucleic acid selected from the group consisting of the nucleotide sequences 1-1587, 1729-2000, 2095-2414, 2558-3235, 3848-3991, 4156-7043, 7396-7958, 8237-9596, 9666-9874, 9921-10039, 10083-11742, 11825-15173, 15267-15916, 16075-16750, 16916-22304, 22443-23269, 23384-24834, 24927-25952, 26048-28683, 28829-34694, 37282-37458, 37765-37894, 38563-38932, 39178-39451, 39692-39821, 40038-40445, and 40846-41587 of SEQ ID NO: 1 or a variant thereof or a sequence complementary thereto.

The formation of stable hybrids depends on the melting temperature (Tm) of the DNA. The Tm depends on the length of the primer or probe, the ionic strength of the solution and the G+C content. The higher the G+C content of the primer or probe, the higher is the melting temperature because G:C pairs are held by three H bonds whereas A:T pairs have only two. The GC content in the probes of the invention usually ranges between 10 and 75%, preferably between 35 and 60%, and more preferably between 40 and 55%.

A probe or a primer according to the invention has between 8 and 1000 nucleotides in length, or is specified to be at least 12, 15, 18, 20, 25, 35, 40, 50, 60, 70, 80, 100, 250, 500 or 1000 nucleotides in length. More particularly, the length of these probes can range from 8, 10, 15, 20, or 30 to 100 nucleotides, preferably from 10 to 50, more preferably from 15 to 30 nucleotides. Shorter probes tend to lack specificity for a target nucleic acid sequence and generally require cooler temperatures to form sufficiently stable hybrid complexes with the template. Longer probes are expensive to produce and can sometimes self-hybridize to form hairpin structures. The appropriate length for primers and probes under a particular set of assay conditions may be empirically determined by one of skill in the art.

A preferred probe or primer consists of a nucleic acid comprising a polynucleotide selected from the group of the nucleotide sequences of P1 to P42 and the complementary sequence thereto, B1 to B34, C1 to C34, D1 to D42, E1 to E42, for which the respective locations in the sequence listing are provided in Tables 1, 2 and 3.

Additionally, another preferred embodiment of a probe according to the invention consists of a nucleic acid comprising a biallelic marker selected from the group consisting of A1 to A43 or the complements thereto, for which the respective locations in the sequence listing are provided in Table 2.

The invention also relates to a purified and/or isolated nucleotide sequence comprising a polymorphic base of a purH-related biallelic marker, preferably of a biallelic marker selected from the group consisting of A1 to A43, and the complements thereof. The sequence has between 8 and 1000 nucleotides in length, and preferably comprises at least 8, 10, 12, 15, 18, 20, 25, 35, 40, 50, 60, 70, 80, 100, 250, 500 or 1000 contiguous nucleotides, to the extent that such lengths are consistent with the specific sequence, of a nucleotide sequence selected from the group consisting of SEQ ID NOs: 1, 2, and 4 to 22 or a variant thereof or a complementary sequence thereto. In one embodiment the invention encompasses isolated, purified, and recombinant polynucleotides consisting of, or consisting essentially of a contiguous span of 8 to 50 nucleotides of any one of SEQ ID NOs: 1, 2, or 4 to 22 and the complement thereof, wherein said span includes a purH-related biallelic marker in said sequence; optionally, wherein said purH-related biallelic marker is selected from the group consisting of A1 to A43, and the complements thereof, or optionally the biallelic markers in linkage disequilibrium therewith; optionally, wherein said purH-related biallelic marker is selected from the group consisting of A1, A3 to A14, A16 to A17, A34, and A35, and the complements thereof, or optionally the biallelic markers in linkage disequilibrium therewith; optionally, wherein said purH-related biallelic marker is selected from the group consisting of A2 and A15, and the complements thereof, or optionally the biallelic markers in linkage disequilibrium therewith; optionally, wherein said purH-related biallelic marker is selected from the group consisting of A18 to A33 and A36 to A43; optionally, wherein said purH-related biallelic marker is selected from the group consisting of A29, A7, A20, A10 and A13, and the complements thereof, or optionally the biallelic markers in linkage disequilibrium therewith; optionally, wherein said purH-related biallelic marker is selected from the group consisting of A30, A17, A28, A25, A21, and A14, and the complements thereof, or optionally the biallelic markers in linkage disequilibrium therewith. These nucleotide sequences comprise the polymorphic base of either allele 1 or allele 2 of the considered biallelic marker. Optionally, said biallelic marker may be within 6, 5, 4, 3, 2, or 1 nucleotides of the center of said polynucleotide or at the center of said polynucleotide; optionally, wherein said contiguous span is 18 to 35 nucleotides in length and said biallelic marker is within 4 nucleotides of the center of said polynucleotide; optionally, wherein said polynucleotide consists of said contiguous span and said contiguous span is 25 nucleotides in length and said biallelic marker is at the center of said polynucleotide; optionally, wherein the 3' end of said contiguous span is present at the 3' end of said polynucleotide; and optionally, wherein the 3' end of said contiguous span is located at the 3' end of said polynucleotide and said biallelic marker is present at the 3' end of said polynucleotide. Optionally, said polynucleotide may further comprise a label. Optionally, said polynucleotide can be attached to solid support. In a further embodiment, the polynucleotides defined above can be used alone or in any combination. In a preferred embodiment, said probes comprises, consists of, or consists essentially of a sequence selected from the following sequences: P1 to P42 and the complementary sequences thereto.

In another embodiment the invention encompasses isolated, purified and recombinant polynucleotides comprising, consisting of, or consisting essentially of a contiguous span of 8 to 50 nucleotides of SEQ ID NOs: 1, 2, or 4 to 22 or the complements thereof, wherein the 3' end of said contiguous span is located at the 3' end of said polynucleotide, and wherein the 3' end of said polynucleotide is located within or at least 2, 4, 6, 8, 10, 12, 15, 18, 20, 25, 50, 100, 250, 500, or 1000 nucleotides upstream of a purH-related biallelic marker in said sequence, preferably within 20 nucleotides upstream; optionally, wherein said purH-related biallelic marker is selected from the group consisting of A1 to A43, and the complements thereof, or optionally the biallelic markers in linkage disequilibrium therewith; optionally, wherein said purH-related biallelic marker is selected from the group consisting of A1, A3 to A14, A16 to A17, A34, and A35, and the complements thereof, or optionally the biallelic markers in linkage disequilibrium therewith; optionally, wherein said purH-related biallelic marker is selected from the group consisting of A2 and A15, and the complements thereof, or optionally the biallelic markers in linkage disequilibrium therewith; optionally, wherein said purH-related biallelic marker is selected from the group consisting of A18 to A33 and A36 to A43; optionally, wherein said purH-related biallelic marker is selected from the group consisting of A29, A7, A20, A10 and A13, and the complements thereof, or optionally the biallelic markers in linkage disequilibrium therewith; optionally, wherein said purH-related biallelic marker is selected from the group consisting of A30, A17, A28, A25, A21, and A14, and the complements thereof, or optionally the biallelic markers in linkage disequilibrium therewith; optionally, wherein the 3' end of said polynucleotide is located 1 nucleotide upstream of said purH-related biallelic marker in said sequence; and optionally, wherein said polynucleotide consists essentially of a sequence selected from the following sequences: D1 to D42 and E1 to E42. Optionally, said polynucleotide may further comprise a label. Optionally, said polynucleotide can be attached to solid support. In a further embodiment, the polynucleotides defined above can be used alone or in any combination.

In a further embodiment, the invention encompasses isolated, purified, or recombinant polynucleotides comprising, consisting of, or consisting essentially of a sequence selected from the following sequences: B1 to B34 and C1 to C34.

In an additional embodiment, the invention encompasses the use of any polynucleotide, or polynucleotides, for use in determining the identity of the nucleotide at a purH-related biallelic marker or the complements thereof, as well as polynucleotides for use or use of polynucleotides in amplifying segments of nucleotides comprising a purH-related biallelic marker or the complements thereof; optionally, said determining may be performed in a hybridization assay, sequencing assay, microsequencing assay, or an enzyme-based mismatch detection assay; optionally, said amplifying may be performed by a PCR or LCR. Optionally, wherein said purH-related biallelic marker is selected from the group consisting of A1 to A43, and the complements thereof, or optionally the biallelic markers in linkage disequilibrium therewith; optionally, wherein said purH-related biallelic marker is selected from the group consisting of A1, A3 to A14, A16 to A17, A34, and A35, and the complements thereof, or optionally the biallelic markers in linkage disequilibrium therewith; optionally, wherein said purH-related biallelic marker is selected from the group consisting of A2 and A15, and the complements thereof, or optionally the biallelic markers in linkage disequilibrium therewith; optionally, wherein said purH-related biallelic marker is selected from the group consisting of A18 to A33 and A36 to A43; optionally, wherein said purH-related biallelic marker is selected from the group consisting of A29, A7, A20, A10 and A13, and the complements thereof, or optionally the biallelic markers in linkage disequilibrium therewith; optionally, wherein said purH-related biallelic marker is selected from the group consisting of A30, A17, A28, A25, A21, and A14, and the complements thereof, or optionally the biallelic markers in linkage disequilibrium therewith; optionally, said polynucleotide may be attached to a solid support, array, or addressable array; optionally, said polynucleotide may be labeled.

The invention concerns the use of the polynucleotides according to the invention for determining the identity of the nucleotide at a purH-related biallelic marker, preferably in hybridization assay, sequencing assay, microsequencing assay, or an enzyme-based mismatch detection assay and in amplifying segments of nucleotides comprising a purH-related biallelic marker. In addition, the polynucleotides of the invention for use or the use of polynucleotides in determining the identity of one or more nucleotides at a purH-related biallelic marker encompass polynucleotides with any further limitation described in this disclosure, or those following, specified alone or in any combination.

The primers and probes can be prepared by any suitable method, including, for example, cloning and restriction of appropriate sequences and direct chemical synthesis by a method such as the phosphodiester method of Narang et al. (1979), the phosphodiester method of Brown et al. (1979), the diethylphosphoramidite method of Beaucage et al. (1981) and the solid support method described in EP 0 707 592. The disclosures of the preceding documents are incorporated herein by reference in their entirety.

Detection probes are generally nucleic acid sequences or uncharged nucleic acid analogs such as, for example peptide nucleic acids which are disclosed in International Patent Application WO 92/20702, morpholino analogs which are described in U.S. Pat. Nos. 5,185,444; 5,034,506 and 5,142,047. The probe may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified, U.S. patent application Ser. No. 07/049,061 filed Apr. 19, 1993 describes modifications, which can be used to render a probe non-extendable.

Any of the polynucleotides of the present invention can be labeled, if desired, by incorporating a label detectable by spectroscopic, photochemical, biochemical, immunochemical, or chemical means. For example, useful labels include radioactive substances ($^{32}P$, $^{35}S$, $^{3}H$, $^{125}I$), fluorescent dyes (5-bromodesoxyuridin, fluorescein, acetylaminofluorene, digoxigenin) or biotin. Preferably, polynucleotides are labeled at their 3' and 5' ends. Examples of non-radioactive labeling of nucleic acid fragments are described in the French patent No. FR-7810975 or by Urdea et al (1988) or Sanchez-Pescador et al (1988), the disclosures of which are incorporated herein by reference. In addition, the probes according to the present invention may have structural characteristics such that they allow the signal amplification, such structural characteristics being, for example, branched DNA probes as those described by Urdea et al. in 1991 or in the European patent No. EP 0 225 807 (Chiron), the disclosures of which are incorporated by reference herein in their entirety.

A label can also be used to capture the primer, so as to facilitate the immobilization of either the primer or a primer extension product, such as amplified DNA, on a solid support. A capture label is attached to the primers or probes and can be a specific binding member which forms a binding pair with the solid's phase reagent's specific binding member (e.g. biotin and streptavidin). Therefore depending upon the type of label carried by a polynucleotide or a probe, it may be employed to capture or to detect the target DNA. Further, it will be understood that the polynucleotides, primers or probes provided herein, may, themselves, serve as the capture label. For example, in the case where a solid phase reagent's binding member is a nucleic acid sequence, it may be selected such that it binds a complementary portion of a primer or probe to thereby immobilize the primer or probe to the solid phase. In cases where a polynucleotide probe itself serves as the binding member, those skilled in the art will recognize that the probe will contain a sequence or "tail" that is not complementary to the target. In the case where a polynucleotide primer itself serves as the capture label, at least a portion of the primer will be free to hybridize with a nucleic acid on a solid phase. DNA labeling techniques are well known to the skilled technician.

The probes of the present invention are useful for a number of purposes. They can be notably used in Southern hybridization to genomic DNA. The probes can also be used to detect PCR amplification products. They may also be used to detect mismatches in the purH gene or mRNA using other techniques.

Any of the polynucleotides, primers and probes of the present invention can be conveniently immobilized on a solid support. Solid supports are known to those skilled in the art and include the walls of wells of a reaction tray, test tubes, polystyrene beads, magnetic beads, nitrocellulose strips, membranes, microparticles such as latex particles, sheep (or other animal) red blood cells, duracytes and others. The solid support is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, duracytes® and other configurations known to those of ordinary skill in the art. The polynucleotides of the invention can be attached to or immobilized on a solid support individually or in groups of at least 2, 5, 8, 10, 12, 15, 20, or 25 distinct polynucleotides of the invention to a single solid support. In addition, polynucleotides other than those of the invention may be attached to the same solid support as one or more polynucleotides of the invention.

Consequently, the invention also deals with a method for detecting the presence of a nucleic acid comprising a nucleotide sequence selected from a group consisting of SEQ ID NOs: 1, 2, a fragment or a variant thereof and a complementary sequence thereto in a sample, said method comprising the following steps of:

a) bringing into contact a nucleic acid probe or a plurality of nucleic acid probes which can hybridize with a nucleotide sequence included in a nucleic acid selected from the group consisting of the nucleotide sequences of SEQ ID NOs: 1, 2, a fragment or a variant thereof and a complementary sequence thereto and the sample to be assayed.

b) detecting the hybrid complex formed between the probe and a nucleic acid in the sample.

The invention further concerns a kit for detecting the presence of a nucleic acid comprising a nucleotide sequence selected from a group consisting of SEQ ID NOs: 1, 2, a fragment or a variant thereof and a complementary sequence thereto in a sample, said kit comprising:

a) a nucleic acid probe or a plurality of nucleic acid probes which can hybridize with a nucleotide sequence included in a nucleic acid selected from the group consisting of the nucleotide sequences of SEQ ID NOs: 1, 2, a fragment or a variant thereof and a complementary sequence thereto;

b) optionally, the reagents necessary for performing the hybridization reaction.

In a first preferred embodiment of this detection method and kit, said nucleic acid probe or the plurality of nucleic acid probes are labeled with a detectable molecule. In a second preferred embodiment of said method and kit, said nucleic acid probe or the plurality of nucleic acid probes has been immobilized on a substrate. In a third preferred embodiment, the nucleic acid probe or the plurality of nucleic acid probes comprise either a sequence which is selected from the group consisting of the nucleotide sequences of P1 to P42 and the complementary sequence thereto, B1 to B34, C1 to C34, D1 to D42, E1 to E42, or a biallelic marker selected from the group consisting of A1 to A43 and the complements thereto.

Oligonucleotide Arrays

A substrate comprising a plurality of oligonucleotide primers or probes of the invention may be used either for detecting or amplifying targeted sequences in the purH gene and may also be used for detecting mutations in the coding or in the non-coding sequences of the purH gene.

Any polynucleotide provided herein may be attached in overlapping areas or at random locations on the solid support. Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotide's location makes these "addressable" arrays particularly useful in hybridization assays. Any addressable array technology known in the art can be employed with the polynucleotides of the invention. One particular embodiment of these polynucleotide arrays is known as the Genechips™, and has been generally described in U.S. Pat. No. 5,143,854; PCT publications WO 90/15070 and 92/10092, the disclosures of which are incorporated by reference herein in their entirety. These arrays may generally be produced using mechanical synthesis methods or light directed synthesis methods which incorporate a combination of photolithographic methods and solid phase oligonucleotide synthesis (Fodor et al., 1991), the disclosure of which is incorporated herein by reference. The immobilization of arrays of oligonucleotides on solid supports has been rendered possible by the development of a technology generally identified as "Very Large Scale Immobilized Polymer Synthesis" (VLSIPS™) in which, typically, probes are immobilized in a high density array on a solid surface of a chip. Examples of VLSIPS™ technologies are provided in U.S. Pat. Nos. 5,143,854; and 5,412,087 and in PCT Publications WO 90/15070, WO 92/10092 and WO 95/11995, the disclosures of which are incorporated by reference herein in their entirety, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256, the disclosures of which are incorporated by reference herein in their entirety.

In another embodiment of the oligonucleotide arrays of the invention, an oligonucleotide probe matrix may advantageously be used to detect mutations occurring in the purH gene and preferably in its regulatory region. For this particular purpose, probes are specifically designed to have a nucleotide sequence allowing their hybridization to the genes that carry known mutations (either by deletion, insertion or substitution of one or several nucleotides). By known mutations, it is meant, mutations on the purH gene that have been identified according, for example to the technique used by Huang et al. (1996) or Samson et al. (1996), the disclosures of which are incorporated herein by reference.

Another technique that is used to detect mutations in the purH gene is the use of a high-density DNA array. Each oligonucleotide probe constituting a unit element of the high density DNA array is designed to match a specific subsequence of the purH genomic DNA or cDNA. Thus, an array consisting of oligonucleotides complementary to subsequences of the target gene sequence is used to determine the identity of the target sequence with the wild gene sequence, measure its amount, and detect differences between the target sequence and the reference wild gene sequence of the purH gene. In one such design, termed 4L tiled array, is implemented a set of four probes (A, C, G, T), preferably 15-nucleotide oligomers. In each set of four probes, the perfect complement will hybridize more strongly than mismatched probes. Consequently, a nucleic acid target of length L is scanned for mutations with a tiled array containing 4L probes, the whole probe set containing all the possible mutations in the known wild reference sequence. The hybridization signals of the 15-mer probe set tiled array are perturbed by a single base change in the target sequence. As a consequence, there is a characteristic loss of signal or a "footprint" for the probes flanking a mutation position. This technique was described by Chee et al. in 1996, which is herein incorporated by reference.

Consequently, the invention concerns an array of nucleic acid molecules comprising at least one polynucleotide described above as probes and primers. Preferably, the invention concerns an array of nucleic acid comprising at least two polynucleotides described above as probes and primers.

A further object of the invention consists of an array of nucleic acid sequences comprising either at least one of the sequences selected from the group consisting of P1 to P42, B1 to B34, C1 to C34, D1 to D42, E1 to E42, the sequences complementary thereto, a fragment thereof of at least 8, 10, 12, 15, 18, 20, 25, 30, or 40 consecutive nucleotides thereof, and at least one sequence comprising a biallelic marker selected from the group consisting of A1 to A43 and the complements thereto.

The invention also pertains to an array of nucleic acid sequences comprising either at least two of the sequences selected from the group consisting of P1 to P42, B1 to B34, C1 to C34, D1 to D42, E1 to E42, the sequences complementary thereto, a fragment thereof of at least 8 consecutive nucleotides thereof, and at least two sequences comprising a biallelic marker selected from the group consisting of A1 to A43 and the complements thereof.

purH Proteins and Polypeptide Fragments

The term "purH polypeptides" is used herein to embrace all of the proteins and polypeptides of the present invention. Also forming part of the invention are polypeptides encoded by the polynucleotides of the invention, as well as fusion polypeptides comprising such polypeptides.

The invention concerns the polypeptide encoded by a nucleotide sequence selected from the group consisting of SEQ ID NO: 1 or 2, a complementary sequence thereof or a fragment thereto.

The invention embodies purH proteins from humans, including isolated or purified purH proteins consisting, consisting essentially, or comprising the sequence of SEQ ID NO: 3. It should be noted the purH proteins of the invention are based on the naturally-occurring variant of the amino acid sequence of human purH, wherein the threonine residue of amino acid position 116 has been replaced with a serine residue. This variant protein and the fragments thereof which contain a serine at the amino acid position 116 of SEQ ID NO: 3 are collectively referred to herein as "116-Ser variants."

The present invention embodies isolated, purified, and recombinant polypeptides comprising a contiguous span of at least 6 amino acids, preferably at least 8 to 10 amino acids, more preferably at least 12, 15, 20, 25, 30, 40, 50, or 100 amino acids of SEQ ID NO: 3, wherein said contiguous span includes a serine residue at amino acid position 116 in SEQ ID NO: 3. In other preferred embodiments the contiguous stretch of amino acids comprises the site of a mutation or functional mutation, including a deletion, addition, swap or truncation of the amino acids in the purH protein sequence.

purH proteins are preferably isolated from human or mammalian tissue samples or expressed from human or mammalian genes. The purH polypeptides of the invention can be made using routine expression methods known in the art. The polynucleotide encoding the desired polypeptide is ligated into an expression vector suitable for any convenient host. Both eukaryotic and prokaryotic host systems are used in forming recombinant polypeptides, and a summary of some of the more common systems. The polypeptide is then isolated from lysed cells or from the culture medium and purified to the extent needed for its intended use. Purification is by any technique known in the art, for example, differential extraction, salt fractionation, chromatography, centrifugation, and the like. See, for example, Methods in Enzymology for a variety of methods for purifying proteins.

In addition, shorter protein fragments are produced by chemical synthesis. Alternatively the proteins of the invention are extracted from cells or tissues of humans or non-human animals. Methods for purifying proteins are known in the art, and include the use of detergents or chaotropic agents to disrupt particles followed by differential extraction and separation of the polypeptides by ion exchange chromatography, affinity chromatography, sedimentation according to density, and gel electrophoresis.

Any purH cDNA, including SEQ ID NO: 2, is used to express purH proteins and polypeptides. The nucleic acid encoding the purH protein or polypeptide to be expressed is operably linked to a promoter in an expression vector using conventional cloning technology. The purH insert in the expression vector may comprise the full coding sequence for the purH protein or a portion thereof. For example, the purH derived insert may encode a polypeptide comprising at least 10 consecutive amino acids of the purH protein of SEQ ID NO: 3, wherein said consecutive amino acids comprise a serine residue in amino acid position 116.

The expression vector is any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence is optimized for the particular expression organism in which the expression vector is introduced, as explained by Hatfield, et al., U.S. Pat. No. 5,082,767, the disclosures of which are incorporated by reference herein in their entirety.

In one embodiment, the entire coding sequence of the purH cDNA through the poly A signal of the cDNA is operably linked to a promoter in the expression vector. Alternatively, if the nucleic acid encoding a portion of the purH protein lacks a methionine to serve as the initiation site, an initiating methionine can be introduced next to the first codon of the nucleic acid using conventional techniques. Similarly, if the insert from the purH cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene. The nucleic acid encoding the purH protein or a portion thereof is obtained by PCR from a bacterial vector containing the purH cDNA of SEQ ID NO: 2 using oligonucleotide primers complementary to the purH cDNA or portion thereof and containing restriction endonuclease sequences for Pst I incorporated into the 5' primer and BglII at the 5' end of the corresponding cDNA 3' primer, taking care to ensure that the sequence encoding the purH protein or a portion thereof is positioned properly with respect to the poly A signal. The purified fragment obtained from the resulting PCR reaction is digested with PstI, blunt ended with an exonuclease, digested with Bgl II, purified and ligated to pXT1, now containing a poly A signal and digested with BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.).

Alternatively, the nucleic acids encoding the purH protein or a portion thereof is cloned into pED6dpc2 (Genetics Institute, Cambridge, Mass.). The resulting pED6dpc2 constructs is transfected into a suitable host cell, such as COS 1 cells. Methotrexate resistant cells are selected and expanded.

The above procedures may also be used to express a mutant purH protein responsible for a detectable phenotype or a portion thereof.

The expressed proteins are purified using conventional purification techniques such as ammonium sulfate precipitation or chromatographic separation based on size or charge. The protein encoded by the nucleic acid insert may also be purified using standard immunochromatography techniques. In such procedures, a solution containing the expressed purH protein or portion thereof, such as a cell extract, is applied to a column having antibodies against the purH protein or portion thereof attached to the chromatography matrix. The expressed protein is allowed to bind to the immunochromatography column. Thereafter, the column is washed to remove non-specifically bound proteins. The specifically bound expressed protein is then released from the column and recovered using standard techniques.

To confirm expression of the purH protein or a portion thereof, the proteins expressed from host cells containing an expression vector containing an insert encoding the purH protein or a portion thereof can be compared to the proteins expressed in host cells containing the expression vector without an insert. The presence of a band in samples from cells containing the expression vector with an insert which is absent in samples from cells containing the expression vector without an insert indicates that the purH protein or a portion thereof is being expressed. Generally, the band will have the mobility expected for the purH protein or portion thereof. However, the band may have a mobility different than that expected as a result of modifications such as glycosylation, ubiquitination, or enzymatic cleavage.

Antibodies capable of specifically recognizing the expressed purH protein or a portion thereof are described below.

If antibody production is not possible, the nucleic acids encoding the purH protein or a portion thereof are incorporated into expression vectors designed for use in purification schemes employing chimeric polypeptides. In such strategies the nucleic acid encoding the purH protein or a portion thereof is inserted in frame with the gene encoding the other half of the chimera. The other half of the chimera is β-globin or a nickel binding polypeptide encoding sequence. A chromatography matrix having antibody to β-globin or nickel attached thereto is then used to purify the chimeric protein. Protease cleavage sites are engineered between the β-globin gene or the nickel binding polypeptide and the purH protein or portion thereof. Thus, the two polypeptides of the chimera are separated from one another by protease digestion.

One useful expression vector for generating β-globin chimeric proteins is pSG5 (Stratagene), which encodes rabbit β-globin. Intron II of the rabbit β-globin gene facilitates splicing of the expressed transcript, and the polyadenylation signal incorporated into the construct increases the level of expression. These techniques are well known to those skilled in the art of molecular biology. Standard methods are published in methods texts such as Davis et al., (1986) and many of the methods are available from Stratagene, Life Technologies, Inc., or Promega. Polypeptide may additionally be produced from the construct using in vitro translation systems such as the In vitro Express™ Translation Kit (Stratagene).

Antibodies that Bind purH Polypeptides of the Invention

Any purH polypeptide or whole protein may be used to generate antibodies capable of specifically binding to expressed purH protein or fragments thereof as described. The antibody compositions of the invention are capable of specifically binding or specifically bind to the 116-Ser variant of the purH protein. For an antibody composition to specifically bind to the 116-Ser variant of purH it must demonstrate at least a 5%, 10%, 15%, 20%, 25%, 50%, or 100% greater binding affinity for full length 116-Ser variant of purH than for full length 116-Thr variant of purH in an ELISA, RIA, or other antibody-based binding assay.

In a preferred embodiment of the invention antibody compositions are capable of selectively binding, or selectively bind to an epitope-containing fragment of a polypeptide comprising a contiguous span of at least 6 amino acids, preferably at least 8 to 10 amino acids, more preferably at least 12, 15, 20, 25, 30, 40, 50, or 100 amino acids of SEQ ID NO: 3, wherein said epitope comprises a serine residue at amino acid position 116 in SEQ ID NO: 3, wherein said antibody composition is optionally either polyclonal or monoclonal.

The present invention also contemplates the use of polypeptides comprising a contiguous span of at least 6 amino acids, preferably at least 8 to 10 amino acids, more preferably at least 12, 15, 20, 25, 50, or 100 amino acids of a purH polypeptide in the manufacture of antibodies, wherein said contiguous span comprises a serine residue at amino acid position 116 of SEQ ID NO: 3. In a preferred embodiment such polypeptides are useful in the manufacture of antibodies to detect the presence and absence of the 116-Ser variant.

Non-human animals or mammals, whether wild-type or transgenic, which express a different species of purH than the one to which antibody binding is desired, and animals which do not express purH (i.e. a purH knock out animal as described in herein) are particularly useful for preparing antibodies. purH knock out animals will recognize all or most of the exposed regions of purH as foreign antigens, and therefore produce antibodies with a wider array of purH epitopes. Moreover, smaller polypeptides with only 10 to 30 amino acids may be useful in obtaining specific binding to the 116-Ser variant. In addition, the humoral immune system of animals which produce a species of purH that resembles the antigenic sequence will preferentially recognize the differences between the animal's native purH species and the antigen sequence, and produce antibodies to these unique sites in the antigen sequence. Such a technique will be particularly useful in obtaining antibodies that specifically bind to the 116-Ser variant.

Preparation of Antibody Compositions to the 116-Ser Variant of purH

Substantially pure protein or polypeptide is isolated from transfected or transformed cells containing an expression vector encoding the purH protein or a portion thereof. The concentration of protein in the final preparation is adjusted, for example, by concentration on an Amicon filter device, to the level of a few micrograms/ml. Monoclonal or polyclonal antibody to the protein can then be prepared as follows:

A. Monoclonal Antibody Production by Hybridoma Fusion

Monoclonal antibody to epitopes in the purH protein or a portion thereof can be prepared from murine hybridomas according to the classical method of Kohler, G. and Milstein, C., (1975) or derivative methods thereof. Also see Harlow, E., and D. Lane. 1988.

Briefly, a mouse is repetitively inoculated with a few micrograms of the purH protein or a portion thereof over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, N.Y. Section 21-2.

B. Polyclonal Antibody Production by Immunization

Polyclonal antiserum containing antibodies to heterogeneous epitopes in the purH protein or a portion thereof can be prepared by immunizing a suitable non-human animal with the purH protein or a portion thereof, which can be unmodified or modified to enhance immunogenicity. A suitable non-human animal, preferably a non-human mammal and, is selected, usually, from a mouse, rat, rabbit, goat, or horse. Alternatively, a crude preparation which has been enriched for purH concentration can be used to generate antibodies. Such proteins, fragments or preparations are introduced into the non-human mammal in the presence of an appropriate adjuvant (e.g. aluminum hydroxide, RIBI, etc.) which is known in the art. In addition the protein, fragment or preparation can be pretreated with an agent which will increase antigenicity; such agents are known in the art and include, for example, methylated bovine serum albumin (mBSA), bovine serum albumin (BSA), Hepatitis B surface antigen, and keyhole limpet hemocyanin (KLH). Serum from the immunized animal is collected, treated and tested according to known procedures. If the serum contains polyclonal antibodies to undesired epitopes, the polyclonal antibodies can be purified by immunoaffinity chromatography.

Effective polyclonal antibody production is affected by many factors related both to the antigen and the host species. Also, host animals vary in response to site of inoculations and dose, with both inadequate or excessive doses of antigen resulting in low titer antisera. Small doses (ng level) of antigen administered at multiple intradermal sites appears to be most reliable. Techniques for producing and processing polyclonal antisera are known in the art, see for example, Mayer and Walker (1987). An effective immunization protocol for rabbits can be found in Vaitukaitis, J. et al. (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., (1973). Plateau concentration of antibody is usually in the range of 0.1 to 0.2 mg/ml of serum (about 12 µM). Affinity of the antisera for the antigen is determined by preparing competitive binding curves, as described, for example, by Fisher, D., (1980).

Antibody preparations prepared according to either the monoclonal or the polyclonal protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

The antibodies of the invention may be labeled, either by a radioactive, a fluorescent or an enzymatic label.

Consequently, the invention is also directed to a method for detecting specifically the presence of a human purH polypeptide according to the invention in a biological sample, said method comprising the following steps:

a) bringing into contact the biological sample with a polyclonal or monoclonal antibody directed against the purH polypeptide of the amino acid sequence of SEQ ID NO: 3, or to a peptide fragment or variant thereof;

b) detecting the antigen-antibody complex formed.

The invention also concerns a diagnostic kit for detecting in vitro the presence of a human BAP28 polypeptide according to the present invention in a biological sample, wherein said kit comprises:

a) a polyclonal or monoclonal antibody directed against the purH polypeptide of the amino acid sequence of SEQ ID NO: 3, or to a peptide fragment or variant thereof, optionally labeled;

b) a reagent allowing the detection of the antigen-antibody complexes formed, said reagent carrying optionally a label, or being able to be recognized itself by a labeled reagent, more particularly in the case when the above-mentioned monoclonal or polyclonal antibody is not labeled by itself.

In a preferred embodiment of the detection method and kit, the purH polypeptide comprises a Serine residue in position 116 of the SEQ ID NO: 3.

purH-Related Biallelic Markers

Advantages of the Biallelic Markers of the Present Invention

The purH-related biallelic markers of the present invention offer a number of important advantages over other genetic markers such as RFLP (Restriction fragment length polymorphism) and VNTR (Variable Number of Tandem Repeats) markers.

The first generation of markers were RFLPs, which are variations that modify the length of a restriction fragment. But methods used to identify and to type RFLPs are relatively wasteful of materials, effort, and time. The second generation of genetic markers were VNTRs, which can be categorized as either minisatellites or microsatellites. Minisatellites are tandemly repeated DNA sequences present in units of 5-50 repeats which are distributed along regions of the human chromosomes ranging from 0.1 to 20 kilobases in length. Since they present many possible alleles, their informative content is very high. Minisatellites are scored by performing Southern blots to identify the number of tandem repeats present in a nucleic acid sample from the individual being tested. However, there are only 10 potential VNTRs that can be typed by Southern blotting. Moreover, both RFLP and VNTR markers are costly and time-consuming to develop and assay in large numbers.

SNP or biallelic markers can be used in the same manner as RFLPs and VNTRs but offer several advantages. SNP are densely spaced in the human genome and represent the most frequent type of variation. An estimated number of more than $10^7$ sites are scattered along the $3\times10^9$ base pairs of the human genome. Therefore, SNP occur at a greater frequency and with greater uniformity than RFLP or VNTR markers which means that there is a greater probability that such a marker will be found in close proximity to a genetic locus of interest. SNP are less variable than VNTR markers but are mutationally more stable.

Also, the different forms of a characterized single nucleotide polymorphism, such as the biallelic markers of the present invention, are often easier to distinguish and can therefore be typed easily on a routine basis. Biallelic markers have single nucleotide based alleles and they have only two common alleles, which allows highly parallel detection and automated scoring. The biallelic markers of the present invention offer the possibility of rapid, high throughput genotyping of a large number of individuals.

Biallelic markers are densely spaced in the genome, sufficiently informative and can be assayed in large numbers. The combined effects of these advantages make biallelic markers extremely valuable in genetic studies. Biallelic markers can be used in linkage studies in families, in allele sharing methods, in linkage disequilibrium studies in populations, in association studies of case-control populations or of trait positive and trait negative populations. An important aspect of the present invention is that biallelic markers allow association studies to be performed to identify genes involved in complex traits. Association studies examine the frequency of marker alleles in unrelated case- and control-populations and are generally employed in the detection of polygenic or sporadic traits. Association studies may be conducted within the general population and are not limited to studies performed on related individuals in affected families (linkage studies). Biallelic markers in different genes can be screened in parallel for direct association with disease or response to a treatment. This multiple gene approach is a powerful tool for a variety of human genetic studies as it provides the necessary statistical power to examine the synergistic effect of multiple genetic factors on a particular phenotype, drug response, sporadic trait, or disease state with a complex genetic etiology.

purH-Related Biallelic Markers and Polynucleotides Related Thereto

The invention also concerns purH-related biallelic markers. As used herein the term "purH-related biallelic marker" relates to a set of biallelic markers in linkage disequilibrium with the purH gene. The term purH-related biallelic marker includes the biallelic markers designated A1 to A43.

A portion of the biallelic markers of the present invention are disclosed in Table 2. Their location on the purH gene is indicated in Table 2 and also as a single base polymorphism in the features of the related SEQ ID NOs: 1, 2, and 4 to 22. The pairs of primers allowing the amplification of a nucleic acid containing the polymorphic base of one purH biallelic marker are listed in Table 1 of Example 2.

19 purH-related biallelic markers, A1 to A17, A34 and A35, are located in the genomic sequence of purH. Two of them are located in exonic sequence, namely A2 and A15. The biallelic marker A2 provides an amino acid change in which a threonine residue in position 116 of the protein sequence is replaced by a serine residue. 24 purH-related biallelic markers, A18 to A33 and A36 to A43, are located outside of the genomic sequence of purH. However, these are in linkage disequilibrium with the purH gene. 12 of them, A18 to A20, A26, A28, A32, A33, A39, A42 to A44, and A46, are located in intergenic regions. The others are located in a gene localized near the purH gene. This gene is the fibronectin gene.

In a preferred embodiment, the sequences comprising a polymorphic base of one of the biallelic markers listed in Table 2 are selected from the group consisting of the nucleotide sequences that have a contiguous span of, that consist of, that are comprised in, or that comprise a polynucleotide selected from the group consisting of the nucleic acids of the sequences set forth as the amplicons listed in Table 1 or a variant thereof or a complementary sequence thereto.

The invention further concerns a nucleic acid encoding the purH protein, wherein said nucleic acid comprises a polymorphic base of a biallelic marker selected from the group consisting of A1 to A17, A34 and A35 and the complements thereof.

The primers for amplification or sequencing reaction of a polynucleotide comprising a biallelic marker of the invention may be designed from the disclosed sequences for any method known in the art. A preferred set of primers are fashioned such that the 3' end of the contiguous span of identity with a sequence selected from the group consisting of SEQ ID NOs: 1, 2, and 4 to 22 or a sequence complementary thereto or a variant thereof is present at the 3' end of the primer. Such a configuration allows the 3' end of the primer to hybridize to a selected nucleic acid sequence and dramatically increases the efficiency of the primer for amplification or sequencing reactions. Allele specific primers may be designed such that a polymorphic base of a biallelic marker is at the 3' end of the contiguous span and the contiguous span is present at the 3' end of the primer. Such allele specific primers tend to selectively prime an amplification or sequencing reaction so long as they are used with a nucleic acid sample that contains one of the two alleles present at a biallelic marker. The 3' end of the primer of the invention may be located within or at least 2, 4, 6, 8, 10, 12, 15, 18, 20, 25, 50, 100, 250, 500, or 1000 nucleotides upstream of a purH-related biallelic marker in said sequence or at any other location which is appropriate for their intended use in sequencing, amplification or the location of novel sequences or markers. Thus, another set of preferred amplification primers comprise an isolated polynucleotide consisting essentially of a contiguous span of 8 to 50 nucleotides in a sequence selected from the group consisting of SEQ ID NOs: 1, 2, and 4 to 22 or a sequence complementary thereto or a variant thereof, wherein the 3' end of said contiguous span is located at the 3' end of said polynucleotide, and wherein the 3'end of said polynucleotide is located upstream of a purH-related biallelic marker in said sequence. Preferably, those amplification primers comprise a sequence selected from the group consisting of the sequences B1 to B34 and C1 to C34. Primers with their 3' ends located 1 nucleotide upstream of a purH-related biallelic marker have a special utility in microsequencing assays. Preferred microsequencing primers are described in Table 3. Optionally, microsequencing primers are selected from the group consisting of the nucleotide sequences D1 to D42 and E1 to E42.

The probes of the present invention may be designed from the disclosed sequences for any method known in the art, particularly methods which allow for testing if a marker disclosed herein is present. A preferred set of probes may be designed for use in the hybridization assays of the invention in any manner known in the art such that they selectively bind to one allele of a biallelic marker, but not the other allele under any particular set of assay conditions. Preferred hybridization probes comprise the polymorphic base of either allele 1 or allele 2 of the specific biallelic marker. Optionally, said biallelic marker may be within 6, 5, 4, 3, 2, or 1 nucleotides of the center of the hybridization probe or at the center of said probe.

It should be noted that the polynucleotides of the present invention are not limited to having the exact flanking sequences surrounding the polymorphic bases which are enumerated in the Sequence Listing. Rather, it will be appreciated that the flanking sequences surrounding the biallelic markers may be lengthened or shortened to any extent compatible with their intended use and the present invention specifically contemplates such sequences. The flanking regions outside of the contiguous span need not be homologous to native flanking sequences which actually occur in human subjects. The addition of any nucleotide sequence which is compatible with the nucleotide's intended use is specifically contemplated.

Primers and probes may be labeled or immobilized on a solid support as described in "Oligonucleotide probes and primers".

The polynucleotides of the invention which are attached to a solid support encompass polynucleotides with any further limitation described in this disclosure, or those following, specified alone or in any combination: Optionally, said polynucleotides may be specified as attached individually or in groups of at least 2, 5, 8, 10, 12, 15, 20, or 25 distinct polynucleotides of the invention to a single solid support. Optionally, polynucleotides other than those of the invention may attached to the same solid support as polynucleotides of the invention. Optionally, when multiple polynucleotides are attached to a solid support they may be attached at random locations, or in an ordered array. Optionally, said ordered array may be addressable.

The present invention also encompasses diagnostic kits comprising one or more polynucleotides of the invention with a portion or all of the necessary reagents and instructions for genotyping a test subject by determining the identity of a nucleotide at a purH-related biallelic marker. The polynucleotides of a kit may optionally be attached to a solid support, or be part of an array or addressable array of polynucleotides. The kit may provide for the determination of the identity of the nucleotide at a marker position by any method known in the art including, but not limited to, a sequencing assay method, a microsequencing assay method, a hybridization assay method, or an enzyme-based mismatch detection method. Optionally such a kit may include instructions for scoring the results of the determination with respect to the test subjects' risk of suffering from a form of cancer or prostate cancer, the level of aggressiveness of cancer tumors or prostate cancer tumors, an early onset of cancer or prostate cancer, a beneficial response to or side effects related to treatment against cancer or prostate cancer.

Methods for De Novo Identification of Biallelic Markers

Any of a variety of methods can be used to screen a genomic fragment for single nucleotide polymorphisms such as differential hybridization with oligonucleotide probes, detection of changes in the mobility measured by gel electrophoresis or direct sequencing of the amplified nucleic acid. A preferred method for identifying biallelic markers involves comparative sequencing of genomic DNA fragments from an appropriate number of unrelated individuals.

In a first embodiment, DNA samples from unrelated individuals are pooled together, following which the genomic DNA of interest is amplified and sequenced. The nucleotide sequences thus obtained are then analyzed to identify significant polymorphisms. One of the major advantages of this method resides in the fact that the pooling of the DNA samples substantially reduces the number of DNA amplification reactions and sequencing reactions which must be carried out. Moreover, this method is sufficiently sensitive so that a biallelic marker obtained thereby usually demonstrates a sufficient frequency of its less common allele to be useful in conducting association studies.

In a second embodiment, the DNA samples are not pooled and are therefore amplified and sequenced individually. This method is usually preferred when biallelic markers need to be identified in order to perform association studies within candidate genes. Preferably, highly relevant gene regions such as promoter regions or exon regions may be screened for biallelic markers. A biallelic marker obtained using this method may show a lower degree of informativeness for conducting association studies, e.g. if the frequency of its less frequent allele may be less than about 10%. Such a biallelic marker will, however, be sufficiently informative to conduct association studies and it will further be appreciated that including less informative biallelic markers in the genetic analysis studies of the present invention, may allow in some cases the direct identification of causal mutations, which may, depending on their penetrance, be rare mutations.

The following is a description of the various parameters of a preferred method used by the inventors for the identification of the biallelic markers of the present invention.

Genomic DNA Samples

The genomic DNA samples from which the biallelic markers of the present invention are generated are preferably obtained from unrelated individuals corresponding to a heterogeneous population of known ethnic background. The number of individuals from whom DNA samples are obtained can vary substantially, preferably from about 10 to about 1000, preferably from about 50 to about 200 individuals. It is usually preferred to collect DNA samples from at least about 100 individuals in order to have sufficient polymorphic diversity in a given population to identify as many markers as possible and to generate statistically significant results.

As for the source of the genomic DNA to be subjected to analysis, any test sample can be foreseen without any particular limitation. These test samples include biological samples, which can be tested by the methods of the present invention described herein, and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens including tumor and non-tumor tissue and lymph node tissues; bone marrow aspirates and fixed cell specimens. The preferred source of genomic DNA used in the present invention is from peripheral venous blood of each donor. Techniques to prepare genomic DNA from biological samples are well known to the skilled technician. Details of a preferred embodiment are provided in Example 1. The person skilled in the art can choose to amplify pooled or unpooled DNA samples.

DNA Amplification

The identification of biallelic markers in a sample of genomic DNA may be facilitated through the use of DNA amplification methods. DNA samples can be pooled or unpooled for the amplification step. DNA amplification techniques are well known to those skilled in the art.

Amplification techniques that can be used in the context of the present invention include, but are not limited to, the ligase chain reaction (LCR) described in EP-A-320 308, WO 9320227 and EP-A-439 182, the disclosures of which are incorporated herein by reference, the polymerase chain reaction (PCR, RT-PCR) and techniques such as the nucleic acid sequence based amplification (NASBA) described in Guatelli J. C., et al. (1990) and in Compton J. (1991), Q-beta amplification as described in European Patent Application No 4544610, strand displacement amplification as described in Walker et al. (1996) and EP A 684 315 and, target mediated amplification as described in PCT Publication WO 9322461, the disclosures of which are incorporated herein by reference in their entirety. For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770, or to use Asymmetric Gap LCR (RT-AGLCR) as described by Marshall et al. (1994). AGLCR is a modification of GLCR that allows the amplification of RNA.

The PCR technology is the preferred amplification technique used in the present invention. A variety of PCR techniques are familiar to those skilled in the art. For a review of PCR technology, see White (1997) and the publication entitled "PCR Methods and Applications" (1991, Cold Spring Harbor Laboratory Press). In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195; 4,683,202; and 4,965,188. Each of the preceding publications is incorporated herein by reference in their entirety.

The PCR technology is the preferred amplification technique used to identify new biallelic markers. A typical example of a PCR reaction suitable for the purposes of the present invention is provided in Example 2.

One of the aspects of the present invention is a method for the amplification of the human purH gene, particularly of the genomic sequence of SEQ ID NO: 1 or of the cDNA sequence of SEQ ID NO: 2, or a fragment or a variant thereof in a test sample, preferably using the PCR technology. This method comprises the steps of contacting a test sample suspected of containing the target purH encoding sequence or portion thereof with amplification reaction reagents comprising a pair of amplification primers, and eventually in some instances a detection probe that can hybridize with an internal region of amplicon sequences to confirm that the desired amplification reaction has taken place.

Thus, the present invention also relates to a method for the amplification of a human purH gene sequence, particularly of a portion of the genomic sequences of SEQ ID NO: 1 or of the cDNA sequence of SEQ ID NO: 2, or a variant thereof in a test sample, said method comprising the steps of:

a) contacting a test sample suspected of containing the targeted purH gene sequence comprised in a nucleotide sequence selected from SEQ ID NOs: 1 and 2, or fragments or variants thereof with amplification reaction reagents comprising a pair of amplification primers as described above and located on either side of the polynucleotide region to be amplified, and b) optionally, detecting the amplification products.

The invention also concerns a kit for the amplification of a human purH gene sequence, particularly of a portion of the genomic sequence of SEQ ID NO: 1 or of the cDNA sequence of SEQ ID NO: 2, or a variant thereof in a test sample, wherein said kit comprises:

a) a pair of oligonucleotide primers located on either side of the purH region to be amplified;

b) optionally, the reagents necessary for performing the amplification reaction.

In one embodiment of the above amplification method and kit, the amplification product is detected by hybridization with a labeled probe having a sequence which is complementary to the amplified region. In another embodiment of the above amplification method and kit, primers comprise a sequence which is selected from the group consisting of the nucleotide sequences of B1 to B34, C1 to C34, D1 to D42, and E1 to E42.

In a first embodiment of the present invention, biallelic markers are identified using genomic sequence information generated by the inventors. Sequenced genomic DNA fragments are used to design primers for the amplification of 500 bp fragments. These 500 bp fragments are amplified from genomic DNA and are scanned for biallelic markers. Primers may be designed using the OSP software (Hillier L. and Green P., 1991), the disclosure of which is incorporated herein by reference. All primers may contain, upstream of the specific target bases, a common oligonucleotide tail that serves as a sequencing primer. Those skilled in the art are familiar with primer extensions, which can be used for these purposes.

Preferred primers, useful for the amplification of genomic sequences encoding the candidate genes, focus on promoters, exons and splice sites of the genes. A biallelic marker presents a higher probability to be an eventual causal mutation if it is located in these functional regions of the gene. Preferred amplification primers of the invention include the nucleotide sequences B1 to B34 and C1 to C34, detailed further in Example 2, Table 1.

Sequencing of Amplified Genomic DNA and Identification of Single Nucleotide Polymorphisms The amplification products generated as described above are then sequenced using any method known and available to the skilled technician. Methods for sequencing DNA using either the dideoxy-mediated method (Sanger method) or the Maxam-Gilbert method are widely known to those of ordinary skill in the art. Such methods are for example disclosed in Sambrook et al. (1989). Alternative approaches include hybridization to high-density DNA probe arrays as described in Chee et al. (1996), the disclosure of which is incorporated herein by reference.

Preferably, the amplified DNA is subjected to automated dideoxy terminator sequencing reactions using a dye-primer cycle sequencing protocol. The products of the sequencing reactions are run on sequencing gels and the sequences are determined using gel image analysis. The polymorphism search is based on the presence of superimposed peaks in the electrophoresis pattern resulting from different bases occurring at the same position. Because each dideoxy terminator is labeled with a different fluorescent molecule, the two peaks corresponding to a biallelic site present distinct colors corresponding to two different nucleotides at the same position on the sequence. However, the presence of two peaks can be an artifact due to background noise. To exclude such an artifact, the two DNA strands are sequenced and a comparison between the peaks is carried out. In order to be registered as a polymorphic sequence, the polymorphism has to be detected on both strands.

The above procedure permits those amplification products which contain biallelic markers to be identified. The detection limit for the frequency of biallelic polymorphisms detected by sequencing pools of 100 individuals is approximately 0.1 for the minor allele, as verified by sequencing pools of known allelic frequencies. However, more than 90% of the biallelic polymorphisms detected by the pooling method have a frequency for the minor allele higher than 0.25. Therefore, the biallelic markers selected by this method have a frequency of at least 0.1 for the minor allele and less than 0.9 for the major allele, preferably at least 0.2 for the minor allele and less than 0.8 for the major allele, more preferably at least 0.3 for the minor allele and less than 0.7 for the major allele, thus a heterozygosity rate higher than 0.18, preferably higher than 0.32, more preferably higher than 0.42.

In another embodiment, biallelic markers are detected by sequencing individual DNA samples; the frequency of the minor allele of such a biallelic marker may be less than 0.1.

Validation of the Biallelic Markers of the Present Invention

The polymorphisms are evaluated for their usefulness as genetic markers by validating that both alleles are present in a population. Validation of the biallelic markers is accomplished by genotyping a group of individuals by a method of the invention and demonstrating that both alleles are present.

Microsequencing is a preferred method of genotyping alleles. The validation by genotyping step may be performed on individual samples derived from each individual in the group or by genotyping a pooled sample derived from more than one individual. The group can be as small as one individual if that individual is heterozygous for the allele in question. Preferably the group contains at least three individuals, more preferably the group contains five or six individuals, so that a single validation test will be more likely to result in the validation of more of the biallelic markers that are being tested. It should be noted, however, that when the validation test is performed on a small group it may result in a false negative result if as a result of sampling error none of the individuals tested carries one of the two alleles. Thus, the validation process is less useful in demonstrating that a particular initial result is an artifact, than it is at demonstrating that there is a bonafide biallelic marker at a particular position in a sequence. All of the genotyping, haplotyping, association, and interaction study methods of the invention may optionally be performed solely with validated biallelic markers.

Evaluation of the Frequency of the Biallelic Markers of the Present Invention

Figure 1:
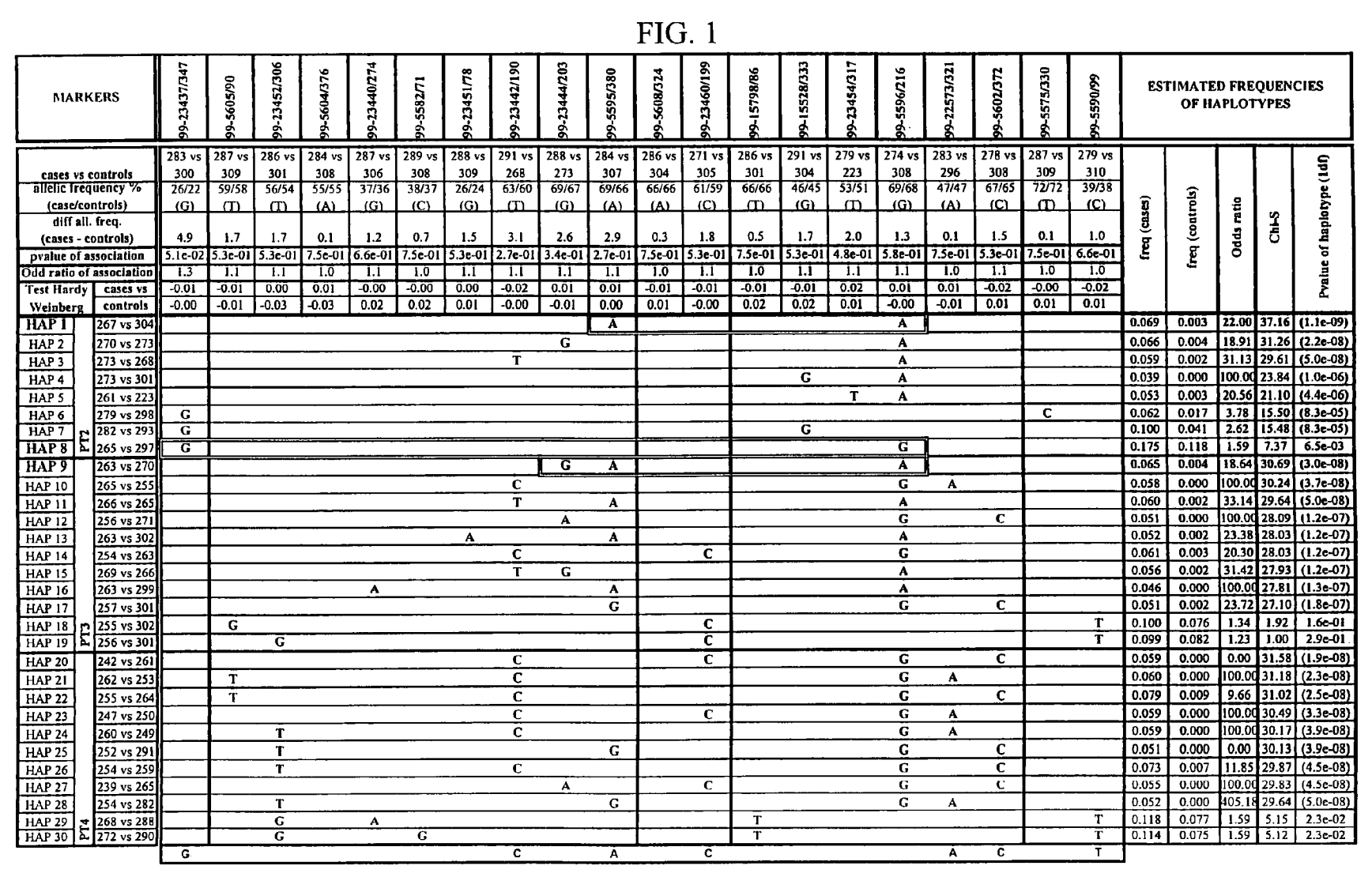

The validated biallelic markers are further evaluated for their usefulness as genetic markers by determining the frequency of the least common allele at the biallelic marker site. The higher the frequency of the less common allele the greater the usefulness of the biallelic marker is for association and interaction studies. The determination of the least common allele is accomplished by genotyping a group of individuals by a method of the invention and demonstrating that both alleles are present. This determination of frequency by genotyping step may be performed on individual samples derived from each individual in the group or by genotyping a pooled sample derived from more than one individual. The group must be large enough to be representative of the population as a whole. Preferably the group contains at least 20 individuals, more preferably the group contains at least 50 individuals, most preferably the group contains at least 100 individuals. Of course the larger the group the greater the accuracy of the frequency determination because of reduced sampling error. For an indication of the frequency for the less common allele of a particular biallelic marker of the invention see FIGS. 1 and 2. A biallelic marker wherein the frequency of the less common allele is 30% or more is termed a "high quality biallelic marker." All of the genotyping, haplotyping, association, and interaction study methods of the invention may optionally be performed solely with high quality biallelic markers.

The invention also relates to methods of estimating the frequency of an allele in a population comprising: a) genotyping individuals from said population for said biallelic marker according to the method of the present invention; and b) determining the proportional representation of said biallelic marker in said population. In addition, the methods of estimating the frequency of an allele in a population of the invention encompass methods with any further limitation described in this disclosure, or those following, specified alone or in any combination; optionally, said purH-related biallelic marker is selected from the group consisting of A1 to A43, and the complements thereof, or optionally the biallelic markers in linkage disequilibrium therewith; optionally, said purH-related biallelic marker is selected from the group consisting of A1, A3 to A14, A16 to A17, A34, and A35, and the complements thereof, or optionally the biallelic markers in linkage disequilibrium therewith; optionally, said purH-related biallelic marker is selected from the group consisting of A2 and A15, and the complements thereof, or optionally the biallelic markers in linkage disequilibrium therewith; optionally, said purH-related biallelic marker is selected from the group consisting of A18 to A33 and A36 to A43; optionally, wherein said purH-related biallelic marker is selected from the group consisting of A29, A7, A20, A10 and A13, and the complements thereof, or optionally the biallelic markers in linkage disequilibrium therewith; optionally, wherein said purH-related biallelic marker is selected from the group consisting of A30, A17, A28, A25, A21, and A14, and the complements thereof, or optionally the biallelic markers in linkage disequilibrium therewith. Optionally, determining the frequency of a biallelic marker allele in a population may be accomplished by determining the identity of the nucleotides for both copies of said biallelic marker present in the genome of each individual in said population and calculating the proportional representation of said nucleotide at said purH-related biallelic marker for the population; optionally, determining the proportional representation may be accomplished by performing a genotyping method of the invention on a pooled biological sample derived from a representative number of individuals, or each individual, in said population, and calculating the proportional amount of said nucleotide compared with the total.

Methods for Genotyping an Individual for Biallelic Markers

Methods are provided to genotype a biological sample for one or more biallelic markers of the present invention, all of which may be performed in vitro. Such methods of genotyping comprise determining the identity of a nucleotide at a purH biallelic marker site by any method known in the art. These methods find use in genotyping case-control populations in association studies as well as individuals in the context of detection of alleles of biallelic markers which are known to be associated with a given trait, in which case both copies of the biallelic marker present in an individual's genome are determined so that an individual may be classified as homozygous or heterozygous for a particular allele.

These genotyping methods can be performed on nucleic acid samples derived from a single individual or pooled DNA samples.

Genotyping can be performed using similar methods as those described above for the identification of the biallelic markers, or using other genotyping methods such as those further described below. In preferred embodiments, the comparison of sequences of amplified genomic fragments from different individuals is used to identify new biallelic markers whereas microsequencing is used for genotyping known biallelic markers in diagnostic and association study applications.

In one embodiment the invention encompasses methods of genotyping comprising determining the identity of a nucleotide at a purH-related biallelic marker or the complement thereof in a biological sample; optionally, said purH-related biallelic marker is selected from the group consisting of A1 to A43, and the complements thereof, or optionally the biallelic markers in linkage disequilibrium therewith; optionally, said purH-related biallelic marker is selected from the group consisting of A1, A3 to A14, A16 to A17, A34, and A35, and the complements thereof, or optionally the biallelic markers in linkage disequilibrium therewith; optionally, said purH-related biallelic marker is selected from the group consisting of A2 and A15, and the complements thereof, or optionally the biallelic markers in linkage disequilibrium therewith; optionally, said purH-related biallelic marker is selected from the group consisting of A18 to A33 and A36 to A43; optionally, wherein said purH-related biallelic marker is selected from the group consisting of A29, A7, A20, A10 and A13, and the complements thereof, or optionally the biallelic markers in linkage disequilibrium therewith; optionally, wherein said purH-related biallelic marker is selected from the group consisting of A30, A17, A28, A25, A21, and A14, and the complements thereof, or optionally the biallelic markers in linkage disequilibrium therewith; optionally, wherein said biological sample is derived from a single subject; optionally, wherein the identity of the nucleotides at said biallelic marker is determined for both copies of said biallelic marker present in said individual's genome; optionally, wherein said biological sample is derived from multiple subjects; optionally, further comprising amplifying a portion of said sequence comprising the biallelic marker prior to said determining step; optionally, wherein said amplifying is performed by PCR; optionally, wherein said determining is performed by a hybridization assay, a sequencing assay, a microsequencing assay, or an enzyme-based mismatch detection assay.

Source of Nucleic Acids for Genotyping

Any source of nucleic acids, in purified or non-purified form, can be utilized as the starting nucleic acid, provided it contains or is suspected of containing the specific nucleic acid sequence desired. DNA or RNA may be extracted from cells, tissues, body fluids and the like as described above. While nucleic acids for use in the genotyping methods of the invention can be derived from any mammalian source, the test subjects and individuals from which nucleic acid samples are taken are generally understood to be human.

Amplification of DNA Fragments Comprising Biallelic Markers

Methods and polynucleotides are provided to amplify a segment of nucleotides comprising one or more biallelic marker of the present invention. It will be appreciated that amplification of DNA fragments comprising biallelic markers may be used in various methods and for various purposes and is not restricted to genotyping. Nevertheless, many genotyping methods, although not all, require the previous amplification of the DNA region carrying the biallelic marker of interest. Such methods specifically increase the concentration or total number of sequences that span the biallelic marker or include that site and sequences located either distal or proximal to it. Diagnostic assays may also rely on amplification of DNA segments carrying a biallelic marker of the present invention. Amplification of DNA may be achieved by any method known in the art. Amplification techniques are described above in the section entitled, "DNA amplification."

Some of these amplification methods are particularly suited for the detection of single nucleotide polymorphisms and allow the simultaneous amplification of a target sequence and the identification of the polymorphic nucleotide as it is further described below.

The identification of biallelic markers as described above allows the design of appropriate oligonucleotides, which can be used as primers to amplify DNA fragments comprising the biallelic markers of the present invention. Amplification can be performed using the primers initially used to discover new biallelic markers which are described herein or any set of primers allowing the amplification of a DNA fragment comprising a biallelic marker of the present invention.

In some embodiments the present invention provides primers for amplifying a DNA fragment containing one or more biallelic markers of the present invention. Preferred amplification primers are listed in Example 2. It will be appreciated that the primers listed are merely exemplary and that any other set of primers which produce amplification products containing one or more biallelic markers of the present invention are also of use.

The spacing of the primers determines the length of the segment to be amplified. In the context of the present invention, amplified segments carrying biallelic markers can range in size from at least about 25 bp to 35 kbp. Amplification fragments from 25-3000 bp are typical, fragments from 50-1000 bp are preferred and fragments from 100-600 bp are highly preferred. It will be appreciated that amplification primers for the biallelic markers may be any sequence which allow the specific amplification of any DNA fragment carrying the markers. Amplification primers may be labeled or immobilized on a solid support as described in "Oligonucleotide probes and primers".

Methods of Genotyping DNA Samples for Biallelic Markers

Any method known in the art can be used to identify the nucleotide present at a biallelic marker site. Since the biallelic marker allele to be detected has been identified and specified in the present invention, detection will prove simple for one of ordinary skill in the art by employing any of a number of techniques. Many genotyping methods require the previous amplification of the DNA region carrying the biallelic marker of interest. While the amplification of target or signal is often preferred at present, ultrasensitive detection methods which do not require amplification are also encompassed by the present genotyping methods. Methods well-known to those skilled in the art that can be used to detect biallelic polymorphisms include methods such as conventional dot blot analyzes, single strand conformational polymorphism analysis (SSCP) described by Orita et al. (1989), denaturing gradient gel electrophoresis (DGGE), heteroduplex analysis, mismatch cleavage detection, and other conventional techniques as described in Sheffield et al. (1991), White et al. (1992), Grompe et al. (1989 and 1993). Another method for determining the identity of the nucleotide present at a particular polymorphic site employs a specialized exonuclease-resistant nucleotide derivative as described in U.S. Pat. No. 4,656,127, the disclosure of which is incorporated herein by reference in its entirety.

Preferred methods involve directly determining the identity of the nucleotide present at a biallelic marker site by sequencing assay, enzyme-based mismatch detection assay, or hybridization assay. The following is a description of some preferred methods. A highly preferred method is the microsequencing technique. The term "sequencing" is generally used herein to refer to polymerase extension of duplex primer/template complexes and includes both traditional sequencing and microsequencing.

1) Sequencing Assays

The nucleotide present at a polymorphic site can be determined by sequencing methods. In a preferred embodiment, DNA samples are subjected to PCR amplification before sequencing as described above. DNA sequencing methods are described in "Sequencing Of Amplified Genomic DNA And Identification Of Single Nucleotide Polymorphisms".

Preferably, the amplified DNA is subjected to automated dideoxy terminator sequencing reactions using a dye-primer cycle sequencing protocol. Sequence analysis allows the identification of the base present at the biallelic marker site.

2) Microsequencing Assays

In microsequencing methods, the nucleotide at a polymorphic site in a target DNA is detected by a single nucleotide primer extension reaction. This method involves appropriate microsequencing primers which hybridize just upstream of the polymorphic base of interest in the target nucleic acid. A polymerase is used to specifically extend the 3' end of the primer with one single ddNTP (chain terminator) complementary to the nucleotide at the polymorphic site. Next the identity of the incorporated nucleotide is determined in any suitable way.

Typically, microsequencing reactions are carried out using fluorescent ddNTPs and the extended microsequencing primers are analyzed by electrophoresis on ABI 377 sequencing machines to determine the identity of the incorporated nucleotide as described in EP 412 883, the disclosure of which is incorporated herein by reference in its entirety. Alternatively capillary electrophoresis can be used in order to process a higher number of assays simultaneously. An example of a typical microsequencing procedure that can be used in the context of the present invention is provided in Example 4.

Different approaches can be used for the labeling and detection of ddNTPs. A homogeneous phase detection method based on fluorescence resonance energy transfer has been described by Chen and Kwok (1997) and Chen et al. (1997), the disclosures of which are incorporated herein by reference. In this method, amplified genomic DNA fragments containing polymorphic sites are incubated with a 5'-fluorescein-labeled primer in the presence of allelic dye-labeled dideoxyribonucleoside triphosphates and a modified Taq polymerase. The dye-labeled primer is extended one base by the dye-terminator specific for the allele present on the template. At the end of the genotyping reaction, the fluorescence intensities of the two dyes in the reaction mixture are analyzed directly without separation or purification. All these steps can be performed in the same tube and the fluorescence changes can be monitored in real time. Alternatively, the extended primer may be analyzed by MALDI-TOF Mass Spectrometry. The base at the polymorphic site is identified by the mass added onto the microsequencing primer (see Haff and Smirnov, 1997), the disclosure of which is incorporated herein by reference.

Microsequencing may be achieved by the established microsequencing method or by developments or derivatives thereof. Alternative methods include several solid-phase microsequencing techniques. The basic microsequencing protocol is the same as described previously, except that the method is conducted as a heterogeneous phase assay, in which the primer or the target molecule is immobilized or captured onto a solid support. To simplify the primer separation and the terminal nucleotide addition analysis, oligonucleotides are attached to solid supports or are modified in such ways that permit affinity separation as well as polymerase extension. The 5' ends and internal nucleotides of synthetic oligonucleotides can be modified in a number of different ways to permit different affinity separation approaches, e.g., biotinylation. If a single affinity group is used on the oligonucleotides, the oligonucleotides can be separated from the incorporated terminator regent. This eliminates the need of physical or size separation. More than one oligonucleotide can be separated from the terminator reagent and analyzed simultaneously if more than one affinity group is used. This permits the analysis of several nucleic acid species or more nucleic acid sequence information per extension reaction. The affinity group need not be on the priming oligonucleotide but could alternatively be present on the template. For example, immobilization can be carried out via an interaction between biotinylated DNA and streptavidin-coated microtitration wells or avidin-coated polystyrene particles. In the same manner, oligonucleotides or templates may be attached to a solid support in a high-density format. In such solid phase microsequencing reactions, incorporated ddNTPs can be radiolabeled (Syvänen, 1994) or linked to fluorescein (Livak and Hainer, 1994). The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such as p-nitrophenyl phosphate). Other possible reporter-detection pairs include: ddNTP linked to dinitrophenyl (DNP) and anti-DNP alkaline phosphatase conjugate (Harju et al., 1993) or biotinylated ddNTP and horseradish peroxidase-conjugated streptavidin with o-phenylenediamine as a substrate (WO 92/15712), the disclosure of which is incorporated herein by reference in its entirety. As yet another alternative solid-phase microsequencing procedure, Nyren et al. (1993) described a method relying on the detection of DNA polymerase activity by an enzymatic luminometric inorganic pyrophosphate detection assay (ELIDA).

Pastinen et al. (1997) describe a method for multiplex detection of single nucleotide polymorphism in which the solid phase minisequencing principle is applied to an oligonucleotide array format. High-density arrays of DNA probes attached to a solid support (DNA chips) are further described below.

In one aspect the present invention provides polynucleotides and methods to genotype one or more biallelic markers of the present invention by performing a microsequencing assay. Preferred microsequencing primers include the nucleotide sequences D1 to D42 and E1 to E42. It will be appreciated that the microsequencing primers listed in Example 4 are merely exemplary and that, any primer having a 3' end immediately adjacent to the polymorphic nucleotide may be used. Similarly, it will be appreciated that microsequencing analysis may be performed for any biallelic marker or any combination of biallelic markers of the present invention. One aspect of the present invention is a solid support which includes one or more microsequencing primers listed in Example 4, or fragments comprising at least 8, 12, 15, 20, 25, 30, 40, or 50 consecutive nucleotides thereof, to the extent that such lengths are consistent with the primer described, and having a 3' terminus immediately upstream of the corresponding biallelic marker, for determining the identity of a nucleotide at a biallelic marker site.

3) Mismatch Detection Assays Based on Polymerases and Ligases

In one aspect the present invention provides polynucleotides and methods to determine the allele of one or more biallelic markers of the present invention in a biological sample, by mismatch detection assays based on polymerases and/or ligases. These assays are based on the specificity of polymerases and ligases. Polymerization reactions place particularly stringent requirements on correct base pairing of the 3' end of the amplification primer and the joining of two oligonucleotides hybridized to a target DNA sequence is quite sensitive to mismatches close to the ligation site, especially at the 3' end. Methods, primers and various parameters to amplify DNA fragments comprising biallelic markers of the present invention are further described above in "Amplification Of DNA Fragments Comprising Biallelic Markers".

Allele Specific Amplification Primers

Discrimination between the two alleles of a biallelic marker can also be achieved by allele specific amplification, a selective strategy, whereby one of the alleles is amplified without amplification of the other allele. This is accomplished by placing the polymorphic base at the 3' end of one of the amplification primers. Because the extension forms from the 3' end of the primer, a mismatch at or near this position has an inhibitory effect on amplification. Therefore, under appropriate amplification conditions, these primers only direct amplification on their complementary allele. Determining the precise location of the mismatch and the corresponding assay conditions are well within the ordinary skill in the art.

Ligation/Amplification Based Methods

The "Oligonucleotide Ligation Assay" (OLA) uses two oligonucleotides which are designed to be capable of hybridizing to abutting sequences of a single strand of a target molecule. One of the oligonucleotides is biotinylated, and the other is detectably labeled. If the precise complementary sequence is found in a target molecule, the oligonucleotides will hybridize such that their termini abut, and create a ligation substrate that can be captured and detected. OLA is capable of detecting single nucleotide polymorphisms and may be advantageously combined with PCR as described by Nickerson et al. (1990). In this method, PCR is used to achieve the exponential amplification of target DNA, which is then detected using OLA.

Other amplification methods which are particularly suited for the detection of single nucleotide polymorphism include LCR (ligase chain reaction) and Gap LCR (GLCR), which are described above in "Amplification of the purH gene". LCR uses two pairs of probes to exponentially amplify a specific target. The sequence of each pair of oligonucleotides is selected to permit the pair to hybridize to abutting sequences of the same strand of the target. Such hybridization forms a substrate for a template-dependant ligase. In accordance with the present invention, LCR can be performed with oligonucleotides having the proximal and distal sequences of the same strand of a biallelic marker site. In one embodiment, either oligonucleotide will be designed to include the biallelic marker site. In such an embodiment, the reaction conditions are selected such that the oligonucleotides can be ligated together only if the target molecule either contains or lacks the specific nucleotide that is complementary to the biallelic marker on the oligonucleotide. In an alternative embodiment, the oligonucleotides will not include the biallelic marker, such that when they hybridize to the target molecule, a "gap" is created as described in WO 90/01069. This gap is then "filled" with complementary dNTPs (as mediated by DNA polymerase), or by an additional pair of oligonucleotides. Thus at the end of each cycle, each single strand has a complement capable of serving as a target during the next cycle and exponential allele-specific amplification of the desired sequence is obtained.

Ligase/Polymerase-mediated Genetic Bit Analysis™ is another method for determining the identity of a nucleotide at a preselected site in a nucleic acid molecule (WO 95/21271), the disclosure of which is incorporated herein by reference in its entirety. This method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

4) Hybridization Assay Methods

A preferred method of determining the identity of the nucleotide present at a biallelic marker site involves nucleic acid hybridization. The hybridization probes, which can be conveniently used in such reactions, preferably include the probes defined herein. Any hybridization assay may be used including Southern hybridization, Northern hybridization, dot blot hybridization and solid-phase hybridization (see Sambrook et al., 1989).

Hybridization refers to the formation of a duplex structure by two single stranded nucleic acids due to complementary base pairing. Hybridization can occur between exactly complementary nucleic acid strands or between nucleic acid strands that contain minor regions of mismatch. Specific probes can be designed that hybridize to one form of a biallelic marker and not to the other and therefore are able to discriminate between different allelic forms. Allele-specific probes are often used in pairs, one member of a pair showing perfect match to a target sequence containing the original allele and the other showing a perfect match to the target sequence containing the alternative allele. Hybridization conditions should be sufficiently stringent that there is a significant difference in hybridization intensity between alleles, and preferably an essentially binary response, whereby a probe hybridizes to only one of the alleles. Stringent, sequence specific hybridization conditions, under which a probe will hybridize only to the exactly complementary target sequence, are well known in the art (Sambrook et al., 1989). Stringent conditions are sequence dependent and will be different in different circumstances. Generally, stringent conditions are selected to be about 5° C. lower than the thermal melting point (Tm) for the specific sequence at a defined ionic strength and pH. Although such hybridization can be performed in solution, it is preferred to employ a solid-phase hybridization assay. The target DNA comprising a biallelic marker of the present invention may be amplified prior to the hybridization reaction. The presence of a specific allele in the sample is determined by detecting the presence or the absence of stable hybrid duplexes formed between the probe and the target DNA. The detection of hybrid duplexes can be carried out by a number of methods. Various detection assay formats are well known which utilize detectable labels bound to either the target or the probe to enable detection of the hybrid duplexes. Typically, hybridization duplexes are separated from unhybridized nucleic acids and the labels bound to the duplexes are then detected. Those skilled in the art will recognize that wash steps may be employed to wash away excess target DNA or probe as well as unbound conjugate. Further, standard heterogeneous assay formats are suitable for detecting the hybrids using the labels present on the primers and probes.

Two recently developed assays allow hybridization-based allele discrimination with no need for separations or washes (see Landegren U. et al., 1998). The TaqMan assay takes advantage of the 5' nuclease activity of Taq DNA polymerase to digest a DNA probe annealed specifically to the accumulating amplification product. TaqMan probes are labeled with a donor-acceptor dye pair that interacts via fluorescence energy transfer. Cleavage of the TaqMan probe by the advancing polymerase during amplification dissociates the donor dye from the quenching acceptor dye, greatly increasing the donor fluorescence. All reagents necessary to detect two allelic variants can be assembled at the beginning of the reaction and the results are monitored in real time (see Livak et al., 1995). In an alternative homogeneous hybridization based procedure, molecular beacons are used for allele discriminations. Molecular beacons are hairpin-shaped oligonucleotide probes that report the presence of specific nucleic acids in homogeneous solutions. When they bind to their targets they undergo a conformational reorganization that restores the fluorescence of an internally quenched fluorophore (Tyagi et al., 1998).

The polynucleotides provided herein can be used to produce probes which can be used in hybridization assays for the detection of biallelic marker alleles in biological samples. These probes are characterized in that they preferably comprise between 8 and 50 nucleotides, and in that they are sufficiently complementary to a sequence comprising a biallelic marker of the present invention to hybridize thereto and preferably sufficiently specific to be able to discriminate the targeted sequence for only one nucleotide variation. A particularly preferred probe is 25 nucleotides in length. Preferably the biallelic marker is within 4 nucleotides of the center of the polynucleotide probe. In particularly preferred probes, the biallelic marker is at the center of said polynucleotide. Preferred probes comprise a nucleotide sequence selected from the group consisting of amplicons listed in Table 1 and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base. In preferred embodiments the polymorphic base(s) are within 5, 4, 3, 2, or 1 nucleotides of the center of the said polynucleotide, more preferably at the center of said polynucleotide.

Preferably the probes of the present invention are labeled or immobilized on a solid support. Labels and solid supports are further described in "Oligonucleotide Probes and Primers". The probes can be non-extendable as described in "Oligonucleotide Probes and Primers".

By assaying the hybridization to an allele specific probe, one can detect the presence or absence of a biallelic marker allele in a given sample. High-Throughput parallel hybridization in array format is specifically encompassed within "hybridization assays" and are described below.

5) Hybridization to Addressable Arrays of Oligonucleotides

Hybridization assays based on oligonucleotide arrays rely on the differences in hybridization stability of short oligonucleotides to perfectly matched and mismatched target sequence variants. Efficient access to polymorphism information is obtained through a basic structure comprising high-density arrays of oligonucleotide probes attached to a solid support (e.g., the chip) at selected positions. Each DNA chip can contain thousands to millions of individual synthetic DNA probes arranged in a grid-like pattern and miniaturized to the size of a dime.

The chip technology has already been applied with success in numerous cases. For example, the screening of mutations has been undertaken in the BRCA1 gene, in *S. cerevisiae* mutant strains, and in the protease gene of HIV-1 virus (Hacia et al., 1996; Shoemaker et al., 1996; Kozal et al., 1996). Chips of various formats for use in detecting biallelic polymorphisms can be produced on a customized basis by Affymetrix (GeneChip™), Hyseq (HyChip and HyGnostics), and Protogene Laboratories.

In general, these methods employ arrays of oligonucleotide probes that are complementary to target nucleic acid sequence segments from an individual which target sequences include a polymorphic marker. EP 785280, the disclosure of which is incorporated herein by reference in its entirety, describes a tiling strategy for the detection of single nucleotide polymorphisms. Briefly, arrays may generally be "tiled" for a large number of specific polymorphisms. By "tiling" is generally meant the synthesis of a defined set of oligonucleotide probes which is made up of a sequence complementary to the target sequence of interest, as well as preselected variations of that sequence, e.g., substitution of one or more given positions with one or more members of the basis set of nucleotides. Tiling strategies are further described in PCT application No. WO 95/11995, the disclosure of which is incorporated herein by reference in its entirety. In a particular aspect, arrays are tiled for a number of specific, identified biallelic marker sequences. In particular, the array is tiled to include a number of detection blocks, each detection block being specific for a specific biallelic marker or a set of biallelic markers. For example, a detection block may be tiled to include a number of probes, which span the sequence segment that includes a specific polymorphism. To ensure probes that are complementary to each allele, the probes are synthesized in pairs differing at the biallelic marker. In addition to the probes differing at the polymorphic base, monosubstituted probes are also generally tiled within the detection block. These monosubstituted probes have bases at and up to a certain number of bases in either direction from the polymorphism, substituted with the remaining nucleotides (selected from A, T, G, C and U). Typically the probes in a tiled detection block will include substitutions of the sequence positions up to and including those that are 5 bases away from the biallelic marker. The monosubstituted probes provide internal controls for the tiled array, to distinguish actual hybridization from artefactual cross-hybridization. Upon completion of hybridization with the target sequence and washing of the array, the array is scanned to determine the position on the array to which the target sequence hybridizes. The hybridization data from the scanned array is then analyzed to identify which allele or alleles of the biallelic marker are present in the sample. Hybridization and scanning may be carried out as described in PCT application No. WO 92/10092 and WO 95/11995 and U.S. Pat. No. 5,424,186, the disclosures of which are incorporated by reference herein in their entirety.

Thus, in some embodiments, the chips may comprise an array of nucleic acid sequences of fragments of about 15 nucleotides in length. In further embodiments, the chip may comprise an array including at least one of the sequences selected from the group consisting of amplicons listed in table 1 and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base. In preferred embodiments the polymorphic base is within 5, 4, 3, 2, or 1 nucleotides of the center of the said polynucleotide, more preferably at the center of said polynucleotide. In some embodiments, the chip may comprise an array of at least 2, 3, 4, 5, 6, 7, 8 or more of these polynucleotides of the invention. Solid supports and polynucleotides of the present invention attached to solid supports are further described in "oligonucleotide probes and primers".

6) Integrated Systems

Another technique which may be used to analyze polymorphisms includes multicomponent integrated systems, which miniaturize and compartmentalize processes such as PCR and capillary electrophoresis reactions in a single functional device. An example of such technique is disclosed in U.S. Pat. No. 5,589,136, the disclosure of which are incorporated by reference herein in its entirety, which describes the integration of PCR amplification and capillary electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip to create functional microscopic valves and pumps with no moving parts.

For genotyping biallelic markers, the microfluidic system may integrate nucleic acid amplification, microsequencing, capillary electrophoresis and a detection method such as laser-induced fluorescence detection.

Methods of Genetic Analysis Using the Biallelic Markers of the Present Invention Different methods are available for the genetic analysis of complex traits (see Lander and Schork, 1994). The search for disease-susceptibility genes is conducted using two main methods: the linkage approach in which evidence is sought for cosegregation between a locus and a putative trait locus using family studies, and the association approach in which evidence is sought for a statistically significant association between an allele and a trait or a trait causing allele (Khoury et al., 1993). In general, the biallelic markers of the present invention find use in any method known in the art to demonstrate a statistically significant correlation between a genotype and a phenotype. The biallelic markers may be used in parametric and non-parametric linkage analysis methods. Preferably, the biallelic markers of the present invention are used to identify genes associated with detectable traits using association studies, an approach which does not require the use of affected families and which permits the identification of genes associated with complex and sporadic traits.

The genetic analysis using the biallelic markers of the present invention may be conducted on any scale. The whole set of biallelic markers of the present invention or any subset of biallelic markers of the present invention corresponding to the candidate gene may be used. Further, any set of genetic markers including a biallelic marker of the present invention may be used. A set of biallelic polymorphisms that could be used as genetic markers in combination with the biallelic markers of the present invention has been described in WO 98/20165, the disclosure of which is incorporated herein by reference in its entirety. As mentioned above, it should be noted that the biallelic markers of the present invention may be included in any complete or partial genetic map of the human genome. These different uses are specifically contemplated in the present invention and claims.

The invention also comprises methods of detecting an association between a genotype and a phenotype, comprising the steps of a) determining the frequency of at least one purH-related biallelic marker in a trait positive population according to a genotyping method of the invention; b) determining the frequency of said purH-related biallelic marker in a control population according to a genotyping method of the invention; and c) determining whether a statistically significant association exists between said genotype and said phenotype. In addition, the methods of detecting an association between a genotype and a phenotype of the invention encompass methods with any further limitation described in this disclosure, or those following, specified alone or in any combination: Optionally, said purH-related biallelic marker is selected from the group consisting of A1 to A43, and the complements thereof, or optionally the biallelic markers in linkage disequilibrium therewith; optionally, said purH-related biallelic marker is selected from the group consisting of A1, A3 to A14, A16 to A17, A34, and A35, and the complements thereof, or optionally the biallelic markers in linkage disequilibrium therewith; optionally, said purH-related biallelic marker is selected from the group consisting of A2 and A15, and the complements thereof, or optionally the biallelic markers in linkage disequilibrium therewith; optionally, said purH-related biallelic marker is selected from the group consisting of A18 to A33 and A36 to A43; optionally, said control population may be a trait negative population, or a random population; optionally, each of said genotyping steps a) and b) may be performed on a pooled biological sample derived from each of said populations; optionally, each of said genotyping of steps a) and b) is performed separately on biological samples derived from each individual in said population or a subsample thereof; optionally, said phenotype is symptoms of, or susceptibility to prostate cancer, the level of aggressiveness of prostate cancer tumors, an early onset of prostate cancer, a beneficial response to or side effects related to treatment against prostate cancer.

The invention also encompasses methods of estimating the frequency of a haplotype for a set of biallelic markers in a population, comprising the steps of: a) genotyping at least one purH-related biallelic marker according to a method of the invention for each individual in said population; b) genotyping a second biallelic marker by determining the identity of the nucleotides at said second biallelic marker for both copies of said second biallelic marker present in the genome of each individual in said population; and c) applying a haplotype determination method to the identities of the nucleotides determined in steps a) and b) to obtain an estimate of said frequency. In addition, the methods of estimating the frequency of a haplotype of the invention encompass methods with any further limitation described in this disclosure, or those following, specified alone or in any combination: Optionally, said purH-related biallelic marker is selected from the group consisting of A1 to A43, and the complements thereof, or optionally the biallelic markers in linkage disequilibrium therewith; optionally, said purH-related biallelic marker is selected from the group consisting of A1, A3 to A14, A16 to A17, A34, and A35, and the complements thereof, or optionally the biallelic markers in linkage disequilibrium therewith; optionally, said purH-related biallelic marker is selected from the group consisting of A2 and A15, and the complements thereof, or optionally the biallelic markers in linkage disequilibrium therewith; optionally, said purH-related biallelic marker is selected from the group consisting of A18 to A33 and A36 to A43; optionally, said haplotype determination method is performed by asymmetric PCR amplification, double PCR amplification of specific alleles, the Clark algorithm, or an expectation-maximization algorithm.

An additional embodiment of the present invention encompasses methods of detecting an association between a haplotype and a phenotype, comprising the steps of: a) estimating the frequency of at least one haplotype in a trait positive population, according to a method of the invention for estimating the frequency of a haplotype; b) estimating the frequency of said haplotype in a control population, according to a method of the invention for estimating the frequency of a haplotype; and c) determining whether a statistically significant association exists between said haplotype and said phenotype. In addition, the methods of detecting an association between a haplotype and a phenotype of the invention encompass methods with any further limitation described in this disclosure, or those following: Optionally, said purH-related biallelic marker is selected from the group consisting of A1 to A43, and the complements thereof, or optionally the biallelic markers in linkage disequilibrium therewith; optionally, said purH-related biallelic marker is selected from the group consisting of A1, A3 to A14, A16 to A17, A34, and A35, and the complements thereof, or optionally the biallelic markers in linkage disequilibrium therewith; optionally, said purH-related biallelic marker is selected from the group consisting of A2 and A15, and the complements thereof, or optionally the biallelic markers in linkage disequilibrium therewith; optionally, said purH-related biallelic marker is selected from the group consisting of A18 to A33 and A36 to A43; optionally, said control population is a trait negative population, or a random population. Optionally, said phenotype is symptoms of, or susceptibility to prostate cancer, the level of aggressiveness of prostate cancer tumors, an early onset of prostate cancer, a beneficial response to or side effects related to treatment against prostate cancer; optionally, said method comprises the additional steps of determining the phenotype in said trait positive and said control populations prior to step c).

Linkage Analysis

Linkage analysis is based upon establishing a correlation between the transmission of genetic markers and that of a specific trait throughout generations within a family. Thus, the aim of linkage analysis is to detect marker loci that show cosegregation with a trait of interest in pedigrees.

Parametric Methods

When data are available from successive generations there is the opportunity to study the degree of linkage between pairs of loci. Estimates of the recombination fraction enable loci to be ordered and placed onto a genetic map. With loci that are genetic markers, a genetic map can be established, and then the strength of linkage between markers and traits can be calculated and used to indicate the relative positions of markers and genes affecting those traits (Weir, 1996). The classical method for linkage analysis is the logarithm of odds (lod) score method (see Morton, 1955; Ott, 1991). Calculation of lod scores requires specification of the mode of inheritance for the disease (parametric method). Generally, the length of the candidate region identified using linkage analysis is between 2 and 20 Mb. Once a candidate region is identified as described above, analysis of recombinant individuals using additional markers allows further delineation of the candidate region. Linkage analysis studies have generally relied on the use of a maximum of 5,000 microsatellite markers, thus limiting the maximum theoretical attainable resolution of linkage analysis to about 600 kb on average.

Linkage analysis has been successfully applied to map simple genetic traits that show clear Mendelian inheritance patterns and which have a high penetrance (i.e., the ratio between the number of trait positive carriers of allele a and the total number of a carriers in the population). However, parametric linkage analysis suffers from a variety of drawbacks. First, it is limited by its reliance on the choice of a genetic model suitable for each studied trait. Furthermore, as already mentioned, the resolution attainable using linkage analysis is limited, and complementary studies are required to refine the analysis of the typical 2 Mb to 20 Mb regions initially identified through linkage analysis. In addition, parametric linkage analysis approaches have proven difficult when applied to complex genetic traits, such as those due to the combined action of multiple genes and/or environmental factors. It is very difficult to model these factors adequately in a lod score analysis. In such cases, too large an effort and cost are needed to recruit the adequate number of affected families required for applying linkage analysis to these situations, as recently discussed by Risch, N. and Merikangas, K. (1996).

Non-Parametric Methods

The advantage of the so-called non-parametric methods for linkage analysis is that they do not require specification of the mode of inheritance for the disease; they tend to be more useful for the analysis of complex traits. In non-parametric methods, one tries to prove that the inheritance pattern of a chromosomal region is not consistent with random Mendelian segregation by showing that affected relatives inherit identical copies of the region more often than expected by chance. Affected relatives should show excess "allele sharing" even in the presence of incomplete penetrance and polygenic inheritance. In non-parametric linkage analysis the degree of agreement at a marker locus in two individuals can be measured either by the number of alleles identical by state (IBS) or by the number of alleles identical by descent (IBD). Affected sib pair analysis is a well-known special case and is the simplest form of these methods.

The biallelic markers of the present invention may be used in both parametric and non-parametric linkage analysis. Preferably biallelic markers may be used in non-parametric methods which allow the mapping of genes involved in complex traits. The biallelic markers of the present invention may be used in both IBD- and IBS-methods to map genes affecting a complex trait. In such studies, taking advantage of the high density of biallelic markers, several adjacent biallelic marker loci may be pooled to achieve the efficiency attained by multi-allelic markers (Zhao et al., 1998).

Population Association Studies

The present invention comprises methods for identifying if the purH gene is associated with a detectable trait using the biallelic markers of the present invention. In one embodiment the present invention comprises methods to detect an association between a biallelic marker allele or a biallelic marker haplotype and a trait. Further, the invention comprises methods to identify a trait causing allele in linkage disequilibrium with any biallelic marker allele of the present invention.

As described above, alternative approaches can be employed to perform association studies: genome-wide association studies, candidate region association studies and candidate gene association studies. In a preferred embodiment, the biallelic markers of the present invention are used to perform candidate gene association studies. The candidate gene analysis clearly provides a short-cut approach to the identification of genes and gene polymorphisms related to a particular trait when some information concerning the biology of the trait is available. Further, the biallelic markers of the present invention may be incorporated in any map of genetic markers of the human genome in order to perform genome-wide association studies. Methods to generate a high-density map of biallelic markers has been described in U.S. Provisional Patent application Ser. No. 60/082,614. The biallelic markers of the present invention may further be incorporated in any map of a specific candidate region of the genome (a specific chromosome or a specific chromosomal segment for example).

As mentioned above, association studies may be conducted within the general population and are not limited to studies performed on related individuals in affected families. Association studies are extremely valuable as they permit the analysis of sporadic or multifactor traits. Moreover, association studies represent a powerful method for fine-scale mapping enabling much finer mapping of trait causing alleles than linkage studies. Studies based on pedigrees often only narrow the location of the trait causing allele. Association studies using the biallelic markers of the present invention can therefore be used to refine the location of a trait causing allele in a candidate region identified by Linkage Analysis methods. Moreover, once a chromosome segment of interest has been identified, the presence of a candidate gene such as a candidate gene of the present invention, in the region of interest can provide a shortcut to the identification of the trait causing allele. Biallelic markers of the present invention can be used to demonstrate that a candidate gene is associated with a trait. Such uses are specifically contemplated in the present invention.

Determining the Frequency of a Biallelic Marker Allele or of a Biallelic Marker Haplotype in a Population Association studies explore the relationships among frequencies for sets of alleles between loci.

Determining the Frequency of an Allele in a Population

Allelic frequencies of the biallelic markers in a populations can be determined using one of the methods described above under the heading "Methods for genotyping an individual for biallelic markers", or any genotyping procedure suitable for this intended purpose. Genotyping pooled samples or individual samples can determine the frequency of a biallelic marker allele in a population. One way to reduce the number of genotypings required is to use pooled samples. A major obstacle in using pooled samples is in terms of accuracy and reproducibility for determining accurate DNA concentrations in setting up the pools. Genotyping individual samples provides higher sensitivity, reproducibility and accuracy and is the preferred method used in the present invention. Preferably, each individual is genotyped separately and simple gene counting is applied to determine the frequency of an allele of a biallelic marker or of a genotype in a given population.

Determining the Frequency of a Haplotype in a Population

The gametic phase of haplotypes is unknown when diploid individuals are heterozygous at more than one locus. Using genealogical information in families, gametic phase can sometimes be inferred (Perlin et al., 1994). When no genealogical information is available, different strategies may be used. One possibility is that the multiple-site heterozygous diploids can be eliminated from the analysis, keeping only the homozygotes and the single-site heterozygote individuals, but this approach might lead to a possible bias in the sample composition and the underestimation of low-frequency haplotypes. Another possibility is that single chromosomes can be studied independently, for example, by asymmetric PCR amplification (see Newton et al, 1989; Wu et al., 1989) or by isolation of single chromosome by limit dilution followed by PCR amplification (see Ruano et al., 1990). Further, a sample may be haplotyped for sufficiently close biallelic markers by double PCR amplification of specific alleles (Sarkar, G. and Sommer S. S., 1991). These approaches are not entirely satisfying either because of their technical complexity, the additional cost they entail, their lack of generalization at a large scale, or the possible biases they introduce. To overcome these difficulties, an algorithm to infer the phase of PCR-amplified DNA genotypes introduced by Clark, A. G. (1990) may be used. Briefly, the principle is to start filling a preliminary list of haplotypes present in the sample by examining unambiguous individuals, that is, the complete homozygotes and the single-site heterozygotes. Then other individuals in the same sample are screened for the possible occurrence of previously recognized haplotypes. For each positive identification, the complementary haplotype is added to the list of recognized haplotypes, until the phase information for all individuals is either resolved or identified as unresolved. This method assigns a single haplotype to each multiheterozygous individual, whereas several haplotypes are possible when there are more than one heterozygous site. Alternatively, one can use methods estimating haplotype frequencies in a population without assigning haplotypes to each individual. Preferably, a method based on an expectation-maximization (EM) algorithm (Dempster et al., 1977) leading to maximum-likelihood estimates of haplotype frequencies under the assumption of Hardy-Weinberg proportions (random mating) is used (see Excoffier L. and Slatkin M., 1995). The EM algorithm is a generalized iterative maximum-likelihood approach to estimation that is useful when data are ambiguous and/or incomplete. The EM algorithm is used to resolve heterozygotes into haplotypes. Haplotype estimations are further described below under the heading "Statistical Methods." Any other method known in the art to determine or to estimate the frequency of a haplotype in a population may be used.

Linkage Disequilibrium Analysis

Linkage disequilibrium is the non-random association of alleles at two or more loci and represents a powerful tool for mapping genes involved in disease traits (see Ajioka R. S. et al., 1997). Biallelic markers, because they are densely spaced in the human genome and can be genotyped in greater numbers than other types of genetic markers (such as RFLP or VNTR markers), are particularly useful in genetic analysis based on linkage disequilibrium.

When a disease mutation is first introduced into a population (by a new mutation or the immigration of a mutation carrier), it necessarily resides on a single chromosome and thus on a single "background" or "ancestral" haplotype of linked markers. Consequently, there is complete disequilibrium between these markers and the disease mutation: one finds the disease mutation only in the presence of a specific set of marker alleles. Through subsequent generations recombination events occur between the disease mutation and these marker polymorphisms, and the disequilibrium gradually dissipates. The pace of this dissipation is a function of the recombination frequency, so the markers closest to the disease gene will manifest higher levels of disequilibrium than those that are further away. When not broken up by recombination, "ancestral" haplotypes and linkage disequilibrium between marker alleles at different loci can be tracked not only through pedigrees but also through populations. Linkage disequilibrium is usually seen as an association between one specific allele at one locus and another specific allele at a second locus.

The pattern or curve of disequilibrium between disease and marker loci is expected to exhibit a maximum that occurs at the disease locus. Consequently, the amount of linkage disequilibrium between a disease allele and closely linked genetic markers may yield valuable information regarding the location of the disease gene. For fine-scale mapping of a disease locus, it is useful to have some knowledge of the patterns of linkage disequilibrium that exist between markers in the studied region. As mentioned above, the mapping resolution achieved through the analysis of linkage disequilibrium is much higher than that of linkage studies. The high density of biallelic markers combined with linkage disequilibrium analysis provides powerful tools for fine-scale mapping. Different methods to calculate linkage disequilibrium are described below under the heading "Statistical Methods".

Population-Based Case-Control Studies of Trait-Marker Associations

As mentioned above, the occurrence of pairs of specific alleles at different loci on the same chromosome is not random and the deviation from random is called linkage disequilibrium. Association studies focus on population frequencies and rely on the phenomenon of linkage disequilibrium. If a specific allele in a given gene is directly involved in causing a particular trait, its frequency will be statistically increased in an affected (trait positive) population, when compared to the frequency in a trait negative population or in a random control population. As a consequence of the existence of linkage disequilibrium, the frequency of all other alleles present in the haplotype carrying the trait-causing allele will also be increased in trait positive individuals compared to trait negative individuals or random controls. Therefore, association between the trait and any allele (specifically a biallelic marker allele) in linkage disequilibrium with the trait-causing allele will suffice to suggest the presence of a trait-related gene in that particular region. Case-control populations can be genotyped for biallelic markers to identify associations that narrowly locate a trait causing allele. As any marker in linkage disequilibrium with one given marker associated with a trait will be associated with the trait. Linkage disequilibrium allows the relative frequencies in case-control populations of a limited number of genetic polymorphisms (specifically biallelic markers) to be analyzed as an alternative to screening all possible functional polymorphisms in order to find trait-causing alleles. Association studies compare the frequency of marker alleles in unrelated case-control populations, and represent powerful tools for the dissection of complex traits.

Case-Control Populations (Inclusion Criteria)

Population-based association studies do not concern familial inheritance but compare the prevalence of a particular genetic marker, or a set of markers, in case-control populations. They are case-control studies based on comparison of unrelated case (affected or trait positive) individuals and unrelated control (unaffected, trait negative or random) individuals. Preferably the control group is composed of unaffected or trait negative individuals. Further, the control group is ethnically matched to the case population. Moreover, the control group is preferably matched to the case-population for the main known confusion factor for the trait under study (for example age-matched for an age-dependent trait). Ideally, individuals in the two samples are paired in such a way that they are expected to differ only in their disease status. The terms "trait positive population", "case population" and "affected population" are used interchangeably herein.

An important step in the dissection of complex traits using association studies is the choice of case-control populations (see Lander and Schork, 1994). A major step in the choice of case-control populations is the clinical definition of a given trait or phenotype. Any genetic trait may be analyzed by the association method proposed here by carefully selecting the individuals to be included in the trait positive and trait negative phenotypic groups. Four criteria are often useful: clinical phenotype, age at onset, family history and severity. The selection procedure for continuous or quantitative traits (such as blood pressure for example) involves selecting individuals at opposite ends of the phenotype distribution of the trait under study, so as to include in these trait positive and trait negative populations individuals with non-overlapping phenotypes. Preferably, case-control populations consist of phenotypically homogeneous populations. Trait positive and trait negative populations consist of phenotypically uniform populations of individuals representing each between 1 and 98%, preferably between 1 and 80%, more preferably between 1 and 50%, and more preferably between 1 and 30%, most preferably between 1 and 20% of the total population under study, and preferably selected among individuals exhibiting non-overlapping phenotypes. The clearer the difference between the two trait phenotypes, the greater the probability of detecting an association with biallelic markers. The selection of those drastically different but relatively uniform phenotypes enables efficient comparisons in association studies and the possible detection of marked differences at the genetic level, provided that the sample sizes of the populations under study are significant enough.

In preferred embodiments, a first group of between 50 and 300 trait positive individuals, preferably about 100 individuals, are recruited according to their phenotypes. A similar number of control individuals are included in such studies.

In the present invention, typical examples of inclusion criteria include prostate cancer.

Association Analysis

The general strategy to perform association studies using biallelic markers derived from a region carrying a candidate gene is to scan two groups of individuals (case-control populations) in order to measure and statistically compare the allele frequencies of the biallelic markers of the present invention in both groups.

If a statistically significant association with a trait is identified for at least one or more of the analyzed biallelic markers, one can assume that either the associated allele is directly responsible for causing the trait (i.e. the associated allele is the trait causing allele), or more likely the associated allele is in linkage disequilibrium with the trait causing allele. The specific characteristics of the associated allele with respect to the candidate gene function usually give further insight into the relationship between the associated allele and the trait (causal or in linkage disequilibrium). If the evidence indicates that the associated allele within the candidate gene is most probably not the trait causing allele but is in linkage disequilibrium with the real trait causing allele, then the trait causing allele can be found by sequencing the vicinity of the associated marker, and performing further association studies with the polymorphisms that are revealed in an iterative manner.

Association studies are usually run in two successive steps. In a first phase, the frequencies of a reduced number of biallelic markers from the candidate gene are determined in the trait positive and control populations. In a second phase of the analysis, the position of the genetic loci responsible for the given trait is further refined using a higher density of markers from the relevant region. However, if the candidate gene under study is relatively small in length, as is the case for purH, a single phase may be sufficient to establish significant associations.

Haplotype Analysis

As described above, when a chromosome carrying a disease allele first appears in a population as a result of either mutation or migration, the mutant allele necessarily resides on a chromosome having a set of linked markers: the ancestral haplotype. This haplotype can be tracked through populations and its statistical association with a given trait can be analyzed. Complementing single point (allelic) association studies with multi-point association studies, also called haplotype studies, increases the statistical power of association studies. Thus, a haplotype association study allows one to define the frequency and the type of the ancestral carrier haplotype. A haplotype analysis is important in that it increases the statistical power of an analysis involving individual markers.

In a first stage of a haplotype frequency analysis, the frequency of the possible haplotypes based on various combinations of the identified biallelic markers of the invention is determined. The haplotype frequency is then compared for distinct populations of trait positive and control individuals. The number of trait positive individuals, which should be, subjected to this analysis to obtain statistically significant results usually ranges between 30 and 300, with a preferred number of individuals ranging between 50 and 150. The same considerations apply to the number of unaffected individuals (or random control) used in the study. The results of this first analysis provide haplotype frequencies in case-control populations; for each evaluated haplotype frequency a p-value and an odd ratio are calculated. If a statistically significant association is found, the relative risk for an individual carrying the given haplotype of being affected with the trait under study can be approximated.

Interaction Analysis

The biallelic markers of the present invention may also be used to identify patterns of biallelic markers associated with detectable traits resulting from polygenic interactions. The analysis of genetic interaction between alleles at unlinked loci requires individual genotyping using the techniques described herein. The analysis of allelic interaction among a selected set of biallelic markers with appropriate level of statistical significance can be considered as a haplotype analysis. Interaction analysis consists in stratifying the case-control populations with respect to a given haplotype for the first loci and performing a haplotype analysis with the second loci with each subpopulation.

Statistical methods used in association studies are further described below.

Testing for Linkage in the Presence of Association

The biallelic markers of the present invention may further be used in TDT (transmission/disequilibrium test). TDT tests for both linkage and association and is not affected by population stratification. TDT requires data for affected individuals and their parents or data from unaffected sibs instead of from parents (see Spielmann S. et al., 1993; Schaid D. J. et al., 1996, Spielmann S. and Ewens W. J., 1998). Such combined tests generally reduce the false-positive errors produced by separate analyses.

Statistical Methods

In general, any method known in the art to test whether a trait and a genotype show a statistically significant correlation may be used.

1) Methods in Linkage Analysis

Statistical methods and computer programs useful for linkage analysis are well-known to those skilled in the art (see Terwilliger J. D. and Ott J., 1994; Ott J., 1991).

2) Methods to Estimate Haplotype Frequencies in a Population

As described above, when genotypes are scored, it is often not possible to distinguish heterozygotes so that haplotype frequencies cannot be easily inferred. When the gametic phase is not known, haplotype frequencies can be estimated from the multilocus genotypic data. Any method known to a person skilled in the art can be used to estimate haplotype frequencies (see Lange K., 1997; Weir, B. S., 1996). Preferably, maximum-likelihood haplotype frequencies are computed using an Expectation-Maximization (EM) algorithm (see Dempster et al., 1977; Excoffier L. and Slatkin M., 1995). This procedure is an iterative process aiming at obtaining maximum-likelihood estimates of haplotype frequencies from multi-locus genotype data when the gametic phase is unknown. Haplotype estimations are usually performed by applying the EM algorithm using, for example, the EM-HAPLO program (Hawley M. E. et al., 1994) or the Arlequin program (Schneider et al., 1997). The EM algorithm is a generalized iterative maximum likelihood approach to estimation and is briefly described below.

Please note that in the present section, "Methods To Estimate Haplotype Frequencies In A Population," of this text, phenotypes will refer to multi-locus genotypes with unknown phase. Genotypes will refer to known-phase multi-locus genotypes.

A sample of N unrelated individuals is typed for K markers. The data observed are the unknown-phase K-locus phenotypes that can categorized in F different phenotypes. Suppose that we have H underlying possible haplotypes (in case of K biallelic markers, $H=2^K$).

For phenotype j, suppose that $c_j$ genotypes are possible. We thus have the following equation $$P_j = \sum_{i=1}^{c_j} pr(genotype_i) = \sum_{i=1}^{c_j} pr(h_k, h_l) \qquad \text{Equation 1}$$

where Pj is the probability of the phenotype j, $h_k$ and $h_l$ are the two haplotypes constituent the genotype i. Under the Hardy-Weinberg equilibrium, $pr(h_k,h_l)$ becomes:

$$pr(h_k,h_l)=pr(h_k)^2 \text{ if } h_k=h_l, pr(h_k,h_l)=2pr(h_k).pr(h_l) \text{ if } h_k \neq h_l. \qquad \text{Equation 2}$$

The successive steps of the E-M algorithm can be described as follows:

Starting with initial values of the haplotypes frequencies, noted $p_1^{(0)}, p_2^{(0)}, \ldots p_H^{(0)}$, these initial values serve to estimate the genotype frequencies (Expectation step) and then estimate another set of haplotype frequencies (Maximization step), noted $p_1^{(1)}, p_2^{(1)}, \ldots p_H^{(1)}$, these two steps are iterated until changes in the sets of haplotypes frequency are very small.

A stop criterion can be that the maximum difference between haplotype frequencies between two iterations is less than $10^{-7}$. These values can be adjusted according to the desired precision of estimations.

At a given iteration s, the Expectation step consists in calculating the genotypes frequencies by the following equation:

$$pr(genotype_i)^{(s)} = pr(phenotype_j) \cdot pr(genotype_i \mid phenotype_j)^{(s)} = \frac{n_j}{N} \cdot \frac{pr(h_k, h_l)^{(s)}}{P_j^{(s)}} \qquad \text{Equation 3}$$

where genotype i occurs in phenotype j, and where $h_k$ and $h_l$ constitute genotype i. Each probability is derived according to eq. 1 and eq. 2, described above.

Then the Maximization step simply estimates another set of haplotype frequencies given the genotypes frequencies. This approach is also known as the gene-counting method (Smith, 1957).

$$p_t^{(s+1)} = \frac{1}{2} \sum_{j=1}^{F} \sum_{i=1}^{c_j} \delta_{it} \cdot pr(genotype_i)^{(s)} \qquad \text{Equation 4}$$

where $\delta_{it}$ is an indicator variable which counts the number of time haplotype t in genotype i. It takes the values of 0, 1 or 2.

To ensure that the estimation finally obtained is the maximum-likelihood estimation several values of departures are required. The estimations obtained are compared and if they are different the estimations leading to the best likelihood are kept.

3) Methods to Calculate Linkage Disequilibrium Between Markers

A number of methods can be used to calculate linkage disequilibrium between any two genetic positions, in practice linkage disequilibrium is measured by applying a statistical association test to haplotype data taken from a population.

Linkage disequilibrium between any pair of biallelic markers comprising at least one of the biallelic markers of the present invention ($M_i$, $M_j$) having alleles ($a_i/b_i$) at marker $M_i$ and alleles ($a_j/b_j$) at marker $M_j$ can be calculated for every allele combination ($a_i,a_j; a_i,b_j; b_i,a_j$ and $b_i,b_j$), according to the Piazza formula:

$$\Delta_{aiaj}=\sqrt{\theta 4}-\sqrt{(\theta 4+\theta 3)(\theta 4+\theta 2)}, \text{ where:}$$

$\theta 4=---$=frequency of genotypes not having allele $a_i$ at $M_i$ and not having allele $a_j$ at $M_j$ θ3=−+=frequency of genotypes not having allele $a_i$ at $M_i$ and having allele $a_j$ at $M_j$ θ2=+−=frequency of genotypes having allele $a_i$ at $M_i$ and not having allele $a_j$ at $M_j$ Linkage disequilibrium (LD) between pairs of biallelic markers ($M_i$, $M_j$) can also be calculated for every allele combination (ai,aj; ai,bj; $b_i,a_j$ and $b_i,b_j$), according to the maximum-likelihood estimate (MLE) for delta (the composite genotypic disequilibrium coefficient), as described by Weir (Weir B. S., 1996). The MLE for the composite linkage disequilibrium is:

$$D_{aiaj}=(2n_1+n_2+n_3+n_4/2)/N-2(pr(a_i).pr(a_j))$$

where $n_1=\Sigma$ phenotype ($a_i/a_i$, $a_j/a_j$), $n_2=\Sigma$ phenotype ($a_i/a_i$, $a_j/b_j$), $n_3=\Sigma$ phenotype ($a_i/b_i$, $a_j/a_j$), $n4=\Sigma$ phenotype ($a_i/b_i$, $a_j/b_j$) and N is the number of individuals in the sample.

This formula allows linkage disequilibrium between alleles to be estimated when only genotype, and not haplotype, data are available.

Another means of calculating the linkage disequilibrium between markers is as follows. For a couple of biallelic markers, $M_i(a_i/b_i)$ and $M_j(a_j/b_j)$, fitting the Hardy-Weinberg equilibrium, one can estimate the four possible haplotype frequencies in a given population according to the approach described above.

The estimation of gametic disequilibrium between ai and aj is simply:

$$D_{aiaj}=pr(\text{haplotype}(a_i,a_j))-pr(a_i).pr(a_j).$$

where $pr(a_i)$ is the probability of allele $a_i$ and $pr(a_j)$ is the probability of allele $a_j$ and where $pr(\text{haplotype} (a_i, a_j))$ is estimated as in Equation 3 above.

For a couple of biallelic markers only one measure of disequilibrium is necessary to describe the association between $M_i$ and $M_j$.

Then a normalized value of the above is calculated as follows:

$$D'_{aiaj}=D_{aiaj}/\max(-pr(a_i).pr(a_j), -pr(b_i).pr(b_j)) \text{ with } D_{aiaj}<0$$

$$D'_{aiaj}=D_{aiaj}/\max(pr(b_i).pr(a_j), pr(a_i).pr(b_j)) \text{ with } D_{aiaj}>0$$

The skilled person will readily appreciate that other linkage disequilibrium calculation methods can be used.

Linkage disequilibrium among a set of biallelic markers having an adequate heterozygosity rate can be determined by genotyping between 50 and 1000 unrelated individuals, preferably between 75 and 200, more preferably around 100.

4) Testing for Association

Methods for determining the statistical significance of a correlation between a phenotype and a genotype, in this case an allele at a biallelic marker or a haplotype made up of such alleles, may be determined by any statistical test known in the art and with any accepted threshold of statistical significance being required. The application of particular methods and thresholds of significance are well within the skill of the ordinary practitioner of the art.

Testing for association is performed by determining the frequency of a biallelic marker allele in case and control populations and comparing these frequencies with a statistical test to determine if there is a statistically significant difference in frequency which would indicate a correlation between the trait and the biallelic marker allele under study. Similarly, a haplotype analysis is performed by estimating the frequencies of all possible haplotypes for a given set of biallelic markers in case and control populations, and comparing these frequencies with a statistical test to determine if there is a statistically significant correlation between the haplotype and the phenotype (trait) under study. Any statistical tool useful to test for a statistically significant association between a genotype and a phenotype may be used. Preferably the statistical test employed is a chi-square test with one degree of freedom. A P-value is calculated (the P-value is the probability that a statistic as large or larger than the observed one would occur by chance).

Statistical Significance

In preferred embodiments, significance for diagnosis purposes, either as a positive basis for further diagnostic tests or as a preliminary starting point for early preventive therapy, the p value related to a biallelic marker association is preferably about $1\times10^{-2}$ or less, more preferably about $1\times10^{-4}$ or less, for a single biallelic marker analysis and about $1\times10^{-3}$ or less, still more preferably $1\times10^{-6}$ or less and most preferably of about $1\times10^{-8}$ or less, for a haplotype analysis involving two or more markers. These values are believed to be applicable to any association studies involving single or multiple marker combinations.

The skilled person can use the range of values set forth above as a starting point in order to carry out association studies with biallelic markers of the present invention. In doing so, significant associations between the biallelic markers of the present invention and prostate cancer, the level of aggressiveness of prostate cancer tumors, an early onset of prostate cancer, or a beneficial response to or side effects related to treatment against prostate cancer can be revealed and used for diagnosis and drug screening purposes.

Phenotypic Permutation

In order to confirm the statistical significance of the first stage haplotype analysis described above, it might be suitable to perform further analyses in which genotyping data from case-control individuals are pooled and randomized with respect to the trait phenotype. Each individual genotyping data is randomly allocated to two groups, which contain the same number of individuals as the case-control populations used to compile the data obtained in the first stage. A second stage haplotype analysis is preferably run on these artificial groups, preferably for the markers included in the haplotype of the first stage analysis showing the highest relative risk coefficient. This experiment is reiterated preferably at least between 100 and 10000 times. The repeated iterations allow the determination of the probability to obtain by chance the tested haplotype.

Assessment of Statistical Association

To address the problem of false positives similar, analysis may be performed with the same case-control populations in random genomic regions. Results in random regions and the candidate region are compared as described in a co-pending US Provisional Patent Application entitled "Methods, Software And Apparati For Identifying Genomic Regions Harboring A Gene Associated With A Detectable Trait," U.S. Ser. No. 60/107,986, filed Nov. 10, 1998, the contents of which are incorporated herein by reference.

5) Evaluation of Risk Factors

The association between a risk factor (in genetic epidemiology the risk factor is the presence or the absence of a certain allele or haplotype at marker loci) and a disease is measured by the odds ratio (OR) and by the relative risk (RR). If $P(R^+)$ is the probability of developing the disease for individuals with R and $P(R^-)$ is the probability for individuals without the risk factor, then the relative risk is simply the ratio of the two probabilities, that is:

$$RR=P(R^+)/P(R^-)$$

In case-control studies, direct measures of the relative risk cannot be obtained because of the sampling design. However, the odds ratio allows a good approximation of the relative risk for low-incidence diseases and can be calculated:

$$OR = \left[\frac{F^+}{1-F^+}\right] / \left[\frac{F^-}{(1-F^-)}\right]$$

$$OR = (F^+/(1-F^+))/(F^-/(1-F^-))$$

$F^+$ is the frequency of the exposure to the risk factor in cases and $F^-$ is the frequency of the exposure to the risk factor in controls. $F^+$ and $F^-$ are calculated using the allelic or haplotype frequencies of the study and further depend on the underlying genetic model (dominant, recessive, additive ...).

One can further estimate the attributable risk (AR) which describes the proportion of individuals in a population exhibiting a trait due to a given risk factor. This measure is important in quantifying the role of a specific factor in disease etiology and in terms of the public health impact of a risk factor. The public health relevance of this measure lies in estimating the proportion of cases of disease in the population that could be prevented if the exposure of interest were absent. AR is determined as follows:

$$AR = P_E(RR-1)/(P_E(RR-1)+1)$$

AR is the risk attributable to a biallelic marker allele or a biallelic marker haplotype. $P_E$ is the frequency of exposure to an allele or a haplotype within the population at large; and RR is the relative risk which is approximated with the odds ratio when the trait under study has a relatively low incidence in the general population.

Association of Biallelic Markers of the Invention with Prostate Cancer

In the context of the present invention, an association between the purH gene and prostate cancer was established. Further details concerning this association study are provided in Example 5, results are briefly summarized below.

Two groups of independent individuals were used in this association study in accordance with the invention: the case-control populations. The two groups corresponded to 491 affected individuals and 313 control individuals. The affected populations may be subdivided into familial cases and sporadic cases. Other subdivision can be done regarding the diagnosis age of prostate cancer and their familial antecedent of the disease.

In the association study described in Example 5, a number of biallelic marker haplotypes were shown to be significantly associated with prostate cancer.

A first preferred haplotype according to the present invention (HAP1 of FIG. 1 or haplotype 3 of FIG. 3) comprises two biallelic markers (99-5595/380 (A29) and 99-5596/216 (A7)). This haplotype presented a p-value of $1.1 \times 10^{-9}$ and an odd-ratio of 22. This haplotype is significant with sporadic prostate cancer, and more significant with sporadic cases under 65 years old. A second preferred haplotype according to the present invention (HAP8 of FIG. 2 or haplotype 4 of FIG. 3) comprises two biallelic markers (99-23437/347 (A20) and 99-5596/216 (A7)). This haplotype had a p-value of $2.6 \times 10^{-7}$ and an odd ratio of 3.15 with informative sporadic cases. Phenotypic permutation tests confirmed the statistical significance of these results. These haplotypes (haplotypes 3 and 4 of FIG. 3) can therefore be considered to be highly significantly associated with prostate cancer, and more particularly sporadic prostate cancer.

A third preferred haplotype according to the present invention (HAP10 of FIG. 2 or haplotype 1 of FIG. 3) comprises three biallelic markers (99-5604/376 (A30), 99-23460/199 (A17) and 99-5590/99 (A28)). This haplotype presented a p-value of $3.7 \times 10^{-5}$ and an odd-ratio of 2.32 for familial prostate cancer. A fourth preferred haplotype according to the present invention (HAP24 of FIG. 2 or haplotype 2 of FIG. 3) comprises four biallelic markers (99-23452/306 (A25), 99-23440/274 (A21), 99-15798/86 (A14) and 99-5590/99 (A28)). This haplotype presented a p-value of $1 \times 10^{-6}$ and an odd-ratio of 2.73 for familial prostate cancer. These haplotypes are significant with familial prostate cancer, and more significant with familial cases >=3CaP or under 65 years old. Phenotypic permutation tests confirmed the statistical significance of these results. These haplotypes (haplotypes 1 and 2 of FIG. 3) can therefore be considered to be highly significantly associated with prostate cancer, and more particularly familial prostate cancer.

A fifth preferred haplotype according to the present invention (HAP1 of FIG. 4 or haplotype of FIG. 5) comprises two markers (5-294-285 (A10), and 99-5596-216 (A7)) and presented for the haplotype frequency test a p-value $2.8 \times 10^{-7}$ and an odd ratio of 100 for the sporadic prostate cancer. A sixth preferred haplotype according to the present invention (HAP2 of FIG. 4) comprises two biallelic markers (99-15528-333 (A13), and 99-5596-216 (A7)), and presented for the haplotype frequency test a p-value of $1 \times 10^{-6}$ and an odd-ratio of 100 for the sporadic prostate cancer. These haplotypes are highly significant for sporadic prostate cancer.

The invention concerns the haplotypes associated with familial prostate cancer comprising at least three biallelic markers selected from the group consisting of 99-5604/376 (A30), 99-23460/199 (A17), 99-5590/99 (A28), 99-23452/306 (A25), 99-23440/274 (A21), and 99-15798/86 (A14).

The invention concerns the haplotypes associated with sporadic prostate cancer comprising at least two biallelic markers selected from the group consisting of 99-5595/380 (A29), 99-5596/216 (A7) 99-23437/347 (A20), 5-294-285 (A10), and 99-15528-333 (A13). Preferably, the invention concerns haplotypes associated with sporadic prostate cancer which comprises the biallelic 99-5596/216 (A7).

This information is extremely valuable. The knowledge of a potential genetic predisposition to prostate cancer, even if this predisposition is not absolute, might contribute in a very significant manner to treatment efficacy of prostate cancer and to the development of new therapeutic and diagnostic tools.

Identification of Biallelic Markers in Linkage Disequilibrium with the Biallelic Markers of the Invention Once a first biallelic marker has been identified in a genomic region of interest, the practitioner of ordinary skill in the art, using the teachings of the present invention, can easily identify additional biallelic markers in linkage disequilibrium with this first marker. As mentioned before any marker in linkage disequilibrium with a first marker associated with a trait will be associated with the trait. Therefore, once an association has been demonstrated between a given biallelic marker and a trait, the discovery of additional biallelic markers associated with this trait is of great interest in order to increase the density of biallelic markers in this particular region. The causal gene or mutation will be found in the vicinity of the marker or set of markers showing the highest correlation with the trait.

Identification of additional markers in linkage disequilibrium with a given marker involves: (a) amplifying a genomic fragment comprising a first biallelic marker from a plurality of individuals; (b) identifying second biallelic markers in the genomic region harboring said first biallelic marker; (c) conducting a linkage disequilibrium analysis between said first biallelic marker and second biallelic markers; and (d) selecting said second biallelic markers as being in linkage disequilibrium with said first marker. Subcombinations comprising steps (b) and (c) are also contemplated.

Methods to identify biallelic markers and to conduct linkage disequilibrium analysis are described herein and can be carried out by the skilled person without undue experimentation. The present invention then also concerns biallelic markers which are in linkage disequilibrium with the specific biallelic markers A1 to A43 and which are expected to present similar characteristics in terms of their respective association with a given trait. In a preferred embodiment, the invention concerns biallelic markers which are in linkage disequilibrium with the specific biallelic markers A29, A7, A20, A10, and A13, more preferably with the biallelic marker A7. In another preferred embodiment, the invention concerns biallelic markers which are in linkage disequilibrium with the specific biallelic markers A30, A17, A28, A25, A21, and A14.

Identification of Functional Mutations

Mutations in the purH gene which are responsible for a detectable phenotype or trait may be identified by comparing the sequences of the purH gene from trait positive and control individuals. Once a positive association is confirmed with a biallelic marker of the present invention, the identified locus can be scanned for mutations. In a preferred embodiment, functional regions such as exons and splice sites, promoters and other regulatory regions of the purH gene are scanned for mutations. In a preferred embodiment the sequence of the purH gene is compared in trait positive and control individuals. Preferably, trait positive individuals carry the haplotype shown to be associated with the trait and trait negative individuals do not carry the haplotype or allele associated with the trait. The detectable trait or phenotype may comprise a variety of manifestations of altered purH function, including susceptibility to prostate cancer, the level of aggressiveness of prostate cancer tumors, an early onset of prostate cancer, a beneficial response to or side effects related to treatment against prostate cancer.

The mutation detection procedure is essentially similar to that used for biallelic marker identification. The method used to detect such mutations generally comprises the following steps:
  amplification of a region of the purH gene comprising a biallelic marker or a group of biallelic markers associated with the trait from DNA samples of trait positive patients and trait-negative controls;
  sequencing of the amplified region;
  comparison of DNA sequences from trait positive and control individuals;
  determination of mutations specific to trait-positive patients.

In one embodiment, said biallelic marker is selected from the group consisting of A1 to A43, and the complements thereof. In a preferred embodiment, said biallelic marker is selected from the group consisting of A29, A7, A20, A10 and A13, and the complements thereof, more preferably the biallelic marker A7 and the complement thereof. In a preferred embodiment, said biallelic marker is selected from the group consisting of A30, A17, A28, A25, A21, and A14, and the complements thereof. It is preferred that candidate polymorphisms be then verified by screening a larger population of cases and controls by means of any genotyping procedure such as those described herein, preferably using a microsequencing technique in an individual test format. Polymorphisms are considered as candidate mutations when present in cases and controls at frequencies compatible with the expected association results. Polymorphisms are considered as candidate "trait-causing" mutations when they exhibit a statistically significant correlation with the detectable phenotype.

Biallelic Markers of the Invention in Methods of Genetic Diagnostics

The biallelic markers of the present invention can also be used to develop diagnostics tests capable of identifying individuals who express a detectable trait as the result of a specific genotype or individuals whose genotype places them at risk of developing a detectable trait at a subsequent time. The trait analyzed using the present diagnostics may be any detectable trait, including susceptibility to prostate cancer, the level of aggressiveness of prostate cancer tumors, an early onset of prostate cancer, a beneficial response to or side effects related to treatment against prostate cancer. Such a diagnosis can be useful in the staging, monitoring, prognosis and/or prophylactic or curative therapy of prostate cancer.

The diagnostic techniques of the present invention may employ a variety of methodologies to determine whether a test subject has a biallelic marker pattern associated with an increased risk of developing a detectable trait or whether the individual suffers from a detectable trait as a result of a particular mutation, including methods which enable the analysis of individual chromosomes for haplotyping, such as family studies, single sperm DNA analysis or somatic hybrids.

The present invention provides diagnostic methods to determine whether an individual is at risk of developing a disease or suffers from a disease resulting from a mutation or a polymorphism in the purH gene. The present invention also provides methods to determine whether an individual has a susceptibility to prostate cancer.

These methods involve obtaining a nucleic acid sample from the individual and determining whether the nucleic acid sample contains at least one allele or at least one biallelic marker haplotype, indicative of a risk of developing the trait or indicative that the individual expresses the trait as a result of possessing a particular purH polymorphism or mutation (trait-causing allele).

Preferably, in such diagnostic methods, a nucleic acid sample is obtained from the individual and this sample is genotyped using methods described above in "Methods Of Genotyping DNA Samples For Biallelic markers." The diagnostics may be based on a single biallelic marker or a on group of biallelic markers.

In each of these methods, a nucleic acid sample is obtained from the test subject and the biallelic marker pattern of one or more of the biallelic markers A1 to A43 is determined.

In one embodiment, a PCR amplification is conducted on the nucleic acid sample to amplify regions in which polymorphisms associated with a detectable phenotype have been identified. The amplification products are sequenced to determine whether the individual possesses one or more purH polymorphisms associated with a detectable phenotype. The primers used to generate amplification products may comprise the primers listed in Table 1. Alternatively, the nucleic acid sample is subjected to microsequencing reactions as described above to determine whether the individual possesses one or more purH polymorphisms associated with a detectable phenotype resulting from a mutation or a polymorphism in the purH gene. The primers used in the microsequencing reactions may include the primers listed in Table 3. In another embodiment, the nucleic acid sample is contacted with one or more allele specific oligonucleotide probes which specifically hybridize to one or more purH alleles associated with a detectable phenotype. The probes used in the hybridization assay may include the probes listed in Table 2. In another embodiment, the nucleic acid sample is contacted with a second purH oligonucleotide capable of producing an amplification product when used with the allele specific oligonucleotide in an amplification reaction. The presence of an amplification product in the amplification reaction indicates that the individual possesses one or more purH alleles associated with a detectable phenotype.

In a preferred embodiment the identity of the nucleotide present at, at least one, biallelic marker selected from the group consisting of A1 to A43 and the complements thereof, preferably A29, A7, A20, A10 and A13, and the complements thereof, still more preferably A7, and the complements thereof, is determined and the detectable trait is cancer, more preferably prostate cancer, more particularly sporadic prostate cancer. In a preferred embodiment the identity of the nucleotide present at, at least one, biallelic marker selected from the group consisting of A1 to A43 and the complements thereof, preferably A30, A17, A28, A25, A21, and A14, and the complements thereof, is determined and the detectable trait is cancer, more preferably prostate cancer, more particularly familial prostate cancer. Diagnostic kits comprise any of the polynucleotides of the present invention.

These diagnostic methods are extremely valuable as they can, in certain circumstances, be used to initiate preventive treatments or to allow an individual carrying a significant haplotype to foresee warning signs such as minor symptoms.

Diagnostics, which analyze and predict response to a drug or side effects to a drug, may be used to determine whether an individual should be treated with a particular drug. For example, if the diagnostic indicates a likelihood that an individual will respond positively to treatment with a particular drug, the drug may be administered to the individual. Conversely, if the diagnostic indicates that an individual is likely to respond negatively to treatment with a particular drug, an alternative course of treatment may be prescribed. A negative response may be defined as either the absence of an efficacious response or the presence of toxic side effects.

Clinical drug trials represent another application for the markers of the present invention. One or more markers indicative of response to an agent acting against prostate cancer or to side effects to an agent acting against prostate cancer may be identified using the methods described above. Thereafter, potential participants in clinical trials of such an agent may be screened to identify those individuals most likely to respond favorably to the drug and exclude those likely to experience side effects. In that way, the effectiveness of drug treatment may be measured in individuals who respond positively to the drug, without lowering the measurement as a result of the inclusion of individuals who are unlikely to respond positively in the study and without risking undesirable safety problems.

Treatment of Cancer or Prostate Cancer

As the metastasis of cancer or prostate cancer can be fatal, it is important to detect cancer or prostate cancer susceptibility of individuals. Consequently, the invention also concerns a method for the treatment of cancer or prostate cancer comprising the following steps:
  selecting an individual whose DNA comprises alleles of a biallelic marker or of a group of biallelic markers, preferably purH-related markers, associated with cancer or prostate cancer;
  following up said individual for the appearance (and optionally the development) of tumors in prostate or elsewhere; and
  administering an effective amount of a medicament acting against cancer or prostate cancer to said individual at an appropriate stage of the cancer or prostate cancer.

In one embodiment, said biallelic marker is selected from the group consisting of A1 to A43, and the complements thereof. In a preferred embodiment, said biallelic marker is selected from the group consisting of A29, A7, A20, A10 and A13, and the complements thereof, more preferably the biallelic marker A7 and the complement thereof. In a preferred embodiment, said biallelic marker is selected from the group consisting of A30, A17, A28, A25, A21, and A14, and the complements thereof.

The prophylactic administration of a treatment serves to prevent, attenuate or inhibit the growth of cancer cells.

Another embodiment of the present invention consists of a method for the treatment of cancer or prostate cancer comprising the following steps:
  selecting an individual whose DNA comprises alleles of a biallelic marker or of a group of biallelic markers, preferably purH-related markers, associated with cancer or prostate cancer;
  administering to said individual, preferably as a preventive treatment of cancer or prostate cancer, an effective amount of a medicament acting against cancer or prostate cancer such as 4HPR.

In one embodiment, said biallelic marker is selected from the group consisting of A1 to A43, and the complements thereof. In a preferred embodiment, said biallelic marker is selected from the group consisting of A29, A7, A20, A10 and A13, and the complements thereof, more preferably the biallelic marker A7 and the complement thereof. In a preferred embodiment, said biallelic marker is selected from the group consisting of A30, A17, A28, A25, A21, and A14, and the complements thereof.

In a further embodiment, the present invention concerns a method for the treatment of cancer or prostate cancer comprising the following steps:
  selecting an individual whose DNA comprises alleles of a biallelic marker or of a group of biallelic markers, preferably purH-related markers, associated with a susceptibility to cancer or prostate cancer;
  administering to said individual, as a preventive treatment of cancer or prostate cancer, an effective amount of a medicament acting against cancer or prostate cancer such as 4HPR;
  following up said individual for the appearance and the development of tumors in prostate or elsewhere; and optionally
  administering an effective amount of a medicament acting against cancer or prostate cancer to said individual at the appropriate stage of the cancer or prostate cancer.

In one embodiment, said biallelic marker is selected from the group consisting of A1 to A43, and the complements thereof. In a preferred embodiment, said biallelic marker is selected from the group consisting of A29, A7, A20, A10 and A13, and the complements thereof, more preferably the biallelic marker A7 and the complement thereof. In a preferred embodiment, said biallelic marker is selected from the group consisting of A30, A17, A28, A25, A21, and A14, and the complements thereof.

To enlighten the choice of the appropriate beginning of the treatment of cancer or prostate cancer, the present invention also concerns a method for the treatment of cancer or prostate cancer comprising the following steps:

selecting an individual suffering from a cancer or prostate cancer whose DNA comprises alleles of a biallelic marker or of a group of biallelic markers, preferably purH-related markers, associated with the aggressiveness of cancer or prostate cancer tumors; and administering an effective amount of a medicament acting against cancer or prostate cancer to said individual.

In one embodiment, said biallelic marker is selected from the group consisting of A1 to A43, and the complements thereof. In a preferred embodiment, said biallelic marker is selected from the group consisting of A29, A7, A20, A10 and A13, and the complements thereof, more preferably the biallelic marker A7 and the complement thereof. In a preferred embodiment, said biallelic marker is selected from the group consisting of A30, A17, A28, A25, A21, and A14, and the complements thereof.

In particular embodiments, the individual is selected by genotyping one or more biallelic markers of the present invention.

Recombinant Vectors

The term "vector" is used herein to designate either a circular or a linear DNA or RNA molecule, which is either double-stranded or single-stranded, and which comprise at least one polynucleotide of interest that is sought to be transferred in a cell host or in a unicellular or multicellular host organism.

The present invention encompasses a family of recombinant vectors that comprise a regulatory polynucleotide derived from the purH genomic sequence, or a coding polynucleotide from the purH genomic sequence. Consequently, the present invention further deals with a recombinant vector comprising either a regulatory polynucleotide comprised in the nucleic acids of SEQ ID NO: 1 or a polynucleotide comprising the purH coding sequence or both.

Generally, a recombinant vector of the invention may comprise any of the polynucleotides described herein, including regulatory sequences and coding sequences, as well as any purH primer or probe as defined above. More particularly, the recombinant vectors of the present invention can comprise any of the polynucleotides described in the "Genomic Sequences Of The purH Gene" section, the "purH cDNA Sequences" section, the "Coding Regions" section, the "Polynucleotide constructs" section, and the "Oligonucleotide Probes And Primers" section.

In a first preferred embodiment, a recombinant vector of the invention is used to amplify the inserted polynucleotide derived from a purH genomic sequence of SEQ ID NO: 1 or a purH cDNA, for example the cDNA of SEQ ID NO: 2 in a suitable cell host, this polynucleotide being amplified at every time that the recombinant vector replicates.

A second preferred embodiment of the recombinant vectors according to the invention consists of expression vectors comprising either a regulatory polynucleotide or a coding nucleic acid of the invention, or both. Within certain embodiments, expression vectors are employed to express the purH polypeptide which can be then purified and, for example be used in ligand screening assays or as an immunogen in order to raise specific antibodies directed against the purH protein.

In other embodiments, the expression vectors are used for constructing transgenic animals and also for gene therapy. Expression requires that appropriate signals are provided in the vectors, said signals including various regulatory elements, such as enhancers/promoters from both viral and mammalian sources that drive expression of the genes of interest in host cells. Dominant drug selection markers for establishing permanent, stable cell clones expressing the products are generally included in the expression vectors of the invention, as they are elements that link expression of the drug selection markers to expression of the polypeptide.

More particularly, the present invention relates to expression vectors which include nucleic acids encoding a purH protein, preferably the purH protein of the amino acid sequence of SEQ ID NO: 3 or variants or fragments thereof, under the control of a regulatory sequence selected among the purH regulatory polynucleotides, or alternatively under the control of an exogenous regulatory sequence.

Consequently, preferred expression vectors of the invention are selected from the group consisting of: (a) the purH regulatory sequence comprised therein drives the expression of a coding polynucleotide operably linked thereto; (b) the purH coding sequence is operably linked to regulation sequences allowing its expression in a suitable cell host and/or host organism.

The invention also pertains to a recombinant expression vector useful for the expression of the purH coding sequence, wherein said vector comprises a nucleic acid of SEQ ID NO: 2.

Recombinant vectors comprising a nucleic acid containing a purH-related biallelic marker are also part of the invention. In a preferred embodiment, said biallelic marker is selected from the group consisting of A1 to A43, and the complements thereof.

Some of the elements which can be found in the vectors of the present invention are described in further detail in the following sections.

1. General Features of the Expression Vectors of the Invention

A recombinant vector according to the invention comprises, but is not limited to, a YAC (Yeast Artificial Chromosome), a BAC (Bacterial Artificial Chromosome), a phage, a phagemid, a cosmid, a plasmid or even a linear DNA molecule which may consist of a chromosomal, non-chromosomal, semi-synthetic or synthetic DNA. Such a recombinant vector can comprise a transcriptional unit comprising an assembly of:

(1) a genetic element or elements having a regulatory role in gene expression, for example promoters or enhancers. Enhancers are cis-acting elements of DNA, usually from about 10 to 300 bp in length that act on the promoter to increase the transcription.

(2) a structural or coding sequence which is transcribed into mRNA and eventually translated into a polypeptide, said structural or coding sequence being operably linked to the regulatory elements described in (1); and (3) appropriate transcription initiation and termination sequences. Structural units intended for use in yeast or eukaryotic expression systems preferably include a leader sequence enabling extracellular secretion of translated protein by a host cell. Alternatively, when a recombinant protein is expressed without a leader or transport sequence, it may include a N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation site, splice donor and acceptor sites, transcriptional termination sequences, and 5'-flanking non-transcribed sequences. DNA sequences derived from the SV40 viral genome, for example SV40 origin, early promoter, enhancer, splice and polyadenylation sites may be used to provide the required non-transcribed genetic elements.

The in vivo expression of a purH polypeptide of SEQ ID NO: 3 or fragments or variants thereof may be useful in order to correct a genetic defect related to the expression of the native gene in a host organism or to the production of a biologically inactive purH protein.

Consequently, the present invention also deals with recombinant expression vectors mainly designed for the in vivo production of the purH polypeptide of SEQ ID NO: 3 or fragments or variants thereof by the introduction of the appropriate genetic material in the organism of the patient to be treated. This genetic material may be introduced in vitro in a cell that has been previously extracted from the organism, the modified cell being subsequently reintroduced in the said organism, directly in vivo into the appropriate tissue.

2. Regulatory Elements

Promoters

The suitable promoter regions used in the expression vectors according to the present invention are chosen taking into account the cell host in which the heterologous gene has to be expressed. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell, such as, for example, a human or a viral promoter.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232-8 and pCM7 vectors.

Preferred bacterial promoters are the LacI, LacZ, the T3 or T7 bacteriophage RNA polymerase promoters, the gpt, lambda PR, PL and trp promoters (EP 0036776), the polyhedrin promoter, or the p10 protein promoter from baculovirus (Kit Novagen) (Smith et al., 1983; O'Reilly et al., 1992), the disclosures of which are incorporated herein by reference, the lambda PR promoter or also the trc promoter.

Eukaryotic promoters include CMV immediate early, HSV thymidine kinase, early and late SV40, LTRs from retrovirus, and mouse metallothionine-L. Selection of a convenient vector and promoter is well within the level of ordinary skill in the art.

The choice of a promoter is well within the ability of a person skilled in the field of genetic engineering. For example, one may refer to the book of Sambrook et al. (1989) or also to the procedures described by Fuller et al. (1996), the disclosure of which is incorporated herein by reference.

Other Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

The vector containing the appropriate DNA sequence as described above, more preferably purH gene regulatory polynucleotide, a polynucleotide encoding the purH polypeptide selected from the group consisting of SEQ ID NO: 1 or a fragment or a variant thereof and SEQ ID NO: 2, or both of them, can be utilized to transform an appropriate host to allow the expression of the desired polypeptide or polynucleotide.

3. Selectable Markers

Such markers would confer an identifiable change to the cell permitting easy identification of cells containing the expression construct. The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. coli*, or levan saccharase for mycobacteria, this latter marker being a negative selection marker.

4. Preferred Vectors

Bacterial Vectors

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), and GEM1 (Promega Biotec, Madison, Wis., USA).

Large numbers of other suitable vectors are known to those of skill in the art, and commercially available, such as the following bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXT1, pSG (Stratagene); pSVK3, pBPV, pMSG, pSVL (Pharmacia); pQE-30 (QIAexpress).

Bacteriophage Vectors

The P1 bacteriophage vector may contain large inserts ranging from about 80 to about 100 kb.

The construction of P1 bacteriophage vectors such as p158 or p158/neo8 are notably described by Sternberg (1992, 1994), the disclosures of which are incorporated herein by reference. Recombinant P1 clones comprising purH nucleotide sequences may be designed for inserting large polynucleotides of more than 40 kb (Linton et al., 1993). To generate P1 DNA for transgenic experiments, a preferred protocol is the protocol described by McCormick et al. (1994). Briefly, *E. coli* (preferably strain NS3529) harboring the P1 plasmid are grown overnight in a suitable broth medium containing 25 µg/ml of kanamycin. The P1 DNA is prepared from the *E. coli* by alkaline lysis using the Qiagen Plasmid Maxi kit (Qiagen, Chatsworth, Calif., USA), according to the manufacturer's instructions. The P1 DNA is purified from the bacterial lysate on two Qiagen-tip 500 columns, using the washing and elution buffers contained in the kit. A phenol/chloroform extraction is then performed before precipitating the DNA with 70% ethanol. After solubilizing the DNA in TE (10 mM Tris-HCl, pH 7.4, 1 mM EDTA), the concentration of the DNA is assessed by spectrophotometry.

When the goal is to express a P1 clone comprising purH nucleotide sequences in a transgenic animal, typically in transgenic mice, it is desirable to remove vector sequences from the P1 DNA fragment, for example by cleaving the P1 DNA at rare-cutting sites within the P1 polylinker (SfiI, NotI or SalI). The P1 insert is then purified from vector sequences on a pulsed-field agarose gel, using methods similar to those originally reported for the isolation of DNA from YACs (Schedl et al., 1993a; Peterson et al., 1993). At this stage, the resulting purified insert DNA can be concentrated, if necessary, on a Millipore Ultrafree-MC Filter Unit (Millipore, Bedford, Mass., USA—30,000 molecular weight limit) and then dialyzed against microinjection buffer (10 mM Tris-HCl, pH 7.4; 250 µM EDTA) containing 100 mM NaCl, 30 µM spermine, 70 µM sperm idine on a microdyalisis membrane (type VS, 0.025 µM from Millipore). The intactness of the purified P1 DNA insert is assessed by electrophoresis on 1% agarose (Sea Kem GTG; FMC Bio-products) pulse-field gel and staining with ethidium bromide.

Baculovirus Vectors

A suitable vector for the expression of the purH polypeptide of SEQ ID NO: 3 or fragments or variants thereof is a baculovirus vector that can be propagated in insect cells and in insect cell lines. A specific suitable host vector system is the pVL1392/1393 baculovirus transfer vector (Pharmingen) that is used to transfect the SF9 cell line (ATCC No CRL 1711) which is derived from *Spodoptera frugiperda*.

Other suitable vectors for the expression of the purH polypeptide of SEQ ID NO: 3 or fragments or variants thereof in a baculovirus expression system include those described by Chai et al. (1993), Vlasak et al. (1983) and Lenhard et al. (1996).

Viral Vectors

In one specific embodiment, the vector is derived from an adenovirus. Preferred adenovirus vectors according to the invention are those described by Feldman and Steg (1996) or Ohno et al. (1994). Another preferred recombinant adenovirus according to this specific embodiment of the present invention is the human adenovirus type 2 or 5 (Ad 2 or Ad 5) or an adenovirus of animal origin (French patent application No FR-93.05954).

Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acids are stably integrated into the chromosomal DNA of the host.

Particularly preferred retroviruses for the preparation or construction of retroviral in vitro or in vitro gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos VR-334, VR-657, VR-726, VR-659 and VR-728). Other preferred retroviral vectors are those described in Roth et al. (1996), PCT Application No WO 93/25234, PCT Application No WO 94/06920, Roux et al., 1989, Julan et al., 1992 and Neda et al., 1991, the disclosures of which are incorporated by reference herein in their entirety.

Yet another viral vector system that is contemplated by the invention consists of the adeno-associated virus (AAV). The adeno-associated virus is a naturally occurring defective virus that requires another virus, such as an adenovirus or a herpes virus, as a helper virus for efficient replication and a productive life cycle (Muzyczka et al., 1992). It is also one of the few viruses that may integrate its DNA into non-dividing cells, and exhibits a high frequency of stable integration (Flotte et al., 1992; Samulski et al., 1989; McLaughlin et al., 1989). One advantageous feature of AAV derives from its reduced efficacy for transducing primary cells relative to transformed cells.

BAC Vectors

The bacterial artificial chromosome (BAC) cloning system (Shizuya et al., 1992) has been developed to stably maintain large fragments of genomic DNA (100-300 kb) in *E. coli*. A preferred BAC vector consists of pBeloBAC11 vector that has been described by Kim et al. (1996). BAC libraries are prepared with this vector using size-selected genomic DNA that has been partially digested using enzymes that permit ligation into either the Bam HI or HindIII sites in the vector. Flanking these cloning sites are T7 and SP6 RNA polymerase transcription initiation sites that can be used to generate end probes by either RNA transcription or PCR methods. After the construction of a BAC library in *E. coli*, BAC DNA is purified from the host cell as a supercoiled circle. Converting these circular molecules into a linear form precedes both size determination and introduction of the BACs into recipient cells. The cloning site is flanked by two Not I sites, permitting cloned segments to be excised from the vector by Not I digestion. Alternatively, the DNA insert contained in the pBeloBAC11 vector may be linearized by treatment of the BAC vector with the commercially available enzyme lambda terminase that leads to the cleavage at the unique cosN site, but this cleavage method results in a full length BAC clone containing both the insert DNA and the BAC sequences.

5. Delivery of the Recombinant Vectors

In order to effect expression of the polynucleotides and polynucleotide constructs of the invention, these constructs must be delivered into a cell. This delivery may be accomplished in vitro, as in laboratory procedures for transforming cell lines, or in vivo or ex vivo, as in the treatment of certain disease states.

One mechanism is viral infection where the expression construct is encapsulated in an infectious viral particle.

Several non-viral methods for the transfer of polynucleotides into cultured mammalian cells are also contemplated by the present invention, and include, without being limited to, calcium phosphate precipitation (Graham et al., 1973; Chen et al., 1987;), DEAE-dextran (Gopal, 1985), electroporation (Tur-Kaspa et al., 1986; Potter et al., 1984), direct microinjection (Harland et al., 1985), DNA-loaded liposomes (Nicolau et al., 1982; Fraley et al., 1979), and receptor-mediate transfection (Wu and Wu, 1987; 1988). Some of these techniques may be successfully adapted for in vivo or ex vivo use.

Once the expression polynucleotide has been delivered into the cell, it may be stably integrated into the genome of the recipient cell. This integration may be in the cognate location and orientation via homologous recombination (gene replacement) or it may be integrated in a random, non specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

Compositions for use in vitro and in vivo comprising a "naked" polynucleotide are described in PCT application No WO 90/11092 (Vical Inc.) and also in PCT application No. WO 95/11307 (Institut Pasteur, INSERM, Université d'Ottawa) as well as in the articles of Tacson et al. (1996) and of Huygen et al. (1996), the disclosures of which are incorporated by reference herein in their entirety.

In still another embodiment of the invention, the transfer of a naked polynucleotide of the invention, including a polynucleotide construct of the invention, into cells may be proceeded with a particle bombardment (biolistic), said particles being DNA-coated microprojectiles accelerated to a high velocity allowing them to pierce cell membranes and enter cells without killing them, such as described by Klein et al. (1987).

In a further embodiment, the polynucleotide of the invention may be entrapped in a liposome (Ghosh and Bacchawat, 1991; Wong et al., 1980; Nicolau et al., 1987).

In a specific embodiment, the invention provides a composition for the in vivo production of the purH protein or polypeptide described herein. It comprises a naked polynucleotide operatively coding for this polypeptide, in solution in a physiologically acceptable carrier, and suitable for introduction into a tissue to cause cells of the tissue to express the said protein or polypeptide.

The amount of vector to be injected into the desired host organism varies according to the site of injection. As an indicative dose, it will be injected between 0.1 and 100 µg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired purH polypeptide or the desired fragment thereof is reintroduced into the animal body in order to deliver the recombinant protein within the body either locally or systemically.

Cell Hosts

Another object of the invention consists of a host cell that has been transformed or transfected with one of the polynucleotides described herein, and in particular a polynucleotide either comprising a purH regulatory polynucleotide or the coding sequence of the purH polypeptide selected from the group consisting of SEQ ID NO: 1 or a fragment or a variant thereof and SEQ ID NO: 2. Also included are host cells that are transformed (prokaryotic cells) or that are transfected (eukaryotic cells) with a recombinant vector such as one of those described above.

Generally, a recombinant host cell of the invention comprises any one of the polynucleotides or the recombinant vectors described herein. More particularly, the cell hosts of the present invention can comprise any of the polynucleotides described in the "Genomic Sequences Of The purH Gene" section, the "purH cDNA Sequences" section, the "Coding Regions" section, the "Polynucleotide constructs" section, and the "Oligonucleotide Probes And Primers" section.

A further recombinant cell host according to the invention comprises a polynucleotide containing a biallelic marker selected from the group consisting of A1 to A43, and the complements thereof.

Preferred host cells used as recipients for the expression vectors of the invention are the following:

a) Prokaryotic host cells: *Escherichia coli* strains (I.E.DH5-α strain), *Bacillus subtilis*, *Salmonella typhimurium*, and strains from species like *Pseudomonas*, *Streptomyces* and *Staphylococcus*.

b) Eukaryotic host cells: HeLa cells (ATCC No CCL2; No CCL2.1; No CCL2.2), Cv 1 cells (ATCC No CCL70), COS cells (ATCC No CRL1650; No CRL1651), Sf-9 cells (ATCC No CRL1711), C127 cells (ATCC No CRL-1804), 3T3 (ATCC No CRL-6361), CHO (ATCC No CCL-61), human kidney 293 (ATCC No 45504; No CRL-1573) and BHK (ECACC No 84100501; No 84111301).

c) Other mammalian host cells.

The purH gene expression in mammalian, and typically human, cells may be rendered defective, or alternatively it may be proceeded with the insertion of a purH genomic or cDNA sequence with the replacement of the purH gene counterpart in the genome of an animal cell by a purH polynucleotide according to the invention. These genetic alterations may be generated by homologous recombination events using specific DNA constructs that have been previously described.

One kind of cell hosts that may be used are mammal zygotes, such as murine zygotes. For example, murine zygotes may undergo microinjection with a purified DNA molecule of interest, for example a purified DNA molecule that has previously been adjusted to a concentration range from 1 ng/ml—for BAC inserts—3 ng/µl—for P1 bacteriophage inserts—in 10 mM Tris-HCl, pH 7.4, 250 µM EDTA containing 100 mM NaCl, 30 µM spermine, and 70 µM spermidine. When the DNA to be microinjected has a large size, polyamines and high salt concentrations can be used in order to avoid mechanical breakage of this DNA, as described by Schedl et al (1993b).

Any one of the polynucleotides of the invention, including the DNA constructs described herein, may be introduced in an embryonic stem (ES) cell line, preferably a mouse ES cell line. ES cell lines are derived from pluripotent, uncommitted cells of the inner cell mass of pre-implantation blastocysts. Preferred ES cell lines are the following: ES-E14TG2a (ATCC no CRL-1821), ES-D3 (ATCC no CRL1934 and no CRL-11632), YS001 (ATCC no CRL-11776), 36.5 (ATCC no CRL-11116). To maintain ES cells in an uncommitted state, they are cultured in the presence of growth inhibited feeder cells which provide the appropriate signals to preserve this embryonic phenotype and serve as a matrix for ES cell adherence. Preferred feeder cells consist of primary embryonic fibroblasts that are established from tissue of day 13-day 14 embryos of virtually any mouse strain, that are maintained in culture, such as described by Abbondanzo et al. (1993) and are inhibited in growth by irradiation, such as described by Robertson (1987), or by the presence of an inhibitory concentration of LIF, such as described by Pease and Williams (1990).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

Cells are typically harvested by centrifugation, disrupted by physical or chemical means, and the resulting crude extract retained for further purification.

Microbial cells employed in the expression of proteins can be disrupted by any convenient method, including freeze-thaw cycling, sonication, mechanical disruption, or use of cell lysing agents. Such methods are well known by the skilled artisan.

Transgenic Animals

The terms "transgenic animals" or "host animals" are used herein to designate animals that have their genome genetically and artificially manipulated so as to include one of the nucleic acids according to the invention. Preferred animals are non-human mammals and include those belonging to a genus selected from *Mus* (e.g. mice), *Rattus* (e.g. rats) and *Oryctogalus* (e.g. rabbits) which have their genome artificially and genetically altered by the insertion of a nucleic acid according to the invention. In one embodiment, the invention encompasses non-human host mammals and animals comprising a recombinant vector of the invention or a purH gene disrupted by homologous recombination with a knock out vector.

The transgenic animals of the invention all include within a plurality of their cells a cloned recombinant or synthetic DNA sequence, more specifically one of the purified or isolated nucleic acids comprising a purH coding sequence, a purH regulatory polynucleotide or a DNA sequence encoding an antisense polynucleotide such as described in the present specification.

Generally, a transgenic animal according the present invention comprises any one of the polynucleotides, the recombinant vectors and the cell hosts described in the present invention. More particularly, the transgenic animals of the present invention can comprise any of the polynucleotides described in the "Genomic Sequences Of The purH Gene" section, the "purH cDNA Sequences" section, the "Coding Regions" section, the "Polynucleotide constructs" section, the "Oligonucleotide Probes And Primers" section, the "Recombinant Vectors" section and the "Cell Hosts" section.

A further transgenic animals according to the invention contains in their somatic cells and/or in their germ line cells a polynucleotide comprising a biallelic marker selected from the group consisting of A1 to A43, and the complements thereof.

In a first preferred embodiment, these transgenic animals may be good experimental models in order to study the diverse pathologies related to cell differentiation, in particular concerning the transgenic animals within the genome of which has been inserted one or several copies of a polynucleotide encoding a native purH protein, or alternatively a mutant purH protein.

In a second preferred embodiment, these transgenic animals may express a desired polypeptide of interest under the control of the regulatory polynucleotides of the purH gene, leading to good yields in the synthesis of this protein of interest, and eventually a tissue specific expression of this protein of interest.

The design of the transgenic animals of the invention may be made according to the conventional techniques well known from the one skilled in the art. For more details regarding the production of transgenic animals, and specifically transgenic mice, it may be referred to U.S. Pat. No. 4,873,191, issued Oct. 10, 1989; U.S. Pat. No. 5,464,764 issued Nov. 7, 1995; and U.S. Pat. No. 5,789,215, issued Aug. 4, 1998; these documents being herein incorporated by reference to disclose methods producing transgenic mice.

Transgenic animals of the present invention are produced by the application of procedures which result in an animal with a genome that has incorporated exogenous genetic material. The procedure involves obtaining the genetic material, or a portion thereof, which encodes either a purH coding sequence, a purH regulatory polynucleotide or a DNA sequence encoding a purH antisense polynucleotide such as described in the present specification.

A recombinant polynucleotide of the invention is inserted into an embryonic or ES stem cell line. The insertion is preferably made using electroporation, such as described by Thomas et al. (1987). The cells subjected to electroporation are screened (e.g. by selection via selectable markers, by PCR or by Southern blot analysis) to find positive cells which have integrated the exogenous recombinant polynucleotide into their genome, preferably via an homologous recombination event. An illustrative positive-negative selection procedure that may be used according to the invention is described by Mansour et al. (1988).

Then, the positive cells are isolated, cloned and injected into 3.5 days old blastocysts from mice, such as described by Bradley (1987). The blastocysts are then inserted into a female host animal and allowed to grow to term.

Alternatively, the positive ES cells are brought into contact with embryos at the 2.5 days old 8-16 cell stage (morulae) such as described by Wood et al. (1993) or by Nagy et al. (1993), the ES cells being internalized to colonize extensively the blastocyst including the cells which will give rise to the germ line.

The offspring of the female host are tested to determine which animals are transgenic e.g. include the inserted exogenous DNA sequence and which are wild-type.

Thus, the present invention also concerns a transgenic animal containing a nucleic acid, a recombinant expression vector or a recombinant host cell according to the invention.

Recombinant Cell Lines Derived from the Transgenic Animals of the Invention.

A further object of the invention consists of recombinant host cells obtained from a transgenic animal described herein. In one embodiment the invention encompasses cells derived from non-human host mammals and animals comprising a recombinant vector of the invention or a purH gene disrupted by homologous recombination with a knock out vector.

Recombinant cell lines may be established in vitro from cells obtained from any tissue of a transgenic animal according to the invention, for example by transfection of primary cell cultures with vectors expressing one-genes such as SV40 large T antigen, as described by Chou (1989) and Shay et al. (1991).

Method for Screening Substances Interacting with the Regulatory Sequences of the purH Gene The present invention also concerns a method for screening substances or molecules that are able to interact with the regulatory sequences of the purH gene, such as for example promoter or enhancer sequences.

Nucleic acids encoding proteins which are able to interact with the regulatory sequences of the purH gene, more particularly a nucleotide sequence selected from the group consisting of the polynucleotides of the 5' and 3' regulatory region or a fragment or variant thereof, and preferably a variant comprising one of the biallelic markers of the invention, may be identified by using a one-hybrid system, such as that described in the booklet enclosed in the Matchmaker One-Hybrid System kit from Clontech (Catalog Ref. no K1603-1), the technical teachings of which are herein incorporated by reference. Briefly, the target nucleotide sequence is cloned upstream of a selectable reporter sequence and the resulting DNA construct is integrated in the yeast genome (*Saccharomyces cerevisiae*). The yeast cells containing the reporter sequence in their genome are then transformed with a library consisting of fusion molecules between cDNAs encoding candidate proteins for binding onto the regulatory sequences of the purH gene and sequences encoding the activator domain of a yeast transcription factor such as GAL4. The recombinant yeast cells are plated in a culture broth for selecting cells expressing the reporter sequence. The recombinant yeast cells thus selected contain a fusion protein that is able to bind onto the target regulatory sequence of the purH gene. Then, the cDNAs encoding the fusion proteins are sequenced and may be cloned into expression or transcription vectors in vitro. The binding of the encoded polypeptides to the target regulatory sequences of the purH gene may be confirmed by techniques familiar to one skilled in the art, such as gel retardation assays or DNAse protection assays.

Gel retardation assays may also be performed independently in order to screen candidate molecules that are able to interact with the regulatory sequences of the purH gene, such as described by Fried and Crothers (1981), Garner and Revzin (1981) and Dent and Latchman (1993), the teachings of these publications being herein incorporated by reference. These techniques are based on the principle according to which a DNA fragment which is bound to a protein migrates slower than the same unbound DNA fragment. Briefly, the target nucleotide sequence is labeled. Then the labeled target nucleotide sequence is brought into contact with either a total nuclear extract from cells containing transcription factors, or with different candidate molecules to be tested. The interaction between the target regulatory sequence of the purH gene and the candidate molecule or the transcription factor is detected after gel or capillary electrophoresis through a retardation in the migration.

Method for Screening Ligands that Modulate the Expression of the purH Gene

Another subject of the present invention is a method for screening molecules that modulate the expression of the purH protein. Such a screening method comprises the steps of:
a) cultivating a prokaryotic or an eukaryotic cell that has been transfected with a nucleotide sequence encoding the purH protein or a variant or a fragment thereof, placed under the control of its own promoter;
b) bringing into contact the cultivated cell with a molecule to be tested;
c) quantifying the expression of the purH protein or a variant or a fragment thereof.

In an embodiment, the nucleotide sequence encoding the purH protein or a variant or a fragment thereof comprises an allele of at least one of the biallelic markers A1 to A17, A34 and A35, and the complements thereof.

Using DNA recombination techniques well known by one skilled in the art, the purH protein encoding DNA sequence is inserted into an expression vector, downstream from its promoter sequence. As an illustrative example, the promoter sequence of the purH gene is contained in the nucleic acid of the 5' regulatory region.

The quantification of the expression of the purH protein may be realized either at the mRNA level or at the protein level. In the latter case, polyclonal or monoclonal antibodies may be used to quantify the amounts of the purH protein that have been produced, for example in an ELISA or a RIA assay.

In a preferred embodiment, the quantification of the purH mRNA is realized by a quantitative PCR amplification of the cDNA obtained by a reverse transcription of the total mRNA of the cultivated purH-transfected host cell, using a pair of primers specific for purH.

The present invention also concerns a method for screening substances or molecules that are able to increase, or in contrast to decrease, the level of expression of the purH gene. Such a method may allow one skilled in the art to select substances exerting a regulating effect on the expression level of the purH gene and which may be useful as active ingredients included in pharmaceutical compositions for treating patients suffering from prostate cancer.

Thus, part of the present invention is also a method for screening of a candidate substance or molecule that modulated the expression of the purH gene; this method comprises the following steps:
providing a recombinant cell host containing a nucleic acid, wherein said nucleic acid comprises a nucleotide sequence of the 5' regulatory region or a biologically active fragment or variant thereof located upstream of a polynucleotide encoding a detectable protein;
obtaining a candidate substance; and
determining the ability of the candidate substance to modulate the expression levels of the polynucleotide encoding the detectable protein.

In a further embodiment, the nucleic acid comprising the nucleotide sequence of the 5' regulatory region or a biologically active fragment or variant thereof also includes a 5'UTR region of the purH cDNA of SEQ ID NO: 2, or one of its biologically active fragments or variants thereof.

Among the preferred polynucleotides encoding a detectable protein, there may be cited polynucleotides encoding beta galactosidase, green fluorescent protein (GFP) and chloramphenicol acetyl transferase (CAT).

The invention also pertains to kits useful for performing the herein described screening method. Preferably, such kits comprise a recombinant vector that allows the expression of a nucleotide sequence of the 5' regulatory region or a biologically active fragment or variant thereof located upstream and operably linked to a polynucleotide encoding a detectable protein or the purH protein or a fragment or a variant thereof.

Another embodiment of a method for the screening of a candidate substance or molecule that modulates the expression of the purH gene comprises the following steps:
a) providing a recombinant host cell containing a nucleic acid, wherein said nucleic acid comprises a 5'UTR sequence of the purH cDNA of SEQ ID NO: 2, or one of its biologically active fragments or variants, the 5'UTR sequence or its biologically active fragment or variant being operably linked to a polynucleotide encoding a detectable protein;
b) obtaining a candidate substance; and
c) determining the ability of the candidate substance to modulate the expression levels of the polynucleotide encoding the detectable protein.

In a specific embodiment of the above screening method, the nucleic acid that comprises a nucleotide sequence selected from the group consisting of the 5'UTR sequence of the purH cDNA of SEQ ID NO: 2 or one of its biologically active fragments or variants, includes a promoter sequence which is endogenous with respect to the purH 5'UTR sequence.

In another specific embodiment of the above screening method, the nucleic acid that comprises a nucleotide sequence selected from the group consisting of the 5'UTR sequence of the purH cDNA of SEQ ID NO: 2 or one of its biologically active fragments or variants, includes a promoter sequence which is exogenous with respect to the purH 5'UTR sequence defined therein.

In a further preferred embodiment, the nucleic acid comprising the 5'-UTR sequence of the purH cDNA or SEQ ID NO: 2 or the biologically active fragments thereof includes a biallelic marker selected from the group consisting of A1 to A17, A34 and A35 or the complements thereof.

The invention further deals with a kit for the screening of a candidate substance modulating the expression of the purH gene, wherein said kit comprises a recombinant vector that comprises a nucleic acid including a 5'UTR sequence of the purH cDNA of SEQ ID NO: 2, or one of their biologically active fragments or variants, the 5'UTR sequence or its biologically active fragment or variant being operably linked to a polynucleotide encoding a detectable protein.

For the design of suitable recombinant vectors useful for performing the screening methods described above, refer to the section of the present specification wherein the preferred recombinant vectors of the invention are detailed.

Expression levels and patterns of purH may be analyzed by solution hybridization with long probes as described in International Patent Application No. WO 97/05277, the entire contents of which are incorporated herein by reference. Briefly, the purH cDNA or the purH genomic DNA described above, or fragments thereof, is inserted at a cloning site immediately downstream of a bacteriophage (T3, T7 or SP6) RNA polymerase promoter to produce antisense RNA. Preferably, the purH insert comprises at least 100 or more consecutive nucleotides of the genomic DNA sequence or the cDNA sequences. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridization is performed under standard stringent conditions (40-50° C. for 16 hours in an 80% formamide, 0.4 M NaCl buffer, pH 7-8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

Quantitative analysis of purH gene expression may also be performed using arrays. As used herein, the term array means a one dimensional, two dimensional, or multidimensional arrangement of a plurality of nucleic acids of sufficient length to permit specific detection of expression of mRNAs capable of hybridizing thereto. For example, the arrays may contain a plurality of nucleic acids derived from genes whose expression levels are to be assessed. The arrays may include the purH genomic DNA, the purH cDNA sequences or the sequences complementary thereto or fragments thereof, particularly those comprising at least one of the biallelic markers according the present invention, preferably at least one of the biallelic markers A1 to A43. Preferably, the fragments are at least 15 nucleotides in length. In other embodiments, the fragments are at least 25 nucleotides in length. In some embodiments, the fragments are at least 50 nucleotides in length. More preferably, the fragments are at least 100 nucleotides in length. In another preferred embodiment, the fragments are more than 100 nucleotides in length. In some embodiments the fragments may be more than 500 nucleotides in length.

For example, quantitative analysis of purH gene expression may be performed with a complementary DNA microarray as described by Schena et al. (1995 and 1996). Full length purH cDNAs or fragments thereof are amplified by PCR and arrayed from a 96-well microtiter plate onto silylated microscope slides using high-speed robotics. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

Cell or tissue mRNA is isolated or commercially obtained and probes are prepared by a single round of reverse transcription. Probes are hybridized to 1 cm$^2$ microarrays under a 14×14 mm glass coverslip for 6-12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of purH gene expression may also be performed with full length purH cDNAs or fragments thereof in complementary DNA arrays as described by Pietu et al. (1996). The full length purH cDNA or fragments thereof is PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis using the purH genomic DNA, the purH cDNA, or fragments thereof can be done through high density nucleotide arrays as described by Lockhart et al. (1996) and Sosnowsky et al. (1997). Oligonucleotides of 15-50 nucleotides from the sequences of the purH genomic DNA, the purH cDNA sequences particularly those comprising at least one of biallelic markers according the present invention, preferably at least one biallelic marker selected from the group consisting of A1 to A17, A34 and A35, or the sequences complementary thereto, are synthesized directly on the chip (Lockhart et al., supra) or synthesized and then addressed to the chip (Sosnowski et al., supra). Preferably, the oligonucleotides are about 20 nucleotides in length.

purH cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip. After washing as described in Lockhart et al., supra and application of different electric fields (Sosnowsky et al., 1997), the dyes or labeling compounds are detected and quantified. Duplicate hybridizations are performed. Comparative analysis of the intensity of the signal originating from cDNA probes on the same target oligonucleotide in different cDNA samples indicates a differential expression of purH mRNA.

Methods for Inhibiting the Expression of a purH Gene

Other therapeutic compositions according to the present invention comprise advantageously an oligonucleotide fragment of the nucleic sequence of purH as an antisense tool or a triple helix tool that inhibits the expression of the corresponding purH gene. A preferred fragment of the nucleic sequence of purH comprises an allele of at least one of the biallelic markers A1 to A17, A34 and A35.

Antisense Approach

Preferred methods using antisense polynucleotides according to the present invention are the procedures described by Sczakiel et al. (1995).

Preferably, the antisense tools are chosen among the polynucleotides (15-200 bp long) that are complementary to the 5' end of the purH mRNA. In another embodiment, a combination of different antisense polynucleotides complementary to different parts of the desired targeted gene are used.

Preferred antisense polynucleotides according to the present invention are complementary to a sequence of the mRNAs of purH that contains either the translation initiation codon ATG or a splicing donor or acceptor site.

The antisense nucleic acids should have a length and melting temperature sufficient to permit formation of an intracellular duplex having sufficient stability to inhibit the expression of the purH mRNA in the duplex. Strategies for designing antisense nucleic acids suitable for use in gene therapy are disclosed in Green et al., (1986) and Izant and Weintraub, (1984), the disclosures of which are incorporated herein by reference.

In some strategies, antisense molecules are obtained by reversing the orientation of the PURH coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of purH antisense nucleic acids in vivo by operably linking DNA containing the antisense sequence to a promoter in a suitable expression vector.

Alternatively, suitable antisense strategies are those described by Rossi et al. (1991), in the International Applications Nos. WO 94/23026, WO 95/04141, WO 92/18522 and in the European Patent Application No. EP 0 572 287 A2, the disclosures of which are incorporated by reference herein in their entirety An alternative to the antisense technology that is used according to the present invention consists in using ribozymes that will bind to a target sequence via their complementary polynucleotide tail and that will cleave the corresponding RNA by hydrolyzing its target site (namely "hammerhead ribozymes"). Briefly, the simplified cycle of a hammerhead ribozyme consists of (1) sequence specific binding to the target RNA via complementary antisense sequences; (2) site-specific hydrolysis of the cleavable motif of the target strand; and (3) release of cleavage products, which gives rise to another catalytic cycle. Indeed, the use of long-chain antisense polynucleotide (at least 30 bases long) or ribozymes with long antisense arms are advantageous. A preferred delivery system for antisense ribozyme is achieved by covalently linking these antisense ribozymes to lipophilic groups or using liposomes as a convenient vector. Preferred antisense ribozymes according to the present invention are prepared as described by Sczakiel et al. (1995), the specific preparation procedures being referred to in said article being herein incorporated by reference.

Triple Helix Approach

The purH genomic DNA may also be used to inhibit the expression of the purH gene based on intracellular triple helix formation.

Triple helix oligonucleotides are used to inhibit transcription from a genome. They are particularly useful for studying alterations in cell activity when it is associated with a particular gene.

Similarly, a portion of the purH genomic DNA can be used to study the effect of inhibiting purH transcription within a cell. Traditionally, homopurine sequences were considered the most useful for triple helix strategies. However, homopyrimidine sequences can also inhibit gene expression. Such homopyrimidine oligonucleotides bind to the major groove at homopurine:homopyrimidine sequences. Thus, both types of sequences from the purH genomic DNA are contemplated within the scope of this invention.

To carry out gene therapy strategies using the triple helix approach, the sequences of the purH genomic DNA are first scanned to identify 10-mer to 20-mer homopyrimidine or homopurine stretches which could be used in triple-helix based strategies for inhibiting purH expression. Following identification of candidate homopyrimidine or homopurine stretches, their efficiency in inhibiting purH expression is assessed by introducing varying amounts of oligonucleotides containing the candidate sequences into tissue culture cells which express the purH gene.

The oligonucleotides can be introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced purH expression using techniques such as Northern blotting, RNase protection assays, or PCR based strategies to monitor the transcription levels of the purH gene in cells which have been treated with the oligonucleotide.

The oligonucleotides which are effective in inhibiting gene expression in tissue culture cells may then be introduced in vivo using the techniques described above in the antisense approach at a dosage calculated based on the in vitro results, as described in the antisense approach.

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al. (1989), which is hereby incorporated by this reference.

Computer-Related Embodiments

As used herein the term "nucleic acid codes of the invention" encompass the nucleotide sequences comprising, consisting essentially of, or consisting of any one of the following: a) a contiguous span of at least 12, 15, 18, 20, 25, 30, 35, 40, 50, 60, 70, 80, 90, 100, 150, 200, 500, or 1000 nucleotides of SEQ ID NO: 1, wherein said contiguous span comprises at least 1 of the following nucleotide positions of SEQ ID NO: 1: 1-1587, 1729-2000, 2095-2414, 2558-3235, 3848-3991, 4156-7043, 7396-7958, 8237-9596, 9666-9874, 9921-10039, 10083-11742, 11825-15173, 15267-15916, 16075-16750, 16916-22304, 22443-23269, 23384-24834, 24927-25952, 26048-28683, 28829-34694, 37282-37458, 37765-37894, 38563-38932, 39178-39451, 39692-39821, 40038-

40445, and 40846-41587; b) a contiguous span of at least 12, 15, 18, 20, 25, 30, 35, 40, 50, 60, 70, 80, 90, 100, 150, 200, 500, or 1000 nucleotides of SEQ ID NO: 1, wherein said contiguous span comprises a nucleotide selected from the group consisting of a G at position 15234, and a G at position 36801 of SEQ ID NO: 1; c) a contiguous span of at least 12, 15, 18, 20, 25, 30, 35, 40, 50, 60, 70, 80, 90, 100, 150, 200, 500, or 1000 nucleotides of SEQ ID NO: 2, wherein said contiguous span comprises a nucleotide selected from the group consisting of a G at position 424, and a G at position 1520 of SEQ ID NO: 2; d) a contiguous span of at least 12, 15, 18, 20, 25, 30, 35, 40, 50, 60, 70, 80, 90, 100, 150, 200, or 500 nucleotides, to the extent that such lengths are consistent with the specific sequence, of a sequence selected from the group consisting of SEQ ID NOs: 4 to 22, and the complements thereof, optionally wherein said contiguous span comprises either allele 1 or allele 2 of a purH-related biallelic marker selected from the group consisting of A18 to A33 and A36 to A43; and e) a nucleotide sequence complementary to any one of the preceding nucleotide sequences.

The "nucleic acid codes of the invention" further encompass nucleotide sequences homologous to a contiguous span of at least 30, 35, 40, 50, 60, 70, 80, 90, 100, 150, 200, 500, or 1000 nucleotides of the following nucleotide position range: 1-1587, 1729-2000, 2095-2414, 2558-3235, 3848-3991, 4156-7043, 7396-7958, 8237-9596, 9666-9874, 9921-10039, 10083-11742, 11825-15173, 15267-15916, 16075-16750, 16916-22304, 22443-23269, 23384-24834, 24927-25952, 26048-28683, 28829-34694, 37282-37458, 37765-37894, 38563-38932, 39178-39451, 39692-39821, 40038-40445, and 40846-41587 of SEQ ID NO: 1, and sequences complementary to all of the preceding sequences. Homologous sequences refer to a sequence having at least 99%, 98%, 97%, 96%, 95%, 90%, 85%, 80%, or 75% homology to $$ these contiguous spans. Homology may be determined using any method described herein, including BLAST2N with the default parameters or with any modified parameters. Homologous sequences also may include RNA sequences in which uridines replace the thymines in the nucleic acid codes of the invention. It will be appreciated that the nucleic acid codes of the invention can be represented in the traditional single character format (See the inside back cover of Stryer, Lubert. *Biochemistry*, $3^{rd}$ edition. W. H Freeman & Co., New York.) or in any other format or code which records the identity of the nucleotides in a sequence.

As used herein the term "polypeptide codes of the invention" encompasses the polypeptide sequences comprising a contiguous span of at least 6, 8, 10, 12, 15, 20, 25, 30, 40, 50, or 100 amino acids of SEQ ID NO: 3, wherein said contiguous span includes a serine residue at amino acid position 116 of SEQ ID NO: 3. It will be appreciated that the polypeptide codes of the invention can be represented in the traditional single character format or three letter format (See the inside back cover of Stryer, Lubert. Biochemistry, $3^{rd}$ edition. W. H Freeman & Co., New York.) or in any other format or code which records the identity of the polypeptides in a sequence.

It will be appreciated by those skilled in the art that the nucleic acid codes of the invention and polypeptide codes of the invention can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid codes of the invention, or one or more of the polypeptide codes of the invention. Another aspect of the present invention is a computer readable medium having recorded thereon at least 2, 5, 10, 15, 20, 25, 30, or 50 nucleic acid codes of the invention. Another aspect of the present invention is a computer readable medium having recorded thereon at least 2, 5, 10, 15, 20, 25, 30, or 50 polypeptide codes of the invention.

Computer readable media include magnetically readable media, optically readable media, electronically readable media and magnetic/optical media. For example, the computer readable media may be a hard disc, a floppy disc, a magnetic tape, CD-ROM, DVD, RAM, or ROM as well as other types of other media known to those skilled in the art.

Embodiments of the present invention include systems, particularly computer systems which contain the sequence information described herein. As used herein, "a computer system" refers to the hardware components, software components, and data storage components used to store and/or analyze the nucleotide sequences of the nucleic acid codes of the invention, the amino acid sequences of the polypeptide codes of the invention, or other sequences. The computer system preferably includes the computer readable media described above, and a processor for accessing and manipulating the sequence data.

Preferably, the computer is a general purpose system that comprises a central processing unit (CPU), one or more data storage components for storing data, and one or more data retrieving devices for retrieving the data stored on the data storage components. A skilled artisan can readily appreciate that any one of the currently available computer systems is suitable.

In one particular embodiment, the computer system includes a processor connected to a bus which is connected to a main memory, preferably implemented as RAM, and one or more data storage devices, such as a hard drive and/or other computer readable media having data recorded thereon. In some embodiments, the computer system further includes one or more data retrieving devices for reading the data stored on the data storage components. The data retrieving device may represent, for example, a floppy disk drive, a compact disk drive, a magnetic tape drive, a hard disk drive, a CD-ROM drive, a DVD drive, etc. In some embodiments, the data storage component is a removable computer readable medium such as a floppy disk, a compact disk, a magnetic tape, etc. containing control logic and/or data recorded thereon. The computer system may advantageously include or be programmed by appropriate software for reading the control logic and/or the data from the data storage component once inserted in the data retrieving device. Software for accessing and processing the nucleotide sequences of the nucleic acid codes of the invention, or the amino acid sequences of the polypeptide codes of the invention (such as search tools, compare tools, modeling tools, etc.) may reside in main memory during execution.

In some embodiments, the computer system may further comprise a sequence comparer for comparing the nucleic acid codes of the invention or polypeptide codes of the invention stored on a computer readable medium to reference nucleotide or polypeptide sequences stored on a computer readable medium. A "sequence comparer" refers to one or more programs which are implemented on the computer system to compare a nucleotide or polypeptide sequence with other nucleotide or polypeptide sequences and/or compounds including but not limited to peptides, peptidomimetics, and chemicals the sequences or structures of which are stored within the data storage means. For example, the sequence comparer may compare the nucleotide sequences of the nucleic acid codes of the invention, or the amino acid sequences of the polypeptide codes of the invention stored on a computer readable medium to reference sequences stored on a computer readable medium to identify homologies, motifs implicated in biological function, or structural motifs. The various sequence comparer programs identified elsewhere in this patent specification are particularly contemplated for use in this aspect of the invention.

Accordingly, one aspect of the present invention is a computer system comprising a processor, a data storage device having stored thereon a nucleic acid code of the invention or a polypeptide code of the invention, a data storage device having retrievably stored thereon reference nucleotide sequences or polypeptide sequences to be compared to the nucleic acid code of the invention or polypeptide code of the invention and a sequence comparer for conducting the comparison. The sequence comparer may indicate a homology level between the sequences compared or identify structural motifs in the nucleic acid code of the invention and polypeptide codes of the invention or it may identify structural motifs in sequences which are compared to these nucleic acid codes and polypeptide codes. In some embodiments, the data storage device may have stored thereon the sequences of at least 2, 5, 10, 15, 20, 25, 30, or 50 of the nucleic acid codes of the invention or polypeptide codes of the invention.

Another aspect of the present invention is a method for determining the level of homology between a nucleic acid code of the invention and a reference nucleotide sequence, comprising the steps of reading the nucleic acid code and the reference nucleotide sequence through the use of a computer program which determines homology levels and determining homology between the nucleic acid code and the reference nucleotide sequence with the computer program. The computer program may be any of a number of computer programs for determining homology levels, including those specifically enumerated herein, including BLAST2N with the default parameters or with any modified parameters. The method may be implemented using the computer systems described above. The method may also be performed by reading 2, 5, 10, 15, 20, 25, 30, or 50 of the above described nucleic acid codes of the invention through the use of the computer program and determining homology between the nucleic acid codes and reference nucleotide sequences.

Alternatively, the computer program may be a computer program which compares the nucleotide sequences of the nucleic acid codes of the present invention, to reference nucleotide sequences in order to determine whether the nucleic acid code of the invention differs from a reference nucleic acid sequence at one or more positions. Optionally such a program records the length and identity of inserted, deleted or substituted nucleotides with respect to the sequence of either the reference polynucleotide or the nucleic acid code of the invention. In one embodiment, the computer program may be a program which determines whether the nucleotide sequences of the nucleic acid codes of the invention contain one or more biallelic marker or single nucleotide polymorphisms (SNP) with respect to a reference nucleotide sequence. These single nucleotide polymorphisms may each comprise a single base substitution, insertion, or deletion, while the biallelic markers may each comprise nucleotide substitutions, insertions, or deletions of 1 to 10 contiguous nucleotides, preferably 1 to 5 contiguous nucleotides.

Another aspect of the present invention is a method for determining the level of homology between a polypeptide code of the invention and a reference polypeptide sequence, comprising the steps of reading the polypeptide code of the invention and the reference polypeptide sequence through use of a computer program which determines homology levels and determining homology between the polypeptide code and the reference polypeptide sequence using the computer program.

Accordingly, another aspect of the present invention is a method for determining whether a nucleic acid code of the invention differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer systems described above. The method may also be performed by reading at least 2, 5, 10, 15, 20, 25, 30, or 50 of the nucleic acid codes of the invention and the reference nucleotide sequences through the use of the computer program and identifying differences between the nucleic acid codes and the reference nucleotide sequences with the computer program.

In other embodiments the computer based system may further comprise an identifier for identifying features within the nucleotide sequences of the nucleic acid codes of the invention or the amino acid sequences of the polypeptide codes of the invention.

An "identifier" refers to one or more programs which identifies certain features within the above-described nucleotide sequences of the nucleic acid codes of the invention or the amino acid sequences of the polypeptide codes of the invention.

The nucleic acid codes of the invention or the polypeptide codes of the invention may be stored and manipulated in a variety of data processor programs in a variety of formats. For example, they may be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparers, identifiers, or sources of reference nucleotide or polypeptide sequences to be compared to the nucleic acid codes of the invention or the polypeptide codes of the invention. The following list is intended not to limit the invention but to provide guidance to programs and databases which are useful with the nucleic acid codes of the invention or the polypeptide codes of the invention. The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, 1990), FASTA (Pearson and Lipman, 1988), FASTDB (Brutlag et al., 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the EMBL/Swissprotein database, the MDL Available Chemicals Directory database, the MDL Drug Data Report data base, the Comprehensive Medicinal Chemistry database, Derwents's World Drug Index database, the BioByteMasterFile database, the Genbank database, and the Genseqn database. Many other programs and data bases would be apparent to one of skill in the art given the present disclosure.

Throughout this application, various publications, patents, and published patent applications are cited. The disclosures of the publications, patents, and published patent specifications referenced in this application are hereby incorporated by reference into the present disclosure to more fully describe the state of the art to which this invention pertains.

EXAMPLES

Example 1

Identification of Biallelic Markers—DNA Extraction

Donors were unrelated and healthy. They presented a sufficient diversity for being representative of a French heterogeneous population. The DNA from 100 individuals was extracted and tested for the detection of the biallelic markers.

30 ml of peripheral venous blood were taken from each donor in the presence of EDTA. Cells (pellet) were collected after centrifugation for 10 minutes at 2000 rpm. Red cells were lysed by a lysis solution (50 ml final volume: 10 mM Tris pH7.6; 5 mM MgCl$_2$; 10 mM NaCl). The solution was centrifuged (10 minutes, 2000 rpm) as many times as necessary to eliminate the residual red cells present in the supernatant, after resuspension of the pellet in the lysis solution.

The pellet of white cells was lysed overnight at 42° C. with 3.7 ml of lysis solution composed of:
  3 ml TE 10-2 (Tris-HCl 10 mM, EDTA 2 mM)/NaCl 0.4 M
  200 µl SDS 10%
  500 µl K-proteinase (2 mg K-proteinase in TE 10-2/NaCl 0.4 M).

For the extraction of proteins, 1 ml saturated NaCl (6M) (1/3.5 v/v) was added. After vigorous agitation, the solution was centrifuged for 20 minutes at 10000 rpm.

For the precipitation of DNA, 2 to 3 volumes of 100% ethanol were added to the previous supernatant, and the solution was centrifuged for 30 minutes at 2000 rpm. The DNA solution was rinsed three times with 70% ethanol to eliminate salts, and centrifuged for 20 minutes at 2000 rpm. The pellet was dried at 37° C., and resuspended in 1 ml TE 10-1 or 1 ml water. The DNA concentration was evaluated by measuring the OD at 260 nm (1 unit OD=50 µg/ml DNA).

To determine the presence of proteins in the DNA solution, the OD 260/OD 280 ratio was determined. Only DNA preparations having a OD 260/OD 280 ratio between 1.8 and 2 were used in the subsequent examples described below.

The pool was constituted by mixing equivalent quantities of DNA from each individual.

Example 2

Identification of Biallelic Markers: Amplification of Genomic DNA by PCR

The amplification of specific genomic sequences of the DNA samples of Example 1 was carried out on the pool of DNA obtained previously. In addition, 50 individual samples were similarly amplified.

| PCR assays were performed using the following protocol: | |
|---|---|
| Final volume | 25 µl |
| DNA | 2 ng/µl |
| MgCl$_2$ | 2 mM |
| dNTP (each) | 200 µM |
| primer (each) | 2.9 ng/µl |
| Ampli Taq Gold DNA polymerase | 0.05 unit/µl |
| PCR buffer (10x = 0.1 M TrisHCl pH8.3 0.5M KCl) | 1x |

Each pair of first primers was designed using the sequence information of the purH gene disclosed herein and the OSP software (Hillier & Green, 1991). This first pair of primers was about 20 nucleotides in length and had the sequences disclosed in Table 1 in the columns labeled "Position range of amplification primer in SEQ ID NO: 1," "Complementary position range of amplification primer in SEQ ID NO: 1," "Position range of amplification primer," and "Complementary position range of amplification primer."

TABLE 1

| Amplicon | Position range of the amplicon in SEQ ID 1 | | Primer name | Position range of amplification primer in SEQ ID NO: 1 | | Primer name | Complementary position range of amplification primer in SEQ ID NO: 1 | |
|---|---|---|---|---|---|---|---|---|
| 99-32284 | 6137 | 6597 | B1 | 6137 | 6157 | C1 | 6577 | 6597 |
| 99-5602 | 14864 | 15312 | B2 | 14864 | 14882 | C2 | 15292 | 15312 |
| 5-290 | 15837 | 16266 | B3 | 15837 | 15855 | C3 | 16249 | 16266 |
| 99-22573 | 16599 | 17049 | B4 | 16599 | 16617 | C4 | 17030 | 17049 |
| 99-22586 | 18131 | 18610 | B5 | 18131 | 18150 | C5 | 18592 | 18610 |
| 99-5596 | 22710 | 23149 | B6 | 22710 | 22727 | C6 | 23130 | 23149 |
| 5-293 | 23100 | 23530 | B7 | 23100 | 23118 | C7 | 23512 | 23530 |
| 5-294 | 25822 | 26241 | B8 | 25822 | 25840 | C8 | 26222 | 26241 |
| 99-23454 | 30332 | 30773 | B9 | 30332 | 30352 | C9 | 30754 | 30773 |
| 99-15528 | 30918 | 31408 | B10 | 30918 | 30935 | C10 | 31390 | 31408 |
| 99-15798 | 34780 | 35233 | B11 | 34780 | 34799 | C11 | 35215 | 35233 |
| 5-297 | 36593 | 37036 | B12 | 36593 | 36610 | C12 | 37017 | 37036 |
| 99-32281 | 37060 | 37561 | B13 | 37060 | 37080 | C13 | 37541 | 37561 |
| 5-298 | 38946 | 39365 | B14 | 38946 | 38965 | C14 | 39346 | 39365 |
| 99-23460 | 39439 | 39886 | B15 | 39439 | 39459 | C15 | 39868 | 39886 |

TABLE 1-continued

| Amplicon | Position range of the amplicon | Primer name | Position range of amplification primer | Primer name | Complementary position range of amplification primer |
|---|---|---|---|---|---|
| 99-22578 | 1    450 SEQ ID NO: 4 | B16 | 1    18 SEQ ID NO: 4 | C16 | 430    450 SEQ ID NO: 4 |
| 99-22580 | 1    506 SEQ ID NO: 5 | B17 | 1    18 SEQ ID NO: 5 | C17 | 488    506 SEQ ID NO: 5 |
| 99-22585 | 1    514 SEQ ID NO: 6 | B18 | 1    21 SEQ ID NO: 6 | C18 | 494    514 SEQ ID NO: 6 |
| 99-23437 | 1    497 SEQ ID NO: 7 | B19 | 1    20 SEQ ID NO: 7 | C19 | 478    497 SEQ ID NO: 7 |
| 99-23440 | 1    448 SEQ ID NO: 8 | B20 | 1    21 SEQ ID NO: 8 | C20 | 428    448 SEQ ID NO: 8 |
| 99-23442 | 1    457 SEQ ID NO: 9 | B21 | 1    20 SEQ ID NO: 9 | C21 | 437    457 SEQ ID NO: 9 |
| 99-23444 | 1    399 SEQ ID NO: 10 | B22 | 1    19 SEQ ID NO: 10 | C22 | 379    399 SEQ ID NO: 10 |
| 99-23451 | 1    547 SEQ ID NO: 11 | B23 | 1    20 SEQ ID NO: 11 | C23 | 529    547 SEQ ID NO: 11 |
| 99-23452 | 1    400 SEQ ID NO: 12 | B24 | 1    20 SEQ ID NO: 12 | C24 | 380    400 SEQ ID NO: 12 |
| 99-28437 | 1    450 SEQ ID NO: 13 | B25 | 1    20 SEQ ID NO: 13 | C25 | 431    450 SEQ ID NO: 13 |
| 99-32278 | 1    494 SEQ ID NO: 14 | B26 | 1    20 SEQ ID NO: 14 | C26 | 474    494 SEQ ID NO: 14 |
| 99-5574 | 1    533 SEQ ID NO: 15 | B27 | 1    20 SEQ ID NO: 15 | C27 | 513    533 SEQ ID NO: 15 |
| 99-5575 | 1    472 SEQ ID NO: 16 | B28 | 1    20 SEQ ID NO: 16 | C28 | 452    472 SEQ ID NO: 16 |
| 99-5582 | 1    516 SEQ ID NO: 17 | B29 | 1    19 SEQ ID NO: 17 | C29 | 497    516 SEQ ID NO: 17 |
| 99-5590 | 1    461 SEQ ID NO: 18 | B30 | 1    19 SEQ ID NO: 18 | C30 | 441    461 SEQ ID NO: 18 |
| 99-5595 | 1    453 SEQ ID NO: 19 | B31 | 1    18 SEQ ID NO: 19 | C31 | 436    453 SEQ ID NO: 19 |
| 99-5604 | 1    467 SEQ ID NO: 20 | B32 | 1    20 SEQ ID NO: 20 | C32 | 447    467 SEQ ID NO: 20 |
| 99-5605 | 1    399 SEQ ID NO: 21 | B33 | 1    18 SEQ ID NO: 21 | C33 | 380    399 SEQ ID NO: 21 |
| 99-5608 | 1    529 SEQ ID NO: 22 | B34 | 1    19 SEQ ID NO: 22 | C34 | 509    529 SEQ ID NO: 22 |

Preferably, the primers contained a common oligonucleotide tail upstream of the specific bases targeted for amplification which was useful for sequencing.

Primers from the columns labeled "Position range of amplification primer in SEQ ID NO: 1," and "Position range of amplification primer" contain the following additional PU 5' sequence: TGTAAAACGACGGCCAGT; and primers from the columns labeled "Complementary position range of amplification primer in SEQ ID NO: 1," and "Complementary position range of amplification primer" contain the following RP 5' sequence: CAGGAAACAGCTATGACC. The primer containing the additional PU 5' sequence is listed in SEQ ID NO: 23. The primer containing the additional RP 5' sequence is listed in SEQ ID NO: 24.

The synthesis of these primers was performed following the phosphoramidite method, on a GENSET UFPS 24.1 synthesizer.

DNA amplification was performed on a Genius II thermocycler. After heating at 95° C. for 10 min, 40 cycles were performed. Each cycle comprised: 30 sec at 95° C., 54° C. for 1 min, and 30 $$ sec at 72° C. For final elongation, 10 min at 72° C. ended the amplification. The quantities of the amplification products obtained were determined on 96-well microtiter plates, using a fluorometer and Picogreen as intercalant agent (Molecular Probes).

Example 3

Identification of Biallelic Markers—Sequencing of Amplified Genomic DNA and Identification of Polymorphisms The sequencing of the amplified DNA obtained in Example 2 was carried out on ABI 377 sequencers. The sequences of the amplification products were determined using automated dideoxy terminator sequencing reactions with a dye terminator cycle sequencing protocol. The products of the sequencing reactions were run on sequencing gels and the sequences were determined using gel image analysis (ABI Prism DNA Sequencing Analysis software (2.1.2 version)).

The sequence data were further evaluated to detect the presence of biallelic markers within the amplified fragments. The polymorphism search was based on the presence of superimposed peaks in the electrophoresis pattern resulting from different bases occurring at the same position as described previously.

In the 30 fragments of amplification, 33 biallelic markers were detected. The localization of these biallelic markers are as shown in Table 2.

TABLE 2

Genic purH-related biallelic markers

| Amplicon | BM | Marker Name | Localization in purH gene | Polymorphism all1 | Polymorphism all2 | BM position in SEQ ID No 1 | BM position in SEQ ID No 2 | Position of probes in SEQ ID NO: | | Probes |
|---|---|---|---|---|---|---|---|---|---|---|
| 99-32284 | A1 | 99-32284-107 | Intron 2 | C | T | 6491 | | 6479 | 6503 | P1 |
| 99-5602 | A2 | 99-5602-372 | Exon 5 T or S (116) | G | C | 15234 | 424 | 15222 | 15246 | P2 |
| 5-290 | A3 | 5-290-32 | Intron 5 | C | T | 15868 | | 15856 | 15880 | P3 |
| 99-22573 | A4 | 99-22573-321 | Intron 6 | C | T | 16729 | | 16717 | 16741 | P4 |
| 99-22586 | A5 | 99-22586-300 | Intron 7 | G | C | 18311 | | 18299 | 18323 | P5 |
| 99-22586 | A6 | 99-22586-39 | Intron 7 | C | T | 18572 | | 18560 | 18584 | P6 |
| 99-5596 | A7 | 99-5596-216 | Intron 8 | A | G | 22906 | | 22894 | 22918 | P7 |
| 5-293 | A8 | 5-293-76 | Intron 8 | C | T | 23175 | | 23163 | 23187 | P8 |
| 5-293 | A9 | 5-293-155 | Intron 8 | A | G | 23253 | | 23241 | 23265 | P9 |
| 5-294 | A10 | 5-294-285 | Intron 11 | G | C | 26106 | | 26094 | 26118 | P10 |
| 99-23454 | A11 | 99-23454-317 | Intron 12 | A | G | 30464 | | 30452 | 30476 | P11 |
| 99-23454 | A12 | 99-23454-105 | Intron 12 | G | C | 30669 | | 30657 | 30681 | P12 |
| 99-15528 | A13 | 99-15528-333 | Intron 12 | A | G | 31250 | | 31238 | 31262 | P13 |
| 99-15798 | A14 | 99-15798-86 | Intron 13 | A | G | 35148 | | 35136 | 35160 | P14 |
| 5-297 | A15 | 5-297-209 | Exon 14 | A | G | 36801 | 1520 | 36789 | 36813 | P15 |
| 99-32281 | A34 | 99-32281-276 | Intron 14 | C | T | 37286 | | 37274 | 37298 | P33 |
| 99-32281 | A35 | 99-32281-26 | Intron 14 | C | T | 37536 | | 37524 | 37548 | P34 |
| 5-298 | A16 | 5-298-376 | Intron 15 | A | G | 39321 | | 39309 | 39333 | P16 |
| 99-23460 | A17 | 99-23460-199 | 3'regulatory region | G | T | 39689 | | 39677 | 39701 | P17 |

Non-genic purH-related biallelic markers

| Amplicon | BM | Marker Name | Localization | Polymorphism all1 | Polymorphism all2 | BM position | Position of probes | Probes |
|---|---|---|---|---|---|---|---|---|
| 99-22578 | A18 | 99-22578-78 | Intergenic region | C | T | 78 in SEQ ID NO: 4 | 66 90 SEQ ID NO: 4 | P18 |
| 99-22580 | A19 | 99-22580-72 | Intergenic region | A | T | 72 in SEQ ID NO: 5 | 60 84 SEQ ID NO: 5 | P19 |
| 99-22585 | A36 | 99-22585-462 | Intergenic region | G | C | 462 in SEQ ID NO: 6 | 450 474 SEQ ID NO: 6 | P35 |
| 99-23437 | A20 | 99-23437-347 | Intergenic region | A | G | 347 in SEQ ID NO: 7 | 335 359 SEQ ID NO: 7 | P20 |
| 99-23440 | A21 | 99-23440-274 | Fibronectin gene | A | G | 273 in SEQ ID NO: 8 | 261 285 SEQ ID NO: 8 | P21 |
| 99-23442 | A22 | 99-23442-190 | Fibronectin gene | C | T | 190 in SEQ ID NO: 9 | 178 202 SEQ ID NO: 9 | P22 |
| 99-23442 | A37 | 99-23442-396 | Fibronectin gene | A | C | 396 in SEQ ID NO: 9 | 384 408 SEQ ID NO: 9 | P36 |
| 99-23444 | A23 | 99-23444-203 | Fibronectin gene | A | G | 203 in SEQ ID NO: 10 | 191 215 SEQ ID NO: 10 | P23 |
| 99-23451 | A24 | 99-23451-78 | Fibronectin gene | A | G | 77 in SEQ ID NO: 11 | 65 89 SEQ ID NO: 11 | P24 |
| 99-23452 | A25 | 99-23452-306 | Fibronectin gene | G | T | 306 in SEQ ID NO: 12 | 294 318 SEQ ID NO: 12 | P25 |
| 99-28437 | A38 | 99-28437-417 | Intergenic region | C | T | 417 in SEQ ID NO: 13 | 405 429 SEQ ID NO: 13 | P37 |
| 99-32278 | A39 | 99-32278-218 | Intergenic region | A | G | 218 in SEQ ID NO: 14 | 206 230 SEQ ID NO: 14 | P38 |
| 99-32278 | A40 | 99-32278-414 | Intergenic region | C | T | 414 in SEQ ID NO: 14 | 402 426 SEQ ID NO: 14 | P39 |
| 99-5575 | A26 | 99-5575-330 | Intergenic region | C | T | 327 in SEQ ID NO: 16 | 315 339 SEQ ID NO: 16 | P26 |

TABLE 2-continued

| | | | | | | | | | |
|---|---|---|---|---|---|---|---|---|---|
| 99-5582 | A27 | 99-5582-71 | Fibronectin gene | G | C | 71 in SEQ ID NO: 17 | 59 | 83 SEQ ID NO: 17 | P27 |
| 99-5582 | A41 | 99-5582-354 | Fibronectin gene | A | G | 354 in SEQ ID NO: 17 | 342 | 366 SEQ ID NO: 17 | P40 |
| 99-5590 | A28 | 99-5590-99 | Intergenic region | C | T | 99 in SEQ ID NO: 18 | 87 | 111 SEQ ID NO: 18 | P28 |
| 99-5590 | A42 | 99-5590-425 | Intergenic region | G | C | 424 in SEQ ID NO: 18 | 412 | 436 SEQ ID NO: 18 | P41 |
| 99-5595 | A29 | 99-5595-380 | Fibronectin gene | A | G | 379 in SEQ ID NO: 19 | 367 | 391 SEQ ID NO: 19 | P29 |
| 99-5604 | A30 | 99-5604-376 | Fibronectin gene | A | G | 374 in SEQ ID NO: 20 | 362 | 386 SEQ ID NO: 20 | P30 |
| 99-5605 | A31 | 99-5605-90 | Fibronectin gene | G | T | 90 in SEQ ID NO: 21 | 78 | 102 SEQ ID NO: 21 | P31 |
| 99-5605 | A43 | 99-5605-135 | Fibronectin gene | G | T | 135 in SEQ ID NO: 21 | 123 | 147 SEQ ID NO: 21 | P42 |
| 99-5608 | A32 | 99-5608-324 | Intergenic region | A | G | 323 in SEQ ID NO: 22 | 311 | 335 SEQ ID NO: 22 | P32 |
| 99-5574 | A33 | 99-5574-388 | Intergenic region | Del AA | | 382 in SEQ ID NO: 15 | | | |

BM refers to "biallelic marker". All1 and all2 refer respectively to allele 1 and allele 2 of the biallelic marker. "Freq. Of all2" refers to the frequency of the allele 2 in percentage in control population. Frequencies corresponded to a population of random blood donors of French Caucasian origin.

Example 4

Validation of the Polymorphisms Through Microsequencing

The biallelic markers identified in Example 3 were further confirmed and their respective frequencies were determined through microsequencing. Microsequencing was carried out for each individual DNA sample described in Example 1.

TABLE 3

| Marker Name | Biallelic Marker | Mis. 1 | Position range of microsequencing primer mis. 1 in SEQ ID NO: 1 | | Mis. 2 | Complementary position range of microsequencing primer mis. 2 in SEQ ID NO: 1 | |
|---|---|---|---|---|---|---|---|
| 99-32284-107 | A1 | D1 | 6472 | 6490 | E1 | 6492 | 6510 |
| 99-5602-372 | A2 | D2 | 15215 | 15233 | E2 | 15235 | 15253 |
| 5-290-32 | A3 | D3 | 15849 | 15867 | E3 | 15869 | 15887 |
| 99-22573-321 | A4 | D4 | 16710 | 16728 | E4 | 16730 | 16748 |
| 99-22586-300 | A5 | D5 | 18292 | 18310 | E5 | 18312 | 18330 |
| 99-22586-39 | A6 | D6 | 18553 | 18571 | E6 | 18573 | 18591 |
| 99-5596-216 | A7 | D7 | 22887 | 22905 | E7 | 22907 | 22925 |
| 5-293-76 | A8 | D8 | 23156 | 23174 | E8 | 23176 | 23194 |
| 5-293-155 | A9 | D9 | 23234 | 23252 | E9 | 23254 | 23272 |
| 5-294-285 | A10 | D10 | 26087 | 26105 | E10 | 26107 | 26125 |
| 99-23454-317 | A11 | D11 | 30445 | 30463 | E11 | 30465 | 30483 |
| 99-23454-105 | A12 | D12 | 30650 | 30668 | E12 | 30670 | 30688 |
| 99-15528-333 | A13 | D13 | 31231 | 31249 | E13 | 31251 | 31269 |
| 99-15798-86 | A14 | D14 | 35129 | 35147 | E14 | 35149 | 35167 |
| 5-297-209 | A15 | D15 | 36782 | 36800 | E15 | 36802 | 36820 |
| 99-32281-276 | A34 | D16 | 37267 | 37285 | E16 | 37287 | 37305 |
| 99-32281-26 | A35 | D17 | 37517 | 37535 | E17 | 37537 | 37555 |
| 5-298-376 | A16 | D18 | 39302 | 39320 | E18 | 39322 | 39340 |
| 99-23460-199 | A17 | D19 | 39670 | 39688 | E19 | 39690 | 39708 |

TABLE 3-continued

| Marker Name | BM | Mis. 1 | Position range of microsequencing primer | | Mis. 2 | Complementary position range of microsequencing primer | |
|---|---|---|---|---|---|---|---|
| 99-22578-78 | A18 | D20 | 59 | 77 | E20 | 79 | 97 |
| | | | SEQ ID NO: 4 | | | SEQ ID NO: 4 | |
| 99-22580-72 | A19 | D21 | 53 | 71 | E21 | 73 | 91 |
| | | | SEQ ID NO: 5 | | | SEQ ID NO: 5 | |
| 99-22585-462 | A36 | D22 | 443 | 461 | E22 | 463 | 481 |
| | | | SEQ ID NO: 6 | | | SEQ ID NO: 6 | |
| 99-23437-347 | A20 | D23 | 328 | 346 | E23 | 348 | 366 |
| | | | SEQ ID NO: 7 | | | SEQ ID NO: 7 | |
| 99-23440-274 | A21 | D24 | 254 | 272 | E24 | 274 | 292 |
| | | | SEQ ID NO: 8 | | | SEQ ID NO: 8 | |
| 99-23442-190 | A22 | D25 | 171 | 189 | E25 | 191 | 209 |
| | | | SEQ ID NO: 9 | | | SEQ ID NO: 9 | |
| 99-23442-396 | A37 | D26 | 377 | 395 | E26 | 397 | 415 |
| | | | SEQ ID NO: 9 | | | SEQ ID NO: 9 | |
| 99-23444-203 | A23 | D27 | 184 | 202 | E27 | 204 | 222 |
| | | | SEQ ID NO: 10 | | | SEQ ID NO: 10 | |
| 99-23451-78 | A24 | D28 | 58 | 76 | E28 | 78 | 96 |
| | | | SEQ ID NO: 11 | | | SEQ ID NO: 11 | |
| 99-23452-306 | A25 | D29 | 287 | 305 | E29 | 307 | 325 |
| | | | SEQ ID NO: 12 | | | SEQ ID NO: 12 | |
| 99-28437-417 | A38 | D30 | 398 | 416 | E30 | 418 | 436 |
| | | | SEQ ID NO: 13 | | | SEQ ID NO: 13 | |
| 99-32278-218 | A39 | D31 | 199 | 217 | E31 | 219 | 237 |
| | | | SEQ ID NO: 14 | | | SEQ ID NO: 14 | |
| 99-32278-414 | A40 | D32 | 395 | 413 | E32 | 415 | 433 |
| | | | SEQ ID NO: 14 | | | SEQ ID NO: 14 | |
| 99-5575-330 | A26 | D33 | 308 | 326 | E33 | 328 | 346 |
| | | | SEQ ID NO: 16 | | | SEQ ID NO: 16 | |
| 99-5582-71 | A27 | D34 | 52 | 70 | E34 | 72 | 90 |
| | | | SEQ ID NO: 17 | | | SEQ ID NO: 17 | |
| 99-5582-354 | A41 | D35 | 335 | 353 | E35 | 355 | 373 |
| | | | SEQ ID NO: 17 | | | SEQ ID NO: 17 | |
| 99-5590-99 | A28 | D36 | 80 | 98 | E36 | 100 | 118 |
| | | | SEQ ID NO: 18 | | | SEQ ID NO: 18 | |
| 99-5590-425 | A42 | D37 | 405 | 423 | E37 | 425 | 443 |
| | | | SEQ ID NO: 18 | | | SEQ ID NO: 18 | |
| 99-5595-380 | A29 | D38 | 360 | 378 | E38 | 380 | 398 |
| | | | SEQ ID NO: 19 | | | SEQ ID NO: 19 | |
| 99-5604-376 | A30 | D39 | 355 | 373 | E39 | 375 | 393 |
| | | | SEQ ID NO: 20 | | | SEQ ID NO: 20 | |
| 99-5605-90 | A31 | D40 | 71 | 89 | E40 | 91 | 109 |
| | | | SEQ ID NO: 21 | | | SEQ ID NO: 21 | |
| 99-5605-135 | A43 | D41 | 116 | 134 | E41 | 136 | 154 |
| | | | SEQ ID NO: 21 | | | SEQ ID NO: 21 | |
| 99-5608-324 | A32 | D42 | 303 | 322 | E42 | 324 | 343 |
| | | | SEQ ID NO: 14 | | | SEQ ID NO: 14 | |

Amplification from genomic DNA of individuals was performed by PCR as described above for the detection of the biallelic markers with the same set of PCR primers (Table 1).

The preferred primers used in microsequencing were about 19 nucleotides in length and hybridized just upstream of the considered polymorphic base. According to the invention, the primers used in microsequencing are detailed in Table 3.

The microsequencing reaction was performed as follows:

After purification of the amplification products, the microsequencing reaction mixture was prepared by adding, in a 20 µl final volume: 10 pmol microsequencing oligonucleotide, 1 U Thermosequenase (Amersham E79000G), 1.25 µl Thermosequenase buffer (260 mM Tris HCl pH 9.5, 65 mM $MgCl_2$), and the two appropriate fluorescent ddNTPs (Perkin Elmer, Dye Terminator Set 401095) complementary to the nucleotides at the polymorphic site of each biallelic marker tested, following the manufacturer's recommendations. After 4 minutes at 94° C., 20 PCR cycles of 15 sec at 55° C., 5 sec at 72° C., and 10 sec at 94° C. were carried out in a Tetrad PTC-225 thermocycler (MJ Research). The unincorporated dye terminators were then removed by ethanol precipitation. Samples were finally resuspended in formamide-EDTA loading buffer and heated for 2 min at 95° C. before being loaded on a polyacrylamide sequencing gel. The data were collected by an ABI PRISM 377 DNA sequencer and processed using the GENESCAN software (Perkin Elmer).

Following gel analysis, data were automatically processed with software that allows the determination of the alleles of biallelic markers present in each amplified fragment.

The software evaluates such factors as whether the intensities of the signals resulting from the above microsequencing procedures are weak, normal, or saturated, or whether the signals are ambiguous. In addition, the software identifies significant peaks (according to shape and height criteria). Among the significant peaks, peaks corresponding to the targeted site are identified based on their position. When two significant peaks are detected for the same position, each sample is categorized as homozygous or heterozygous type based on the height ratio.

Example 5

Association Study Between Prostate Cancer and the purH-Related Biallelic Markers Collection of DNA Samples from Affected and Non-Affected Individuals Affected Population:

The positive trait followed in this association study was prostate cancer. Prostate cancer patients were recruited according to a combination of clinical, histological and biological inclusion criteria. Clinical criteria can include rectal examination and prostate biopsies. Biological criteria can include PSA assays. The affected individuals were recorded as familial forms when at least two persons affected by prostate cancer have been diagnosed in the family. Familial forms in which at least three persons are affected by prostate cancer in the family are described in the present application as >3CaP. Remaining cases were classified as informative sporadic cases when at least two sibs of the case both aged over 50 years old are unaffected, or uninformative sporadic cases when no information about sibs over 50 years old is available. All affected individuals included in the statistical analysis of this patent were unrelated. Cases were also separated following the criteria of diagnosis age: early onset prostate cancer (under 65 years old) and late onset prostate cancer (65 years old or more).

Unaffected Population:

Control individuals included in this study were checked for both the absence of all clinical and biological criteria defining the presence or the risk of prostate cancer (PSA<4) (WO 96/21042), and for their age (aged 65 years old or more). All unaffected individuals included in the statistical analysis of this patent were unrelated.

The affected group was composed of 491 unrelated individuals, comprising 197 familial cases and 294 sporadic cases. Among the familial cases, 85 individuals are >3CaP. Among the sporadic cases, 70 individuals are informative sporadic cases. The unaffected group contained 313 individuals aged 65 years old or more.

Genotyping of Affected and Control Individuals

The general strategy to perform the Association studies was to individually scan the DNA samples from all individuals in each of the populations described above in order to establish the allele frequencies of the above described biallelic markers in each of these populations.

Allelic frequencies of the above-described biallelic marker alleles in each population were determined by performing microsequencing reactions on amplified fragments obtained by genomic PCR performed on the DNA samples from each individual. Genomic PCR and microsequencing were performed as detailed above in Examples 1 and 2 using the described PCR and microsequencing primers.

Haplotype Frequency Analysis

None of the single marker alleles showed a significant association with prostate cancer except the biallelic marker 99-23437/347 (A20) in the informative sporadic individuals (p value of $1.9 \cdot 10^{-3}$). However, significant results were obtained in haplotype studies. Allelic frequencies were useful to check that the markers used in the haplotype studies meet the Hardy-Weinberg proportions (random mating).

For sets of 2 and 3 markers haplotype frequency estimation can be derived using the E-M algorithm (see above). It has to be noted that all of these approaches are applied to markers under Hardy-Weinberg equilibrium, and only these markers are included.

The profile of haplotypes frequencies can be compared by two main approaches.

Omnibus Likelihood Ratio Tests

For one combination of 2 and 3 markers, this procedure allows us to compare the profile of haplotype frequency differences between the two populations under study. The null hypothesis is that both cases and controls are samples derived from the same population, i.e., the haplotypes frequencies are only due to the sampling process. Using the E-M algorithm, one can calculate the haplotype frequencies in cases, in controls and in the overall population. Once the haplotype frequencies are estimated, a likelihood ratio test (LR test) can be derived which gathers all the haplotype frequency differences in one statistic.

As 1) haplotype frequencies are inferred via the E-M algorithm and not observed and 2) rare haplotypes occur, the LR test does not follow a chi-square with h−1 degrees of freedom (h being the number of haplotypes). A permutation procedure then allows assessment of the significance of the LR test. The permutation procedure is performed as follows:

The affected status (case/controls) is shuffled in individuals and replicate samples of original size are generated. For each generated replicate sample haplotype frequencies are derived and a LR test is calculated. This procedure mimics the null hypothesis of the test, i.e. the two samples are derived from a single population. The process is repeated generally a hundred times. The proportion of test superior to the observed value (the real value) is the level of significance of the test.

Haplo-max Test

Another procedure is based on the haplotype frequency difference of each haplotype between the two groups. For one combination of marker with h haplotypes, h differences of haplotype frequencies can be compared via a Pearson chi-square statistic (1 degree of freedom). The haplo-max test selects the difference showing the maximum positive (Max-M) or negative (Max-S) test value between cases and controls, rejecting test values based on rare haplotype frequencies (with an estimated number of haplotypes inferior to 10). Here, for one combination of marker, there is one Max-M and one Max-S test value.

The significance of this test can be compared by several means:

First, significance thresholds taking into account the multiple testing procedure due to selection of the maximum test value can be arbitrarily set, Secondly, one can assess the observed distribution of the statistics based on all Max-M (or Max-S) statistics derived from the analysis and estimate signification thresholds, Thirdly, one can use the permutation procedure to evaluate a level of significance not based on chi-square with one degree of freedom.

Figure 2:
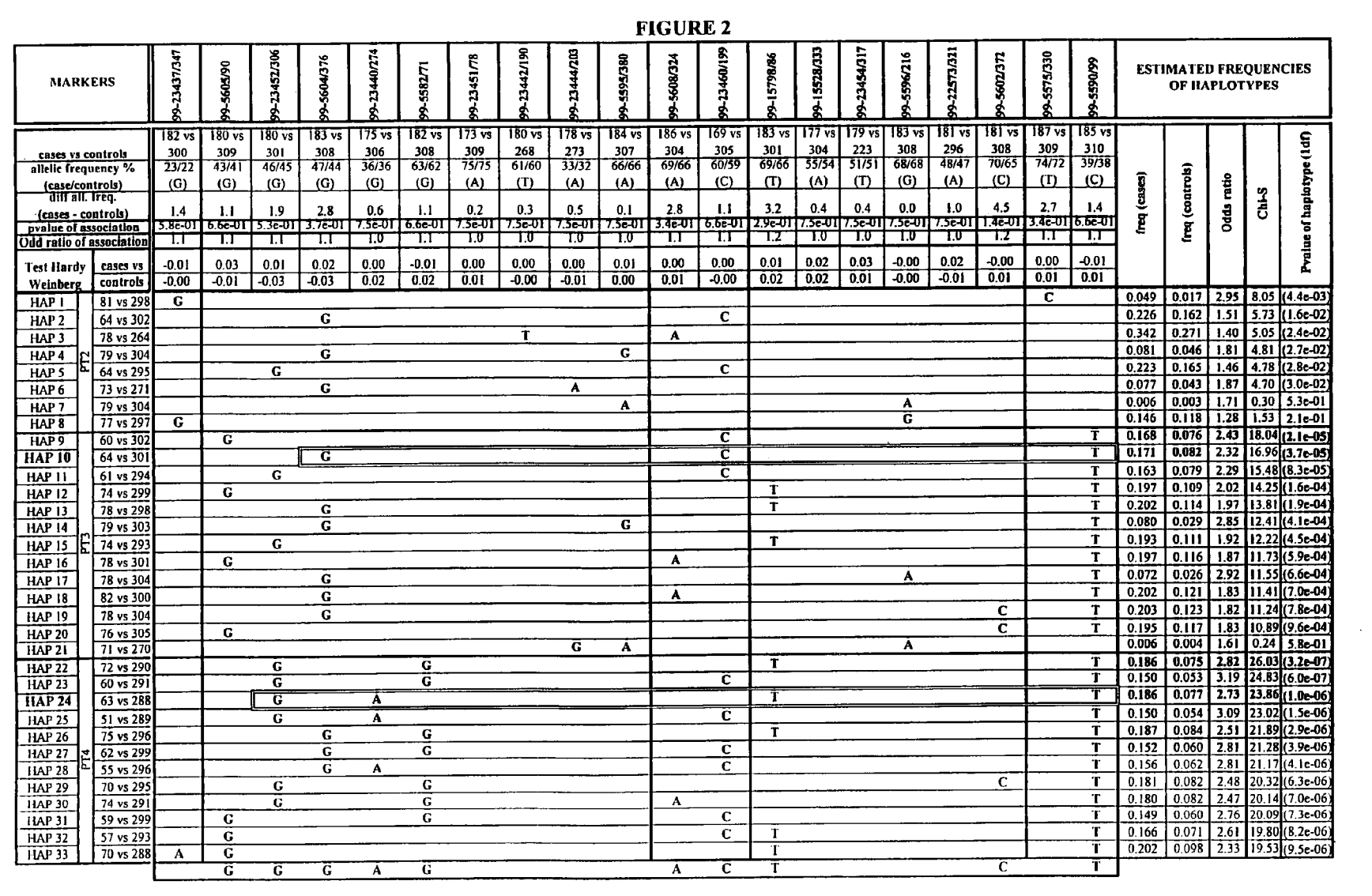

The results of the haplotype analysis using 20 biallelic markers (99-23437/347 (A20), 99-5605/90 (A31), 99-23452/306 (A25), 99-5604/376 (A30), 99-23440/274 (A21), 99-5582/71 (A27), 99-23451/78 (A24), 99-23442/190 (A22), 99-23444/203 (A23), 99-5595/380 (A29), 99-5608/324 (A32), 99-23460/199 (A17), 99-15798/86 (A14), 99-15528/333 (A13), 99-23454/317 (A11), 99-5596/216 (A7), 99-22573/321 (A4), 99-5602/372 (A2), 99-5575/330 (A26), and 99-5590/99 (A28)) are shown in FIGS. 1 and 2. Haplotype analysis for association of purH-related biallelic markers and prostate was performed by estimating the frequencies of all possible 2, 3 and 4 marker haplotypes in the affected and control populations described above. Haplotype estimations were performed by applying the Expectation-Maximization (EM) algorithm (Excoffier and Slatkin, 1995), using the EM- HAPLO program (Hawley et al., 1994) as described above. Estimated haplotype frequencies in the affected and control population were compared by means of a chi-square statistical test (one degree of freedom).

Sporadic Cases

FIG. 1 shows the most significant haplotypes obtained with the sporadic cases.

Haplotype no. 1 (HAP1) consisting of two biallelic markers (99-5595/380 (A29) allele A, and 99-5596/216 (A7) allele A), presented a p-value of $1.1 \times 10^{-9}$ and an odd-ratio of 22. Estimated haplotype frequencies were 6.9% in the sporadic cases and 0.3% in the controls. The association between the HAP 1 haplotype and prostate cancer was still more significant in the sporadic cases under 65 years old with a p-value of $2 \times 10^{-13}$ (see FIG. 3)

However, six other two-markers haplotypes are also highly significant, namely HAP2, HAP3, HAP4, HAP5, HAP6, and HAP7. These haplotypes presented p-value comprised in the range between $2.2 \times 10^{-8}$ and $8.3 \times 10^{-5}$. They often comprised the biallelic marker 99-5596/216 (A7) allele A. Haplotype HAP8 had a highly significant p value in the informative sporadic population ($2.6 \times 10^{-7}$) (see FIG. 3).

Haplotype no. 9 (HAP9) consisting of three biallelic markers (99-23444/203 (A23) allele G, 99-5595/380 (A29) allele A and 99-5596/216 (A7) allele A), had a p-value of $3 \times 10^{-8}$ and an odd ratio of 18.64. Estimated haplotype frequencies were 6.5% in the cases and 0.4% in the controls. The three-markers haplotypes HAP10 to HAP17 and the four-markers haplotypes HAP20 to HAP28 also showed very significant association. The haplotypes HAP10 to HAP17 and HAP20 to HAP28 all comprise the biallelic marker 99-5596/216 (A7).

The more preferred haplotypes HAP1 and HAP9 are both strongly associated with sporadic prostate cancer. They can be used in diagnosis of prostate cancer.

The statistical significance of the results obtained for the haplotype analysis was evaluated by a phenotypic permutation test reiterated 1000 times on a computer. For this computer simulation, data from the affected and control individuals were pooled and randomly allocated to two groups which contained the same number of individuals as the case-control populations used to produce the data summarized in FIG. 1. A haplotype analysis was then run on these artificial groups for the 2 markers included in the haplotype HAP1 and in the haplotype HAP8, which showed the strongest association with sporadic prostate cancer, more particularly with informative sporadic prostate cancer for the HAP8. This experiment was reiterated 1000 times and the results are shown in FIG. 3. These results demonstrate for the HAP1 haplotype of FIG. 1 that among 1000 iterations none of the obtained haplotypes in the simulation had a p-value comparable to the one obtained for the haplotype HAP1. These results clearly validate the statistical significance of the association between the HAP1 haplotype and prostate cancer, preferably sporadic prostate cancer. The permutation test also shows for the HAP8 of FIG. 1 haplotype that among 1000 iterations none of the obtained haplotypes in the simulation had a p-value comparable to the one obtained for the haplotype HAP8 with the informative sporadic cases.

Haplotype Analysis with Genic Biallelic Markers of the purH Gene

The results of the haplotype analysis using 7 biallelic markers (5-297-209 (A15), 99-15798-86 (A14), 99-15528-333 (A13), 5-294-285 (A10), 99-5596-216 (A7), 99-22573-321 (A4), and 99-5602-372 (A2)) are shown in FIGS. 4 and 5. Haplotype analysis for association of genic purH-related biallelic markers and prostate was performed by estimating the frequencies of all possible 2 and 3 marker haplotypes in the affected and control populations described above.

FIG. 4 shows the most significant haplotypes obtained with the sporadic cases (FIG. 4A: 2-markers haplotypes; FIG. 4B: 3-markers haplotypes).

Two 2-biallelic markers haplotypes, namely Haplotype no. 1 and 2, showed a highly significant association with sporadic prostate cancer.

Haplotype no. 1 (HAP1) consisting of two biallelic markers (5-294-285 (A10) allele G, and 99-5596-216 (A7) allele A), presented for the haplotype frequency test a p-value of $2.8 \times 10^{-7}$ and an odd-ratio of 100. Estimated haplotype frequencies were 4.5% in the sporadic cases and 0% in the controls. This haplotype presented a p-value for the likelihood ratio test of $3.2 \times 10^{-7}$. The association between the HAP 1 haplotype and prostate cancer was still more significant in the sporadic cases under 65 years old with a p-value of $10.9 \times 10^{-8}$ and in the informative sporadic cases with a p-value of $1.2 \times 10^{-11}$ (see FIG. 5).

Haplotype no. 2 (HAP2) consisting of two biallelic markers (99-15528-333 (A13) allele G, and 99-5596-216 (A7) allele A), presented for the haplotype frequency test a p-value of $1 \times 10^{-6}$ and an odd-ratio of 100. Estimated haplotype frequencies were 3.9% in the sporadic cases and 0% in the controls. This haplotype presented a p-value for the likelihood ratio test of $1.1 \times 10^{-5}$.

Two 3-biallelic markers haplotypes, namely Haplotype no. 18 and 19, showed a highly significant association with sporadic prostate cancer. Compared to the 2-markers haplotypes, these 3-markers haplotypes further comprise the biallelic marker 5-297-209 (A15), allele A.

Haplotype no. 18 (HAP18) consisting of three biallelic markers (5-294-285 (A10) allele G, 99-5596-216 (A7) allele A and 5-297-209 (A15), allele A), presented for the haplotype frequency test a p-value of $3.8 \times 10^{-7}$ and an odd-ratio of 100. Estimated haplotype frequencies were 4.5% in the sporadic cases and 0% in the controls. This haplotype presented a p-value for the likelihood ratio test of $3.5 \times 10^{-6}$.

Haplotype no. 19 (HAP19) consisting of three biallelic markers (99-15528-333 (A13) allele G, 99-5596-216 (A7) allele A and 5-297-209 (A15), allele A), presented for the haplotype frequency test a p-value of $1.2 \times 10^{-6}$ and an odd-ratio of 100. Estimated haplotype frequencies were 4% in the sporadic cases and 0% in the controls. This haplotype presented a p-value for the likelihood ratio test of $1.1 \times 10^{-4}$.

The more preferred haplotypes HAP1 and HAP2 are both strongly associated with sporadic prostate cancer. They can be used in diagnosis of prostate cancer.

The statistical significance of the results obtained for the haplotype analysis was evaluated by a phenotypic permutation test reiterated 1000 times on a computer. The permutation tests demonstrate for the HAP1, HAP2, HAP18 and HAP19 haplotypes of FIG. 4 that among 100 iterations none of the obtained haplotypes in the simulation had a p-value comparable to the one obtained for these haplotypes. Moreover, the permuation test for the HAP1 haplotype of FIG. 4 demonstrates that among 1000 iterations none of the obtained haplotypes in the simulation had a p-value comparable to the one obtained for the HAP1 haplotype for the sporadic cases. These results clearly validate the statistical significance of the association between the HAP1, HAP2, HAP18 and HAP19 haplotypes of FIG. 4, more particularly HAP1 haplotype, and prostate cancer, preferably sporadic prostate cancer.

HAP1, HAP2, HAP18 and HAP19 haplotypes of FIG. 4, preferably HAP1 haplotype, can be used in diagnosis of prostate cancer, more particularly sporadic prostate cancer.

Familial Cases

FIG. 2 shows the most significant haplotypes obtained with the familial cases.

Two three-markers haplotypes, namely HAP9 and HAP10, showed a highly significant association with familial prostate cancer. The haplotype HAP9 consisting of three biallelic markers (99-5605/90 allele G, 99-23460/199 (A17) allele C and 99-5590/99 (A28) allele T), presented a p-value of $2.1 \times 10^{-5}$ and an odd-ratio of 2.43. Estimated haplotype frequencies were 16.8% in the familial cases and 7.6% in the controls. The haplotype HAP10 consisting of three biallelic markers (99-5604/376 (A30) allele G, 99-23460/199 (A17) allele C and 99-5590/99 (A28) allele T), presented a p-value of $3.7 \times 10^{-5}$ and an odd-ratio of 2.32. Estimated haplotype frequencies were 17.1% in the familial cases and 8.2% in the controls. The association between the HAP 10 haplotype and prostate cancer was more significant in the familial cases which are either >=3CaP or under 65 years old with a p-value of $1.4 \times 10^{-7}$ or $7.1 \times 10^{-7}$, respectively (see FIG. 3). However, ten other three-markers haplotypes are also significant, namely HAP11 to HAP20. These haplotypes presented p-value comprised in the range between $8.3 \times 10^{-5}$ and $9.6 \times 10^{-4}$.

The four-markers haplotypes HAP 22 to HAP 33 showed a highly significant association with familial prostate cancer and presented p-values comprised in the range between $3.2 \times 10^{-7}$ and $9.5 \times 10^{-6}$. One preferred haplotype HAP22 consisting of the four biallelic markers (99-23452/306 (A25) allele G, 99-5582/71 (A27) allele G, 99-15798/86 (A14) allele T and 99-5590/99 (A28) allele T), presented a p-value of $3.2 \times 10^{-7}$ and an odd-ratio of 2.82. Estimated haplotype frequencies were 18.6% in the familial cases and 7.5% in the controls. An other preferred haplotype HAP 24 consisting of the four biallelic markers (99-23452/306 (A25) allele G, 99-23440/274 (A21) allele A, 99-15798/86 (A14) allele T and 99-5590/99 (A28) allele T), presented a p-value of $1 \times 10^{-6}$ and an odd-ratio of 2.73. Estimated haplotype frequencies were 18.6% in the familial cases and 7.7% in the controls. The association between the HAP 24 haplotype and prostate cancer was still more significant in the familial cases which are either >=3CaP or under 65 years old with a p-value of $9.1 \times 10^{-11}$ or $3.5 \times 10^{-9}$, respectively (see FIG. 3).

The haplotypes HAP10 and HAP24 are the more preferred haplotypes of the invention. They can be used in diagnosis of prostate cancer and more particularly familial prostate cancer.

The statistical significance of the results obtained for the haplotype analysis was evaluated by a phenotypic permutation test reiterated 1000 times on a computer. For this computer simulation, data from the affected and control individuals were pooled and randomly allocated to two groups which contained the same number of individuals as the case-control populations used to produce the data summarized in FIG. 2. A haplotype analysis was then run on these artificial groups for the 3 markers included in the haplotype HAP10 and for the 4 markers included in the haplotype HAP24, which showed the strongest association with familial prostate cancer, more particularly with prostate cancer >=3CaP or under 65 years old. This experiment was reiterated 1000 times and the results are shown in FIG. 3. These results demonstrate for the HAP10 haplotype that among 1000 iterations none or only one of the obtained haplotypes had a p-value comparable to the one obtained for the haplotype HAP10 with the familial cases, and more particularly familial cases >=3CaP or under 65 years old. The permutation test also shows for the HAP24 haplotype that among 1000 iterations none of the obtained haplotypes had a p-value comparable to the one obtained for the haplotype HAP24 with the familial cases, and more particularly familial cases >=3CaP or under 65 years old. These results clearly validate the statistical significance of the association between the HAP10 and HAP24 haplotypes and prostate cancer, more particularly familial prostate cancer and more preferably either >=3CaP familial prostate cancer or familial prostate cancer under 65 years old.

All references cited herein are incorporated by reference herein in their entirety.

REFERENCES

The following references are cited herein and are incorporated herein by reference in their entirety.

Abbondanzo S. J. et al. (1993) Methods in Enzymology, Academic Press, New York. pp. 803-823./Ajioka R. S. et al. (1997) Am. J. Hum. Genet. 60:1439-1447./Altschul et al., 1990, J. Mol. Biol. 215(3):403-410;/Altschul et al., 1993, Nature Genetics 3:266-272/Altschul et al., 1997, Nuc. Acids Res. 25:3389-3402/Anton M. et al., 1995, J. Virol., 69: 4600-4606./Araki K et al. (1995) Proc. Natl. Acad. Sci. USA. 92(1):160-4./Baubonis W. (1993) Nucleic Acids Res. 21(9): 2025-9./Beaucage et al., Tetrahedron Lett 1981, 22: 1859-1862/Bradley A., (1987) Production and analysis of chimaeric mice. In: E. J. Robertson (Ed.), Teratocarcinomas and embryonic stem cells: A practical approach. IRL Press, Oxford, pp. 113./Brown E L, Belagaje R, Ryan M J, Khorana H G, Methods Enzymol 1979;68:109-151/Brutlag et al. Comp. App. Biosci. 6:237-245, 1990/Chai H. et al. (1993) Biotechnol. Appl. Biochem. 18:259-273./Chee et al. (1996) Science. 274:610-614./Chen and Kwok Nucleic Acids Research 25:347-353 1997/Chen et al. (1987) Mol. Cell. Biol. 7:2745-2752./Chen et al. Proc. Nat. Acad. Sci. USA 94/20 10756-10761, 1997/Chou J. Y. (1989) Mol. Endocrinol. 3:1511-1514./Clark A. G. (1990) Mol. Biol. Evol. 7:111-122./Coles et al. Hum. Mol. Genet., 7:791-800, 1998/Compton J. (1991) Nature. 350(6313):91-92./Davis et al., Basic Methods in Molecular Biology, ed., Elsevier Press, NY, 1986/Dempster et al., (1977) J. R. Stat. Soc., 39B: 1-38./Dent D. S. and Latchman D. S. (1993) The DNA mobility shift assay. In: Transcription Factors: A Practical Approach (Latchman D S, ed.) Oxford: IRL Press. pp 1-26./Eckner R. et al. (1991) EMBO J. 10:3513-3522./Engvall, E., Meth. Enzymol. 70:419 (1980)/Excoffier L. and Slatkin M. (1995) Mol. Biol. Evol., 12(5): 921-927./Feldman and Steg, 1996, Medecine/Sciences, synthese, 12:47-55/Fisher, D., Chap. 42 in: Manual of Clinical Immunology, 2d Ed. (Rose and Friedman, Eds.) Amer. Soc. For Microbiol., Washington, D.C. (1980)/Flotte et al. (1992) Am. J. Respir. Cell Mol. Biol. 7:349-356./Fodor et al. (1991) Science 251:767-777./Fraley et al. (1979) Proc. Natl. Acad. Sci. USA. 76:3348-3352./Fried M. and Crothers D. M. (1981) Nucleic Acids Res. 9:6505-6525./Fuller S. A. et al. (1996) Immunology in Current Protocols in Molecular Biology, Ausubel et al. Eds, John Wiley & Sons, Inc., USA./Furth P. A. et al. (1994) Proc. Natl. Acad. Sci USA. 91:9302-9306./Garner M. M. and Revzin A. (1981) Nucleic Acids Res. 9:3047-3060./Geysen H. Mario et al. 1984. Proc. Natl. Acad. Sci. U.S.A. 81:3998-4002/Ghosh and Bacchawat (1991) Targeting of liposomes to hepatocytes, IN: Liver Diseases, Targeted diagnosis and therapy using specific receptors and ligands. Wu et al. Eds., Marcel Dekeker, New York, pp. 87-104./Gonnet et al., 1992, Science 256:1443-1445;/Gopal (1985) Mol. Cell. Biol., 5:1188-1190./Gossen M. et al. (1992) Proc. Natl. Acad. Sci. USA. 89:5547-5551./Gossen M. et al. (1995) Science. 268:1766-1769./Graham et al. (1973) Virology 52:456-457./Green et al. (1986) Ann. Rev. Biochem. 55:569-597./Griffin et al. (1989) Science. 245:967-971./Grompe, M. (1993) Nature Genetics. 5:111-117./Grompe, M. et al. (1989) Proc. Natl. Acad. Sci. U.S.A. 86:5855-5892./Gu H. et al. (1993) Cell 73:1155-1164./Gu H. et al. (1994) Science 265:103-106./Guatelli J C et al. Proc. Natl. Acad. Sci.

USA. 35:273-286./Hacia J G, Brody L C, Chee M S, Fodor S P, Collins F S, Nat Genet 1996; 14(4):441-447/Haff L. A. and Smirnov I. P. (1997) Genome Research, 7:378-388./Hames B. D. and Higgins S. J. (1985) Nucleic Acid Hybridization: A Practical Approach. Hames and Higgins Ed., IRL Press, Oxford./Harju L, Weber T, Alexandrova L, Lukin M, Ranki M, Jalanko A, Clin Chem 1993; 39(11Pt 1):2282-2287/Harland et al. (1985) J. Cell. Biol. 101:1094-1095./Harlow, E., and D. Lane. 1988. Antibodies A Laboratory Manual. Cold Spring Harbor Laboratory. pp. 53-242/Hawley M. E. et al. (1994) Am. J. Phys. Anthropol. 18:104./Henikoff and Henikoff, 1993, Proteins 17:49-61/Higgins et al., 1996, Methods Enzymol. 266:383-402;/Hillier L. and Green P. Methods Appl., 1991, 1: 124-8. Gu H. et al. (1994) Science 265:103-106./Hoess et al. (1986) Nucleic Acids Res. 14:2287-2300./Huang L. et al. (1996) Cancer Res 56(5):1137-1141./Huygen et al. (1996) Nature Medicine. 2(8):893-898./Izant J. G. and Weintraub H. (1984) Cell 36(4):1007-1015./Julan et al. (1992) J. Gen. Virol. 73:3251-3255./Kanegae Y. et al., Nucl. Acids Res. 23:3816-3821./Karlin and Altschul, 1990, Proc. Natl. Acad. Sci. USA 87:2267-2268;/Khoury J. et al. (1993) Fundamentals of Genetic Epidemiology, Oxford University Press, NY./Kim U-J. et al. (1996) Genomics 34:213-218./Klein et al. (1987) Nature. 327:70-73./Kohler, G. and Milstein, C., Nature 256:495 (1975)/Koller et al. (1992) Annu. Rev. Immunol. 10:705-730./Kozal M J, Shah N, Shen N, Yang R, Fucini R, Merigan T C, Richman D D, Morris D, Hubbell E, Chee M, Gingeras T R, Nat Med 1996; 2(7):753-759/ Landegren U. et al. (1998) Genome Research, 8:769-776./Lander and Schork, Science, 265, 2037-2048, 1994/Lange K. (1997) *Mathematical and Statistical Methods for Genetic Analysis*. Springer, New York./Lenhard T. et al. (1996) Gene. 169:187-190./Linton M. F. et al. (1993) J. Clin. Invest. 92:3029-3037. Liu Z. et al. (1994) Proc. Natl. Acad. Sci. USA. 91: 4528-4262./Livak et al., Nature Genetics, 9:341-342, 1995/Livak K J, Hainer J W, Hum Mutat 1994; 3(4):379-385/Lockhart et al. (1996) Nature Biotechnology 14:1675-1680./Mansour S. L. et al. (1988) Nature. 336:348-352./Marshall R. L. et al. (1994) PCR Methods and Applications. 4:80-84./McCormick et al. (1994) Genet. Anal. Tech. Appl. 11:158-164./McLaughlin B. A. et al. (1996) Am. J. Hum. Genet. 59:561-569./Morton N. E. (1955) Am. J. Hum. Genet. 7:277-318./Muzyczka et al. (1992) Curr. Topics in Micro. and Immunol. 158:97-129./Nada S. et al. (1993) Cell 73:1125-1135./Nagy A. et al. (1993) Proc. Natl. Acad. Sci. USA. 90: 8424-8428./Narang S A, Hsiung H M, Brousseau R, Methods Enzymol 1979; 68:90-98/Neda et al. (1991) J. Biol. Chem. 266:14143-14146./Newton et al. (1989) Nucleic Acids Res. 17:2503-2516./Nickerson D. A. et al. (1990) Proc. Natl. Acad. Sci. U.S.A. 87:8923-8927./Nicolau et al. (1982) Biochim. Biophys. Acta. 721:185-190./Nyren P, Pettersson B, Uhlen M, Anal Biochem 1993; 208(1):171-175/O'Reilly et al. (1992) Baculovirus Expression Vectors: A Laboratory Manual. W. H. Freeman and Co., New York./Ohno et al. (1994) Science. 265:781-784./Orita et al. (1989) Proc. Natl. Acad. Sci. U.S.A. 86: 2776-2770./Ott J. (1991) Analysis of Human Genetic Linkage. John Hopkins University Press, Baltimore./Ouchterlony, O. et al., Chap. 19 in: Handbook of Experimental Immunology D. Wier (ed) Blackwell (1973)/Pastinen et al., Genome Research 1997; 7:606-614/Pearson and Lipman, 1988, Proc. Natl. Acad. Sci. USA 85(8):2444-2448;/Pease S. and William R. S. (1990) Exp. Cell. Res. 190:09-211./Perlin et al. (1994) Am. J. Hum. Genet. 55:777-787./Peterson et al. (1993) Proc. Natl. Acad. Sci. USA. 90: 7593-7597./Pietu et al. (1996) Genome Research. 6:492-503./Potter et al. (1984) Proc. Natl. Acad. Sci. U.S.A. 81(22): 7161-7165./Rayl et al., (1996) J. Bio. Chem, 271, 2225-2233./Reid L. H. et al. (1990) Proc. Natl. Acad. Sci. U.S.A. 87:4299-4303./Risch, N. and Merikangas, K. (1996) Science. 273:1516-1517./Robertson E. (1987) "Embryo-Derived Stem Cell Lines." In: E. J. Robertson Ed. Teratocarcinomas And Embryonic Stem Cells: A Practical Approach. IRL Press, Oxford, pp. 71./Rossi et al. (1991) Pharmacol. Ther. 50:245-254./Roth J. A. et al. (1996) Nature Medicine. 2(9): 985-991./Roux et al. (1989) Proc. Natl. Acad. Sci. U.S.A. 86:9079-9083./Ruano et al. (1990) Proc. Natl. Acad. Sci. U.S.A. 87:6296-6300./Sambrook, J., Fritsch, E. F., and T. Maniatis. (1989) Molecular Cloning: A Laboratory Manual. 2ed. Cold Spring Harbor Laboratory, Cold Spring Harbor, N.Y./Samson M, et al. (1996) Nature, 382(6593):722-725./Samulski et al. (1989) J. Virol. 63:3822-3828./Sanchez-Pescador R. (1988) J. Clin. Microbiol. 26(10):1934-1938./Sarkar, G. and Sommer S. S. (1991) Biotechniques./Sauer B. et al. (1988) Proc. Natl. Acad. Sci. U.S.A. 85:5166-5170./Schaid D. J. et al. (1996) Genet. Epidemiol. 13:423-450./Schedl A. et al. (1993a) Nature. 362:258-261./Schedl et al. (1993b) Nucleic Acids Res. 21:4783-4787./Schena et al. (1995) Science. 270:467-470./Schena et al. (1996) Proc. Natl. Acad. Sci. U.S.A. 93(20):10614-10619./Schneider et al. (1997) Arlequin: A Software For Population Genetics Data Analysis. University of Geneva./Schwartz and Dayhoff, eds., 1978, Matrices for Detecting Distance Relationships: Atlas of Protein Sequence and Structure, Washington: National Biomedical Research Foundation/Sczakiel G. et al. (1995) Trends Microbiol. 3(6):213-217./Shay J. W. et al. (1991) Biochem. Biophys. Acta. 1072:1-7./Sheffield, V. C. et al. (1991) Proc. Natl. Acad. Sci. U.S.A. 49:699-706./Shizuya et al. (1992) Proc. Natl. Acad. Sci. U.S.A. 89:8794-8797. Shoemaker D D, Lashkari D A, Morris D, Mittmann M, Davis R W, Nat Genet 1996; 14(4):450-456/Smith (1957) Ann. Hum. Genet. 21:254-276./Smith et al. (1983) Mol. Cell. Biol. 3:2156-2165./Sosnowski R. G. et al. (1997) Proc. Natl. Acad. Sci. U.S.A. 94:1119-1123./Spielmann S. and Ewens W. J. (1998) Am. J. Hum. Genet. 62:450-458./Spielmann S. et al. (1993) Am. J. Hum. Genet. 52:506-516./Sternberg N. L. (1992) Trends Genet. 8:1-16./Sternberg N. L. (1994) Mamm. Genome. 5:397-404./Sugita et al, (1997) J. Biochem. 122, 309-313/Syvanen A C, Clin Chim Acta 1994; 226(2):225-236/Tacson et al. (1996) Nature Medicine. 2(8):888-892./Te Riele et al. (1990) Nature. 348:649-651./Terwilliger J. D. and Ott J. (1994) Handbook of Human Genetic Linkage. John Hopkins University Press, London./Thomas K. R. et al. (1986) Cell. 44:419-428./Thomas K. R. et al. (1987) Cell. 51:503-512./Thompson et al., 1994, Nucleic Acids Res. 22(2):4673-4680;/Tur-Kaspa et al. (1986) Mol. Cell. Biol. 6:716-718./Tyagi et al. (1998) Nature Biotechnology. 16:49-53./Urdea M. S. (1988) Nucleic Acids Research. 11:4937-4957./Urdea M. S. et al. (1991) Nucleic Acids Symp. Ser. 24:197-200./Vaitukaitis, J. et al. J. Clin. Endocrinol. Metab. 33:988-991 (1971)/Van der Lugt et al. (1991) Gene. 105:263-267./Vlasak R. et al. (1983) Eur. J. Biochem. 135:123-126./Wabiko et al. (1986) DNA. 5(4):305-314./Walker et al. (1996) Clin. Chem. 42:9-13./Weir, B. S. (1996) Genetic data Analysis II: Methods for Discrete population genetic Data, Sinauer Assoc., Inc., Sunderland, Mass., U.S.A./White, M. B. et al. (1992) Genomics. 12:301-306./White, M. B. et al. (1997) Genomics. 12:301-306./Wong et al. (1980) Gene. 10:87-94./Wood S. A. et al. (1993) Proc. Natl. Acad. Sci. U.S.A. 90:4582-4585./Wu and Wu (1987) J. Biol. Chem. 262:4429-4432./Wu and Wu (1988) Biochemistry. 27:887-892./Wu et al. (1989) Proc. Natl. Acad. Sci. U.S.A. 86:2757./Yagi T. et al. (1990) Proc. Natl. Acad. Sci. U.S.A. 87:9918-9922./Zhao et al. (1998) Am. J. Hum. Genet. 63:225-240./Zou Y. R. et al. (1994) Curr. Biol. 4:1099-1103/

We claim:

1. A method of determining whether a human individual is at an increased risk for developing sporadic prostate cancer comprising the steps of:
   a) obtaining a biological sample comprising a nucleic acid from said human individual;
   b) determining the identity of a biallelic marker at position 22906 of SEQ ID NO: 1 (A7) and position 379 of SEQ ID NO: 19 (A29) within said biological sample; and
   c) evaluating whether said human individual is at an increased risk of sporadic prostate cancer; wherein the presence of both an A at position 22906 of SEQ ID NO: 1 (A7) and an A at position 379 of SEQ ID NO: 19 (A29) is indicative of an increased risk for developing sporadic prostate cancer.

2. The method according to claim 1, further comprising the steps of:
   a) determining the identity of a biallelic marker at position 203 of SEQ ID NO: 10 (A23) within said biological sample; and
   b) evaluating whether an individual is at an increased risk of sporadic prostate cancer; wherein the presence of all of:
      (i) a G at position 203 of SEQ ID NO: 10 (A23);
      (ii) an A at position 22906 of SEQ ID NO: 1 (A7); and
      (iii) an A at position 379 of SEQ ID NO: 19 (A29);
   is indicative of an increased risk for developing sporadic prostate cancer.

3. The method according to claim 1, further comprising the step of amplifying a portion of said purH gene comprising said biallelic marker prior to determining the identity of said nucleotides.

4. The method according to claim 3, wherein said amplifying is performed by PCR.

5. The method according to claim 1, wherein said nucleotide is determined by performing a microsequencing assay.

6. The method according to claim 1, wherein said nucleotide is determined by performing a hybridization assay.

7. The method according to claim 1, wherein said nucleotide is determined by performing a sequencing assay.

8. The method according to claim 2, wherein said nucleotide is determined by performing a microsequencing assay.

9. The method according to claim 2, wherein said nucleotide is determined by performing a hybridization assay.

10. The method according to claim 2, wherein said nucleotide is determined by performing a sequencing assay.

11. The method according to claim 1, further comprising the steps of:
    a) determining the identity of the biallelic marker at position 190 of SEQ ID NO: 9 (A22) within said biological sample; and
    b) evaluating whether a human individual is at an increased risk of sporadic prostate cancer; wherein the presence of the following biallelic markers is indicative of an increased risk for developing sporadic prostate cancer:
       (i) a T at position 190 of SEQ ID NO: 9 (A22);
       (ii) an A at position 22906 of SEQ ID NO: 1 (A7); and
       (iii) an A at position 379 of SEQ ID NO: 19 (A29).

12. The method according to claim 11, wherein said nucleotide is determined by performing a microsequencing assay.

13. The method according to claim 11, wherein said nucleotide is determined by performing a hybridization assay.

14. The method according to claim 11, wherein said nucleotide is determined by performing a sequencing assay.

15. The method according to claim 1, further comprising the steps of:
    a) determining the identity of the biallelic marker at position 77 of SEQ ID NO: 11 (A24) within said biological sample; and
    b) evaluating whether a human individual is at an increased risk of sporadic prostate cancer; wherein the presence of the following biallelic markers is indicative of an increased risk for developing sporadic prostate cancer:
       (i) an A at position 77 of SEQ ID NO: 11 (A24);
       (ii) an A at position 22906 of SEQ ID NO: 1 (A7); and
       (iii) an A at position 379 of SEQ ID NO: 19 (A29).

16. The method according to claim 15, wherein said nucleotide is determined by performing a microsequencing assay.

17. The method according to claim 15, wherein said nucleotide is determined by performing a hybridization assay.

18. The method according to claim 15, wherein said nucleotide is determined by performing a sequencing assay.

19. The method according to claim 1, further comprising the steps of:
    a) determining the identity of the biallelic marker at position 273 of SEQ ID NO: 8 (A21) within said biological sample; and
    b) evaluating whether a human individual is at an increased risk of sporadic prostate cancer; wherein the presence of the following biallelic markers is indicative of an increased risk for developing sporadic prostate cancer:
       (i) anAat position 273 of SEQ ID NO: 8 (A21);
       (ii) an A at position 22906 of SEQ ID NO: 1 (A7); and
       (iii) an A at position 379 of SEQ ID NO: 19 (A29).

20. The method according to claim 19, wherein said nucleotide is determined by performing a microsequencing assay.

21. The method according to claim 19, wherein said nucleotide is determined by performing a hybridization assay.

22. The method according to claim 19, wherein said nucleotide is determined by performing a sequencing assay.

* * * * *

UNITED STATES PATENT AND TRADEMARK OFFICE
CERTIFICATE OF CORRECTION

PATENT NO. : 7,427,482 B2
APPLICATION NO. : 11/285466
DATED : September 23, 2008
INVENTOR(S) : Marta Blumenfeld et al.

It is certified that error appears in the above-identified patent and that said Letters Patent is hereby corrected as shown below:

Column 4,
Line 52, "an cytosine" should read --a cytosine--.

Column 5,
Line 21, "acids" should read --acid--.

Column 7,
Line 27, "as wells as" should read --as well as--.
Line 66, "one modifications" should read --one modification--.

Column 10,
Line 9, "in an other gene" should read --in another gene--.

Column 16,
Line 2, "two others TATA box have" should read --two other TATA boxes have--.

Column 19,
Line 15, "a polypeptides" should read --a polypeptide--.

Column 24,
Line 3, "selected in the group" should read --selected from the group--.

Column 25,
Line 50, "probes" should read --probe--.

Column 30,
Line 55, "acid" should read --acids--.

Column 32,
Line 56, "constructs" should read --construct--.

Column 36,
Line 40, "10" should read --$10^4$--.

Column 46,
Lines 30-31, "analyzes" should read --analysis--.

UNITED STATES PATENT AND TRADEMARK OFFICE
CERTIFICATE OF CORRECTION

PATENT NO. : 7,427,482 B2
APPLICATION NO. : 11/285466
DATED : September 23, 2008
INVENTOR(S) : Marta Blumenfeld et al.

It is certified that error appears in the above-identified patent and that said Letters Patent is hereby corrected as shown below:

Column 62,
Line 45, "time" should read --times--.

Column 70,
Line 17, "A 10" should read --A10--.

Column 93,
Line 65, "30 $$ sec" should read --30 sec--.

Column 103,
Line 15, "2x10-$^{13}$" should read --2x10$^{-13}$--.

Column 104,
Lines 17-18, "10.9x10$^{-8}$" should read --1.9x10$^{-8}$--.

Column 105,
Line 30, "An other preferred" should read --Another preferred--.

Column 106,
Line 57, "Dekeker" should read --Deker--.

Signed and Sealed this

Twenty-first Day of April, 2009

JOHN DOLL
*Acting Director of the United States Patent and Trademark Office*